US008383641B2

(12) United States Patent
Grandel et al.

(10) Patent No.: US 8,383,641 B2
(45) Date of Patent: Feb. 26, 2013

(54) ARYLOXYETHYLAMINE COMPOUNDS SUITABLE FOR TREATING DISORDERS THAT RESPOND TO MODULATION OF THE DOPAMINE D3 RECEPTOR

(75) Inventors: Roland Grandel, Dossenheim (DE); Wilfried Martin Braje, Rinteln (DE); Andreas Haupt, Schwetzingen (DE); Sean Colm Turner, Mannheim (DE); Udo Lange, Berlin (DE); Karla Drescher, Dossenheim (DE); Liliane Unger, Ludwigshafen (DE)

(73) Assignee: Abbott GmbH & Co. KG, Wiesbaden (DE)

( * ) Notice: Subject to any disclaimer, the term of this patent is extended or adjusted under 35 U.S.C. 154(b) by 207 days.

(21) Appl. No.: 12/296,739

(22) PCT Filed: Apr. 13, 2007

(86) PCT No.: PCT/EP2007/053633
§ 371 (c)(1),
(2), (4) Date: Dec. 18, 2008

(87) PCT Pub. No.: WO2007/118859
PCT Pub. Date: Oct. 25, 2007

(65) Prior Publication Data
US 2009/0143383 A1 Jun. 4, 2009

Related U.S. Application Data

(60) Provisional application No. 60/793,671, filed on Apr. 20, 2006.

(30) Foreign Application Priority Data

Apr. 14, 2006 (EP) .................................... 06007923

(51) Int. Cl.
*A61K 31/44* (2006.01)
*A61K 31/4965* (2006.01)
*C07D 213/62* (2006.01)
*C07D 239/34* (2006.01)
(52) U.S. Cl. ......... 514/274; 514/349; 544/316; 546/293
(58) Field of Classification Search .................. 544/316; 546/293
See application file for complete search history.

(56) References Cited

FOREIGN PATENT DOCUMENTS
WO       9958499   A    11/1999
WO     2006040179  A1   4/2006

OTHER PUBLICATIONS

Dementia [online], [retrieved on May 24, 2007]. Retrieved from the internet, URL; http://en.wikipedia.org/wiki/Dementia.*
Parkinson's Disease [online], [retrieved on May 23, 2010]. Retrieved from the internet, URL; http://www.mayoclinic.com/health/parkinsons-disease/ds00295.*
J.C. Schwartz et al., "The Dopamine D3 Receptor as a Target for Antipsychotics", Raven Press, New York, 1992, pp. 135-144.
Dooley, et al., "Pramipexole", Drugs and Aging 1998, 12, pp. 495-514.
Joyce, et al., "Dopamine D3 Receptor Antagonists as Therapeutic Agents", Pharmacology and Therapeutics 2001, 90, pp. 231-259.
Laszlovszky, et al., "Substituted Phenoxyalkylpiperazines as Dopamine D3 Receptor Ligands", XP-001093755.
International Search Report as filed Jul. 2, 2007 in PCT/EP2007/053633.
Benoit S.C., et al. Altered feeding responses in mice with targeted disruption of the dopamine-3 receptor gene. Behavioral Neuroscience, 2003;117(1):46-54.
Laszy, J., et al. Dopamine D3 receptor antagonists improve the learning performance in memory-impaired rats. Pscyhopharmacology, 2005;179:567-75.
Heidbreder, C.A., et al. The role of central dopamine D3 receptors in drug addiction: a review of pharmacological evidence. Brain Research Reviews, 2005;49:77-105.
Rogoz, Z., et al. Anxiolytic-like effects of preferential dopamine D3 receptor agonists in an animal model. Polish Journal of Pharmacology, 2003;55:449-54.
Muhlbauer B., et al.. Dopamine D3 receptors in the rat kidney: role in physiology and pathophysiology. Acta Physiologica Scandinavica, 2000;168(1):219-23.
Joyce, J.N. Dopamine D3 receptor as a therapeutic target for antipsychotic and antiparkinsonian drugs. Pharmacology and Therapeutics. Pharmacology and Therapeutics, 2001;90:231-59.

* cited by examiner

*Primary Examiner* — Shawquia Yong
(74) *Attorney, Agent, or Firm* — Lisa V. Mueller; Michael Best & Friedrich LLP

(57) ABSTRACT

The present invention relates to aryloxyethylamine compounds of the formula I (I)

and the physiologically tolerated acid addition salts thereof. The variables have the meanings given in the claims and the description. The invention also relates to the use of a compound of the formula I or a pharmaceutically acceptable salt thereof for preparing a pharmaceutical composition for the treatment of a medical disorder susceptible to treatment with a dopamine D3 receptor ligand.

28 Claims, No Drawings

ARYLOXYETHYLAMINE COMPOUNDS SUITABLE FOR TREATING DISORDERS THAT RESPOND TO MODULATION OF THE DOPAMINE D3 RECEPTOR

CROSS REFERENCE TO RELATED APPLICATION

This application is a 371 national stage filing based upon International PCT Application No. PCT/EP2007/053633, with an international filing date of Apr. 13, 2007, which claims the benefit of priority to U.S. Provisional Application No. 60/793,671, filed Apr. 20, 2006, and benefit under 35 U.S.C. §119(b) to EP Application No. 06007923.3, filed Apr. 14, 2006, each of which are fully incorporated herein by reference as though fully set forth herein.

BACKGROUND OF THE INVENTION

The present invention relates to novel aryloxyethylamine compounds. The compounds possess valuable therapeutic properties and are suitable, in particular, for treating diseases that respond to modulation of the dopamine $D_3$ receptor.

Neurons obtain their information by way of G protein-coupled receptors, inter alia. A large number of substances exert their effect by way of these receptors. One of them is dopamine. Confirmed findings exist with regard to the presence of dopamine and its physiological function as a neurotransmitter. Disorders in the dopaminergic transmitter system result in diseases of the central nervous system which include, for example, schizophrenia, depression and Parkinson's disease. These diseases, and others, are treated with drugs which interact with the dopamine receptors.

Up until 1990, two subtypes of dopamine receptor had been clearly defined pharmacologically, namely the $D_1$ and $D_2$ receptors. More recently, a third subtype was found, namely the $D_3$ receptor which appears to mediate some effects of antipsychotics and antiparkinsonians (J. C. Schwartz et al., The Dopamine $D_3$ Receptor as a Target for Antipsychotics, in Novel Antipsychotic Drugs, H. Y. Meltzer, Ed. Raven Press, New York 1992, pages 135-144; M. Dooley et al., Drugs and Aging 1998, 12, 495-514, J. N. Joyce, Pharmacology and Therapeutics 2001, 90, pp. 231-59 "The Dopamine $D_3$ Receptor as a Therapeutic Target for Antipsychotic and Antiparkinsonian Drugs").

Since then, the dopamine receptors have been divided into two families. On the one hand, there is the $D_2$ group, consisting of $D_2$, $D_3$ and $D_4$ receptors, and, on the other hand, the $D_1$ group, consisting of $D_1$ and $D_5$ receptors. Whereas $D_1$ and $D_2$ receptors are widely distributed, $D_3$ receptors appear to be expressed regioselectively. Thus, these receptors are preferentially to be found in the limbic system and the projection regions of the mesolimbic dopamine system, especially in the nucleus accumbens, but also in other regions, such as the amygdala. Because of this comparatively regioselective expression, $D_3$ receptors are regarded as being a target having few side-effects and it is assumed that while a selective $D_3$ ligand would have the properties of known antipsychotics, it would not have their dopamine $D_2$ receptor-mediated neurological side-effects (P. Sokoloff et al., Localization and Function of the $D_3$ Dopamine Receptor, Arzneim. Forsch./Drug Res. 42(1), 224 (1992); P. Sokoloff et al. Molecular Cloning and Characterization of a Novel Dopamine Receptor ($D_3$) as a Target for Neuroleptics, Nature, 347, 146 (1990)).

SUMMARY OF THE INVENTION

The invention is based on the object of providing compounds which act as highly selective dopamine $D_3$ receptor ligands. This object is surprisingly achieved by means of aryloxyethylamine compounds of the formula I

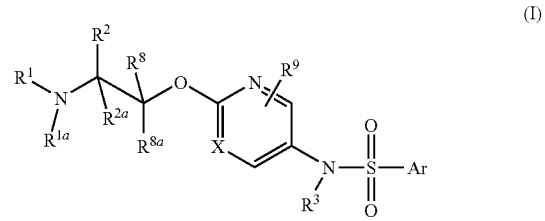

wherein
Ar is phenyl or an aromatic 5- or 6-membered C-bound heteroaromatic radical, wherein Ar may carry 1 radical Ra and wherein Ar may also carry 1 or 2 radicals Rb;
$R^a$ is selected from the group consisting of $C_1$-$C_6$-alkyl, fluorinated $C_1$-$C_6$-alkyl, $C_2$-$C_6$-alkenyl, fluorinated $C_2$-$C_6$-alkenyl, $C_3$-$C_6$-cycloalkyl, fluorinated $C_3$-$C_6$-cycloalkyl, $C_1$-$C_6$-alkoxy, fluorinated $C_1$-$C_6$-alkoxy, $C_1$-$C_6$-hydroxyalkyl, $C_1$-$C_6$-alkoxy-$C_1$-$C_4$-alkyl, $C_1$-$C_6$-hydroxyalkoxy, $C_1$-$C_6$-alkoxy-$C_1$-$C_4$-alkoxy, COOH, $NR^4R^5$, $CH_2NR^4R^5$, $ONR^4R^5$, $NHC(O)NR^4R^5$, $C(O)NR^4R^5$, $SO_2NR^4R^5$, $C_1$-$C_6$-alkylcarbonyl, fluorinated $C_1$-$C_6$-alkylcarbonyl, $C_1$-$C_6$-alkylcarbonylamino, fluorinated $C_1$-$C_6$-alkylcarbonylamino, $C_1$-$C_6$-alkylcarbonyloxy, fluorinated $C_1$-$C_6$-alkylcarbonyloxy, $C_1$-$C_6$-alkoxycarbonyl, fluorinated $C_1$-$C_6$-alkoxycarbonyl, $C_1$-$C_6$-alkylthio, fluorinated $C_1$-$C_6$-alkylthio, $C_1$-$C_6$-alkylsulfinyl, fluorinated $C_1$-$C_6$-alkylsulfinyl, $C_1$-$C_6$-alkylsulfonyl, fluorinated $C_1$-$C_6$-alkylsulfonyl, phenylsulfonyl, phenyl, phenoxy, benzyloxy, pyridin-2-yloxy and a 3- to 7-membered heterocyclic radical, wherein the phenyl groups, the pyridyl group and the heterocyclyl group in the six last mentioned radicals may carry 1, 2, 3 or 4 radicals selected from halogen, cyano, OH, oxo, CN, and a radical $R^{aa}$, wherein
$R^{aa}$ is selected from $C_1$-$C_6$-alkyl, fluorinated $C_1$-$C_6$-alkyl, $C_2$-$C_6$-alkenyl, fluorinated $C_2$-$C_6$-alkenyl, $C_3$-$C_6$-cycloalkyl, fluorinated $C_3$-$C_6$-cycloalkyl, $C_1$-$C_6$-alkoxy, fluorinated $C_1$-$C_6$-alkoxy, $C_1$-$C_6$-hydroxyalkyl, $C_1$-$C_6$-alkoxy-$C_1$-$C_4$-alkyl, $C_1$-$C_6$-hydroxyalkoxy, $C_1$-$C_6$-alkoxy-$C_1$-$C_4$-alkoxy, COOH, $NR^4R^5$, $CH_2NR^4R^5$, $ONR^4R^5$, $NHC(O)NR^4R^5$, $C(O)NR^4R^5$, $SO_2NR^4R^5$, $C_1$-$C_6$-alkylcarbonyl, fluorinated $C_1$-$C_6$-alkylcarbonyl, $C_1$-$C_6$-alkylcarbonylamino, fluorinated $C_1$-$C_6$-alkylcarbonylamino, $C_1$-$C_6$-alkylcarbonyloxy, fluorinated $C_1$-$C_6$-alkylcarbonyloxy, $C_1$-$C_6$-alkoxycarbonyl, fluorinated $C_1$-$C_6$-alkoxycarbonyl, $C_1$-$C_6$-alkylthio, fluorinated $C_1$-$C_6$-alkylthio, $C_1$-$C_6$-alkylsulfinyl, fluorinated $C_1$-$C_6$-alkylsulfinyl, $C_1$-$C_6$-alkylsulfonyl, fluorinated $C_1$-$C_6$-alkylsulfonyl,
each $R^b$ is selected from halogen, cyano, nitro, OH, methyl, methoxy, fluoromethyl, difluoromethyl, trifluoromethyl, fluormethoxy, difluoromethoxy and trifluoromethoxy, or
the radical $R^a$ and one radical $R^b$, if present, which are bound to two adjacent carbon atoms of phenyl, may form a 5- or 6-membered heterocyclic or carbocyclic ring which is fused to the phenyl ring and which is unsubstituted or which may carry 1, 2 or 3 radicals selected from halogen, $NO_2$, $NH_2$, OH, CN, $C_1$-$C_6$-alkyl, fluorinated $C_1$-$C_6$-alkyl, $C_3$-$C_6$-cycloalkyl, fluorinated $C_3$-$C_6$-cycloalkyl, $C_1$-$C_6$-alkoxy, fluorinated $C_1$-$C_6$-alkoxy, $C_1$-$C_6$-hydroxyalkyl, $C_1$-$C_4$-alkoxy-$C_2$-$C_4$-alkyl, $C_1$-$C_6$-hydroxyalkoxy, $C_1$-$C_4$-alkoxy-$C_2$-$C_4$-alkoxy, $C_1$-$C_6$-alkylcarbonyl, fluorinated $C_1$-$C_6$-alkylcarbonyl, $C_1$-$C_6$-alkylamino, di-$C_1$-$C_6$-alkylamino, $C_1$-$C_6$-alkylaminocarbonyl, di-$C_1$-$C_6$-alkylaminocarbonyl, $C_1$-$C_6$-alkylcarbonylamino, fluorinated $C_1$-$C_6$-alkylcarbonylamino, $C_1$-$C_6$-alkylcarbonyloxy, fluorinated $C_1$-$C_6$-alkylcarbonyloxy, $C_1$-$C_6$-alkoxycarbonyl, $C_1$-$C_6$-alkylthio, fluorinated $C_1$-$C_6$-alkylthio, $C_1$-$C_6$-alkylsulfinyl, fluorinated $C_1$-$C_6$-alkylsulfinyl, $C_1$-$C_6$-alkylsulfonyl and fluorinated $C_1$-$C_6$-alkylsulfonyl, X is N or CH;

$R^1$ is H, $C_1$-$C_4$-alkyl, $C_3$-$C_4$-cycloalkyl, $C_3$-$C_4$-cycloalkylmethyl, $C_3$-$C_4$-alkenyl, fluorinated $C_1$-$C_4$-alkyl, fluorinated $C_3$-$C_4$-cycloalkyl, fluorinated $C_3$-$C_4$-cycloalkylmethyl, fluorinated $C_3$-$C_4$-alkenyl, formyl or $C_1$-$C_3$-alkylcarbonyl;

$R^{1a}$ is H, $C_1$-$C_4$-alkyl, $C_3$-$C_4$-cycloalkyl, $C_3$-$C_4$-cycloalkylmethyl, $C_3$-$C_4$-alkenyl, fluorinated $C_1$-$C_4$-alkyl, fluorinated $C_3$-$C_4$-cycloalkyl, fluorinated $C_3$-$C_4$-cycloalkylmethyl, or fluorinated $C_3$-$C_4$-alkenyl; or $R^1$ and $R^{1a}$ together are $(CR^6R^7)_r$ with r being 3, 4 or 5;

$R^2$ and $R^{2a}$ are independently of each other H, fluorine, $C_1$-$C_4$-alkyl or fluorinated $C_1$-$C_4$-alkyl or $R^{2a}$ and $R^2$ together may form a ring member $(CR^6R^7)_m$ with m being 2, 3, 4 or 5; or $R^{1a}$ and $R^{2a}$ together are $(CR^6R^7)_n$ with n being 2, 3 or 4, $R^3$ is H or $C_1$-$C_4$-alkyl;

$R^4$, $R^5$ independently of each other and independently of their individual occurrence are selected from H, $C_1$-$C_3$-alkyl, $C_1$-$C_3$-alkoxy and fluorinated $C_1$-$C_3$-alkyl;

$R^6$, $R^7$ independently of each other and independently of their individual occurrence are selected from H, fluorine, $C_1$-$C_4$-alkyl and fluorinated $C_1$-$C_4$-alkyl;

$R^8$, $R^{8a}$ independently of each other are H, fluorine, $C_1$-$C_4$-alkyl or fluorinated $C_1$-$C_4$-alkyl or $R^{8a}$ and $R^8$ together may form a ring member $(CR^6R^7)_q$ with q being 2, 3, 4 or 5; or $R^{1a}$ and $R^{8a}$ together are $(CR^6R^7)_s$ with s being 2 or 3; and $R^9$ is H, $C_1$-$C_4$-alkyl, fluorinated $C_1$-$C_4$-alkyl, $C_1$-$C_4$-alkoxy or fluorinated $C_1$-$C_4$-alkoxy;

and the physiologically tolerated acid addition salts of these compounds.

The present invention therefore relates to aryloxyethylamine compounds of the general formula I and to their physiologically tolerated acid addition salts.

The present invention also relates to a pharmaceutical composition which comprises at least one aryloxyethylamine compound of the formula I and/or at least one physiologically tolerated acid addition salt of I, where appropriate together with physiologically acceptable carriers and/or auxiliary substances.

The present invention also relates to a method for treating disorders which respond to influencing by dopamine $D_3$ receptor antagonists or dopamine $D_3$ agonists, said method comprising administering an effective amount of at least one aryloxyethylamine compound of the formula I and/or at least one physiologically tolerated acid addition salt of I to a subject in need thereof.

DETAILED DESCRIPTION OF THE INVENTION

The diseases which respond to the influence of dopamine $D_3$ receptor antagonists or agonists include, in particular, disorders and diseases of the central nervous system, in particular affective disturbances, neurotic disturbances, stress disturbances and somatoform disturbances and psychoses, especially schizophrenia and depression and, in addition, disturbances of kidney function, in particular kidney function disturbances which are caused by diabetes mellitus (see WO 00/67847).

According to the invention, at least one compound of the general formula I having the meanings mentioned at the outset is used for treating the above mentioned indications. Provided the compounds of the formula I of a given constitution may exist in different spatial arrangements, for example if they possess one or more centers of asymmetry, polysubstituted rings or double bonds, or as different tautomers, it is also possible to use enantiomeric mixtures, in particular racemates, diastereomeric mixtures and tautomeric mixtures, preferably, however, the respective essentially pure enantiomers, diastereomers and tautomers of the compounds of formula I and/or of their salts.

It is likewise possible to use physiologically tolerated salts of the compounds of the formula I, especially acid addition salts with physiologically tolerated acids. Examples of suitable physiologically tolerated organic and inorganic acids are hydrochloric acid, hydrobromic acid, phosphoric acid, sulfuric acid, $C_1$-$C_4$-alkylsulfonic acids, such as methanesulfonic acid, aromatic sulfonic acids, such as benzenesulfonic acid and toluenesulfonic acid, oxalic acid, maleic acid, fumaric acid, lactic acid, tartaric acid, adipic acid and benzoic acid. Other utilizable acids are described in Fortschritte der Arzneimittelforschung [Advances in drug research], Volume 10, pages 224 ff., Birkhäuser Verlag, Basel and Stuttgart, 1966.

The organic moieties mentioned in the above definitions of the variables are—like the term halogen—collective terms for individual listings of the individual group members. The prefix $C_n$-$C_m$ indicates in each case the possible number of carbon atoms in the group.

The term halogen denotes in each case fluorine, bromine, chlorine or iodine, in particular fluorine or chlorine.

$C_1$-$C_4$ Alkyl (and likewise in $C_1$-$C_4$ hydroxyalkyl, $C_1$-$C_6$ alkoxy-$C_1$-$C_4$-alkyl, $C_1$-$C_4$ alkylcarbonyl, $C_1$-$C_4$alkylcarbonylamino, $C_1$-$C_4$alkylcarbonyloxy, $C_1$-$C_4$alkylthio, $C_1$-$C_4$ alkylsulfinyl, $C_1$-$C_4$ alkylsulfonyl etc.) is a straight-chain or branched alkyl group having from 1 to 4 carbon atoms. Examples of an alkyl group are methyl, ethyl, n-propyl, iso-propyl, n-butyl, 2-butyl, iso-butyl or tert-butyl.

$C_1$-$C_6$ Alkyl (and likewise in $C_1$-$C_6$ hydroxyalkyl, $C_1$-$C_6$ alkoxy-$C_1$-$C_4$-alkyl, $C_1$-$C_6$ alkylcarbonyl, $C_1$-$C_6$ alkylcarbonylamino, $C_1$-$C_6$ alkylcarbonyloxy, $C_1$-$C_6$ alkylthio, $C_1$-$C_6$ alkylsulfinyl, $C_1$-$C_6$ alkylsulfonyl etc.) is a straight-chain or branched alkyl group having from 1 to 6 carbon atoms. Examples include $C_1$-$C_4$ alkyl as mentioned above and also pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl;

Fluorinated $C_1$-$C_6$ alkyl (and likewise in fluorinated $C_1$-$C_6$ alkylcarbonyl, fluorinated $C_1$-$C_6$ alkylcarbonylamino, fluorinated $C_1$-$C_6$ alkylcarbonyloxy, fluorinated $C_1$-$C_6$ alkylthio, fluorinated $C_1$-$C_6$ alkylsulfinyl, fluorinated $C_1$-$C_6$ alkylsulfonyl etc.) is a straight-chain or branched alkyl group having from 1 to 6, in particular 1 to 4 carbon atoms, more preferably 1 to 3 carbon atoms, wherein at least one, e.g. 1, 2, 3, 4 or all of the hydrogen atoms are replaced by a fluorine atom such as in fluoromethyl, difluoromethyl, trifluoromethyl, (R)-1-fluoroethyl, (S)-1-fluoroethyl, 2-fluoroethyl, 1,1-difluoroethyl, 2,2-difluoroethyl, 2,2,2-trifluoroethyl, (R)-1-fluoropropyl, (S)-1-fluoropropyl, 2-fluoropropyl, 3-fluoropropyl, 1,1-difluoropropyl, 2,2-difluoropropyl, 3,3-difluoropropyl, 3,3,3-trifluoropropyl, (R)-2-fluoro-1-methylethyl, (S)-2-fluoro-1- methylethyl, (R-2,2-difluoro-1-methylethyl, (S)-2,2-difluoro-1-methylethyl, (R)-1,2-difluoro-1-methylethyl, (S)-1,2-difluoro-1-methylethyl, (R)-2,2,2-trifluoro-1-methylethyl, (S)-2,2,2-trifluoro-1-methylethyl, 2-fluoro-1-(fluoromethyl)ethyl, 1-(difluoromethyl)-2,2-difluoroethyl, (R)-1-fluorobutyl, (S)-1-fluorobutyl, 2-fluorobutyl, 3-fluorobutyl, 4-fluorobutyl, 1,1-difluorobutyl, 2,2-difluorobutyl, 3,3-difluorobutyl, 4,4-difluorobutyl, 4,4,4-trifluorobutyl, etc.;

Branched $C_3$-$C_6$ alkyl is alkyl having 3 to 6 carbon atoms at least one being a secondary or tertiary carbon atom. Examples are isopropyl, tert.-butyl, 2-butyl, isobutyl, 2-pentyl, 2-hexyl, 3-methylpentyl, 1,1-dimethylbutyl, 1,2-dimethylbutyl 1-methyl-1-ethylpropyl.

$C_1$-$C_6$ Alkoxy (and likewise in $C_1$-$C_6$ alkoxycarbonyl, $C_1$-$C_6$ alkoxy-$C_1$-$C_4$ alkyl, $C_1$-$C_6$ alkoxy-$C_1$-$C_4$ alkoxy and $C_1$-$C_6$ hydroxyalkoxy) is a straight-chain or branched alkyl group having from 1 to 6, in particular 1 to 4 carbon atoms, which is bound to the remainder of the molecule via an oxygen atom. Examples include methoxy, ethoxy, n-propoxy, isopropoxy, n-butoxy, 2-butoxy, iso-butoxy, tert.-butoxy, pentyloxy, 1-methylbutoxy, 2-methylbutoxy, 3-methylbutoxy, 2,2-dimethylpropoxy, 1-ethylpropoxy, hexyloxy, 1,1-dimethylpropoxy, 1,2-dimethylpropoxy, 1-methylpentyloxy, 2-methylpentyloxy, 3-methylpentyloxy, 4-methylpentyloxy, 1,1-dimethylbutyloxy, 1,2-dimethylbutyloxy, 1,3-dimethylbutyloxy, 2,2-dimethylbutyloxy, 2,3-dimethylbutyloxy, 3,3-dimethylbutyloxy, 1-ethylbutyloxy, 2-ethylbutyloxy, 1,1,2-trimethylpropoxy, 1,2,2-trimethylpropoxy, 1-ethyl-1-methyl propoxy and 1-ethyl-2-methylpropoxy;

Fluorinated $C_1$-$C_6$ alkoxy (and likewise in fluorinated $C_1$-$C_6$ alkoxycarbonyl) is a straight-chain or branched alkoxy group having from 1 to 6, in particular 1 to 4 carbon atoms, wherein at least one, e.g. 1, 2, 3, 4 or all of the hydrogen atoms are replaced by a fluorine atom such as in fluoromethoxy, difluoromethoxy, trifluoromethoxy, (R)-1-fluoroethoxy, (S)-1-fluoroethoxy, 2-fluoroethoxy, 1,1-difluoroethoxy, 2,2-difluoroethoxy, 2,2,2-trifluoroethoxy, (R)-1-fluoropropoxy, (S)-1-fluoropropoxy, 2-fluoropropoxy, 3-fluoropropoxy, 1,1-difluoropropoxy, 2,2-difluoropropoxy, 3,3-difluoropropoxy, 3,3,3-trifluoropropoxy, (R)-2-fluoro-1-methylethoxy, (S)-2-fluoro-1-methylethoxy, (R)-2,2-difluoro-1-methylethoxy, (S)-2,2-difluoro-1-methylethoxy, (R)-1,2-difluoro-1-methylethoxy, (S)-1,2-difluoro-1-methylethoxy, (R)-2,2,2-trifluoro-1-methylethoxy, (S)-2,2,2-trifluoro-1-methylethoxy, 2-fluoro-1-(fluoromethyl)ethoxy, 1-(difluoromethyl)-2,2-difluoroethoxy, (R)-1-fluorobutoxy, (S)-1-fluorobutoxy, 2-fluorobutoxy, 3-fluorobutoxy, 4-fluorobutoxy, 1,1-difluorobutoxy, 2,2-difluorobutoxy, 3,3-difluorobutoxy, 4,4-difluorobutoxy, 4,4,4-trifluorobutoxy, etc.;

$C_3$-$C_6$ Cycloalkyl is a cycloaliphatic radical having from 3 to 6 C atoms, such as cyclopropyl, cyclobutyl and cyclopentyl. The cycloalkyl radical may be unsubstituted or may carry 1, 2, 3 or 4 $C_1$-$C_4$ alkyl radicals, preferably a methyl radical. One alkyl radical is preferably located in the 1-position of the cycloalkyl radical, such as in 1-methylcyclopropyl or 1-methylcyclobutyl.

Fluorinated $C_3$-$C_6$ cycloalkyl is a cycloaliphatic radical having from 3 to 6 C atoms, such as cyclopropyl, cyclobutyl and cyclopentyl, wherein at least one, e.g. 1, 2, 3, 4 or all of the hydrogen atoms are replaced by a fluorine atom such as in 1-fluorocyclopropyl, 2-fluorocyclopropyl, 2,2-difluorocyclopropyl, 1,2-difluorocyclopropyl, 2,3-difluorocyclopropyl, pentafluorocyclopropyl, 1-fluorocyclobutyl, 2-fluorocyclobutyl, 3-fluorocyclobutyl, 2,2-difluorocyclobutyl, 3,3-difluorocyclobutyl, 1,2-difluorocyclobutyl, 1,3-difluorocyclobutyl, 2,3-difluorocyclobutyl, 2,4-difluorocyclobutyl, or 1,2,2-trifluorocyclobutyl.

$C_3$-$C_6$ cycloalkylmethyl is methyl which carries a cycloaliphatic radical having from 3 to 6 C atoms as mentioned above Fluorinated $C_3$-$C_6$ cycloalkylmethyl is methyl which carries a cycloaliphatic radical having from 3 to 6 C atoms, wherein at least one, e.g. 1, 2, 3, 4 or all of the hydrogen atoms are replaced by a fluorine atom.

$C_2$-$C_6$-Alkenyl is a singly unsaturated hydrocarbon radical having 2, 3, 4, 5 or 6 C-atoms, e.g. vinyl, allyl(2-propen-1-yl), 1-propen-1-yl, 2-propen-2-yl, methallyl(2-methylprop-2-en-1-yl) and the like. $C_3$-$C_4$-Alkenyl is, in particular, allyl, 1-methylprop-2-en-1-yl, 2-buten-1-yl, 3-buten-1-yl, methallyl, 2-penten-1-yl, 3-penten-1-yl, 4-penten-1-yl, 1-methylbut-2-en-1-yl or 2-ethylprop-2-en-1-yl.

Fluorinated $C_2$-$C_6$-alkenyl is a singly unsaturated hydrocarbon radical having 2, 3, 4, 5 or 6 C-atoms, wherein at least one, e.g. 1, 2, 3, 4 or all of the hydrogen atoms are replaced by a fluorine atom such as in 1-fluorovinyl, 2-fluorovinyl, 2,2-fluorovinyl, 3,3,3-fluoropropenyl, 1,1-difluoro-2-propenyl 1-fluoro-2-propenyl and the like.

$C_1$-$C_6$ hydroxyalkyl is an alkyl radical having from 1 to 6 carbon atoms as defined above, wherein one hydrogen atom is replaced by hydroxy. Examples comprise hydroxymethyl, 2-hydroxyethyl, 1-hydroxyethyl, 3-hydroxypropyl, 2-hydroxypropyl, 1-methyl-1-hydroxyethyl and the like.

$C_1$-$C_6$ hydroxyalkoxy is an alkoxy radical having from 1 to 6, preferably from 2 to 4 carbon atoms as defined above, wherein one hydrogen atom is replaced by hydroxy. Examples comprise 2-hydroxyethoxy, 3-hydroxypropoxy, 2-hydroxypropoxy, 1-methyl-2-hydroxyethoxy and the like.

$C_1$-$C_6$ alkoxy-$C_1$-$C_4$-alkyl is an alkyl radical having from 1 to 4 carbon atoms as defined above, wherein one hydrogen atom is replaced by $C_1$-$C_6$ alkoxy. Examples comprise methoxymethyl, 2-methoxyethyl, 1-methoxyethyl, 3-methoxypropyl, 2-methoxypropyl, 1-methyl-1-methoxyethyl, ethoxymethyl, 2-ethoxyethyl, 1-ethoxyethyl, 3-ethoxypropyl, 2-ethoxypropyl, 1-methyl-1-ethoxyethyl and the like.

$C_1$-$C_6$ alkoxy-$C_1$-$C_4$-alkoxy is an alkoxy radical having from 1 to 4 carbon atoms as defined above, wherein one hydrogen atom is replaced by $C_1$-$C_6$ alkoxy. Examples comprise methoxymethoxy, 2-methoxyethoxy, 1-methoxyethoxy, 3-methoxypropoxy, 2-methoxypropoxy, 1-methyl-1-methoxyethoxy, ethoxymethoxy, 2-ethoxyethoxy, 1-ethoxyethoxy, 3-ethoxypropoxy, 2-ethoxypropoxy, 1-methyl-1-ethoxyethoxy and the like.

$C_1$-$C_6$ alkylcarbonyl is a radical of the formula R—C(O)—, wherein R is an alkyl radical having from 1 to 6 carbon atoms as defined above. Examples comprise acetyl, propionyl, n-butylryl, 2-methylpropionyl, pivalyl and the like.

$C_1$-$C_6$ alkylcarbonylamino is a radical of the formula R—C(O)—NH—, wherein R is an alkyl radical having from 1 to 6 carbon atoms as defined above. Examples comprise acetamido, propionamido, n-butyramido, 2-methylpropionamido, 2,2-dimethylpropionamido and the like.

$C_1$-$C_6$ alkylcarbonyloxy is a radical of the formula R—C(O)—O—, wherein R is an alkyl radical having from 1 to 6 carbon atoms as defined above. Examples comprise acetyloxy, propionyloxy, n-butyryloxy, 2-methylpropionyloxy, 2,2-dimethylpropionyloxy and the like.

$C_1$-$C_6$ alkylthio is a radical of the formula R—S—, wherein R is an alkyl radical having from 1 to 6 carbon atoms as defined above. Examples comprise methylthio, ethylthio, propylthio, butylthio, pentylthio, 1-methylbutylthio, 2-methylbutylthio, 3-methylbutylthio, 2,2-dimethylpropylthio, 1-ethylpropylthio, hexylthio, 1,1-dimethylpropylthio, 1,2-dimethylpropylthio, 1-methylpentylthio, 2-methylpentylthio, 3-methylpentylthio, 4-methylpentylthio, 1,1-dimethylbutylthio, 1,2-dimethylbutylthio, 1,3-dimethylbutylthio, 2,2-dimethylbutylthio, 2,3-dimethylbutylthio, 3,3-dimethylbutylthio, 1-ethylbutylthio, 2-ethylbutylthio, 1,1,2-trimethylpropylthio, 1,2,2-trimethylpropylthio, 1-ethyl-1-methylpropyl and 1-ethyl-2-methylpropyl;

$C_1$-$C_6$ alkylsulfinyl is a radical of the formula R—S(O)—, wherein R is an alkyl radical having from 1 to 6 carbon atoms as defined above. Examples comprise methylsulfinyl, ethylsulfinyl, propylsulfinyl, butylsulfinyl, pentylsulfinyl, 1-methylbutylsulfinyl, 2-methylbutylsulfinyl, 3-methylbutylsulfinyl, 2,2-dimethylpropylsulfinyl, 1-ethylpropylsulfinyl, hexylsulfinyl, 1,1-dimethylpropylsulfinyl, 1,2-dimethylpropylsulfinyl, 1-methylpentylsulfinyl, 2-methylpentylsulfinyl, 3-methylpentylsulfinyl, 4-methylpentylsulfinyl, 1,1-dimethylbutylsulfinyl, 1,2-dimethylbutylsulfinyl, 1,3-dimethylbutylsulfinyl, 2,2-dimethylbutylsulfinyl, 2,3-dimethylbutylsulfinyl, 3,3-dimethylbutylsulfinyl, 1-ethylbutylsulfinyl, 2-ethylbutylsulfinyl, 1,1,2-trimethylpropylsulfinyl, 1,2,2-trimethylpropylsulfinyl, 1-ethyl-1-methylpropyl and 1-ethyl-2-methylpropyl;

$C_1$-$C_6$ alkylsulfonyl is a radical of the formula R—S(O)$_2$—, wherein R is an alkyl radical having from 1 to 6 carbon atoms as defined above. Examples comprise methylsulfonyl, ethylsulfonyl, propylsulfonyl, butylsulfonyl, pentylsulfonyl, 1-methylbutylsulfonyl, 2-methylbutylsulfonyl, 3-methylbutylsulfonyl, 2,2-dimethylpropylsulfonyl, 1-ethylpropylsulfonyl, hexylsulfonyl, 1,1-dimethylpropylsulfonyl, 1,2-dimethylpropylsulfonyl, 1-methylpentylsulfonyl, 2-methylpentylsulfonyl, 3-methylpentylsulfonyl, 4-methylpentylsulfonyl, 1,1-dimethylbutylsulfonyl, 1,2-dimethylbutylsulfonyl, 1,3-dimethylbutylsulfonyl, 2,2-dimethylbutylsulfonyl, 2,3-dimethylbutylsulfonyl, 3,3-dimethylbutylsulfonyl, 1-ethylbutylsulfonyl, 2-ethylbutylsulfonyl, 1,1,2-trimethylpropylsulfonyl, 1,2,2-trimethylpropylsulfonyl, 1-ethyl-1-methylpropyl and 1-ethyl-2-methylpropyl;

fluorinated $C_1$-$C_6$ alkylcarbonyl is a radical of the formula R—C(O)—, wherein R is a fluorinated alkyl radical having from 1 to 6 carbon atoms as defined above. Examples comprise fluoroacetyl, difluoroacetyl, trifluoroacetyl, (R)-1-fluoroethylcarbonyl, (S)-1-fluoroethylcarbonyl, 2-fluoroethylcarbonyl, 1,1-difluoroethylcarbonyl, 2,2-difluoroethylcarbonyl, 2,2,2-trifluoroethylcarbonyl, (R)-1-fluoropropylcarbonyl, (S)-1-fluoropropylcarbonyl, 2-fluoropropylcarbonyl, 3-fluoropropylcarbonyl, 1,1-difluoropropylcarbonyl, 2,2-difluoropropylcarbonyl, 3,3-difluoropropylcarbonyl, 3,3,3-trifluoropropylcarbonyl, (R)-2-fluoro-1-methylethylcarbonyl, (S)-2-fluoro-1-methylethylcarbonyl, (R)-2,2-difluoro-1-methylethylcarbonyl, (S)-2,2-difluoro-1-methylethylcarbonyl, (R)-1,2-difluoro-1-methylethylcarbonyl, (S)-1,2-difluoro-1-methylethylcarbonyl, (R)-2,2,2-trifluoro-1-methylethylcarbonyl, (S)-2,2,2-trifluoro-1-methylethylcarbonyl, 2-fluoro-1-(fluoromethyl)ethylcarbonyl, 1-(difluoromethyl)-2,2-difluoroethylcarbonyl, (R)-1-fluorobutylcarbonyl, (S)-1-fluorobutylcarbonyl, 2-fluorobutylcarbonyl, 3-fluorobutylcarbonyl, 4-fluorobutylcarbonyl, 1,1-difluorobutylcarbonyl, 2,2-difluorobutylcarbonyl, 3,3-difluorobutylcarbonyl, 4,4-difluorobutylcarbonyl, 4,4,4-trifluorobutylcarbonyl, etc.;

fluorinated $C_1$-$C_6$ alkylcarbonylamino is a radical of the formula R—C(O)—NH—, wherein R is a fluorinated alkyl radical having from 1 to 6 carbon atoms as defined above. Examples comprise fluoroacetamido, difluoroacetamido, trifluoroacetamido, (R)-1-fluoroethylcarbonylamino, (S)-1-fluoroethylcarbonylamino, 2-fluoroethylcarbonylamino, 1,1-difluoroethylcarbonylamino, 2,2-difluoroethylcarbonylamino, 2,2,2-trifluoroethylcarbonylamino, (R)-1-fluoropropylcarbonylamino, (S)-1-fluoropropylcarbonylamino, 2-fluoropropylcarbonylamino, 3-fluoropropylcarbonylamino, 1,1-difluoropropylcarbonylamino, 2,2-difluoropropylcarbonylamino, 3,3-difluoropropylcarbonylamino, 3,3,3-trifluoropropylcarbonylamino, (R)-2-fluoro-1-methylethylcarbonylamino, (S)-2-fluoro-1-methylethylcarbonylamino, (R)-2,2-difluoro-1-methylethylcarbonylamino, (S)-2,2-difluoro-1-methylethylcarbonylamino, (R)-1,2-difluoro-1-methylethylcarbonylamino, (S)-1,2-difluoro-1-methylethylcarbonylamino, (R)-2,2,2-trifluoro-1-methylethylcarbonylamino, (S)-2,2,2-trifluoro-1-methylethylcarbonylamino, 2-fluoro-1-(fluoromethyl)ethylcarbonylamino, 1-(difluoromethyl)-2,2-difluoroethylcarbonylamino, (R)-1-fluorobutylcarbonylamino, (S)-1-fluorobutylcarbonylamino, 2-fluorobutylcarbonylamino, 3-fluorobutylcarbonylamino, 4-fluorobutylcarbonylamino, 1,1-difluorobutylcarbonylamino, 2,2-difluorobutylcarbonylamino, 3,3-difluorobutylcarbonylamino, 4,4-difluorobutylcarbonylamino, 4,4,4-trifluorobutylcarbonylamino, etc., fluorinated $C_1$-$C_6$ alkylcarbonyloxy is a radical of the formula R—C(O)—O—, wherein R is a fluorinated alkyl radical having from 1 to 6 carbon atoms as defined above fluoroacetyl, difluoroacetyl, trifluoroacetyl, (R)-1-fluoroethylcarbonyloxy, (S)-1-fluoroethylcarbonyloxy, 2-fluoroethylcarbonyloxy, 1,1-difluoroethylcarbonyloxy, 2,2-difluoroethylcarbonyloxy, 2,2,2-trifluoroethylcarbonyloxy, (R)-1-fluoropropylcarbonyloxy, (S)-1-fluoropropylcarbonyloxy, 2-fluoropropylcarbonyloxy, 3-fluoropropylcarbonyloxy, 1,1-difluoropropylcarbonyloxy, 2,2-difluoropropylcarbonyloxy, 3,3-difluoropropylcarbonyloxy, 3,3,3-trifluoropropylcarbonyloxy, (R)-2-fluoro-1-methylethylcarbonyloxy, (S)-2-fluoro-1-methylethylcarbonyloxy, (R)-2,2-difluoro-1-methylethylcarbonyloxy, (S)-2,2-difluoro-1-methylethylcarbonyloxy, (R)-1,2-difluoro-1-methylethylcarbonyloxy, (S)-1,2-difluoro-1-methylethylcarbonyloxy, (R)-2,2,2-trifluoro-1-methylethylcarbonyloxy, (S)-2,2,2-trifluoro-1-methylethylcarbonyloxy, 2-fluoro-1-(fluoromethyl)ethylcarbonyloxy, 1-(difluoromethyl)-2,2-difluoroethylcarbonyloxy, (R)-1-fluorobutylcarbonyloxy, (S)-1-fluorobutylcarbonyloxy, 2-fluorobutylcarbonyloxy, 3-fluorobutylcarbonyloxy, 4-fluorobutylcarbonyloxy, 1,1-difluorobutylcarbonyloxy, 2,2-difluorobutylcarbonyloxy, 3,3-difluorobutylcarbonyloxy, 4,4-difluorobutylcarbonyloxy, 4,4,4-trifluorobutylcarbonyloxy, etc.;

fluorinated $C_1$-$C_6$ alkylthio is a radical of the formula R—S—, wherein R is a fluorinated alkyl radical having from 1 to 6 carbon atoms as defined above. Examples comprise fluoromethylthio, difluoromethylthio, trifluoromethylthio, (R)-1-fluoroethylthio, (S)-1-fluoroethylthio, 2-fluoroethylthio, 1,1-difluoroethylthio, 2,2-difluoroethylthio, 2,2,2-trifluoroethylthio, (R)-1-fluoropropylthio, (S)-1-fluoropropylthio, 2-fluoropropylthio, 3-fluoropropylthio, 1,1-difluoropropylthio, 2,2-difluoropropylthio, 3,3-difluoropropylthio, 3,3,3-trifluoropropylthio, (R)-2-fluoro-1-methylethylthio, (S)-2-fluoro-1-methylethylthio, (R)-2,2-difluoro-1-methylethylthio, (S)-2,2-difluoro-1-methylethylthio, (R)-1,2-difluoro-1-methylethylthio, (S)-1,2-difluoro-1-methylethylthio, (R)-2,2,2-trifluoro-1-methylethylthio, (S)-2,2,2-trifluoro-1-methylethylthio, 2-fluoro-1-(fluoromethyl)ethylthio, 1-(difluoromethyl)-2,2-difluoroethylthio, (R)-1-fluorobutylthio, (S)-1-fluorobutylthio, 2-fluorobutylthio, 3-fluorobutylthio, 4-fluorobutylthio, 1,1-difluorobutylthio, 2,2-difluorobutylthio, 3,3-difluorobutylthio, 4,4-difluorobutylthio, 4,4,4-trifluorobutylthio, etc.;

fluorinated $C_1$-$C_6$ alkylsulfinyl is a radical of the formula R—S(O)—, wherein R is a fluorinated alkyl radical having from 1 to 6 carbon atoms as defined above. Examples comprise fluoromethylsulfinyl, difluoromethylsulfinyl, trifluoromethylsulfinyl, (R)-1-fluoroethylsulfinyl, (S)-1-fluoroethylsulfinyl, 2-fluoroethylsulfinyl, 1,1-difluoroethylsulfinyl, 2,2-difluoroethylsulfinyl, 2,2,2-trifluoroethylsulfinyl, (R)-1-fluoropropylsulfinyl, (S)-1-fluoropropylsulfinyl, 2-fluoropropylsulfinyl, 3-fluoropropylsulfinyl, 1,1-difluoropropylsulfinyl, 2,2-difluoropropylsulfinyl, 3,3-difluoropropylsulfinyl, 3,3,3-trifluoropropylsulfinyl, (R)-2-fluoro-1-methylethylsulfinyl, (S)-2-fluoro-1-methylethylsulfinyl, (R)-2,2-difluoro-1-methylethylsulfinyl, (S)-2,2-difluoro-1-methylethylsulfinyl, (R)-1,2-difluoro-1-methylethylsulfinyl, (S)-1,2-difluoro-1-methylethylsulfinyl, (R)-2,2,2-trifluoro-1-methylethylsulfinyl, (S)-2,2,2-trifluoro-1-methylethylsulfinyl, 2-fluoro-1-(fluoromethyl)ethylsulfinyl, 1-(difluoromethyl)-2,2-difluoroethylsulfinyl, (R)-1-fluorobutylsulfinyl, (S)-1-fluorobutylsulfinyl, 2-fluorobutylsulfinyl, 3-fluorobutylsulfinyl, 4-fluorobutylsulfinyl, 1,1-difluorobutylsulfinyl, 2,2-difluorobutylsulfinyl, 3,3-difluorobutylsulfinyl, 4,4-difluorobutylsulfinyl, 4,4,4-trifluorobutylsulfinyl, etc.;

fluorinated $C_1$-$C_6$ alkylsulfonyl is a radical of the formula R—S(O)$_2$—, wherein R is a fluorinated alkyl radical having from 1 to 6 carbon atoms as defined above. Examples comprise fluoromethylsulfonyl, difluoromethylsulfonyl, trifluoromethylsulfonyl, (R)-1-fluoroethylsulfonyl, (S)-1-fluoroethylsulfonyl, 2-fluoroethylsulfonyl, 1,1-difluoroethylsulfonyl, 2,2-difluoroethylsulfonyl, 2,2,2-trifluoroethylsulfonyl, (R)-1-fluoropropylsulfonyl, (S)-1-fluoropropylsulfonyl, 2-fluoropropylsulfonyl, 3-fluoropropylsulfonyl, 1,1-difluoropropylsulfonyl, 2,2-difluoropropylsulfonyl, 3,3-difluoropropylsulfonyl, 3,3,3-trifluoropropylsulfonyl, (R)-2-fluoro-1-methylethylsulfonyl, (S)-2-fluoro-1-methylethylsulfonyl, (R)-2,2-difluoro-1-methylethylsulfonyl, (S)-2,2-difluoro-1-methylethylsulfonyl, (R)-1,2-difluoro-1-methylethylsulfonyl, (S)-1,2-difluoro-1-methylethylsulfonyl, (R)-2,2,2-trifluoro-1-methylethylsulfonyl, (S)-2,2,2-trifluoro-1-methylethylsulfonyl, 2-fluoro-1-(fluoromethyl)ethylsulfonyl, 1-(difluoromethyl)-2,2-difluoroethylsulfonyl, (R)-1-fluorobutylsulfonyl, (S)-1-fluorobutylsulfonyl, 2-fluorobutylsulfonyl, 3-fluorobutylsulfonyl, 4-fluorobutylsulfonyl, 1,1-difluorobutylsulfonyl, 2,2-difluorobutylsulfonyl, 3,3-difluorobutylsulfonyl, 4,4-difluorobutylsulfonyl, 4,4,4-trifluorobutylsulfonyl, etc.

3- to 7-membered heterocyclic radicals comprise saturated heterocyclic radicals, which generally have 3-, 4-, 5-, 6- or 7 ring forming atoms (ring members), unsaturated non-aromatic heterocyclic radicals, which generally have 5-, 6- or 7 ring forming atoms, and heteroaromatic radicals, which generally have 5-, 6- or 7 ring forming atoms. The heterocylcic radicals may be bound via a carbon atom (C-bound) or an nitrogen atom (N-bound). Preferred heterocyclic radicals comprise 1 nitrogen atom as ring member atom and optionally 1, 2 or 3 further heteroatoms as ring members, which are selected, independently of each other from O, S and N. Likewise preferred heterocyclic radicals comprise 1 heteroatom as ring member, which is selected from O, S and N, and optionally 1, 2 or 3 further nitrogen atoms as ring members.

Examples of 3- to 7-membered, saturated heterocyclic radicals comprise 1- or 2-aziridinyl, 1-, 2- or 3-azetidinyl, 1-, 2- or 3-pyrrolidinyl, 1-, 2-, 3- or 4-piperidinyl, 1-, 2- or 3-morpholinyl, 1-, 2- or 3-thiomorpholinyl, 1-, 2- or 3-piperazinyl, 1-, 2- or 4-oxazolidinyl, 1-, 3- or 4-isoxazolidinyl, 2-oxiranyl, 2- or 3-oxetanyl, 2- or 3-oxolanyl, 2-, 3- or 4-oxanyl, 1,3-dioxolan-2- or 4-yl and the like, which may be unsubstituted or which may carry 1, 2 or 3 of the aforementioned radicals $R^a$ and/or $R^b$.

Unsaturated non-aromatic heterocyclic radicals, are heterocyclic radicals which generally have 5-, 6- or 7 ring forming atoms and which have 1 or 2 doublebonds that do not form an aromatic p-electron system. Examples are 2,3-dihydropyrrolyl, 3,4-dihydropyrrolyl, 2,3-dihydrofuranyl, 3,4-dihydrofuranyl, 2,3-dihydrothiophenyl, 3,4-dihydrothiophenyl, 1,2-dihydropyridinyl, 2,3-Dihydropyridiynl, 3,4-dihydropyridinyl, 1,2,3,4-tetrahydropyridinyl, 2,3,4,5-tetrahydropyridinyl, and the like.

5- or 6-membered heteroaromatic radicals are heteroaromatic cyclic radicals, wherein the cyclic radical has 5 or 6 atoms which form the ring (ring members) and wherein generally 1, 2, 3 or 4 ring member atoms are selected from O, S and N, the other ring member atoms being carbon atoms. More precisely, the heteroaromatic radicals comprise one heteroatom selected from O, S and N as ring member and optionally 1, 2 or 3 further N atoms as ring members The heteroaromatic radicals may be bound via a carbon atom (C-bound) or an nitrogen atom (N-bound). Preferred heteroaromatic radicals comprise 1 nitrogen atom as ring member atom and optionally 1, 2 or 3 further heteroatoms as ring members, which are selected, independently of each other from O, S and N. As a matter of course, only one of the further heteroatom ring members can be O or S and only 5-membered heteroaromatic radicals may comprise O or S as ring members. Likewise preferred heteroaromatic radicals comprise 1 heteroatom as ring member, which is selected from O, S and N, and optionally 1, 2 or 3 further nitrogen atoms as ring members. Examples of 5- or 6-membered heteroaromatic radicals comprise 2-, 3-, or 4-pyridyl, 2-, 4- or 5-pyrimidinyl, pyrazinyl, 3- or 4-pyridazinyl, 2- or 3-thienyl, 2- or 3-furyl, 1-, 2- or 3-pyrrolyl, 1-, 2- or 4-imidazolyl, 1-, 3- or 4-pyrazolyl, 1- or 3-[1,2,4]-triazolyl, 1- or 4-[1,2,3]-triazolyl, 1-, 2- or 5-tetrazolyl, 2-, 3- or 5-oxazolyl, 3-, 4- or 5-isoxazolyl, 2-, 3- or 5-thiazolyl, 3-, 4- or 5-isothiazolyl, 4- or 5-[1,2,3]-oxadiazolyl, [1,2,5]-oxadiazolyl (=furazanyl), 3- or 5-[1,2,4]-oxadizolyl, [1,3,4]-oxadizolyl, 4- or 5-[1,2,3]-thiadiazolyl, [1,2,5]-thiadiazolyl, 3- or 5-[1,2,4]-thiadiazolyl or [1,3,4]-thiadiazolyl, which may be unsubstituted or which may carry one of the aforementioned radicals $R^a$ and optionally 1 or 2 of the aforementioned radicals $R^b$.

A skilled person will appreciate that the radical $R^9$ may be bound to any of the carbon atoms of the pyridine or pyrimidine moiety in formula I, thereby substituting a hydrogen atom. Preferably, $R^9$ is bound at the 2-position with respect to the 1-position of the nitrogen ring atom and the 3-position of the $NR^3$—$SO_2$—Ar group.

Preferably, Ar is phenyl or an aromatic 5- or 6-membered C-bound heteroaromatic radical, comprising 1 nitrogen atom as ring member and 0, 1, 2 or 3 further heteroatoms, independently of each other, selected from O, S and N, as ring members which may be unsubstituted or which may carry 1, 2 or 3 of the aforementioned radicals $R^a$ and/or $R^b$. Amongst these heteroaromatic radicals those are preferred which comprise 1, 2 or 3 nitrogen atoms and no further heteroatom as ring members, or 1 or 2 nitrogen atoms and 1 atom, selected from and S, as ring members. However, thienyl and furyl are likewise preferred. Particularly preferred heteroaromatic radicals Ar are 2- or 3-thienyl, 2-, 3- or 4-pyridyl, 2-, 4- or 5-pyrimidinyl, 2-, 3- or 5-thiazolyl, 1,2,4-triazol-3-yl, 1,2,3-triazol-4-yl, 1,3,4-thiadiazol-2-yl, in particular 2-thienyl, 2-pyrimidinyl, 5-pyrimidinyl and 2-pyridinyl which may be unsubstituted or which may carry one of the aforementioned radicals $R^a$ and optionally 1 or 2 of the aforementioned radicals $R^b$. More preferably, Ar is phenyl which may carry one of the aforementioned radicals $R^a$ and optionally 1 or 2 of the aforementioned radicals $R^b$.

Preferably, the aromatic radical Ar carries one radical $R^a$ and optionally one or two further radicals $R^b$ as mentioned above, $R^b$ being particularly selected from methyl, fluorinated methyl, halogen, more preferably from fluorine or chlorine.

The aforementioned 5-membered heteroaromatic radicals Ar preferably carry one radical $R^a$ in the 3-position (related to the position of the $SO_2$-radical) and optionally one or two further radicals $R^b$, which are preferably selected from halogen, in particular fluorine or chlorine.

Phenyl and the aforementioned 6-membered heteroaromatic radicals Ar preferably carry one radical $R^a$ in the 4-position (related to the position of the $SO_2$-radical) and optionally one or two further radicals $R^b$, which are preferably selected from halogen, in particular fluorine or chlorine.

In a very preferred embodiment of the invention Ar is phenyl that carries a radical $R^a$ in the 4-position of the phenyl ring and optionally 1 or 2 further radicals $R^b$, which are preferably selected from halogen, in particular from fluorine or chlorine.

In another preferred embodiment of the invention Ar is 2-pyrimidinyl that carries a radical $R^a$ in the 5-position of the pyrimidine ring and optionally 1 or 2 further radicals $R^b$, which are preferably selected from halogen, in particular from fluorine or chlorine.

In a further preferred embodiment of the invention Ar is 5-pyrimidinyl that carries a radical $R^a$ in the 2-position of the pyrimidine ring and optionally 1 or 2 further radicals $R^b$, which are preferably selected from halogen, in particular from fluorine or chlorine.

In a further preferred embodiment of the invention Ar is 2-thienyl that carries a radical $R^a$ in the 3-position of the thiophen ring and optionally 1 or 2 further radicals $R^b$, which are preferably selected from halogen, in particular from fluorine or chlorine.

In a preferred embodiment Ar carries 1 radical $R^a$ which is selected from the group consisting of $C_1$-$C_6$-alkyl, fluorinated $C_1$-$C_6$-alkyl, $C_3$-$C_6$-cycloalkyl, fluorinated $C_3$-$C_6$-cycloalkyl, $C_1$-$C_6$-alkoxy, fluorinated $C_1$-$C_6$-alkoxy, $NR^4R^5$, 1-aziridinyl, azetidin-1-yl, pyrrolidin-1-yl, piperidin-1-yl, wherein the last four mentioned radicals may be fluorinated, a phenyl group and an aromatic 5- or 6-membered C-bound heteroaromatic radical comprising 1 nitrogen atom as ring member and 0, 1, 2 or 3 further heteroatoms, independently of each other, selected from O, S and N, wherein the last two mentioned radicals may carry 1, 2, 3 or 4 radicals selected from halogen, $C_1$-$C_6$-alkyl, fluorinated $C_1$-$C_6$-alkyl, $C_3$-$C_6$-cycloalkyl, fluorinated $C_3$-$C_6$-cycloalkyl, $C_1$-$C_6$-alkoxy, fluorinated $C_1$-$C_6$-alkoxy and $NR^4R^5$; and wherein Ar may carry 1 or 2 further radicals $R^b$, which are independently from each other selected from halogen, cyano, methyl, fluoromethyl, difluoromethyl, trifluoromethyl, difluoromethoxy and trifluoromethoxy. In this embodiment $R^4$, $R^5$ are, independently of each other, preferably selected from H, $C_1$-$C_2$-alkyl and fluorinated $C_1$-$C_2$-alkyl. Preferably one of the radicals $R^4$ or $R^5$ is different from hydrogen. One of the radicals $R^4$ or $R^5$ may also be $C_1$-$C_2$-alkoxy.

In a very preferred embodiment, the radical Ar preferably carries one radical $R^a$, which has the formula $R^{a'}$

wherein
Y is N, CH or CF,
$R^1$ and $R^{a2}$ are independently of each other selected from $C_1$-$C_2$-alkyl, $C_1$-$C_2$-alkoxy, fluorinated $C_1$-$C_2$-alkyl, provided for Y being CH or CF one of the radicals $R^{a1}$ or $R^{a2}$ may also be hydrogen or fluorine, or
$R^1$ and $R^{a2}$ together form a radical $(CH_2)_k$ wherein 1 or 2 of the hydrogen atoms may be replaced by fluorine, hydroxy, oxo, $C_1$-$C_2$-alkyl or $C_1$-$C_2$-alkoxy, wherein one $CH_2$ moiety may be replaced by O, S, S=O, $SO_2$ or N—$R^c$, $R^c$ being hydrogen or $C_1$-$C_2$-alkyl and wherein k is 2, 3, 4, 5 or 6;

In particular
$R^1$ or $R^{a2}$ are independently of each other selected from $C_1$-$C_2$-alkyl, fluorinated $C_1$-$C_2$-alkyl, in particular fluoromethyl, difluoromethyl or trifluoromethyl, provided for Y being CH or CF one of the radicals $R^1$ or $R^{a2}$ may also be hydrogen or fluorine, or
$R^1$ and $R^{a2}$ form a radical $(CH_2)_k$ wherein 1 or 2 of the hydrogen atoms may be replaced by fluorine and wherein k is 2, 3 or 4, in particular $CH_2$—$CH_2$, $CHF$—$CH_2CF_2$—$CH_2$, $CH_2$—$CH_2$—$CH_2$, $CHF$—$CH_2$—$CH_2$, $CF_2$—$CH_2$—$CH_2$, $CH_2$—$CHF$—$CH_2$, $CH_2$—$CF_2$—$CH_2$.

In case $R^1$ and $R^{a2}$ are different from each other, the radical of the aforementioned formula $R^{a'}$ may have either (R)- or (S)-configuration with regard to the Y-moiety.

Examples for preferred radicals $R^{a'}$ comprise isopropyl, (R)-1-fluoroethyl, (S)-1-fluoroethyl, 2-fluoroethyl, 1,1-difluoroethyl, 2,2-difluoroethyl, 2,2,2-trifluoroethyl, (R)-1-fluoropropyl, (S)-1-fluoropropyl, 2-fluoropropyl, 3-fluoropropyl, 1,1-difluoropropyl, 2,2-difluoropropyl, 3,3-difluoropropyl, 3,3,3-trifluoropropyl, (R)-2-fluoro-1-methylethyl, (S)-2-fluoro-1-methylethyl, (R)-2,2-difluoro-1-methylethyl, (S)-2,2-difluoro-1-methylethyl, (R)-1,2-difluoro-1-methylethyl, (S)-1,2-difluoro-1-methylethyl, (R)-2,2,2-trifluoro-1-methylethyl, (S)-2,2,2-trifluoro-1-methylethyl, 2-fluoro-1-(fluoromethyl)ethyl, 1-(difluoromethyl)-2,2-difluoroethyl cyclopropyl, cyclobutyl, 1-fluorocyclopropyl, and 2-fluorocyclopropyl Also preferred are radicals $R^{a'}$ wherein one of $R^1$ or $R^{a2}$ is $C_1$-$C_2$-alkoxy and the other of $R^{a1}$ or $R^{a2}$ is selected from H, $C_1$-$C_2$-alkyl, in particular methyl, fluorinated $C_1$-$C_2$-alkyl, in particular fluoromethyl, difluoromethyl or trifluoromethyl. Examples comprise N-methoxy-N-methylamino, N-methoxyamino and N-ethoxyamino.

Preferred radicals of the formula $R^{a'}$ also comprise those wherein Y is nitrogen and wherein $R^{a1}$ and $R^{a2}$ form a radical $(CH_2)_t$ wherein 1 or 2 of the hydrogen atoms may be replaced by fluorine, methyl, trifluoromethyl, methoxy or oxo and wherein t is 2, 3, 4 or 5. Examples comprise azetidin-1-yl, 2-methylazetidin-1-yl, (S)-2-methylazetidin-1-yl, (R)-2-methylazetidin-1-yl, 3-fluoroazetidin-1-yl, 3-methoxyazetidin-1-yl, 3-hydroxyazetidin-1-yl, 1,3-oxazol-5-yl, pyrrolidin-1-yl, (S)-2-fluoropyrrolidin-1-yl, (R)-2-fluoropyrrolidin-1-yl, 3-fluoropyrrolidin-1-yl, (S)-3-fluoropyrrolidin-1-yl, (R)-3-fluoropyrrolidin-1-yl, 2,2-difluoropyrrolidin-1-yl, 3,3-difluoropyrrolidin-1-yl, 2-methylpyrrolidin-1-yl, (S)-2-methylpyrrolidin-1-yl, (R)-2-methylpyrrolidin-1-yl, 3-methylpyrrolidin-1-yl, (S)-3-methylpyrrolidin-1-yl, (R)-3-methylpyrrolidin-1-yl, 2,2-dimethylpyrrolidin-1-yl, 3,3-dimethylpyrrolidin-1-yl, 2-trifluoromethylpyrrolidin-1-yl, (S)-2-trifluoromethylpyrrolidin-1-yl, (R)-2-trifluoromethylpyrrolidin-1-yl, 3-trifluoromethylpyrrolidin-1-yl, (S)-3-trifluoromethylpyrrolidin-1-yl, (R)-3-trifluoromethylpyrrolidin-1-yl, 2-oxopyrrolidin-1-yl, piperidin-1-yl, 2-methylpiperidin-1-yl, (S)-2-methylpiperidin-1-yl and (R)-2-methylpiperidin-1-yl.

Likewise preferred are radicals $R^{a'}$, wherein $R^{a1}$ and $R^{a2}$ together form a radical $(CH_2)_u$ wherein 1 or 2 of the hydrogen atoms may be replaced by fluorine, hydroxy, oxo, $C_1$-$C_2$-alkyl or $C_1$-$C_2$-alkoxy, wherein one $CH_2$ moiety is replaced by O, S, S=O, $SO_2$ or N—$R^c$, $R^c$ being hydrogen or $C_1$-$C_2$-alkyl and wherein u is 2, 3, 4, 5 or 6. Examples for preferred radicals of the formula $R^{a'}$ also comprise 4-morpholinyl, 4-thiomorpholinyl, 4-(1,1-dioxo)thiomorpholinyl, piperazin-1-yl, 4-methylpiperazin-1-yl, 2-oxo-oxazolidin-3-yl, pyrrolidin-2-yl, (S)-pyrrolidin-2-yl, (R)-pyrrolidin-2-yl, pyrrolidin-3-yl, (S)-pyrrolidin-3-yl, (R)-pyrrolidin-3-yl, 2-fluoropyrrolidin-1-yl, 1-methylpyrrolidin-2-yl, (S)-1-methylpyrrolidin-2-yl, (R)-1-methylpyrrolidin-2-yl, 1-methylpyrrolidin-3-yl, (S)-1-methylpyrrolidin-3-yl and (R)-1-methylpyrrolidin-3-yl.

Amongst the radicals of the formula $R^{a'}$ those are preferred which carry 1, 2, 3 or 4, in particular 1, 2 or 3 fluorine atoms.

In a further preferred embodiment Ar carries one radical $R^a$, which is selected from 5- or 6-membered heteroaromatic radicals having as ring members 1 heteroatom selected from O, S and N and which may further have 1, 2 or 3 nitrogen atoms as ring members, and wherein the 5- or 6-membered heteroaromatic radical may carry 1, 2 or 3 substituents selected from halogen, $NO_2$, $NH_2$, OH, CN, $C_1$-$C_6$-alkyl, $C_3$-$C_6$-cycloalkyl, $C_1$-$C_6$-alkoxy, fluorinated $C_1$-$C_6$-alkyl, fluorinated $C_3$-$C_6$-cycloalkyl, fluorinated $C_1$-$C_6$-alkoxy, $C_1$-$C_6$-hydroxyalkyl, $C_1$-$C_4$-alkoxy-$C_2$-$C_4$-alkyl, $C_1$-$C_6$-hydroxyalkoxy, $C_1$-$C_4$-alkoxy-$C_2$-$C_4$-alkoxy, $C_1$-$C_6$-alkylcarbonyl, $C_1$-$C_6$-alkylamino, di-$C_1$-$C_6$-alkylamino, $C_1$-$C_6$-alkylaminocarbonyl, di-$C_1$-$C_6$-alkylaminocarbonyl, fluorinated $C_1$-$C_6$-alkylcarbonyl, $C_1$-$C_6$-alkylcarbonylamino, fluorinated $C_1$-$C_6$-alkylcarbonylamino, $C_1$-$C_6$-alkylcarbonyloxy, fluorinated $C_1$-$C_6$-alkylcarbonyloxy, $C_1$-$C_6$-alkoxycarbonyl, $C_1$-$C_6$-alkylthio, fluorinated $C_1$-$C_6$-alkylthio, $C_1$-$C_6$-alkylsulfinyl, $C_1$-$C_6$-alkylsulfonyl, fluorinated $C_1$-$C_6$-alkylsulfinyl and fluorinated $C_1$-$C_6$-alkylsulfonyl. Amongst these radicals $R^a$, preference is given to radicals selected from 2-, 3-, or 4-pyridyl, 2-, 4- or 5-pyrimidinyl, pyrazinyl, 3- or 4-pyridazinyl, 2- or 3-thienyl, 2- or 3-furyl, 1-, 2- or 3-pyrrolyl, 1-, 2-, 4- or 5-imidazolyl, 1-, 3-, 4- or 5-pyrazolyl, 1-, 3- or 5-[1,2,4]-triazolyl, 1-, 4- or 5-[1,2,3]-triazolyl, 1- or 5-(1H)-tetrazolyl, 2- or 5-(2H)-tetrazolyl, 2-, 4- or 5-oxazolyl, 3-, 4- or 5-isoxazolyl, 2-, 4- or 5-thiazolyl, 3-, 4- or 5-isothiazolyl, 4- or 5-[1,2,3]-oxadiazolyl, 3- or 4-[1,2,5]-oxadiazolyl (=furazanyl), 3- or 5-[1,2,4]-oxadiazolyl, 2- or 5-[1,3,4]-oxadizolyl, 4- or 5-[1,2,3]-thiadiazolyl, 3- or 4-[1,2,5]-thiadiazolyl, 3- or 5-[1,2,4]-thiadizolyl or 2- or 5-[1,3,4]-thiadiazolyl, in particular from 2- or 3-furanyl, 2- or 3-thienyl, 1-, 2- or 3-pyrrolyl, 1-, 3-, 4- or 5-pyrazolyl, 1-, 2-, 4- or 5-imidazolyl, 2-, 4- or 5-oxazolyl, 3-, 4- or 5-isoxazolyl, 2- or 5-[1,3,4]-thiadiazolyl, 1-, 3- or 5-[1,2,4]-triazolyl, 1-, 4- or 5-[1,2,3]-triazolyl, 1- or 5-(1H)-tetrazolyl and 2- or 5-(2H)-tetrazolyl, and specifically from 1-, 3-, 4- or 5-pyrazolyl, in particular 1-pyrazolyl, and 2-, 4- or 5-oxazolyl, in particular 4- or 5-oxazolyl. The heteroaromatic radical may be unsubstituted or may carry 1 to 3 substituents as given above. Preferred substituents on heteroaromatic $R^a$ are selected from halogen, $C_1$-$C_4$-alkyl, $C_1$-$C_4$-alkoxy, fluorinated $C_1$-$C_4$-alkyl and fluorinated $C_1$-$C_4$-alkoxy.

In a further preferred embodiment Ar carries 1 radical $R^a$ which is selected from the group consisting of $(CH_2)_vCF_3$, $(CH_2)_vCHF_2$, $(CH_2)_vCH_2F$, $O(CH_2)_vCF_3$, $O(CH_2)_vCHF_2$, $O(CH_2)_vCH_2F$, wherein v is 0, 1, 2 or 3. In this embodiment Ar may also carry 1 or 2 further radicals $R^b$, which are independently from each other selected from halogen, cyano, methyl, fluoromethyl, difluoromethyl, trifluoromethyl, difluoromethoxy and trifluoromethoxy. Preferably Ar carries no further radical $R^b$. In this embodiment Ar is preferably phenyl which carries 1 radical $R^a$ which is selected from the group consisting of $(CH_2)_vCF_3$, $(CH_2)_vCHF_2$, $(CH_2)_vCH_2F$, $O(CH_2)_vCF_3$, $O(CH_2)_vCHF_2$, $O(CH_2)_vCH_2F$, wherein v is 0, 1, 2 or 3. In this embodiment Ar is preferably phenyl, which carries $R^a$ in the 4 position with respect to the $SO_2$-group.

In another embodiment of the invention, Ar carries 1 radical $R^a$ which is selected from the group consisting of $C_2$-$C_6$-alkenyl, fluorinated $C_2$-$C_6$-alkenyl, $C_1$-$C_6$-hydroxyalkyl, $C_1$-$C_6$-alkoxy-$C_1$-$C_4$-alkyl, $C_1$-$C_6$-hydroxyalkoxy, $C_1$-$C_6$-alkoxy-$C_1$-$C_4$-alkoxy, COOH, $CH_2NR^4R^5$, $ONR^4R^5$, $NHC(O)NR^4R^5$, $C(O)NR^4R^5$, $SO_2NR^4R^5$, $C_1$-$C_6$-alkylcarbonyl, fluorinated $C_2$-$C_6$-alkylcarbonyl, $C_1$-$C_6$-alkylcarbonylamino, fluorinated $C_1$-$C_6$-alkylcarbonylamino, $C_1$-$C_6$-alkylcarbonyloxy, fluorinated $C_1$-$C_6$-alkylcarbonyloxy, $C_1$-$C_6$-alkoxycarbonyl, $C_1$-$C_6$-alkylthio, fluorinated $C_1$-$C_6$-alkylthio, $C_1$-$C_6$-alkylsulfinyl, $C_1$-$C_6$-alkylsulfonyl, fluorinated $C_1$-$C_6$-alkylsulfinyl, fluorinated $C_1$-$C_6$-alkylsulfonyl, phenylsulfonyl, phenoxy, benzyloxy, pyridine-2-yloxy, and a 5- or 6-membered N-bound heteroaromatic radical, wherein the six last mentioned radicals may carry 1, 2, 3 or 4 radicals selected from halogen, $NO_2$, $NH_2$, OH, CN, $C_1$-$C_6$-alkyl, $C_3$-$C_6$-cycloalkyl, $C_1$-$C_6$-alkoxy, fluorinated $C_1$-$C_6$-alkyl, fluorinated $C_3$-$C_6$-cycloalkyl, fluorinated $C_1$-$C_6$-alkoxy, $C_1$-$C_6$-hydroxyalkyl, $C_1$-$C_4$-alkoxy-$C_2$-$C_4$-alkyl, $C_1$-$C_6$-hydroxyalkoxy, $C_1$-$C_4$-alkoxy-$C_2$-$C_4$-alkoxy, $C_1$-$C_6$-alkylcarbonyl, $C_1$-$C_6$-alkylamino, di-$C_1$-$C_6$-alkylamino, $C_1$-$C_6$-alkylaminocarbonyl, di-$C_1$-$C_6$-alkylaminocarbonyl, fluorinated $C_1$-$C_6$-alkylcarbonyl, $C_1$-$C_6$-alkylcarbonylamino, fluorinated $C_1$-$C_6$-alkylcarbonylamino, $C_1$-$C_6$-alkylcarbonyloxy, fluorinated $C_1$-$C_6$-alkylcarbonyloxy, $C_1$-$C_6$-alkoxycarbonyl, $C_1$-$C_6$-alkylthio, fluorinated $C_1$-$C_6$-alkylthio, $C_1$-$C_6$-alkylsulfinyl, $C_1$-$C_6$-alkylsulfonyl, fluorinated $C_1$-$C_6$-alkylsulfinyl and fluorinated $C_1$-$C_6$-alkylsulfonyl.

In another embodiment of the invention, Ar is phenyl, which carries 1 radical $R^a$ and at least one radical $R^b$ and wherein $R^a$ and one radical $R^b$ are bound to two adjacent carbon atoms of phenyl and form a 5- or 6-membered heterocyclic or carbocyclic ring which is fused to the phenyl ring and which is unsubstituted or which may carry 1, 2 or 3 radicals as given above. Examples of a phenyl ring fused to a saturated or unsaturated 5- or 6-membered carbocyclic or heterocyclic ring comprise indenyl, indanyl, naphthyl, tetralin, benzofuranyl, 2,3-dihydrobenzofuranyl, benzothienyl, indolyl, indazolyl, benzimidazolyl, benzoxathiazolyl, benzoxadiazolyl, benzothiadiazolyl, benzoxazinyl, dihydrobenzoxazinyl, chinolinyl, isochinolinyl, tetrahydroisochinolinyl, chromenyl, chromanyl and the like, which may be unsubstituted or which may carry 1, 2 or 3 of the aforementioned radicals. Preferred substituents for the saturated or unsaturated 5- or 6-membered carbocyclic or heterocyclic ring fused to the phenyl ring are selected from halogen, $C_1$-$C_4$-alkyl, $C_1$-$C_4$-alkoxy, fluorinated $C_1$-$C_4$-alkyl and fluorinated $C_1$-$C_4$-alkoxy.

Specifically, $R^a$ is selected from $C_1$-$C_4$-alkyl, fluorinated $C_1$-$C_4$-alkyl, in particular $(CH_2)_vCF_3$, $(CH_2)_vCHF_2$ and $(CH_2)_vCH_2F$, $C_1$-$C_4$-alkoxy and fluorinated $C_1$-$C_4$-alkoxy, in particular $O(CH_2)_vCF_3$, $O(CH_2)_vCHF_2$ and $O(CH_2)_vCH_2F$.

Alternatively, $R^a$ is specifically selected from a 5- or 6-membered heteroaromatic radical having as ring members 1 heteroatom selected from O, S and N and which may further have 1, 2 or 3 nitrogen atoms as ring members, and wherein the 5- or 6-membered heteroaromatic radical may be substituted as described above. Preferred 5- or 6-membered heteroaromatic radicals $R^a$ and preferred substituents thereof are as described above.

More specifically, Ar is phenyl which carries, preferably in the 4-position with respect to the 1-position of the sulfonyl group, one radical Ra which is selected from $C_1$-$C_4$-alkyl, fluorinated $C_1$-$C_4$-alkyl, in particular $(CH_2)_vCF_3$, $(CH_2)_vCHF_2$ and $(CH_2)_vCH_2F$, $C_1$-$C_4$-alkoxy, fluorinated $C_1$-$C_4$-alkoxy, in particular $O(CH_2)_vCF_3$, $O(CH_2)_vCHF_2$ and $O(CH_2)_vCH_2F$, and a 5- or 6-membered heteroaromatic radical as described above.

The radical $R^1$ is preferably H, $C_1$-$C_4$-alkyl, $C_3$-$C_4$-cycloalkyl, $C_3$-$C_4$-cycloalkylmethyl, $C_3$-$C_4$-alkenyl, fluorinated $C_2$-$C_4$-alkyl, fluorinated $C_3$-$C_4$-cycloalkyl, fluorinated $C_3$-$C_4$-cycloalkylmethyl, fluorinated $C_3$-$C_4$-alkenyl, formyl or $C_1$-$C_3$-alkylcarbonyl, in particular H, $C_1$-$C_4$-alkyl, $C_3$-$C_4$-alkenyl, fluorinated $C_2$-$C_4$-alkyl, fluorinated $C_3$-$C_4$-alkenyl, more preferably H, methyl, ethyl, n-propyl, fluorinated $C_2$-$C_3$-alkyl or 1-propen-3-yl (allyl), specifically H, methyl or n-propyl, in particular n-propyl.

A preferred embodiment of the invention relates to compounds, wherein $R^{1a}$ is hydrogen. In these compounds $R^1$ has the meanings given above and is preferably different from hydrogen. In particular $R^1$ is n-propyl. In this embodiment $R^{2a}$ is preferably hydrogen while $R^2$ is preferably hydrogen, methyl or fluorinated methyl. In particular, both $R^{2a}$ and $R^2$ are hydrogen or one of the radicals $R^{2a}$ and $R^2$ is hydrogen while the other is methyl. In this embodiment both $R^{8a}$ and $R^8$ are preferably hydrogen.

In a further preferred embodiment, $R^{1a}$ is different from hydrogen and is preferably $C_1$-$C_4$-alkyl, $C_3$-$C_4$-alkenyl, fluorinated $C_2$-$C_4$-alkyl, fluorinated $C_3$-$C_4$-alkenyl, more preferably methyl, n-propyl, fluorinated $C_2$-$C_3$-alkyl or 1-propen-3-yl, in particular n-propyl. In these compounds $R^1$ has the meanings given above. In particular $R^1$ is H, methyl or n-propyl. In this embodiment, $R^1$ and $R^{1a}$ have the same meaning and are in particular both methyl or both n-propyl. In this embodiment $R^{2a}$ is preferably hydrogen while $R^2$ is preferably hydrogen, methyl or fluorinated methyl. In particular both $R^{2a}$ and $R^2$ are hydrogen or one of the radicals $R^{2a}$ and $R^2$ is hydrogen while the other is methyl. In this embodiment both, $R^{8a}$ and $R^8$ are preferably hydrogen.

In a further preferred embodiment, $R^{2a}$ and $R^{1a}$ together are $(CR^6R^7)_n$ with n being 2, 3 or 4 and specifically 3. $R^6$ and $R^7$ are preferably H. $R^2$ is preferably hydrogen. In these compounds $R^1$ has the meanings given above. In particular $R^1$ is H, n-propyl, 1-propen-3-yl. In this embodiment both $R^{8a}$ and $R^8$ are preferably hydrogen.

In a further preferred embodiment, $R^{8a}$ and $R^{1a}$ together are $(CR^6R^7)_s$ with s being 2 or 3 and specifically 2. $R^6$ and $R^7$ are preferably H. $R^2$ and $R^{2a}$ are preferably H. $R^8$ is preferably hydrogen. In these compounds, $R^1$ has the meanings given above. In particular, $R^1$ is H, n-propyl, 1-propen-3-yl and specifically H or n-propyl.

In a further preferred embodiment, $R^1$ and $R^{1a}$ together are $(CR^6R^7)_r$ with r being 3, 4 or 5 and specifically 4. $R^6$ and $R^7$ are preferably H. In this embodiment both $R^{2a}$ and $R^2$ as well as both $R^{8a}$ and $R^3$ are preferably hydrogen.

One preferred embodiment of the invention relates to compounds of the formula I, wherein X is CH.

Another preferred embodiment of the invention relates to compounds of the formula I, wherein X is N.

Preferably, $R^3$ is H or methyl and more preferably H.

One preferred embodiment of the invention relates to compounds of the formula I, wherein $R^9$ is selected from $C_1$-$C_4$-alkyl, in particular methyl, $C_1$-$C_4$-alkoxy, in particular methoxy, and hydrogen.

In a further preferred embodiment, $R^9$ is bound next to the ring nitrogen of the pyridine and pyrimidine moiety, and $R^9$ is preferably $C_1$-$C_4$-alkoxy, in particular methoxy.

In a further preferred embodiment $R^9$ is bound next to the ring nitrogen of the pyridine and pyrimidine moiety respectively, and $R^9$ is preferably $C_1$-$C_4$-alkyl, in particular methyl.

Another preferred embodiment relates to compounds wherein X is CH, and $R^{1a}$, $R^2$, $R^{2a}$, $R^8$ and $R^{8a}$ are H, $R^9$ is methoxy and $R^a$ and Ar are as defined above.

Another preferred embodiment relates to compounds wherein X is N, $R^{1a}$, $R^2$, $R^{2a}$, $R^8$ and $R^{8a}$ are H, $R^9$ is methoxy and $R^a$ and Ar are as defined above.

In one preferred embodiment, Ar (together with $R^a$) has one of the meanings given in Table B below.

Preferred embodiments of the invention are compounds of the following formulae Ia, Ib, Ic, Id, Ie, If, Ig, Ih, Ii, Ij, Ik, Il, Im, In, Io, Ip, Iq, Ir, Is, It, Iu, Iv, Iw, Ix, Iy and Iz and the physiologically tolerated acid addition salts thereof. With regard to the carbon atom carrying four different groups, compounds of the formulae Ii, Ij, Ik, Ilk, Im, In, Io, Ip, Iq, Ir, Is and It may exist as R-enantiomers or S-enantiomers as well as mixtures of the enantiomers such as racemic mixtures. The preferred embodiments include the R- and S-enantiomers of Ii, Ij, Ik, Il, Im, In, Io, Ip, Iq, Ir, Is and It and the mixtures of the enantiomers.

In the compounds of the formulae Ia, Ib, Ic, Id, Ie, If, Ig, Ih, Ii, Ij, Ik, Il, Im, In, Io, Ip, Iq, Ir, Is and It, $R^1$, Ar and $R^{1a}$ are as defined above with particular preference given to those compounds, wherein $R^1$, Ar and $R^{1a}$ have one of the preferred meanings.

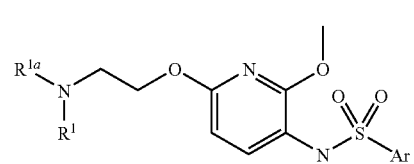

Ia

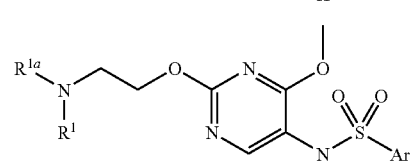

Ib

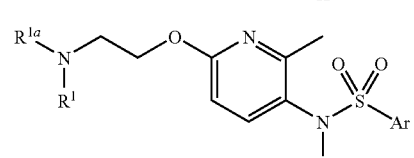

Ic

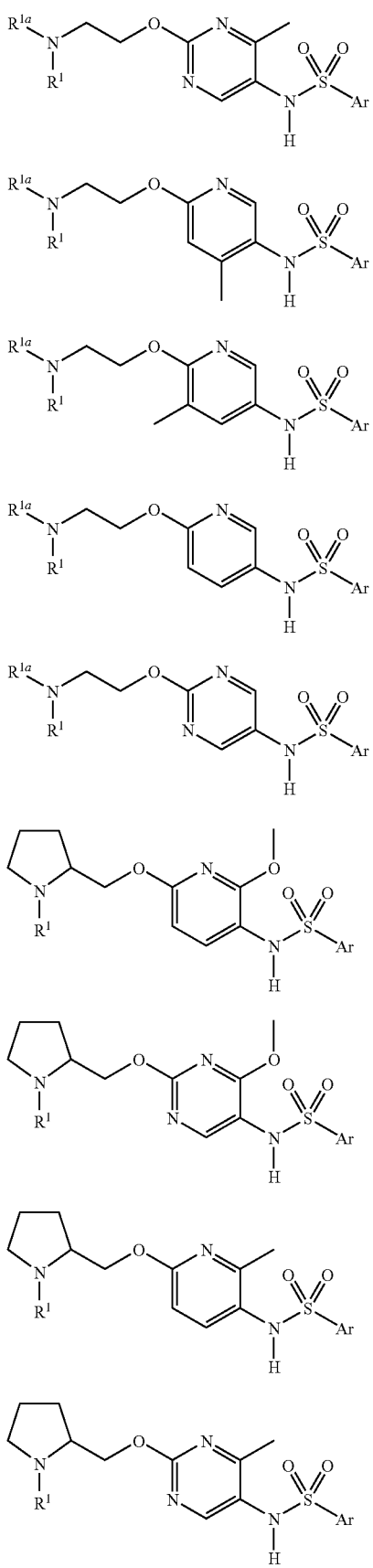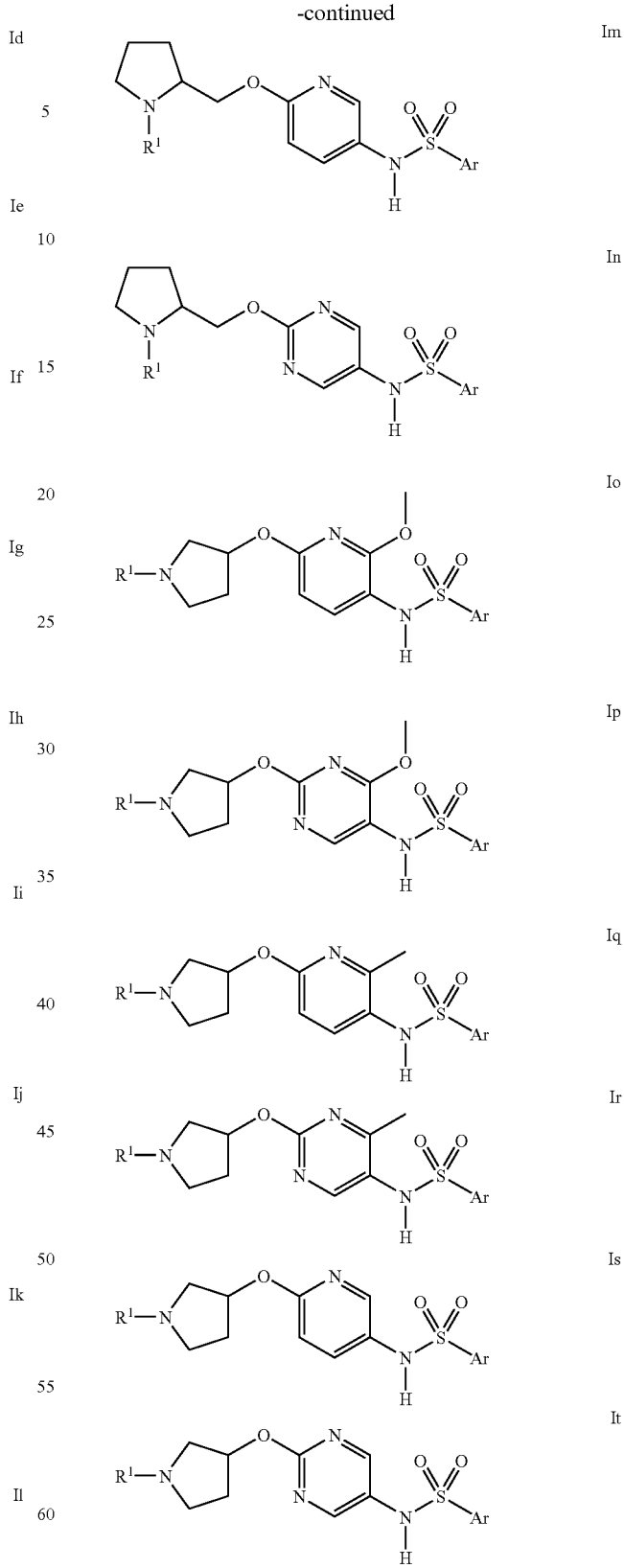
In the compounds of the formulae Iu, Iv, Iw, Ix, Iy and Iz, Ar is as defined above with particular preference given to those compounds wherein Ar has one of the preferred meanings.

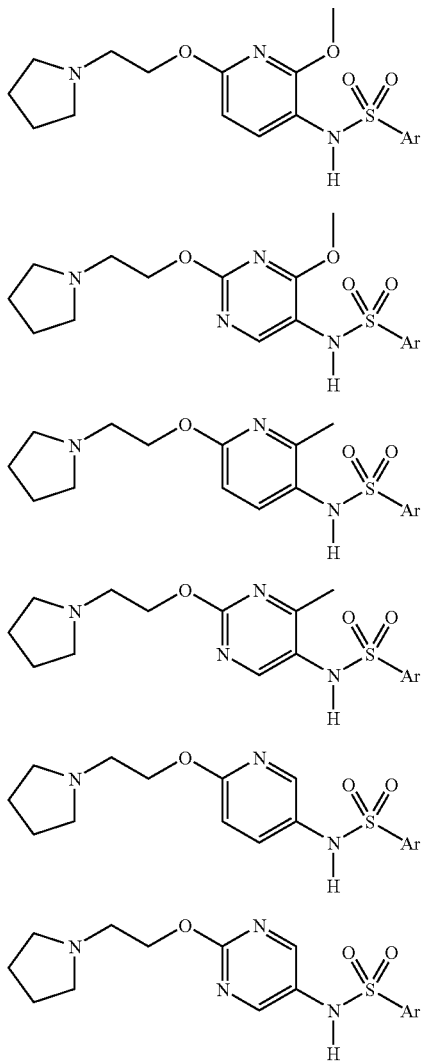

Examples of preferred compounds of the general formula I are given in the following tables A-1, A-2, A-3, A-4, A5, A-6, A-7, A-8, A-9, A-10, A-11, A-12, A-13, A-14, A-15, A-16, A-17, A-18, A-19, A-20, B-1, B-2, B-3, B-4, B-5 and B-6.

Table A-1: Compounds of the formula Ia, wherein $R^{1a}$ is H and Ar and $R^1$ have the meaning given in one of the rows of table A.

Table A-2: Compounds of the formula Ib, wherein $R^{1a}$ is H and Ar and $R^1$ have the meaning given in one of the rows of table A.

Table A-3: Compounds of the formula Ic, wherein $R^{1a}$ is H and Ar and $R^1$ have the meaning given in one of the rows of table A.

Table A-4: Compounds of the formula Id, wherein $R^{1a}$ is H and Ar and $R^1$ have the meaning given in one of the rows of table A.

Table A-5: Compounds of the formula Ie, wherein $R^{1a}$ is H and Ar and $R^1$ have the meaning given in one of the rows of table A.

Table A-6: Compounds of the formula If, wherein $R^{1a}$ is H and Ar and $R^1$ have the meaning given in one of the rows of table A.

Table A-7: Compounds of the formula Ig, wherein Ar and $R^1$ have the meaning given in one of the rows of table A.

Table A-8: Compounds of the formula Ih, wherein Ar and $R^1$ have the meaning given in one of the rows of table A.

Table A-9: Compounds of the formula Ii, including the pure S-isomers, the pure R-isomers and the racemic mixtures, wherein Ar and $R^1$ have the meaning given in one of the rows of table A.

Table A-10: Compounds of the formula Ij, including the pure S-isomers, the pure R-isomers and the racemic mixtures, wherein Ar and $R^1$ have the meaning given in one of the rows of table A.

Table A-11: Compounds of the formula Ik, including the pure S-isomers, the pure R-isomers and the racemic mixtures, wherein Ar and $R^1$ have the meaning given in one of the rows of table A.

Table A-12: Compounds of the formula Il, including the pure S-isomers, the pure R-isomers and the racemic mixtures, wherein Ar and $R^1$ have the meaning given in one of the rows of table A.

Table A-13: Compounds of the formula Im, including the pure S-isomers, the pure R-isomers and the racemic mixtures, wherein Ar and $R^1$ have the meaning given in one of the rows of table A.

Table A-14: Compounds of the formula In, including the pure S-isomers, the pure R-isomers and the racemic mixtures, wherein Ar and $R^1$ have the meaning given in one of the rows of table A.

Table A-15: Compounds of the formula Io, including the pure S-isomers, the pure R-isomers and the racemic mixtures, wherein Ar and $R^1$ have the meaning given in one of the rows of table A.

Table A-16: Compounds of the formula Ip, including the pure S-isomers, the pure R-isomers and the racemic mixtures, wherein Ar and $R^1$ have the meaning given in one of the rows of table A.

Table A-17: Compounds of the formula Iq, including the pure S-isomers, the pure R-isomers and the racemic mixtures, wherein Ar and $R^1$ have the meaning given in one of the rows of table A.

Table A-18: Compounds of the formula Ir, including the pure S-isomers, the pure R-isomers and the racemic mixtures, wherein Ar and $R^1$ have the meaning given in one of the rows of table A.

Table A-19: Compounds of the formula Is, including the pure S-isomers, the pure R-isomers and the racemic mixtures, wherein Ar and $R^1$ have the meaning given in one of the rows of table A.

Table A-20: Compounds of the formula It, including the pure S-isomers, the pure R-isomers and the racemic mixtures, wherein Ar and $R^1$ have the meaning given in one of the rows of table A.

TABLE A

| No. | $R^1$ | Ar |
|---|---|---|
| 1. | methyl | 4-(trifluoromethoxy)-phenyl |
| 2. | methyl | 3-(trifluoromethoxy)-phenyl |
| 3. | methyl | 4-cyanophenyl |
| 4. | methyl | 4-methylphenyl |
| 5. | methyl | 4-ethylphenyl |
| 6. | methyl | 4-propylphenyl |
| 7. | methyl | 4-methoxyphenyl |
| 8. | methyl | 4-fluorophenyl |
| 9. | methyl | 4-chlorophenyl |
| 10. | methyl | 4-bromophenyl |
| 11. | methyl | 3-(trifluoromethyl)phenyl |
| 12. | methyl | 4-(trifluoromethyl)phenyl |
| 13. | methyl | 2-(trifluoromethyl)phenyl |
| 14. | methyl | 3,4-difluorophenyl |

TABLE A-continued

| No. | R¹ | Ar |
|---|---|---|
| 15. | methyl | 4-bromo-3-fluorophenyl |
| 16. | methyl | 4-bromo-2-fluorophenyl |
| 17. | methyl | 4-bromo-2,5-difluorophenyl |
| 18. | methyl | 2-fluoro-4-isopropylphenyl |
| 19. | methyl | 4-hydroxyphenyl |
| 20. | methyl | 4-isopropylphenyl |
| 21. | methyl | 4-sec-butylphenyl |
| 22. | methyl | 4-isobutylphenyl |
| 23. | methyl | 4-(1,1-dimethylpropyl)-phenyl |
| 24. | methyl | 4-vinylphenyl |
| 25. | methyl | 4-isopropenylphenyl |
| 26. | methyl | 4-(fluoromethyl)phenyl |
| 27. | methyl | 3-(fluoromethyl)phenyl |
| 28. | methyl | 2-(fluoromethyl)phenyl |
| 29. | methyl | 4-(difluoromethyl)phenyl |
| 30. | methyl | 3-(difluoromethyl)phenyl |
| 31. | methyl | 2-(difluoromethyl)phenyl |
| 32. | methyl | 4-(1-fluoroethyl)-phenyl |
| 33. | methyl | 4-((S)-1-fluoroethyl)-phenyl |
| 34. | methyl | 4-((R)-1-fluoroethyl)-phenyl |
| 35. | methyl | 4-(2-fluoroethyl)-phenyl |
| 36. | methyl | 4-(1,1-difluoroethyl)-phenyl |
| 37. | methyl | 4-(2,2-difluoroethyl)-phenyl |
| 38. | methyl | 4-(2,2,2-trifluoroethyl)-phenyl |
| 39. | methyl | 4-(3-fluoropropyl)-phenyl |
| 40. | methyl | 4-(2-fluoropropyl)-phenyl |
| 41. | methyl | 4-((S)-2-fluoropropyl)-phenyl |
| 42. | methyl | 4-((R)-2-fluoropropyl)-phenyl |
| 43. | methyl | 4-(3,3-difluoropropyl)-phenyl |
| 44. | methyl | 4-(3,3,3-trifluoropropyl)-phenyl |
| 45. | methyl | 4-(1-fluoro-1-methylethyl)-phenyl |
| 46. | methyl | 4-(2-fluoro-1-methylethyl)-phenyl |
| 47. | methyl | 4-((S)-2-fluoro-1-methylethyl)-phenyl |
| 48. | methyl | 4-((R)-2-fluoro-1-methylethyl)-phenyl |
| 49. | methyl | 4-(2,2-difluoro-1-methylethyl)-phenyl |
| 50. | methyl | 4-((S)-2,2-difluoro-1-methylethyl)-phenyl |
| 51. | methyl | 4-((R)-2,2-difluoro-1-methylethyl)-phenyl |
| 52. | methyl | 4-(2,2,2-trifluoro-1-methylethyl)-phenyl |
| 53. | methyl | 4-((S)-2,2,2-trifluoro-1-methylethyl)-phenyl |
| 54. | methyl | 4-((R)-2,2,2-trifluoro-1-methylethyl)-phenyl |
| 55. | methyl | 4-(2-fluoro-1-fluoromethylethyl)-phenyl |
| 56. | methyl | 4-(1-difluoromethyl-2,2-difluoroethyl)-phenyl |
| 57. | methyl | 4-(1,1-dimethyl-2-fluoroethyl)-phenyl |
| 58. | methyl | 4-ethoxyphenyl |
| 59. | methyl | 4-propoxyphenyl |
| 60. | methyl | 4-isopropoxyphenyl |
| 61. | methyl | 4-butoxyphenyl |
| 62. | methyl | 4-(fluoromethoxy)-phenyl |
| 63. | methyl | 4-(difluoromethoxy)-phenyl |
| 64. | methyl | 4-(2-fluoroethoxy)-phenyl |
| 65. | methyl | 4-(2,2-difluoroethoxy)-phenyl |
| 66. | methyl | 4-(2,2,2-trifluoroethoxy)-phenyl |
| 67. | methyl | 4-(1,1,2,2-tetrafluoroethoxy)-phenyl |
| 68. | methyl | 4-cyclopropylphenyl |
| 69. | methyl | 4-cyclobutylphenyl |
| 70. | methyl | 4-cyclopentylphenyl |
| 71. | methyl | 4-(2,2-difluorocyclopropyl)-phenyl |
| 72. | methyl | 3-fluoro-4-isopropylphenyl |
| 73. | methyl | 4-(1-hydroxy-1-methylethyl)-phenyl |
| 74. | methyl | 4-(2-hydroxy-2-methylpropyl)-phenyl |
| 75. | methyl | 4-acetylphenyl |
| 76. | methyl | 4-carboxyphenyl |
| 77. | methyl | 4-(O-benzyl)-phenyl |
| 78. | methyl | 4-(2-methoxyethoxy)-phenyl |
| 79. | methyl | 4-(CH₂—N(CH₃)₂)-phenyl |
| 80. | methyl | 4-(NH—CO—NH₂)-phenyl |
| 81. | methyl | 4-(methylsulfanyl)-phenyl |
| 82. | methyl | 4-(fluoromethylsulfanyl)-phenyl |
| 83. | methyl | 4-(difluoromethylsulfanyl)-phenyl |
| 84. | methyl | 4-(trifluoromethylsulfanyl)-phenyl |
| 85. | methyl | 4-(methylsulfonyl)-phenyl |
| 86. | methyl | 4-(N-methoxy-N-methyl-amino)-phenyl |
| 87. | methyl | 4-(methoxyamino)-phenyl |
| 88. | methyl | 4-(ethoxyamino)-phenyl |
| 89. | methyl | 4-(N-methylaminooxy)-phenyl |
| 90. | methyl | 4-(N,N-dimethylaminooxy)-phenyl |
| 91. | methyl | 4-(azetidin-1-yl)-phenyl |
| 92. | methyl | 4-(2-methylazetidin-1-yl)-phenyl |
| 93. | methyl | 4-((S)-2-methylazetidin-1-yl)-phenyl |
| 94. | methyl | 4-((R)-2-methylazetidin-1-yl)-phenyl |
| 95. | methyl | 4-(3-fluoroazetidin-1-yl)-phenyl |
| 96. | methyl | 4-(3-methoxyazetidin-1-yl)-phenyl |
| 97. | methyl | 4-(3-hydroxyazetidin-1-yl)-phenyl |
| 98. | methyl | 4-(pyrrolidin-1-yl)-phenyl |
| 99. | methyl | 4-(pyrrolidin-2-yl)-phenyl |
| 100. | methyl | 4-((S)-pyrrolidin-2-yl)-phenyl |
| 101. | methyl | 4-((R)-pyrrolidin-2-yl)-phenyl |
| 102. | methyl | 4-(pyrrolidin-3-yl)-phenyl |
| 103. | methyl | 4-((S)-pyrrolidin-3-yl)-phenyl |
| 104. | methyl | 4-((R)-pyrrolidin-3-yl)-phenyl |
| 105. | methyl | 4-(2-fluoropyrrolidin-1-yl)-phenyl |
| 106. | methyl | 4-((S)-2-fluoropyrrolidin-1-yl)-phenyl |
| 107. | methyl | 4-((R)-2-fluoropyrrolidin-1-yl)-phenyl |
| 108. | methyl | 4-(3-fluoropyrrolidin-1-yl)-phenyl |
| 109. | methyl | 4-((S)-3-fluoropyrrolidin-1-yl)-phenyl |
| 110. | methyl | 4-((R)-3-fluoropyrrolidin-1-yl)-phenyl |
| 111. | methyl | 4-(2,2-difluoropyrrolidin-1-yl)-phenyl |
| 112. | methyl | 4-(3,3-difluoropyrrolidin-1-yl)-phenyl |
| 113. | methyl | 4-(2-methylpyrrolidin-1-yl)-phenyl |
| 114. | methyl | 4-((S)-2-methylpyrrolidin-1-yl)-phenyl |
| 115. | methyl | 4-((R)-2-methylpyrrolidin-1-yl)-phenyl |
| 116. | methyl | 4-(3-methylpyrrolidin-1-yl)-phenyl |
| 117. | methyl | 4-((S)-3-methylpyrrolidin-1-yl)-phenyl |
| 118. | methyl | 4-((R)-3-methylpyrrolidin-1-yl)-phenyl |
| 119. | methyl | 4-(1-methylpyrrolidin-2-yl)-phenyl |
| 120. | methyl | 4-((S)-1-methylpyrrolidin-2-yl)-phenyl |
| 121. | methyl | 4-((R)-1-methylpyrrolidin-2-yl)-phenyl |
| 122. | methyl | 4-(1-methylpyrrolidin-3-yl)-phenyl |
| 123. | methyl | 4-((S)-1-methylpyrrolidin-3-yl)-phenyl |
| 124. | methyl | 4-((R)-1-methylpyrrolidin-3-yl)-phenyl |
| 125. | methyl | 4-(2,2-dimethylpyrrolidin-1-yl)-phenyl |
| 126. | methyl | 4-(3,3-dimethylpyrrolidin-1-yl)-phenyl |
| 127. | methyl | 4-(2-trifluoromethylpyrrolidin-1-yl)-phenyl |
| 128. | methyl | 4-((S)-2-trifluoromethylpyrrolidin-1-yl)-phenyl |
| 129. | methyl | 4-((R)-2-trifluoromethylpyrrolidin-1-yl)-phenyl |
| 130. | methyl | 4-(3-trifluoromethylpyrrolidin-1-yl)-phenyl |
| 131. | methyl | 4-((S)-3-trifluoromethylpyrrolidin-1-yl)-phenyl |
| 132. | methyl | 4-((R)-3-trifluoromethylpyrrolidin-1-yl)-phenyl |
| 133. | methyl | 4-(2-oxopyrrolidin-1-yl)-phenyl |
| 134. | methyl | 4-(2-oxo-oxazolidin-3-yl)-phenyl |
| 135. | methyl | 4-(piperidin-1-yl)-phenyl |
| 136. | methyl | 4-(2-methylpiperidin-1-yl)-phenyl |
| 137. | methyl | 4-((S)-2-methylpiperidin-1-yl)-phenyl |
| 138. | methyl | 4-((R)-2-methylpiperidin-1-yl)-phenyl |
| 139. | methyl | 4-(piperazin-1-yl)-phenyl |
| 140. | methyl | 4-(4-methylpiperazin-1-yl)-phenyl |
| 141. | methyl | 4-(morpholin-4-yl)-phenyl |
| 142. | methyl | 4-(thiomorpholin-4-yl)-phenyl |
| 143. | methyl | 4-(1-oxo-thiomorpholin-4-yl)-phenyl |
| 144. | methyl | 4-(1,1-dioxo-thiomorpholin-4-yl)-phenyl |
| 145. | methyl | 4-(pyrrol-1-yl)-phenyl |
| 146. | methyl | 4-(pyrrol-2-yl)-phenyl |
| 147. | methyl | 4-(pyrrol-3-yl)-phenyl |
| 148. | methyl | 4-(1-methylpyrrol-2-yl)-phenyl |
| 149. | methyl | 4-(1-methylpyrrol-3-yl)-phenyl |
| 150. | methyl | 4-(furan-2-yl)-phenyl |
| 151. | methyl | 4-(furan-3-yl)-phenyl |
| 152. | methyl | 4-(thiophen-2-yl)-phenyl |
| 153. | methyl | 4-(thiophen-3-yl)-phenyl |
| 154. | methyl | 4-(5-propylthien-2-yl)-phenyl |
| 155. | methyl | 4-(pyrazol-1-yl)-phenyl |
| 156. | methyl | 4-(pyrazol-3-yl)-phenyl |
| 157. | methyl | 4-(pyrazol-4-yl)-phenyl |
| 158. | methyl | 4-(1-methyl-1H-pyrazol-4-yl)-phenyl |
| 159. | methyl | 4-(1-ethyl-1H-pyrazol-4-yl)-phenyl |
| 160. | methyl | 4-(1-methyl-1H-pyrazol-5-yl)-phenyl |
| 161. | methyl | 4-(1H-imidazol-2-yl)-phenyl |
| 162. | methyl | 4-(imidazol-1-yl)-phenyl |
| 163. | methyl | 4-(1-methylimidazol-2-yl)-phenyl |
| 164. | methyl | 4-(oxazol-2-yl)-phenyl |
| 165. | methyl | 4-(oxazol-4-yl)-phenyl |

TABLE A-continued

| No. | R¹ | Ar |
|---|---|---|
| 166. | methyl | 4-(oxazol-5-yl)-phenyl |
| 167. | methyl | 4-(isoxazol-3-yl)-phenyl |
| 168. | methyl | 4-(isoxazol-4-yl)-phenyl |
| 169. | methyl | 4-(isoxazol-5-yl)-phenyl |
| 170. | methyl | 4-([1,2,3]-triazol-1-yl)-phenyl |
| 171. | methyl | 4-([1,2,4]-triazol-1-yl)-phenyl |
| 172. | methyl | 4-([1,2,3]-triazol-2-yl)-phenyl |
| 173. | methyl | 4-(4H-[1,2,4]-triazol-3-yl)-phenyl |
| 174. | methyl | 4-([1,2,4]-triazol-4-yl)-phenyl |
| 175. | methyl | 4-(2H-[1,2,3]-triazol-4-yl)-phenyl |
| 176. | methyl | 4-(4-methyl-4H-[1,2,4]-triazol-3-yl)-phenyl |
| 177. | methyl | 4-(2-methyl-2H-[1,2,3]-triazol-4-yl)-phenyl |
| 178. | methyl | 4-([1,3,4]-oxadiazol-2-yl)-phenyl |
| 179. | methyl | 4-([1,2,4]-oxadiazol-3-yl)-phenyl |
| 180. | methyl | 4-([1,2,4]-oxadiazol-5-yl)-phenyl |
| 181. | methyl | 4-([1,2,3]-oxadiazol-4-yl)-phenyl |
| 182. | methyl | 4-([1,2,3]-oxadiazol-5-yl)-phenyl |
| 183. | methyl | 4-([1,2,3]-thiadiazol-4-yl)-phenyl |
| 184. | methyl | 4-(1H-tetrazol-5-yl)-phenyl |
| 185. | methyl | 4-(tetrazol-1-yl)-phenyl |
| 186. | methyl | 4-(2-methyl-2H-tetrazol-5-yl)-phenyl |
| 187. | methyl | 4-(1-methyl-1H-tetrazol-5-yl)-phenyl |
| 188. | methyl | 4-furazan-3-yl-phenyl |
| 189. | methyl | 4-(pyrid-2-yl)-phenyl |
| 190. | methyl | 4-(pyrid-3-yl)-phenyl |
| 191. | methyl | 4-(pyrid-4-yl)-phenyl |
| 192. | methyl | 4-(pyrimidin-2-yl)-phenyl |
| 193. | methyl | 4-(pyrimidin-4-yl)-phenyl |
| 194. | methyl | 4-(pyrimidin-5-yl)-phenyl |
| 195. | methyl | 5-isopropylthiophen-2-yl |
| 196. | methyl | 2-chlorothiophen-5-yl |
| 197. | methyl | 2,5-dichlorothiophen-4-yl |
| 198. | methyl | 2,3-dichlorothiophen-5-yl |
| 199. | methyl | 2-chloro-3-nitrothiophen-5-yl |
| 200. | methyl | 2-(phenylsulfonyl)-thiophen-5-yl |
| 201. | methyl | 2-(pyridin-2-yl)thiophen-5-yl |
| 202. | methyl | 2-(5-(trifluoromethyl)isoxazol-3-yl)-thiophen-5-yl |
| 203. | methyl | 2-(2-methylthiazol-4-yl)-thiophen-5-yl |
| 204. | methyl | 1-methyl-1H-imidazol-4-yl |
| 205. | methyl | 1,2-dimethyl-1H-imidazol-4-yl |
| 206. | methyl | 3,5-dimethylisoxazol-4-yl |
| 207. | methyl | thiazol-2-yl |
| 208. | methyl | 4-methylthiazol-2-yl |
| 209. | methyl | 4-isopropylthiazol-2-yl |
| 210. | methyl | 4-trifluoromethylthiazol-2-yl |
| 211. | methyl | 5-methylthiazol-2-yl |
| 212. | methyl | 5-isopropylthiazol-2-yl |
| 213. | methyl | 5-trifluoromethylthiazol-2-yl |
| 214. | methyl | 2,4-dimethylthiazol-5-yl |
| 215. | methyl | 2-acetamido-4-methylthiazol-5-yl |
| 216. | methyl | 4H-[1,2,4]triazol-3-yl |
| 217. | methyl | 5-methyl-4H-[1,2,4]triazol-3-yl |
| 218. | methyl | 4-methyl-4H-[1,2,4]triazol-3-yl |
| 219. | methyl | 5-isopropyl-4H-[1,2,4]triazol-3-yl |
| 220. | methyl | 5-trifluoromethyl-4H-[1,2,4]triazol-3-yl |
| 221. | methyl | 4,5-dimethyl-4H-[1,2,4]triazol-3-yl |
| 222. | methyl | 5-isopropyl-4-methyl-4H-[1,2,4]triazol-3-yl |
| 223. | methyl | 5-trifluoromethyl-4-methyl-4H-[1,2,4]triazol-3-yl |
| 224. | methyl | [1,3,4]thiadiazol-2-yl |
| 225. | methyl | 5-methyl-[1,3,4]thiadiazol-2-yl |
| 226. | methyl | 5-isopropyl-[1,3,4]thiadiazol-2-yl |
| 227. | methyl | 5-trifluoromethyl-[1,3,4]thiadiazol-2-yl |
| 228. | methyl | 3-bromo-2-chloropyrid-5-yl |
| 229. | methyl | 2-(4-morpholino)-pyrid-5-yl |
| 230. | methyl | 2-phenoxypyrid-5-yl |
| 231. | methyl | (2-isopropyl)-pyrimidin-5-yl |
| 232. | methyl | (5-isopropyl)-pyrimidin-2-yl |
| 233. | methyl | 8-quinolyl |
| 234. | methyl | 5-isoquinolyl |
| 235. | methyl | 2-(trifluoroacetyl)-1,2,3,4-tetrahydroisoquinolin-7-yl |
| 236. | methyl | 5-chloro-3-methylbenzothiophen-2-yl |
| 237. | methyl | 3,4-dihyro-4-methyl-2H-benzo[b][1,4]oxazinyl |
| 238. | methyl | benzothiazol-6-yl |
| 239. | methyl | benzo[2,1,3]oxadiazol-4-yl |
| 240. | methyl | 5-chlorobenzo[2,1,3]oxadiazol-4-yl |
| 241. | methyl | 7-chlorobenzo[2,1,3]oxadiazol-4-yl |
| 242. | methyl | benzo[2,1,3]thiadiazol-4-yl |
| 243. | methyl | 6-chloroimidazo[2,1-b]thiazolyl |
| 244. | ethyl | 4-(trifluoromethoxy)-phenyl |
| 245. | ethyl | 3-(trifluoromethoxy)-phenyl |
| 246. | ethyl | 4-cyanophenyl |
| 247. | ethyl | 4-methylphenyl |
| 248. | ethyl | 4-ethylphenyl |
| 249. | ethyl | 4-propylphenyl |
| 250. | ethyl | 4-methoxyphenyl |
| 251. | ethyl | 4-fluorophenyl |
| 252. | ethyl | 4-chlorophenyl |
| 253. | ethyl | 4-bromophenyl |
| 254. | ethyl | 3-(trifluoromethyl)phenyl |
| 255. | ethyl | 4-(trifluoromethyl)phenyl |
| 256. | ethyl | 2-(trifluoromethyl)phenyl |
| 257. | ethyl | 3,4-difluorophenyl |
| 258. | ethyl | 4-bromo-3-fluorophenyl |
| 259. | ethyl | 4-bromo-2-fluorophenyl |
| 260. | ethyl | 4-bromo-2,5-difluorophenyl |
| 261. | ethyl | 2-fluoro-4-isopropylphenyl |
| 262. | ethyl | 4-hydroxyphenyl |
| 263. | ethyl | 4-isopropylphenyl |
| 264. | ethyl | 4-sec-butylphenyl |
| 265. | ethyl | 4-isobutylphenyl |
| 266. | ethyl | 4-(1,1-dimethylpropyl)-phenyl |
| 267. | ethyl | 4-vinylphenyl |
| 268. | ethyl | 4-isopropenylphenyl |
| 269. | ethyl | 4-(fluoromethyl)phenyl |
| 270. | ethyl | 3-(fluoromethyl)phenyl |
| 271. | ethyl | 2-(fluoromethyl)phenyl |
| 272. | ethyl | 4-(difluoromethyl)phenyl |
| 273. | ethyl | 3-(difluoromethyl)phenyl |
| 274. | ethyl | 2-(difluoromethyl)phenyl |
| 275. | ethyl | 4-(1-fluoroethyl)-phenyl |
| 276. | ethyl | 4-((S)-1-fluoroethyl)-phenyl |
| 277. | ethyl | 4-((R)-1-fluoroethyl)-phenyl |
| 278. | ethyl | 4-(2-fluoroethyl)-phenyl |
| 279. | ethyl | 4-(1,1-difluoroethyl)-phenyl |
| 280. | ethyl | 4-(2,2-difluoroethyl)-phenyl |
| 281. | ethyl | 4-(2,2,2-trifluoroethyl)-phenyl |
| 282. | ethyl | 4-(3-fluoropropyl)-phenyl |
| 283. | ethyl | 4-(2-fluoropropyl)-phenyl |
| 284. | ethyl | 4-((S)-2-fluoropropyl)-phenyl |
| 285. | ethyl | 4-((R)-2-fluoropropyl)-phenyl |
| 286. | ethyl | 4-(3,3-difluoropropyl)-phenyl |
| 287. | ethyl | 4-(3,3,3-trifluoropropyl)-phenyl |
| 288. | ethyl | 4-(1-fluoro-1-methylethyl)-phenyl |
| 289. | ethyl | 4-(2-fluoro-1-methylethyl)-phenyl |
| 290. | ethyl | 4-((S)-2-fluoro-1-methylethyl)-phenyl |
| 291. | ethyl | 4-((R)-2-fluoro-1-methylethyl)-phenyl |
| 292. | ethyl | 4-(2,2-difluoro-1-methylethyl)-phenyl |
| 293. | ethyl | 4-((S)-2,2-difluoro-1-methylethyl)-phenyl |
| 294. | ethyl | 4-((R)-2,2-difluoro-1-methylethyl)-phenyl |
| 295. | ethyl | 4-(2,2,2-trifluoro-1-methylethyl)-phenyl |
| 296. | ethyl | 4-((S)-2,2,2-trifluoro-1-methylethyl)-phenyl |
| 297. | ethyl | 4-((R)-2,2,2-trifluoro-1-methylethyl)-phenyl |
| 298. | ethyl | 4-(2-fluoro-1-fluoromethylethyl)-phenyl |
| 299. | ethyl | 4-(1-difluoromethyl-2,2-difluoroethyl)-phenyl |
| 300. | ethyl | 4-(1,1-dimethyl-2-fluoroethyl)-phenyl |
| 301. | ethyl | 4-ethoxyphenyl |
| 302. | ethyl | 4-propoxyphenyl |
| 303. | ethyl | 4-isopropoxyphenyl |
| 304. | ethyl | 4-butoxyphenyl |
| 305. | ethyl | 4-(fluoromethoxy)-phenyl |
| 306. | ethyl | 4-(difluoromethoxy)-phenyl |
| 307. | ethyl | 4-(2-fluoroethoxy)-phenyl |
| 308. | ethyl | 4-(2,2-difluoroethoxy)-phenyl |
| 309. | ethyl | 4-(2,2,2-trifluoroethoxy)-phenyl |
| 310. | ethyl | 4-(1,1,2,2-tetrafluoroethoxy)-phenyl |
| 311. | ethyl | 4-cyclopropylphenyl |
| 312. | ethyl | 4-cyclobutylphenyl |
| 313. | ethyl | 4-cyclopentylphenyl |
| 314. | ethyl | 4-(2,2-difluorocyclopropyl)-phenyl |
| 315. | ethyl | 3-fluoro-4-isopropylphenyl |
| 316. | ethyl | 4-(1-hydroxy-1-methylethyl)-phenyl |

TABLE A-continued

| No. | R¹ | Ar |
|---|---|---|
| 317. | ethyl | 4-(2-hydroxy-2-methylpropyl)-phenyl |
| 318. | ethyl | 4-acetylphenyl |
| 319. | ethyl | 4-carboxyphenyl |
| 320. | ethyl | 4-(O-benzyl)-phenyl |
| 321. | ethyl | 4-(2-methoxyethoxy)-phenyl |
| 322. | ethyl | 4-(CH$_2$—N(CH$_3$)$_2$)-phenyl |
| 323. | ethyl | 4-(NH—CO—NH$_2$)-phenyl |
| 324. | ethyl | 4-(methylsulfanyl)-phenyl |
| 325. | ethyl | 4-(fluoromethylsulfanyl)-phenyl |
| 326. | ethyl | 4-(difluoromethylsulfanyl)-phenyl |
| 327. | ethyl | 4-(trifluoromethylsulfanyl)-phenyl |
| 328. | ethyl | 4-(methylsulfonyl)-phenyl |
| 329. | ethyl | 4-(N-methoxy-N-methyl-amino)-phenyl |
| 330. | ethyl | 4-(methoxyamino)-phenyl |
| 331. | ethyl | 4-(ethoxyamino)-phenyl |
| 332. | ethyl | 4-(N-methylaminooxy)-phenyl |
| 333. | ethyl | 4-(N,N-dimethylaminooxy)-phenyl |
| 334. | ethyl | 4-(azetidin-1-yl)-phenyl |
| 335. | ethyl | 4-(2-methylazetidin-1-yl)-phenyl |
| 336. | ethyl | 4-((S)-2-methylazetidin-1-yl)-phenyl |
| 337. | ethyl | 4-((R)-2-methylazetidin-1-yl)-phenyl |
| 338. | ethyl | 4-(3-fluoroazetidin-1-yl)-phenyl |
| 339. | ethyl | 4-(3-methoxyazetidin-1-yl)-phenyl |
| 340. | ethyl | 4-(3-hydroxyazetidin-1-yl)-phenyl |
| 341. | ethyl | 4-(pyrrolidin-1-yl)-phenyl |
| 342. | ethyl | 4-(pyrrolidin-2-yl)-phenyl |
| 343. | ethyl | 4-((S)-pyrrolidin-2-yl)-phenyl |
| 344. | ethyl | 4-((R)-pyrrolidin-2-yl)-phenyl |
| 345. | ethyl | 4-(pyrrolidin-3-yl)-phenyl |
| 346. | ethyl | 4-((S)-pyrrolidin-3-yl)-phenyl |
| 347. | ethyl | 4-((R)-pyrrolidin-3-yl)-phenyl |
| 348. | ethyl | 4-(2-fluoropyrrolidin-1-yl)-phenyl |
| 349. | ethyl | 4-((S)-2-fluoropyrrolidin-1-yl)-phenyl |
| 350. | ethyl | 4-((R)-2-fluoropyrrolidin-1-yl)-phenyl |
| 351. | ethyl | 4-(3-fluoropyrrolidin-1-yl)-phenyl |
| 352. | ethyl | 4-((S)-3-fluoropyrrolidin-1-yl)-phenyl |
| 353. | ethyl | 4-((R)-3-fluoropyrrolidin-1-yl)-phenyl |
| 354. | ethyl | 4-(2,2-difluoropyrrolidin-1-yl)-phenyl |
| 355. | ethyl | 4-(3,3-difluoropyrrolidin-1-yl)-phenyl |
| 356. | ethyl | 4-(2-methylpyrrolidin-1-yl)-phenyl |
| 357. | ethyl | 4-((S)-2-methylpyrrolidin-1-yl)-phenyl |
| 358. | ethyl | 4-((R)-2-methylpyrrolidin-1-yl)-phenyl |
| 359. | ethyl | 4-(3-methylpyrrolidin-1-yl)-phenyl |
| 360. | ethyl | 4-((S)-3-methylpyrrolidin-1-yl)-phenyl |
| 361. | ethyl | 4-((R)-3-methylpyrrolidin-1-yl)-phenyl |
| 362. | ethyl | 4-(1-methylpyrrolidin-2-yl)-phenyl |
| 363. | ethyl | 4-((S)-1-methylpyrrolidin-2-yl)-phenyl |
| 364. | ethyl | 4-((R)-1-methylpyrrolidin-2-yl)-phenyl |
| 365. | ethyl | 4-(1-methylpyrrolidin-3-yl)-phenyl |
| 366. | ethyl | 4-((S)-1-methylpyrrolidin-3-yl)-phenyl |
| 367. | ethyl | 4-((R)-1-methylpyrrolidin-3-yl)-phenyl |
| 368. | ethyl | 4-(2,2-dimethylpyrrolidin-1-yl)-phenyl |
| 369. | ethyl | 4-(3,3-dimethylpyrrolidin-1-yl)-phenyl |
| 370. | ethyl | 4-(2-trifluoromethylpyrrolidin-1-yl)-phenyl |
| 371. | ethyl | 4-((S)-2-trifluoromethylpyrrolidin-1-yl)-phenyl |
| 372. | ethyl | 4-((R)-2-trifluoromethylpyrrolidin-1-yl)-phenyl |
| 373. | ethyl | 4-(3-trifluoromethylpyrrolidin-1-yl)-phenyl |
| 374. | ethyl | 4-((S)-3-trifluoromethylpyrrolidin-1-yl)-phenyl |
| 375. | ethyl | 4-((R)-3-trifluoromethylpyrrolidin-1-yl)-phenyl |
| 376. | ethyl | 4-(2-oxopyrrolidin-1-yl)-phenyl |
| 377. | ethyl | 4-(2-oxo-oxazolidin-3-yl)-phenyl |
| 378. | ethyl | 4-(piperidin-1-yl)-phenyl |
| 379. | ethyl | 4-(2-methylpiperidin-1-yl)-phenyl |
| 380. | ethyl | 4-((S)-2-methylpiperidin-1-yl)-phenyl |
| 381. | ethyl | 4-((R)-2-methylpiperidin-1-yl)-phenyl |
| 382. | ethyl | 4-(piperazin-1-yl)-phenyl |
| 383. | ethyl | 4-(4-methylpiperazin-1-yl)-phenyl |
| 384. | ethyl | 4-(morpholin-4-yl)-phenyl |
| 385. | ethyl | 4-(thiomorpholin-4-yl)-phenyl |
| 386. | ethyl | 4-(1-oxo-thiomorpholin-4-yl)-phenyl |
| 387. | ethyl | 4-(1,1-dioxo-thiomorpholin-4-yl)-phenyl |
| 388. | ethyl | 4-(pyrrol-1-yl)-phenyl |
| 389. | ethyl | 4-(pyrrol-2-yl)-phenyl |
| 390. | ethyl | 4-(pyrrol-3-yl)-phenyl |
| 391. | ethyl | 4-(1-methylpyrrol-2-yl)-phenyl |
| 392. | ethyl | 4-(1-methylpyrrol-3-yl)-phenyl |
| 393. | ethyl | 4-(furan-2-yl)-phenyl |
| 394. | ethyl | 4-(furan-3-yl)-phenyl |
| 395. | ethyl | 4-(thiophen-2-yl)-phenyl |
| 396. | ethyl | 4-(thiophen-3-yl)-phenyl |
| 397. | ethyl | 4-(5-propylthien-2-yl)-phenyl |
| 398. | ethyl | 4-(pyrazol-1-yl)-phenyl |
| 399. | ethyl | 4-(pyrazol-3-yl)-phenyl |
| 400. | ethyl | 4-(pyrazol-4-yl)-phenyl |
| 401. | ethyl | 4-(1-methyl-1H-pyrazol-4-yl)-phenyl |
| 402. | ethyl | 4-(1-ethyl-1H-pyrazol-4-yl)-phenyl |
| 403. | ethyl | 4-(1-methyl-1H-pyrazol-5-yl)-phenyl |
| 404. | ethyl | 4-(1H-imidazol-2-yl)-phenyl |
| 405. | ethyl | 4-(imidazol-1-yl)-phenyl |
| 406. | ethyl | 4-(1-methylimidazol-2-yl)-phenyl |
| 407. | ethyl | 4-(oxazol-2-yl)-phenyl |
| 408. | ethyl | 4-(oxazol-4-yl)-phenyl |
| 409. | ethyl | 4-(oxazol-5-yl)-phenyl |
| 410. | ethyl | 4-(isoxazol-3-yl)-phenyl |
| 411. | ethyl | 4-(isoxazol-4-yl)-phenyl |
| 412. | ethyl | 4-(isoxazol-5-yl)-phenyl |
| 413. | ethyl | 4-([1,2,3]-triazol-1-yl)-phenyl |
| 414. | ethyl | 4-([1,2,4]-triazol-1-yl)-phenyl |
| 415. | ethyl | 4-([1,2,3]-triazol-2-yl)-phenyl |
| 416. | ethyl | 4-(4H-[1,2,4]-triazol-3-yl)-phenyl |
| 417. | ethyl | 4-([1,2,4]-triazol-4-yl)-phenyl |
| 418. | ethyl | 4-(2H-[1,2,3]-triazol-4-yl)-phenyl |
| 419. | ethyl | 4-(4-methyl-4H-[1,2,4]-triazol-3-yl)-phenyl |
| 420. | ethyl | 4-(2-methyl-2H-[1,2,3]-triazol-4-yl)-phenyl |
| 421. | ethyl | 4-([1,3,4]-oxadiazol-2-yl)-phenyl |
| 422. | ethyl | 4-([1,2,4]-oxadiazol-3-yl)-phenyl |
| 423. | ethyl | 4-([1,2,4]-oxadiazol-5-yl)-phenyl |
| 424. | ethyl | 4-([1,2,3]-oxadiazol-4-yl)-phenyl |
| 425. | ethyl | 4-([1,2,3]-oxadiazol-5-yl)-phenyl |
| 426. | ethyl | 4-([1,2,3]-thiadiazol-4-yl)-phenyl |
| 427. | ethyl | 4-(1H-tetrazol-5-yl)-phenyl |
| 428. | ethyl | 4-(tetrazol-1-yl)-phenyl |
| 429. | ethyl | 4-(2-methyl-2H-tetrazol-5-yl)-phenyl |
| 430. | ethyl | 4-(1-methyl-1H-tetrazol-5-yl)-phenyl |
| 431. | ethyl | 4-furazan-3-yl-phenyl |
| 432. | ethyl | 4-(pyrid-2-yl)-phenyl |
| 433. | ethyl | 4-(pyrid-3-yl)-phenyl |
| 434. | ethyl | 4-(pyrid-4-yl)-phenyl |
| 435. | ethyl | 4-(pyrimidin-2-yl)-phenyl |
| 436. | ethyl | 4-(pyrimidin-4-yl)-phenyl |
| 437. | ethyl | 4-(pyrimidin-5-yl)-phenyl |
| 438. | ethyl | 5-isopropylthiophen-2-yl |
| 439. | ethyl | 2-chlorothiophen-5-yl |
| 440. | ethyl | 2,5-dichlorothiophen-4-yl |
| 441. | ethyl | 2,3-dichlorothiophen-5-yl |
| 442. | ethyl | 2-chloro-3-nitrothiophen-5-yl |
| 443. | ethyl | 2-(phenylsulfonyl)-thiophen-5-yl |
| 444. | ethyl | 2-(pyridin-2-yl)thiophen-5-yl |
| 445. | ethyl | 2-(5-(trifluoromethyl)isoxazol-3-yl)-thiophen-5-yl |
| 446. | ethyl | 2-(2-methylthiazol-4-yl)-thiophen-5-yl |
| 447. | ethyl | 1-methyl-1H-imidazol-4-yl |
| 448. | ethyl | 1,2-dimethyl-1H-imidazol-4-yl |
| 449. | ethyl | 3,5-dimethylisoxazol-4-yl |
| 450. | ethyl | thiazol-2-yl |
| 451. | ethyl | 4-methylthiazol-2-yl |
| 452. | ethyl | 4-isopropylthiazol-2-yl |
| 453. | ethyl | 4-trifluoromethylthiazol-2-yl |
| 454. | ethyl | 5-methylthiazol-2-yl |
| 455. | ethyl | 5-isopropylthiazol-2-yl |
| 456. | ethyl | 5-trifluoromethylthiazol-2-yl |
| 457. | ethyl | 2,4-dimethylthiazol-5-yl |
| 458. | ethyl | 2-acetamido-4-methylthiazol-5-yl |
| 459. | ethyl | 4H-[1,2,4]triazol-3-yl |
| 460. | ethyl | 5-methyl-4H-[1,2,4]triazol-3-yl |
| 461. | ethyl | 4-methyl-4H-[1,2,4]triazol-3-yl |
| 462. | ethyl | 5-isopropyl-4H-[1,2,4]triazol-3-yl |
| 463. | ethyl | 5-trifluoromethyl-4H-[1,2,4]triazol-3-yl |
| 464. | ethyl | 4,5-dimethyl-4H-[1,2,4]triazol-3-yl |
| 465. | ethyl | 5-isopropyl-4-methyl-4H-[1,2,4]triazol-3-yl |
| 466. | ethyl | 5-trifluoromethyl-4-methyl-4H-[1,2,4]triazol-3-yl |

TABLE A-continued

| No. | R¹ | Ar |
|---|---|---|
| 467. | ethyl | [1,3,4]thiadiazol-2-yl |
| 468. | ethyl | 5-methyl-[1,3,4]thiadiazol-2-yl |
| 469. | ethyl | 5-isopropyl-[1,3,4]thiadiazol-2-yl |
| 470. | ethyl | 5-trifluoromethyl-[1,3,4]thiadiazol-2-yl |
| 471. | ethyl | 3-bromo-2-chloropyrid-5-yl |
| 472. | ethyl | 2-(4-morpholino)-pyrid-5-yl |
| 473. | ethyl | 2-phenoxypyrid-5-yl |
| 474. | ethyl | (2-isopropyl)-pyrimidin-5-yl |
| 475. | ethyl | (5-isopropyl)-pyrimidin-2-yl |
| 476. | ethyl | 8-quinolyl |
| 477. | ethyl | 5-isoquinolyl |
| 478. | ethyl | 2-(trifluoroacetyl)-1,2,3,4-tetrahydroisoquinolin-7-yl |
| 479. | ethyl | 5-chloro-3-methylbenzothiophen-2-yl |
| 480. | ethyl | 3,4-dihydro-4-methyl-2H-benzo[b][1,4]oxazinyl |
| 481. | ethyl | benzothiazol-6-yl |
| 482. | ethyl | benzo[2,1,3]oxadiazol-4-yl |
| 483. | ethyl | 5-chlorobenzo[2,1,3]oxadiazol-4-yl |
| 484. | ethyl | 7-chlorobenzo[2,1,3]oxadiazol-4-yl |
| 485. | ethyl | benzo[2,1,3]thiadiazol-4-yl |
| 486. | ethyl | 6-chloroimidazo[2,1-b]thiazolyl |
| 487. | propyl | 4-(trifluoromethoxy)-phenyl |
| 488. | propyl | 3-(trifluoromethoxy)-phenyl |
| 489. | propyl | 4-cyanophenyl |
| 490. | propyl | 4-methylphenyl |
| 491. | propyl | 4-ethylphenyl |
| 492. | propyl | 4-propylphenyl |
| 493. | propyl | 4-methoxyphenyl |
| 494. | propyl | 4-fluorophenyl |
| 495. | propyl | 4-chlorophenyl |
| 496. | propyl | 4-bromophenyl |
| 497. | propyl | 3-(trifluoromethyl)phenyl |
| 498. | propyl | 4-(trifluoromethyl)phenyl |
| 499. | propyl | 2-(trifluoromethyl)phenyl |
| 500. | propyl | 3,4-difluorophenyl |
| 501. | propyl | 4-bromo-3-fluorophenyl |
| 502. | propyl | 4-bromo-2-fluorophenyl |
| 503. | propyl | 4-bromo-2,5-difluorophenyl |
| 504. | propyl | 2-fluoro-4-isopropylphenyl |
| 505. | propyl | 4-hydroxyphenyl |
| 506. | propyl | 4-isopropylphenyl |
| 507. | propyl | 4-sec-butylphenyl |
| 508. | propyl | 4-isobutylphenyl |
| 509. | propyl | 4-(1,1-dimethylpropyl)-phenyl |
| 510. | propyl | 4-vinylphenyl |
| 511. | propyl | 4-isopropenylphenyl |
| 512. | propyl | 4-(fluoromethyl)phenyl |
| 513. | propyl | 3-(fluoromethyl)phenyl |
| 514. | propyl | 2-(fluoromethyl)phenyl |
| 515. | propyl | 4-(difluoromethyl)phenyl |
| 516. | propyl | 3-(difluoromethyl)phenyl |
| 517. | propyl | 2-(difluoromethyl)phenyl |
| 518. | propyl | 4-(1-fluoroethyl)-phenyl |
| 519. | propyl | 4-((S)-1-fluoroethyl)-phenyl |
| 520. | propyl | 4-((R)-1-fluoroethyl)-phenyl |
| 521. | propyl | 4-(2-fluoroethyl)-phenyl |
| 522. | propyl | 4-(1,1-difluoroethyl)-phenyl |
| 523. | propyl | 4-(2,2-difluoroethyl)-phenyl |
| 524. | propyl | 4-(2,2,2-trifluoroethyl)-phenyl |
| 525. | propyl | 4-(3-fluoropropyl)-phenyl |
| 526. | propyl | 4-(2-fluoropropyl)-phenyl |
| 527. | propyl | 4-((S)-2-fluoropropyl)-phenyl |
| 528. | propyl | 4-((R)-2-fluoropropyl)-phenyl |
| 529. | propyl | 4-(3,3-difluoropropyl)-phenyl |
| 530. | propyl | 4-(3,3,3-trifluoropropyl)-phenyl |
| 531. | propyl | 4-(1-fluoro-1-methylethyl)-phenyl |
| 532. | propyl | 4-(2-fluoro-1-methylethyl)-phenyl |
| 533. | propyl | 4-((S)-2-fluoro-1-methylethyl)-phenyl |
| 534. | propyl | 4-((R)-2-fluoro-1-methylethyl)-phenyl |
| 535. | propyl | 4-(2,2-difluoro-1-methylethyl)-phenyl |
| 536. | propyl | 4-((S)-2,2-difluoro-1-methylethyl)-phenyl |
| 537. | propyl | 4-((R)-2,2-difluoro-1-methylethyl)-phenyl |
| 538. | propyl | 4-(2,2,2-trifluoro-1-methylethyl)-phenyl |
| 539. | propyl | 4-((S)-2,2,2-trifluoro-1-methylethyl)-phenyl |
| 540. | propyl | 4-((R)-2,2,2-trifluoro-1-methylethyl)-phenyl |
| 541. | propyl | 4-(2-fluoro-1-fluoromethylethyl)-phenyl |
| 542. | propyl | 4-(1-difluoromethyl-2,2-difluoroethyl)-phenyl |
| 543. | propyl | 4-(1,1-dimethyl-2-fluoroethyl)-phenyl |
| 544. | propyl | 4-ethoxyphenyl |
| 545. | propyl | 4-propoxyphenyl |
| 546. | propyl | 4-isopropoxyphenyl |
| 547. | propyl | 4-butoxyphenyl |
| 548. | propyl | 4-(fluoromethoxy)-phenyl |
| 549. | propyl | 4-(difluoromethoxy)-phenyl |
| 550. | propyl | 4-(2-fluoroethoxy)-phenyl |
| 551. | propyl | 4-(2,2-difluoroethoxy)-phenyl |
| 552. | propyl | 4-(2,2,2-trifluoroethoxy)-phenyl |
| 553. | propyl | 4-(1,1,2,2-tetrafluoroethoxy)-phenyl |
| 554. | propyl | 4-cyclopropylphenyl |
| 555. | propyl | 4-cyclobutylphenyl |
| 556. | propyl | 4-cyclopentylphenyl |
| 557. | propyl | 4-(2,2-difluorocyclopropyl)-phenyl |
| 558. | propyl | 3-fluoro-4-isopropylphenyl |
| 559. | propyl | 4-(1-hydroxy-1-methylethyl)-phenyl |
| 560. | propyl | 4-(2-hydroxy-2-methylpropyl)-phenyl |
| 561. | propyl | 4-acetylphenyl |
| 562. | propyl | 4-carboxyphenyl |
| 563. | propyl | 4-(O-benzyl)-phenyl |
| 564. | propyl | 4-(2-methoxyethoxy)-phenyl |
| 565. | propyl | 4-(CH₂—N(CH₃)₂)-phenyl |
| 566. | propyl | 4-(NH—CO—NH₂)-phenyl |
| 567. | propyl | 4-(methylsulfanyl)-phenyl |
| 568. | propyl | 4-(fluoromethylsulfanyl)-phenyl |
| 569. | propyl | 4-(difluoromethylsulfanyl)-phenyl |
| 570. | propyl | 4-(trifluoromethylsulfanyl)-phenyl |
| 571. | propyl | 4-(methylsulfonyl)-phenyl |
| 572. | propyl | 4-(N-methoxy-N-methyl-amino)-phenyl |
| 573. | propyl | 4-(methoxyamino)-phenyl |
| 574. | propyl | 4-(ethoxyamino)-phenyl |
| 575. | propyl | 4-(N-methylaminooxy)-phenyl |
| 576. | propyl | 4-(N,N-dimethylaminooxy)-phenyl |
| 577. | propyl | 4-(azetidin-1-yl)-phenyl |
| 578. | propyl | 4-(2-methylazetidin-1-yl)-phenyl |
| 579. | propyl | 4-((S)-2-methylazetidin-1-yl)-phenyl |
| 580. | propyl | 4-((R)-2-methylazetidin-1-yl)-phenyl |
| 581. | propyl | 4-(3-fluoroazetidin-1-yl)-phenyl |
| 582. | propyl | 4-(3-methoxyazetidin-1-yl)-phenyl |
| 583. | propyl | 4-(3-hydroxyazetidin-1-yl)-phenyl |
| 584. | propyl | 4-(pyrrolidin-1-yl)-phenyl |
| 585. | propyl | 4-(pyrrolidin-2-yl)-phenyl |
| 586. | propyl | 4-((S)-pyrrolidin-2-yl)-phenyl |
| 587. | propyl | 4-((R)-pyrrolidin-2-yl)-phenyl |
| 588. | propyl | 4-(pyrrolidin-3-yl)-phenyl |
| 589. | propyl | 4-((S)-pyrrolidin-3-yl)-phenyl |
| 590. | propyl | 4-((R)-pyrrolidin-3-yl)-phenyl |
| 591. | propyl | 4-(2-fluoropyrrolidin-1-yl)-phenyl |
| 592. | propyl | 4-((S)-2-fluoropyrrolidin-1-yl)-phenyl |
| 593. | propyl | 4-((R)-2-fluoropyrrolidin-1-yl)-phenyl |
| 594. | propyl | 4-(3-fluoropyrrolidin-1-yl)-phenyl |
| 595. | propyl | 4-((S)-3-fluoropyrrolidin-1-yl)-phenyl |
| 596. | propyl | 4-((R)-3-fluoropyrrolidin-1-yl)-phenyl |
| 597. | propyl | 4-(2,2-difluoropyrrolidin-1-yl)-phenyl |
| 598. | propyl | 4-(3,3-difluoropyrrolidin-1-yl)-phenyl |
| 599. | propyl | 4-(2-methylpyrrolidin-1-yl)-phenyl |
| 600. | propyl | 4-((S)-2-methylpyrrolidin-1-yl)-phenyl |
| 601. | propyl | 4-((R)-2-methylpyrrolidin-1-yl)-phenyl |
| 602. | propyl | 4-(3-methylpyrrolidin-1-yl)-phenyl |
| 603. | propyl | 4-((S)-3-methylpyrrolidin-1-yl)-phenyl |
| 604. | propyl | 4-((R)-3-methylpyrrolidin-1-yl)-phenyl |
| 605. | propyl | 4-(1-methylpyrrolidin-2-yl)-phenyl |
| 606. | propyl | 4-((S)-1-methylpyrrolidin-2-yl)-phenyl |
| 607. | propyl | 4-((R)-1-methylpyrrolidin-2-yl)-phenyl |
| 608. | propyl | 4-(1-methylpyrrolidin-3-yl)-phenyl |
| 609. | propyl | 4-((S)-1-methylpyrrolidin-3-yl)-phenyl |
| 610. | propyl | 4-((R)-1-methylpyrrolidin-3-yl)-phenyl |
| 611. | propyl | 4-(2,2-dimethylpyrrolidin-1-yl)-phenyl |
| 612. | propyl | 4-(3,3-dimethylpyrrolidin-1-yl)-phenyl |
| 613. | propyl | 4-(2-trifluoromethylpyrrolidin-1-yl)-phenyl |
| 614. | propyl | 4-((S)-2-trifluoromethylpyrrolidin-1-yl)-phenyl |
| 615. | propyl | 4-((R)-2-trifluoromethylpyrrolidin-1-yl)-phenyl |

TABLE A-continued

| No. | R¹ | Ar |
|---|---|---|
| 616. | propyl | 4-(3-trifluoromethylpyrrolidin-1-yl)-phenyl |
| 617. | propyl | 4-((S)-3-trifluoromethylpyrrolidin-1-yl)-phenyl |
| 618. | propyl | 4-((R)-3-trifluoromethylpyrrolidin-1-yl)-phenyl |
| 619. | propyl | 4-(2-oxopyrrolidin-1-yl)-phenyl |
| 620. | propyl | 4-(2-oxo-oxazolidin-3-yl)-phenyl |
| 621. | propyl | 4-(piperidin-1-yl)-phenyl |
| 622. | propyl | 4-(2-methylpiperidin-1-yl)-phenyl |
| 623. | propyl | 4-((S)-2-methylpiperidin-1-yl)-phenyl |
| 624. | propyl | 4-((R)-2-methylpiperidin-1-yl)-phenyl |
| 625. | propyl | 4-(piperazin-1-yl)-phenyl |
| 626. | propyl | 4-(4-methylpiperazin-1-yl)-phenyl |
| 627. | propyl | 4-(morpholin-4-yl)-phenyl |
| 628. | propyl | 4-(thiomorpholin-4-yl)-phenyl |
| 629. | propyl | 4-(1-oxo-thiomorpholin-4-yl)-phenyl |
| 630. | propyl | 4-(1,1-dioxo-thiomorpholin-4-yl)-phenyl |
| 631. | propyl | 4-(pyrrol-1-yl)-phenyl |
| 632. | propyl | 4-(pyrrol-2-yl)-phenyl |
| 633. | propyl | 4-(pyrrol-3-yl)-phenyl |
| 634. | propyl | 4-(1-methylpyrrol-2-yl)-phenyl |
| 635. | propyl | 4-(1-methylpyrrol-3-yl)-phenyl |
| 636. | propyl | 4-(furan-2-yl)-phenyl |
| 637. | propyl | 4-(furan-3-yl)-phenyl |
| 638. | propyl | 4-(thiophen-2-yl)-phenyl |
| 639. | propyl | 4-(thiophen-3-yl)-phenyl |
| 640. | propyl | 4-(5-propylthien-2-yl)-phenyl |
| 641. | propyl | 4-(pyrazol-1-yl)-phenyl |
| 642. | propyl | 4-(pyrazol-3-yl)-phenyl |
| 643. | propyl | 4-(pyrazol-4-yl)-phenyl |
| 644. | propyl | 4-(1-methyl-1H-pyrazol-4-yl)-phenyl |
| 645. | propyl | 4-(1-ethyl-1H-pyrazol-4-yl)-phenyl |
| 646. | propyl | 4-(1-methyl-1H-pyrazol-5-yl)-phenyl |
| 647. | propyl | 4-(1H-imidazol-2-yl)-phenyl |
| 648. | propyl | 4-(imidazol-1-yl)-phenyl |
| 649. | propyl | 4-(1-methylimidazol-2-yl)-phenyl |
| 650. | propyl | 4-(oxazol-2-yl)-phenyl |
| 651. | propyl | 4-(oxazol-4-yl)-phenyl |
| 652. | propyl | 4-(oxazol-5-yl)-phenyl |
| 653. | propyl | 4-(isoxazol-3-yl)-phenyl |
| 654. | propyl | 4-(isoxazol-4-yl)-phenyl |
| 655. | propyl | 4-(isoxazol-5-yl)-phenyl |
| 656. | propyl | 4-([1,2,3]-triazol-1-yl)-phenyl |
| 657. | propyl | 4-([1,2,4]-triazol-1-yl)-phenyl |
| 658. | propyl | 4-([1,2,3]-triazol-2-yl)-phenyl |
| 659. | propyl | 4-(4H-[1,2,4]-triazol-3-yl)-phenyl |
| 660. | propyl | 4-([1,2,4]-triazol-4-yl)-phenyl |
| 661. | propyl | 4-(2H-[1,2,3]-triazol-4-yl)-phenyl |
| 662. | propyl | 4-(4-methyl-4H-[1,2,4]-triazol-3-yl)-phenyl |
| 663. | propyl | 4-(2-methyl-2H-[1,2,3]-triazol-4-yl)-phenyl |
| 664. | propyl | 4-([1,3,4]-oxadiazol-2-yl)-phenyl |
| 665. | propyl | 4-([1,2,4]-oxadiazol-3-yl)-phenyl |
| 666. | propyl | 4-([1,2,4]-oxadiazol-5-yl)-phenyl |
| 667. | propyl | 4-([1,2,3]-oxadiazol-4-yl)-phenyl |
| 668. | propyl | 4-([1,2,3]-oxadiazol-5-yl)-phenyl |
| 669. | propyl | 4-([1,2,3]-thiadiazol-4-yl)-phenyl |
| 670. | propyl | 4-(1H-tetrazol-5-yl)-phenyl |
| 671. | propyl | 4-(tetrazol-1-yl)-phenyl |
| 672. | propyl | 4-(2-methyl-2H-tetrazol-5-yl)-phenyl |
| 673. | propyl | 4-(1-methyl-1H-tetrazol-5-yl)-phenyl |
| 674. | propyl | 4-furazan-3-yl-phenyl |
| 675. | propyl | 4-(pyrid-2-yl)-phenyl |
| 676. | propyl | 4-(pyrid-3-yl)-phenyl |
| 677. | propyl | 4-(pyrid-4-yl)-phenyl |
| 678. | propyl | 4-(pyrimidin-2-yl)-phenyl |
| 679. | propyl | 4-(pyrimidin-4-yl)-phenyl |
| 680. | propyl | 4-(pyrimidin-5-yl)-phenyl |
| 681. | propyl | 5-isopropylthiophen-2-yl |
| 682. | propyl | 2-chlorothiophen-5-yl |
| 683. | propyl | 2,5-dichlorothiophen-4-yl |
| 684. | propyl | 2,3-dichlorothiophen-5-yl |
| 685. | propyl | 2-chloro-3-nitrothiophen-5-yl |
| 686. | propyl | 2-(phenylsulfonyl)-thiophen-5-yl |
| 687. | propyl | 2-(pyridin-2-yl)thiophen-5-yl |
| 688. | propyl | 2-(5-(trifluoromethyl)isoxazol-3-yl)-thiophen-5-yl |
| 689. | propyl | 2-(2-methylthiazol-4-yl)-thiophen-5-yl |
| 690. | propyl | 1-methyl-1H-imidazol-4-yl |
| 691. | propyl | 1,2-dimethyl-1H-imidazol-4-yl |
| 692. | propyl | 3,5-dimethylisoxazol-4-yl |
| 693. | propyl | thiazol-2-yl |
| 694. | propyl | 4-methylthiazol-2-yl |
| 695. | propyl | 4-isopropylthiazol-2-yl |
| 696. | propyl | 4-trifluoromethylthiazol-2-yl |
| 697. | propyl | 5-methylthiazol-2-yl |
| 698. | propyl | 5-isopropylthiazol-2-yl |
| 699. | propyl | 5-trifluoromethylthiazol-2-yl |
| 700. | propyl | 2,4-dimethylthiazol-5-yl |
| 701. | propyl | 2-acetamido-4-methylthiazol-5-yl |
| 702. | propyl | 4H-[1,2,4]triazol-3-yl |
| 703. | propyl | 5-methyl-4H-[1,2,4]triazol-3-yl |
| 704. | propyl | 4-methyl-4H-[1,2,4]triazol-3-yl |
| 705. | propyl | 5-isopropyl-4H-[1,2,4]triazol-3-yl |
| 706. | propyl | 5-trifluoromethyl-4H-[1,2,4]triazol-3-yl |
| 707. | propyl | 4,5-dimethyl-4H-[1,2,4]triazol-3-yl |
| 708. | propyl | 5-isopropyl-4-methyl-4H-[1,2,4]triazol-3-yl |
| 709. | propyl | 5-trifluoromethyl-4-methyl-4H-[1,2,4]triazol-3-yl |
| 710. | propyl | [1,3,4]thiadiazol-2-yl |
| 711. | propyl | 5-methyl-[1,3,4]thiadiazol-2-yl |
| 712. | propyl | 5-isopropyl-[1,3,4]thiadiazol-2-yl |
| 713. | propyl | 5-trifluoromethyl-[1,3,4]thiadiazol-2-yl |
| 714. | propyl | 3-bromo-2-chloropyrid-5-yl |
| 715. | propyl | 2-(4-morpholino)-pyrid-5-yl |
| 716. | propyl | 2-phenoxypyrid-5-yl |
| 717. | propyl | (2-isopropyl)-pyrimidin-5-yl |
| 718. | propyl | (5-isopropyl)-pyrimidin-2-yl |
| 719. | propyl | 8-quinolyl |
| 720. | propyl | 5-isoquinolyl |
| 721. | propyl | 2-(trifluoroacetyl)-1,2,3,4-tetrahydroisoquinolin-7-yl |
| 722. | propyl | 5-chloro-3-methylbenzothiophen-2-yl |
| 723. | propyl | 3,4-dihydro-4-methyl-2H-benzo[b][1,4]oxazinyl |
| 724. | propyl | benzothiazol-6-yl |
| 725. | propyl | benzo[2,1,3]oxadiazol-4-yl |
| 726. | propyl | 5-chlorobenzo[2,1,3]oxadiazol-4-yl |
| 727. | propyl | 7-chlorobenzo[2,1,3]oxadiazol-4-yl |
| 728. | propyl | benzo[2,1,3]thiadiazol-4-yl |
| 729. | propyl | 6-chloroimidazo[2,1-b]thiazolyl |
| 730. | 3-fluoropropyl | 4-methylphenyl |
| 731. | 3-fluoropropyl | 4-ethylphenyl |
| 732. | 3-fluoropropyl | 4-propylphenyl |
| 733. | 3-fluoropropyl | 4-isopropylphenyl |
| 734. | 3-fluoropropyl | 4-sec-butylphenyl |
| 735. | 3-fluoropropyl | 4-isobutylphenyl |
| 736. | 3-fluoropropyl | 4-(1,1-dimethylpropyl)-phenyl |
| 737. | 3-fluoropropyl | 4-vinylphenyl |
| 738. | 3-fluoropropyl | 4-isopropenylphenyl |
| 739. | 3-fluoropropyl | 4-fluorophenyl |
| 740. | 3-fluoropropyl | 4-chlorophenyl |
| 741. | 3-fluoropropyl | 4-bromophenyl |
| 742. | 3-fluoropropyl | 4-(fluoromethyl)phenyl |
| 743. | 3-fluoropropyl | 3-(fluoromethyl)phenyl |
| 744. | 3-fluoropropyl | 2-(fluoromethyl)phenyl |
| 745. | 3-fluoropropyl | 4-(difluoromethyl)phenyl |
| 746. | 3-fluoropropyl | 3-(difluoromethyl)phenyl |
| 747. | 3-fluoropropyl | 2-(difluoromethyl)phenyl |
| 748. | 3-fluoropropyl | 4-(trifluoromethyl)phenyl |
| 749. | 3-fluoropropyl | 3-(trifluoromethyl)phenyl |
| 750. | 3-fluoropropyl | 2-(trifluoromethyl)phenyl |
| 751. | 3-fluoropropyl | 4-(1-fluoroethyl)-phenyl |
| 752. | 3-fluoropropyl | 4-((S)-1-fluoroethyl)-phenyl |
| 753. | 3-fluoropropyl | 4-((R)-1-fluoroethyl)-phenyl |
| 754. | 3-fluoropropyl | 4-(2-fluoroethyl)-phenyl |
| 755. | 3-fluoropropyl | 4-(1,1-difluoroethyl)-phenyl |
| 756. | 3-fluoropropyl | 4-(2,2-difluoroethyl)-phenyl |
| 757. | 3-fluoropropyl | 4-(2,2,2-trifluoroethyl)-phenyl |
| 758. | 3-fluoropropyl | 4-(3-fluoropropyl)-phenyl |
| 759. | 3-fluoropropyl | 4-(2-fluoropropyl)-phenyl |
| 760. | 3-fluoropropyl | 4-((S)-2-fluoropropyl)-phenyl |
| 761. | 3-fluoropropyl | 4-((R)-2-fluoropropyl)-phenyl |
| 762. | 3-fluoropropyl | 4-(3,3-difluoropropyl)-phenyl |
| 763. | 3-fluoropropyl | 4-(3,3,3-trifluoropropyl)-phenyl |

TABLE A-continued

| No. | R¹ | Ar |
|---|---|---|
| 764. | 3-fluoropropyl | 4-(1-fluoro-1-methylethyl)-phenyl |
| 765. | 3-fluoropropyl | 4-(2-fluoro-1-methylethyl)-phenyl |
| 766. | 3-fluoropropyl | 4-((S)-2-fluoro-1-methylethyl)-phenyl |
| 767. | 3-fluoropropyl | 4-((R)-2-fluoro-1-methylethyl)-phenyl |
| 768. | 3-fluoropropyl | 4-(2,2-difluoro-1-methylethyl)-phenyl |
| 769. | 3-fluoropropyl | 4-((S)-2,2-difluoro-1-methylethyl)-phenyl |
| 770. | 3-fluoropropyl | 4-((R)-2,2-difluoro-1-methylethyl)-phenyl |
| 771. | 3-fluoropropyl | 4-(2,2,2-trifluoro-1-methylethyl)-phenyl |
| 772. | 3-fluoropropyl | 4-((S)-2,2,2-trifluoro-1-methylethyl)-phenyl |
| 773. | 3-fluoropropyl | 4-((R)-2,2,2-trifluoro-1-methylethyl)-phenyl |
| 774. | 3-fluoropropyl | 4-(2-fluoro-1-fluoromethylethyl)-phenyl |
| 775. | 3-fluoropropyl | 4-(1-difluoromethyl-2,2-difluoroethyl)-phenyl |
| 776. | 3-fluoropropyl | 4-(1,1-dimethyl-2-fluoroethyl)-phenyl |
| 777. | 3-fluoropropyl | 4-methoxyphenyl |
| 778. | 3-fluoropropyl | 4-ethoxyphenyl |
| 779. | 3-fluoropropyl | 4-propoxyphenyl |
| 780. | 3-fluoropropyl | 4-isopropoxyphenyl |
| 781. | 3-fluoropropyl | 4-butoxyphenyl |
| 782. | 3-fluoropropyl | 4-(fluoromethoxy)-phenyl |
| 783. | 3-fluoropropyl | 4-(difluoromethoxy)-phenyl |
| 784. | 3-fluoropropyl | 4-(trifluoromethoxy)-phenyl |
| 785. | 3-fluoropropyl | 3-(trifluoromethoxy)-phenyl |
| 786. | 3-fluoropropyl | 4-(2-fluoroethoxy)-phenyl |
| 787. | 3-fluoropropyl | 4-(2,2-difluoroethoxy)-phenyl |
| 788. | 3-fluoropropyl | 4-(2,2,2-trifluoroethoxy)-phenyl |
| 789. | 3-fluoropropyl | 4-(1,1,2,2-tetrafluoroethoxy)-phenyl |
| 790. | 3-fluoropropyl | 4-cyclopropylphenyl |
| 791. | 3-fluoropropyl | 4-cyclobutylphenyl |
| 792. | 3-fluoropropyl | 4-cyclopentylphenyl |
| 793. | 3-fluoropropyl | 4-(2,2-difluorocyclopropyl)-phenyl |
| 794. | 3-fluoropropyl | 3,4-difluorophenyl |
| 795. | 3-fluoropropyl | 4-bromo-3-fluorophenyl |
| 796. | 3-fluoropropyl | 4-bromo-2-fluorophenyl |
| 797. | 3-fluoropropyl | 4-bromo-2,5-difluorophenyl |
| 798. | 3-fluoropropyl | 2-fluoro-4-isopropylphenyl |
| 799. | 3-fluoropropyl | 3-fluoro-4-isopropylphenyl |
| 800. | 3-fluoropropyl | 4-(1-hydroxy-1-methylethyl)-phenyl |
| 801. | 3-fluoropropyl | 4-(2-hydroxy-2-methylpropyl)-phenyl |
| 802. | 3-fluoropropyl | 4-acetylphenyl |
| 803. | 3-fluoropropyl | 4-carboxyphenyl |
| 804. | 3-fluoropropyl | 4-cyanophenyl |
| 805. | 3-fluoropropyl | 4-hydroxyphenyl |
| 806. | 3-fluoropropyl | 4-(O-benzyl)-phenyl |
| 807. | 3-fluoropropyl | 4-(2-methoxyethoxy)-phenyl |
| 808. | 3-fluoropropyl | 4-(CH₂—N(CH₃)₂)-phenyl |
| 809. | 3-fluoropropyl | 4-(NH—CO—NH₂)-phenyl |
| 810. | 3-fluoropropyl | 4-(methylsulfanyl)-phenyl |
| 811. | 3-fluoropropyl | 4-(fluoromethylsulfanyl)-phenyl |
| 812. | 3-fluoropropyl | 4-(difluoromethylsulfanyl)-phenyl |
| 813. | 3-fluoropropyl | 4-(trifluoromethylsulfanyl)-phenyl |
| 814. | 3-fluoropropyl | 4-(methylsulfonyl)-phenyl |
| 815. | 3-fluoropropyl | 4-(N-methoxy-N-methyl-amino)-phenyl |
| 816. | 3-fluoropropyl | 4-(methoxyamino)-phenyl |
| 817. | 3-fluoropropyl | 4-(ethoxyamino)-phenyl |
| 818. | 3-fluoropropyl | 4-(N-methylaminooxy)-phenyl |
| 819. | 3-fluoropropyl | 4-(N,N-dimethylaminooxy)-phenyl |
| 820. | 3-fluoropropyl | 4-(azetidin-1-yl)-phenyl |
| 821. | 3-fluoropropyl | 4-(2-methylazetidin-1-yl)-phenyl |
| 822. | 3-fluoropropyl | 4-((S)-2-methylazetidin-1-yl)-phenyl |
| 823. | 3-fluoropropyl | 4-((R)-2-methylazetidin-1-yl)-phenyl |
| 824. | 3-fluoropropyl | 4-(3-fluoroazetidin-1-yl)-phenyl |
| 825. | 3-fluoropropyl | 4-(3-methoxyazetidin-1-yl)-phenyl |
| 826. | 3-fluoropropyl | 4-(3-hydroxyazetidin-1-yl)-phenyl |
| 827. | 3-fluoropropyl | 4-(pyrrolidin-1-yl)-phenyl |
| 828. | 3-fluoropropyl | 4-(pyrrolidin-2-yl)-phenyl |
| 829. | 3-fluoropropyl | 4-((S)-pyrrolidin-2-yl)-phenyl |
| 830. | 3-fluoropropyl | 4-((R)-pyrrolidin-2-yl)-phenyl |
| 831. | 3-fluoropropyl | 4-(pyrrolidin-3-yl)-phenyl |
| 832. | 3-fluoropropyl | 4-((S)-pyrrolidin-3-yl)-phenyl |
| 833. | 3-fluoropropyl | 4-((R)-pyrrolidin-3-yl)-phenyl |
| 834. | 3-fluoropropyl | 4-(2-fluoropyrrolidin-1-yl)-phenyl |
| 835. | 3-fluoropropyl | 4-((S)-2-fluoropyrrolidin-1-yl)-phenyl |
| 836. | 3-fluoropropyl | 4-((R)-2-fluoropyrrolidin-1-yl)-phenyl |
| 837. | 3-fluoropropyl | 4-(3-fluoropyrrolidin-1-yl)-phenyl |
| 838. | 3-fluoropropyl | 4-((S)-3-fluoropyrrolidin-1-yl)-phenyl |
| 839. | 3-fluoropropyl | 4-((R)-3-fluoropyrrolidin-1-yl)-phenyl |
| 840. | 3-fluoropropyl | 4-(2,2-difluoropyrrolidin-1-yl)-phenyl |
| 841. | 3-fluoropropyl | 4-(3,3-difluoropyrrolidin-1-yl)-phenyl |
| 842. | 3-fluoropropyl | 4-(2-methylpyrrolidin-1-yl)-phenyl |
| 843. | 3-fluoropropyl | 4-((S)-2-methylpyrrolidin-1-yl)-phenyl |
| 844. | 3-fluoropropyl | 4-((R)-2-methylpyrrolidin-1-yl)-phenyl |
| 845. | 3-fluoropropyl | 4-(3-methylpyrrolidin-1-yl)-phenyl |
| 846. | 3-fluoropropyl | 4-((S)-3-methylpyrrolidin-1-yl)-phenyl |
| 847. | 3-fluoropropyl | 4-((R)-3-methylpyrrolidin-1-yl)-phenyl |
| 848. | 3-fluoropropyl | 4-(1-methylpyrrolidin-2-yl)-phenyl |
| 849. | 3-fluoropropyl | 4-((S)-1-methylpyrrolidin-2-yl)-phenyl |
| 850. | 3-fluoropropyl | 4-((R)-1-methylpyrrolidin-2-yl)-phenyl |
| 851. | 3-fluoropropyl | 4-(1-methylpyrrolidin-3-yl)-phenyl |
| 852. | 3-fluoropropyl | 4-((S)-1-methylpyrrolidin-3-yl)-phenyl |
| 853. | 3-fluoropropyl | 4-((R)-1-methylpyrrolidin-3-yl)-phenyl |
| 854. | 3-fluoropropyl | 4-(2,2-dimethylpyrrolidin-1-yl)-phenyl |
| 855. | 3-fluoropropyl | 4-(3,3-dimethylpyrrolidin-1-yl)-phenyl |
| 856. | 3-fluoropropyl | 4-(2-trifluoromethylpyrrolidin-1-yl)-phenyl |
| 857. | 3-fluoropropyl | 4-((S)-2-trifluoromethylpyrrolidin-1-yl)-phenyl |
| 858. | 3-fluoropropyl | 4-((R)-2-trifluoromethylpyrrolidin-1-yl)-phenyl |
| 859. | 3-fluoropropyl | 4-(3-trifluoromethylpyrrolidin-1-yl)-phenyl |
| 860. | 3-fluoropropyl | 4-((S)-3-trifluoromethylpyrrolidin-1-yl)-phenyl |
| 861. | 3-fluoropropyl | 4-((R)-3-trifluoromethylpyrrolidin-1-yl)-phenyl |
| 862. | 3-fluoropropyl | 4-(2-oxopyrrolidin-1-yl)-phenyl |
| 863. | 3-fluoropropyl | 4-(2-oxo-oxazolidin-3-yl)-phenyl |
| 864. | 3-fluoropropyl | 4-(piperidin-1-yl)-phenyl |
| 865. | 3-fluoropropyl | 4-(2-methylpiperidin-1-yl)-phenyl |
| 866. | 3-fluoropropyl | 4-((S)-2-methylpiperidin-1-yl)-phenyl |
| 867. | 3-fluoropropyl | 4-((R)-2-methylpiperidin-1-yl)-phenyl |
| 868. | 3-fluoropropyl | 4-(piperazin-1-yl)-phenyl |
| 869. | 3-fluoropropyl | 4-(4-methylpiperazin-1-yl)-phenyl |
| 870. | 3-fluoropropyl | 4-(morpholin-4-yl)-phenyl |
| 871. | 3-fluoropropyl | 4-(thiomorpholin-4-yl)-phenyl |
| 872. | 3-fluoropropyl | 4-(1-oxo-thiomorpholin-4-yl)-phenyl |
| 873. | 3-fluoropropyl | 4-(1,1-dioxo-thiomorpholin-4-yl)-phenyl |
| 874. | 3-fluoropropyl | 4-(pyrrol-1-yl)-phenyl |
| 875. | 3-fluoropropyl | 4-(pyrrol-2-yl)-phenyl |
| 876. | 3-fluoropropyl | 4-(pyrrol-3-yl)-phenyl |
| 877. | 3-fluoropropyl | 4-(1-methylpyrrol-2-yl)-phenyl |
| 878. | 3-fluoropropyl | 4-(1-methylpyrrol-3-yl)-phenyl |
| 879. | 3-fluoropropyl | 4-(furan-2-yl)-phenyl |
| 880. | 3-fluoropropyl | 4-(furan-3-yl)-phenyl |
| 881. | 3-fluoropropyl | 4-(thiophen-2-yl)-phenyl |
| 882. | 3-fluoropropyl | 4-(thiophen-3-yl)-phenyl |
| 883. | 3-fluoropropyl | 4-(5-propylthien-2-yl)-phenyl |
| 884. | 3-fluoropropyl | 4-(pyrazol-1-yl)-phenyl |
| 885. | 3-fluoropropyl | 4-(pyrazol-3-yl)-phenyl |
| 886. | 3-fluoropropyl | 4-(pyrazol-4-yl)-phenyl |
| 887. | 3-fluoropropyl | 4-(1-methyl-1H-pyrazol-4-yl)-phenyl |
| 888. | 3-fluoropropyl | 4-(1-ethyl-1H-pyrazol-4-yl)-phenyl |
| 889. | 3-fluoropropyl | 4-(1-methyl-1H-pyrazol-5-yl)-phenyl |
| 890. | 3-fluoropropyl | 4-(1H-imidazol-2-yl)-phenyl |
| 891. | 3-fluoropropyl | 4-(imidazol-1-yl)-phenyl |
| 892. | 3-fluoropropyl | 4-(1-methylimidazol-2-yl)-phenyl |
| 893. | 3-fluoropropyl | 4-(oxazol-2-yl)-phenyl |
| 894. | 3-fluoropropyl | 4-(oxazol-4-yl)-phenyl |
| 895. | 3-fluoropropyl | 4-(oxazol-5-yl)-phenyl |
| 896. | 3-fluoropropyl | 4-(isoxazol-3-yl)-phenyl |
| 897. | 3-fluoropropyl | 4-(isoxazol-4-yl)-phenyl |
| 898. | 3-fluoropropyl | 4-(isoxazol-5-yl)-phenyl |
| 899. | 3-fluoropropyl | 4-([1,2,3]-triazol-1-yl)-phenyl |
| 900. | 3-fluoropropyl | 4-([1,2,4]-triazol-1-yl)-phenyl |
| 901. | 3-fluoropropyl | 4-([1,2,3]-triazol-2-yl)-phenyl |
| 902. | 3-fluoropropyl | 4-(4H-[1,2,4]-triazol-3-yl)-phenyl |
| 903. | 3-fluoropropyl | 4-([1,2,4]-triazol-4-yl)-phenyl |
| 904. | 3-fluoropropyl | 4-(2H-[1,2,3]-triazol-4-yl)-phenyl |
| 905. | 3-fluoropropyl | 4-(4-methyl-4H-[1,2,4]-triazol-3-yl)-phenyl |
| 906. | 3-fluoropropyl | 4-(2-methyl-2H-[1,2,3]-triazol-4-yl)-phenyl |
| 907. | 3-fluoropropyl | 4-([1,3,4]-oxadiazol-2-yl)-phenyl |
| 908. | 3-fluoropropyl | 4-([1,2,4]-oxadiazol-3-yl)-phenyl |
| 909. | 3-fluoropropyl | 4-([1,2,4]-oxadiazol-5-yl)-phenyl |
| 910. | 3-fluoropropyl | 4-([1,2,3]-oxadiazol-4-yl)-phenyl |
| 911. | 3-fluoropropyl | 4-([1,2,3]-oxadiazol-5-yl)-phenyl |
| 912. | 3-fluoropropyl | 4-([1,2,3]-thiadiazol-4-yl)-phenyl |
| 913. | 3-fluoropropyl | 4-(1H-tetrazol-5-yl)-phenyl |

TABLE A-continued

| No. | R¹ | Ar |
|---|---|---|
| 914. | 3-fluoropropyl | 4-(tetrazol-1-yl)-phenyl |
| 915. | 3-fluoropropyl | 4-(2-methyl-2H-tetrazol-5-yl)-phenyl |
| 916. | 3-fluoropropyl | 4-(1-methyl-1H-tetrazol-5-yl)-phenyl |
| 917. | 3-fluoropropyl | 4-furazan-3-yl-phenyl |
| 918. | 3-fluoropropyl | 4-(pyrid-2-yl)-phenyl |
| 919. | 3-fluoropropyl | 4-(pyrid-3-yl)-phenyl |
| 920. | 3-fluoropropyl | 4-(pyrid-4-yl)-phenyl |
| 921. | 3-fluoropropyl | 4-(pyrimidin-2-yl)-phenyl |
| 922. | 3-fluoropropyl | 4-(pyrimidin-4-yl)-phenyl |
| 923. | 3-fluoropropyl | 4-(pyrimidin-5-yl)-phenyl |
| 924. | 3-fluoropropyl | 5-isopropylthiophen-2-yl |
| 925. | 3-fluoropropyl | 2-chlorothiophen-5-yl |
| 926. | 3-fluoropropyl | 2,5-dichlorothiophen-4-yl |
| 927. | 3-fluoropropyl | 2,3-dichlorothiophen-5-yl |
| 928. | 3-fluoropropyl | 2-chloro-3-nitrothiophen-5-yl |
| 929. | 3-fluoropropyl | 2-(phenylsulfonyl)-thiophen-5-yl |
| 930. | 3-fluoropropyl | 2-(pyridin-2-yl)thiophen-5-yl |
| 931. | 3-fluoropropyl | 2-(5-(trifluoromethyl)isoxazol-3-yl)-thiophen-5-yl |
| 932. | 3-fluoropropyl | 2-(2-methylthiazol-4-yl)-thiophen-5-yl |
| 933. | 3-fluoropropyl | 1-methyl-1H-imidazol-4-yl |
| 934. | 3-fluoropropyl | 1,2-dimethyl-1H-imidazol-4-yl |
| 935. | 3-fluoropropyl | 3,5-dimethylisoxazol-4-yl |
| 936. | 3-fluoropropyl | thiazol-2-yl |
| 937. | 3-fluoropropyl | 4-methylthiazol-2-yl |
| 938. | 3-fluoropropyl | 4-isopropylthiazol-2-yl |
| 939. | 3-fluoropropyl | 4-trifluoromethylthiazol-2-yl |
| 940. | 3-fluoropropyl | 5-methylthiazol-2-yl |
| 941. | 3-fluoropropyl | 5-isopropylthiazol-2-yl |
| 942. | 3-fluoropropyl | 5-trifluoromethylthiazol-2-yl |
| 943. | 3-fluoropropyl | 2,4-dimethylthiazol-5-yl |
| 944. | 3-fluoropropyl | 2-acetamido-4-methylthiazol-5-yl |
| 945. | 3-fluoropropyl | 4H-[1,2,4]triazol-3-yl |
| 946. | 3-fluoropropyl | 5-methyl-4H-[1,2,4]triazol-3-yl |
| 947. | 3-fluoropropyl | 4-methyl-4H-[1,2,4]triazol-3-yl |
| 948. | 3-fluoropropyl | 5-isopropyl-4H-[1,2,4]triazol-3-yl |
| 949. | 3-fluoropropyl | 5-trifluoromethyl-4H-[1,2,4]triazol-3-yl |
| 950. | 3-fluoropropyl | 4,5-dimethyl-4H-[1,2,4]triazol-3-yl |
| 951. | 3-fluoropropyl | 5-isopropyl-4-methyl-4H-[1,2,4]triazol-3-yl |
| 952. | 3-fluoropropyl | 5-trifluoromethyl-4-methyl-4H-[1,2,4]triazol-3-yl |
| 953. | 3-fluoropropyl | [1,3,4]thiadiazol-2-yl |
| 954. | 3-fluoropropyl | 5-methyl-[1,3,4]thiadiazol-2-yl |
| 955. | 3-fluoropropyl | 5-isopropyl-[1,3,4]thiadiazol-2-yl |
| 956. | 3-fluoropropyl | 5-trifluoromethyl-[1,3,4]thiadiazol-2-yl |
| 957. | 3-fluoropropyl | 3-bromo-2-chloropyrid-5-yl |
| 958. | 3-fluoropropyl | 2-(4-morpholino)-pyrid-5-yl |
| 959. | 3-fluoropropyl | 2-phenoxypyrid-5-yl |
| 960. | 3-fluoropropyl | (2-isopropyl)-pyrimidin-5-yl |
| 961. | 3-fluoropropyl | (5-isopropyl)-pyrimidin-2-yl |
| 962. | 3-fluoropropyl | 8-quinolyl |
| 963. | 3-fluoropropyl | 5-isoquinolyl |
| 964. | 3-fluoropropyl | 2-(trifluoroacetyl)-1,2,3,4-tetrahydroisoquinolin-7-yl |
| 965. | 3-fluoropropyl | 5-chloro-3-methylbenzothiophen-2-yl |
| 966. | 3-fluoropropyl | 3,4-dihydro-4-methyl-2H-benzo[b][1,4]oxazinyl |
| 967. | 3-fluoropropyl | benzothiazol-6-yl |
| 968. | 3-fluoropropyl | benzo[2,1,3]oxadiazol-4-yl |
| 969. | 3-fluoropropyl | 5-chlorobenzo[2,1,3]oxadiazol-4-yl |
| 970. | 3-fluoropropyl | 7-chlorobenzo[2,1,3]oxadiazol-4-yl |
| 971. | 3-fluoropropyl | benzo[2,1,3]thiadiazol-4-yl |
| 972. | 3-fluoropropyl | 6-chloroimidazo[2,1-b]thiazolyl |
| 973. | 2-fluoroethyl | 4-methylphenyl |
| 974. | 2-fluoroethyl | 4-ethylphenyl |
| 975. | 2-fluoroethyl | 4-propylphenyl |
| 976. | 2-fluoroethyl | 4-isopropylphenyl |
| 977. | 2-fluoroethyl | 4-sec-butylphenyl |
| 978. | 2-fluoroethyl | 4-isobutylphenyl |
| 979. | 2-fluoroethyl | 4-(1,1-dimethylpropyl)-phenyl |
| 980. | 2-fluoroethyl | 4-vinylphenyl |
| 981. | 2-fluoroethyl | 4-isopropenylphenyl |
| 982. | 2-fluoroethyl | 4-fluorophenyl |
| 983. | 2-fluoroethyl | 4-chlorophenyl |
| 984. | 2-fluoroethyl | 4-bromophenyl |
| 985. | 2-fluoroethyl | 4-(fluoromethyl)phenyl |
| 986. | 2-fluoroethyl | 3-(fluoromethyl)phenyl |
| 987. | 2-fluoroethyl | 2-(fluoromethyl)phenyl |
| 988. | 2-fluoroethyl | 4-(difluoromethyl)phenyl |
| 989. | 2-fluoroethyl | 3-(difluoromethyl)phenyl |
| 990. | 2-fluoroethyl | 2-(difluoromethyl)phenyl |
| 991. | 2-fluoroethyl | 4-(trifluoromethyl)phenyl |
| 992. | 2-fluoroethyl | 3-(trifluoromethyl)phenyl |
| 993. | 2-fluoroethyl | 2-(trifluoromethyl)phenyl |
| 994. | 2-fluoroethyl | 4-(1-fluoroethyl)-phenyl |
| 995. | 2-fluoroethyl | 4-((S)-1-fluoroethyl)-phenyl |
| 996. | 2-fluoroethyl | 4-((R)-1-fluoroethyl)-phenyl |
| 997. | 2-fluoroethyl | 4-(2-fluoroethyl)-phenyl |
| 998. | 2-fluoroethyl | 4-(1,1-difluoroethyl)-phenyl |
| 999. | 2-fluoroethyl | 4-(2,2-difluoroethyl)-phenyl |
| 1000. | 2-fluoroethyl | 4-(2,2,2-trifluoroethyl)-phenyl |
| 1001. | 2-fluoroethyl | 4-(3-fluoropropyl)-phenyl |
| 1002. | 2-fluoroethyl | 4-(2-fluoropropyl)-phenyl |
| 1003. | 2-fluoroethyl | 4-((S)-2-fluoropropyl)-phenyl |
| 1004. | 2-fluoroethyl | 4-((R)-2-fluoropropyl)-phenyl |
| 1005. | 2-fluoroethyl | 4-(3,3-difluoropropyl)-phenyl |
| 1006. | 2-fluoroethyl | 4-(3,3,3-trifluoropropyl)-phenyl |
| 1007. | 2-fluoroethyl | 4-(1-fluoro-1-methylethyl)-phenyl |
| 1008. | 2-fluoroethyl | 4-(2-fluoro-1-methylethyl)-phenyl |
| 1009. | 2-fluoroethyl | 4-((S)-2-fluoro-1-methylethyl)-phenyl |
| 1010. | 2-fluoroethyl | 4-((R)-2-fluoro-1-methylethyl)-phenyl |
| 1011. | 2-fluoroethyl | 4-(2,2-difluoro-1-methylethyl)-phenyl |
| 1012. | 2-fluoroethyl | 4-((S)-2,2-difluoro-1-methylethyl)-phenyl |
| 1013. | 2-fluoroethyl | 4-((R)-2,2-difluoro-1-methylethyl)-phenyl |
| 1014. | 2-fluoroethyl | 4-(2,2,2-trifluoro-1-methylethyl)-phenyl |
| 1015. | 2-fluoroethyl | 4-((S)-2,2,2-trifluoro-1-methylethyl)-phenyl |
| 1016. | 2-fluoroethyl | 4-((R)-2,2,2-trifluoro-1-methylethyl)-phenyl |
| 1017. | 2-fluoroethyl | 4-(2-fluoro-1-fluoromethylethyl)-phenyl |
| 1018. | 2-fluoroethyl | 4-(1-difluoromethyl-2,2-difluoroethyl)-phenyl |
| 1019. | 2-fluoroethyl | 4-(1,1-dimethyl-2-fluoroethyl)-phenyl |
| 1020. | 2-fluoroethyl | 4-methoxyphenyl |
| 1021. | 2-fluoroethyl | 4-ethoxyphenyl |
| 1022. | 2-fluoroethyl | 4-propoxyphenyl |
| 1023. | 2-fluoroethyl | 4-isopropoxyphenyl |
| 1024. | 2-fluoroethyl | 4-butoxyphenyl |
| 1025. | 2-fluoroethyl | 4-(fluoromethoxy)-phenyl |
| 1026. | 2-fluoroethyl | 4-(difluoromethoxy)-phenyl |
| 1027. | 2-fluoroethyl | 4-(trifluoromethoxy)-phenyl |
| 1028. | 2-fluoroethyl | 3-(trifluoromethoxy)-phenyl |
| 1029. | 2-fluoroethyl | 4-(2-fluoroethoxy)-phenyl |
| 1030. | 2-fluoroethyl | 4-(2,2-difluoroethoxy)-phenyl |
| 1031. | 2-fluoroethyl | 4-(2,2,2-trifluoroethoxy)-phenyl |
| 1032. | 2-fluoroethyl | 4-(1,1,2,2-tetrafluoroethoxy)-phenyl |
| 1033. | 2-fluoroethyl | 4-cyclopropylphenyl |
| 1034. | 2-fluoroethyl | 4-cyclobutylphenyl |
| 1035. | 2-fluoroethyl | 4-cyclopentylphenyl |
| 1036. | 2-fluoroethyl | 4-(2,2-difluorocyclopropyl)-phenyl |
| 1037. | 2-fluoroethyl | 3,4-difluorophenyl |
| 1038. | 2-fluoroethyl | 4-bromo-3-fluorophenyl |
| 1039. | 2-fluoroethyl | 4-bromo-2-fluorophenyl |
| 1040. | 2-fluoroethyl | 4-bromo-2,5-difluorophenyl |
| 1041. | 2-fluoroethyl | 2-fluoro-4-isopropylphenyl |
| 1042. | 2-fluoroethyl | 3-fluoro-4-isopropylphenyl |
| 1043. | 2-fluoroethyl | 4-(1-hydroxy-1-methylethyl)-phenyl |
| 1044. | 2-fluoroethyl | 4-(2-hydroxy-2-methylpropyl)-phenyl |
| 1045. | 2-fluoroethyl | 4-acetylphenyl |
| 1046. | 2-fluoroethyl | 4-carboxyphenyl |
| 1047. | 2-fluoroethyl | 4-cyanophenyl |
| 1048. | 2-fluoroethyl | 4-hydroxyphenyl |
| 1049. | 2-fluoroethyl | 4-(O-benzyl)-phenyl |
| 1050. | 2-fluoroethyl | 4-(2-methoxyethoxy)-phenyl |
| 1051. | 2-fluoroethyl | 4-(CH₂—N(CH₃)₂)-phenyl |
| 1052. | 2-fluoroethyl | 4-(NH—CO—NH₂)-phenyl |
| 1053. | 2-fluoroethyl | 4-(methylsulfanyl)-phenyl |
| 1054. | 2-fluoroethyl | 4-(fluoromethylsulfanyl)-phenyl |
| 1055. | 2-fluoroethyl | 4-(difluoromethylsulfanyl)-phenyl |
| 1056. | 2-fluoroethyl | 4-(trifluoromethylsulfanyl)-phenyl |
| 1057. | 2-fluoroethyl | 4-(methylsulfonyl)-phenyl |
| 1058. | 2-fluoroethyl | 4-(N-methoxy-N-methyl-amino)-phenyl |
| 1059. | 2-fluoroethyl | 4-(methoxyamino)-phenyl |
| 1060. | 2-fluoroethyl | 4-(ethoxyamino)-phenyl |
| 1061. | 2-fluoroethyl | 4-(N-methylaminooxy)-phenyl |
| 1062. | 2-fluoroethyl | 4-(N,N-dimethylaminooxy)-phenyl |
| 1063. | 2-fluoroethyl | 4-(azetidin-1-yl)-phenyl |
| 1064. | 2-fluoroethyl | 4-(2-methylazetidin-1-yl)-phenyl |

TABLE A-continued

| No. | R¹ | Ar |
|---|---|---|
| 1065. | 2-fluoroethyl | 4-((S)-2-methylazetidin-1-yl)-phenyl |
| 1066. | 2-fluoroethyl | 4-((R)-2-methylazetidin-1-yl)-phenyl |
| 1067. | 2-fluoroethyl | 4-(3-fluoroazetidin-1-yl)-phenyl |
| 1068. | 2-fluoroethyl | 4-(3-methoxyazetidin-1-yl)-phenyl |
| 1069. | 2-fluoroethyl | 4-(3-hydroxyazetidin-1-yl)-phenyl |
| 1070. | 2-fluoroethyl | 4-(pyrrolidin-1-yl)-phenyl |
| 1071. | 2-fluoroethyl | 4-(pyrrolidin-2-yl)-phenyl |
| 1072. | 2-fluoroethyl | 4-((S)-pyrrolidin-2-yl)-phenyl |
| 1073. | 2-fluoroethyl | 4-((R)-pyrrolidin-2-yl)-phenyl |
| 1074. | 2-fluoroethyl | 4-(pyrrolidin-3-yl)-phenyl |
| 1075. | 2-fluoroethyl | 4-((S)-pyrrolidin-3-yl)-phenyl |
| 1076. | 2-fluoroethyl | 4-((R)-pyrrolidin-3-yl)-phenyl |
| 1077. | 2-fluoroethyl | 4-(2-fluoropyrrolidin-1-yl)-phenyl |
| 1078. | 2-fluoroethyl | 4-((S)-2-fluoropyrrolidin-1-yl)-phenyl |
| 1079. | 2-fluoroethyl | 4-((R)-2-fluoropyrrolidin-1-yl)-phenyl |
| 1080. | 2-fluoroethyl | 4-(3-fluoropyrrolidin-1-yl)-phenyl |
| 1081. | 2-fluoroethyl | 4-((S)-3-fluoropyrrolidin-1-yl)-phenyl |
| 1082. | 2-fluoroethyl | 4-((R)-3-fluoropyrrolidin-1-yl)-phenyl |
| 1083. | 2-fluoroethyl | 4-(2,2-difluoropyrrolidin-1-yl)-phenyl |
| 1084. | 2-fluoroethyl | 4-(3,3-difluoropyrrolidin-1-yl)-phenyl |
| 1085. | 2-fluoroethyl | 4-(2-methylpyrrolidin-1-yl)-phenyl |
| 1086. | 2-fluoroethyl | 4-((S)-2-methylpyrrolidin-1-yl)-phenyl |
| 1087. | 2-fluoroethyl | 4-((R)-2-methylpyrrolidin-1-yl)-phenyl |
| 1088. | 2-fluoroethyl | 4-(3-methylpyrrolidin-1-yl)-phenyl |
| 1089. | 2-fluoroethyl | 4-((S)-3-methylpyrrolidin-1-yl)-phenyl |
| 1090. | 2-fluoroethyl | 4-((R)-3-methylpyrrolidin-1-yl)-phenyl |
| 1091. | 2-fluoroethyl | 4-(1-methylpyrrolidin-2-yl)-phenyl |
| 1092. | 2-fluoroethyl | 4-((S)-1-methylpyrrolidin-2-yl)-phenyl |
| 1093. | 2-fluoroethyl | 4-((R)-1-methylpyrrolidin-2-yl)-phenyl |
| 1094. | 2-fluoroethyl | 4-(1-methylpyrrolidin-3-yl)-phenyl |
| 1095. | 2-fluoroethyl | 4-((S)-1-methylpyrrolidin-3-yl)-phenyl |
| 1096. | 2-fluoroethyl | 4-((R)-1-methylpyrrolidin-3-yl)-phenyl |
| 1097. | 2-fluoroethyl | 4-(2,2-dimethylpyrrolidin-1-yl)-phenyl |
| 1098. | 2-fluoroethyl | 4-(3,3-dimethylpyrrolidin-1-yl)-phenyl |
| 1099. | 2-fluoroethyl | 4-(2-trifluoromethylpyrrolidin-1-yl)-phenyl |
| 1100. | 2-fluoroethyl | 4-((S)-2-trifluoromethylpyrrolidin-1-yl)-phenyl |
| 1101. | 2-fluoroethyl | 4-((R)-2-trifluoromethylpyrrolidin-1-yl)-phenyl |
| 1102. | 2-fluoroethyl | 4-(3-trifluoromethylpyrrolidin-1-yl)-phenyl |
| 1103. | 2-fluoroethyl | 4-((S)-3-trifluoromethylpyrrolidin-1-yl)-phenyl |
| 1104. | 2-fluoroethyl | 4-((R)-3-trifluoromethylpyrrolidin-1-yl)-phenyl |
| 1105. | 2-fluoroethyl | 4-(2-oxopyrrolidin-1-yl)-phenyl |
| 1106. | 2-fluoroethyl | 4-(2-oxo-oxazolidin-3-yl)-phenyl |
| 1107. | 2-fluoroethyl | 4-(piperidin-1-yl)-phenyl |
| 1108. | 2-fluoroethyl | 4-(2-methylpiperidin-1-yl)-phenyl |
| 1109. | 2-fluoroethyl | 4-((S)-2-methylpiperidin-1-yl)-phenyl |
| 1110. | 2-fluoroethyl | 4-((R)-2-methylpiperidin-1-yl)-phenyl |
| 1111. | 2-fluoroethyl | 4-(piperazin-1-yl)-phenyl |
| 1112. | 2-fluoroethyl | 4-(4-methylpiperazin-1-yl)-phenyl |
| 1113. | 2-fluoroethyl | 4-(morpholin-4-yl)-phenyl |
| 1114. | 2-fluoroethyl | 4-(thiomorpholin-4-yl)-phenyl |
| 1115. | 2-fluoroethyl | 4-(1-oxo-thiomorpholin-4-yl)-phenyl |
| 1116. | 2-fluoroethyl | 4-(1,1-dioxo-thiomorpholin-4-yl)-phenyl |
| 1117. | 2-fluoroethyl | 4-(pyrrol-1-yl)-phenyl |
| 1118. | 2-fluoroethyl | 4-(pyrrol-2-yl)-phenyl |
| 1119. | 2-fluoroethyl | 4-(pyrrol-3-yl)-phenyl |
| 1120. | 2-fluoroethyl | 4-(1-methylpyrrol-2-yl)-phenyl |
| 1121. | 2-fluoroethyl | 4-(1-methylpyrrol-3-yl)-phenyl |
| 1122. | 2-fluoroethyl | 4-(furan-2-yl)-phenyl |
| 1123. | 2-fluoroethyl | 4-(furan-3-yl)-phenyl |
| 1124. | 2-fluoroethyl | 4-(thiophen-2-yl)-phenyl |
| 1125. | 2-fluoroethyl | 4-(thiophen-3-yl)-phenyl |
| 1126. | 2-fluoroethyl | 4-(5-propylthien-2-yl)-phenyl |
| 1127. | 2-fluoroethyl | 4-(pyrazol-1-yl)-phenyl |
| 1128. | 2-fluoroethyl | 4-(pyrazol-3-yl)-phenyl |
| 1129. | 2-fluoroethyl | 4-(pyrazol-4-yl)-phenyl |
| 1130. | 2-fluoroethyl | 4-(1-methyl-1H-pyrazol-4-yl)-phenyl |
| 1131. | 2-fluoroethyl | 4-(1-ethyl-1H-pyrazol-4-yl)-phenyl |
| 1132. | 2-fluoroethyl | 4-(1-methyl-1H-pyrazol-5-yl)-phenyl |
| 1133. | 2-fluoroethyl | 4-(1H-imidazol-2-yl)-phenyl |
| 1134. | 2-fluoroethyl | 4-(imidazol-1-yl)-phenyl |
| 1135. | 2-fluoroethyl | 4-(1-methylimidazol-2-yl)-phenyl |
| 1136. | 2-fluoroethyl | 4-(oxazol-2-yl)-phenyl |
| 1137. | 2-fluoroethyl | 4-(oxazol-4-yl)-phenyl |
| 1138. | 2-fluoroethyl | 4-(oxazol-5-yl)-phenyl |
| 1139. | 2-fluoroethyl | 4-(isoxazol-3-yl)-phenyl |
| 1140. | 2-fluoroethyl | 4-(isoxazol-4-yl)-phenyl |
| 1141. | 2-fluoroethyl | 4-(isoxazol-5-yl)-phenyl |
| 1142. | 2-fluoroethyl | 4-([1,2,3]-triazol-1-yl)-phenyl |
| 1143. | 2-fluoroethyl | 4-([1,2,4]-triazol-1-yl)-phenyl |
| 1144. | 2-fluoroethyl | 4-([1,2,3]-triazol-2-yl)-phenyl |
| 1145. | 2-fluoroethyl | 4-(4H-[1,2,4]-triazol-3-yl)-phenyl |
| 1146. | 2-fluoroethyl | 4-([1,2,4]-triazol-4-yl)-phenyl |
| 1147. | 2-fluoroethyl | 4-(2H-[1,2,3]-triazol-4-yl)-phenyl |
| 1148. | 2-fluoroethyl | 4-(4-methyl-4H-[1,2,4]-triazol-3-yl)-phenyl |
| 1149. | 2-fluoroethyl | 4-(2-methyl-2H-[1,2,3]-triazol-4-yl)-phenyl |
| 1150. | 2-fluoroethyl | 4-([1,3,4]-oxadiazol-2-yl)-phenyl |
| 1151. | 2-fluoroethyl | 4-([1,2,4]-oxadiazol-3-yl)-phenyl |
| 1152. | 2-fluoroethyl | 4-([1,2,4]-oxadiazol-5-yl)-phenyl |
| 1153. | 2-fluoroethyl | 4-([1,2,3]-oxadiazol-4-yl)-phenyl |
| 1154. | 2-fluoroethyl | 4-([1,2,3]-oxadiazol-5-yl)-phenyl |
| 1155. | 2-fluoroethyl | 4-([1,2,3]-thiadiazol-4-yl)-phenyl |
| 1156. | 2-fluoroethyl | 4-(1H-tetrazol-5-yl)-phenyl |
| 1157. | 2-fluoroethyl | 4-(tetrazol-1-yl)-phenyl |
| 1158. | 2-fluoroethyl | 4-(2-methyl-2H-tetrazol-5-yl)-phenyl |
| 1159. | 2-fluoroethyl | 4-(1-methyl-1H-tetrazol-5-yl)-phenyl |
| 1160. | 2-fluoroethyl | 4-furazan-3-yl-phenyl |
| 1161. | 2-fluoroethyl | 4-(pyrid-2-yl)-phenyl |
| 1162. | 2-fluoroethyl | 4-(pyrid-3-yl)-phenyl |
| 1163. | 2-fluoroethyl | 4-(pyrid-4-yl)-phenyl |
| 1164. | 2-fluoroethyl | 4-(pyrimidin-2-yl)-phenyl |
| 1165. | 2-fluoroethyl | 4-(pyrimidin-4-yl)-phenyl |
| 1166. | 2-fluoroethyl | 4-(pyrimidin-5-yl)-phenyl |
| 1167. | 2-fluoroethyl | 5-isopropylthiophen-2-yl |
| 1168. | 2-fluoroethyl | 2-chlorothiophen-5-yl |
| 1169. | 2-fluoroethyl | 2,5-dichlorothiophen-4-yl |
| 1170. | 2-fluoroethyl | 2,3-dichlorothiophen-5-yl |
| 1171. | 2-fluoroethyl | 2-chloro-3-nitrothiophen-5-yl |
| 1172. | 2-fluoroethyl | 2-(phenylsulfonyl)-thiophen-5-yl |
| 1173. | 2-fluoroethyl | 2-(pyridin-2-yl)thiophen-5-yl |
| 1174. | 2-fluoroethyl | 2-(5-(trifluoromethyl)isoxazol-3-yl)-thiophen-5-yl |
| 1175. | 2-fluoroethyl | 2-(2-methylthiazol-4-yl)-thiophen-5-yl |
| 1176. | 2-fluoroethyl | 1-methyl-1H-imidazol-4-yl |
| 1177. | 2-fluoroethyl | 1,2-dimethyl-1H-imidazol-4-yl |
| 1178. | 2-fluoroethyl | 3,5-dimethylisoxazol-4-yl |
| 1179. | 2-fluoroethyl | thiazol-2-yl |
| 1180. | 2-fluoroethyl | 4-methylthiazol-2-yl |
| 1181. | 2-fluoroethyl | 4-isopropylthiazol-2-yl |
| 1182. | 2-fluoroethyl | 4-trifluoromethylthiazol-2-yl |
| 1183. | 2-fluoroethyl | 5-methylthiazol-2-yl |
| 1184. | 2-fluoroethyl | 5-isopropylthiazol-2-yl |
| 1185. | 2-fluoroethyl | 5-trifluoromethylthiazol-2-yl |
| 1186. | 2-fluoroethyl | 2,4-dimethylthiazol-5-yl |
| 1187. | 2-fluoroethyl | 2-acetamido-4-methylthiazol-5-yl |
| 1188. | 2-fluoroethyl | 4H-[1,2,4]triazol-3-yl |
| 1189. | 2-fluoroethyl | 5-methyl-4H-[1,2,4]triazol-3-yl |
| 1190. | 2-fluoroethyl | 4-methyl-4H-[1,2,4]triazol-3-yl |
| 1191. | 2-fluoroethyl | 5-isopropyl-4H-[1,2,4]triazol-3-yl |
| 1192. | 2-fluoroethyl | 5-trifluoromethyl-4H-[1,2,4]triazol-3-yl |
| 1193. | 2-fluoroethyl | 4,5-dimethyl-4H-[1,2,4]triazol-3-yl |
| 1194. | 2-fluoroethyl | 5-isopropyl-4-methyl-4H-[1,2,4]triazol-3-yl |
| 1195. | 2-fluoroethyl | 5-trifluoromethyl-4-methyl-4H-[1,2,4]triazol-3-yl |
| 1196. | 2-fluoroethyl | [1,3,4]thiadiazol-2-yl |
| 1197. | 2-fluoroethyl | 5-methyl-[1,3,4]thiadiazol-2-yl |
| 1198. | 2-fluoroethyl | 5-isopropyl-[1,3,4]thiadiazol-2-yl |
| 1199. | 2-fluoroethyl | 5-trifluoromethyl-[1,3,4]thiadiazol-2-yl |
| 1200. | 2-fluoroethyl | 3-bromo-2-chloropyrid-5-yl |
| 1201. | 2-fluoroethyl | 2-(4-morpholino)-pyrid-5-yl |
| 1202. | 2-fluoroethyl | 2-phenoxypyrid-5-yl |
| 1203. | 2-fluoroethyl | (2-isopropyl)-pyrimidin-5-yl |
| 1204. | 2-fluoroethyl | (5-isopropyl)-pyrimidin-2-yl |
| 1205. | 2-fluoroethyl | 8-quinolyl |
| 1206. | 2-fluoroethyl | 5-isoquinolyl |
| 1207. | 2-fluoroethyl | 2-(trifluoroacetyl)-1,2,3,4-tetrahydroisoquinolin-7-yl |
| 1208. | 2-fluoroethyl | 5-chloro-3-methylbenzothiophen-2-yl |
| 1209. | 2-fluoroethyl | 3,4-dihydro-4-methyl-2H-benzo[b][1,4]oxazinyl |
| 1210. | 2-fluoroethyl | benzothiazol-6-yl |
| 1211. | 2-fluoroethyl | benzo[2,1,3]oxadiazol-4-yl |
| 1212. | 2-fluoroethyl | 5-chlorobenzo[2,1,3]oxadiazol-4-yl |

TABLE A-continued

| No. | R¹ | Ar |
|---|---|---|
| 1213. | 2-fluoroethyl | 7-chlorobenzo[2,1,3]oxadiazol-4-yl |
| 1214. | 2-fluoroethyl | benzo[2,1,3]thiadiazol-4-yl |
| 1215. | 2-fluoroethyl | 6-chloroimidazo[2,1-b]thiazolyl |
| 1216. | cyclopropylmethyl | 4-methylphenyl |
| 1217. | cyclopropylmethyl | 4-ethylphenyl |
| 1218. | cyclopropylmethyl | 4-propylphenyl |
| 1219. | cyclopropylmethyl | 4-isopropylphenyl |
| 1220. | cyclopropylmethyl | 4-sec-butylphenyl |
| 1221. | cyclopropylmethyl | 4-isobutylphenyl |
| 1222. | cyclopropylmethyl | 4-(1,1-dimethylpropyl)-phenyl |
| 1223. | cyclopropylmethyl | 4-vinylphenyl |
| 1224. | cyclopropylmethyl | 4-isopropenylphenyl |
| 1225. | cyclopropylmethyl | 4-fluorophenyl |
| 1226. | cyclopropylmethyl | 4-chlorophenyl |
| 1227. | cyclopropylmethyl | 4-bromophenyl |
| 1228. | cyclopropylmethyl | 4-(fluoromethyl)phenyl |
| 1229. | cyclopropylmethyl | 3-(fluoromethyl)phenyl |
| 1230. | cyclopropylmethyl | 2-(fluoromethyl)phenyl |
| 1231. | cyclopropylmethyl | 4-(difluoromethyl)phenyl |
| 1232. | cyclopropylmethyl | 3-(difluoromethyl)phenyl |
| 1233. | cyclopropylmethyl | 2-(difluoromethyl)phenyl |
| 1234. | cyclopropylmethyl | 4-(trifluoromethyl)phenyl |
| 1235. | cyclopropylmethyl | 3-(trifluoromethyl)phenyl |
| 1236. | cyclopropylmethyl | 2-(trifluoromethyl)phenyl |
| 1237. | cyclopropylmethyl | 4-(1-fluoroethyl)-phenyl |
| 1238. | cyclopropylmethyl | 4-((S)-1-fluoroethyl)-phenyl |
| 1239. | cyclopropylmethyl | 4-((R)-1-fluoroethyl)-phenyl |
| 1240. | cyclopropylmethyl | 4-(2-fluoroethyl)-phenyl |
| 1241. | cyclopropylmethyl | 4-(1,1-difluoroethyl)-phenyl |
| 1242. | cyclopropylmethyl | 4-(2,2-difluoroethyl)-phenyl |
| 1243. | cyclopropylmethyl | 4-(2,2,2-trifluoroethyl)-phenyl |
| 1244. | cyclopropylmethyl | 4-(3-fluoropropyl)-phenyl |
| 1245. | cyclopropylmethyl | 4-(2-fluoropropyl)-phenyl |
| 1246. | cyclopropylmethyl | 4-((S)-2-fluoropropyl)-phenyl |
| 1247. | cyclopropylmethyl | 4-((R)-2-fluoropropyl)-phenyl |
| 1248. | cyclopropylmethyl | 4-(3,3-difluoropropyl)-phenyl |
| 1249. | cyclopropylmethyl | 4-(3,3,3-trifluoropropyl)-phenyl |
| 1250. | cyclopropylmethyl | 4-(1-fluoro-1-methylethyl)-phenyl |
| 1251. | cyclopropylmethyl | 4-(2-fluoro-1-methylethyl)-phenyl |
| 1252. | cyclopropylmethyl | 4-((S)-2-fluoro-1-methylethyl)-phenyl |
| 1253. | cyclopropylmethyl | 4-((R)-2-fluoro-1-methylethyl)-phenyl |
| 1254. | cyclopropylmethyl | 4-(2,2-difluoro-1-methylethyl)-phenyl |
| 1255. | cyclopropylmethyl | 4-((S)-2,2-difluoro-1-methylethyl)-phenyl |
| 1256. | cyclopropylmethyl | 4-((R)-2,2-difluoro-1-methylethyl)-phenyl |
| 1257. | cyclopropylmethyl | 4-(2,2,2-trifluoro-1-methylethyl)-phenyl |
| 1258. | cyclopropylmethyl | 4-((S)-2,2,2-trifluoro-1-methylethyl)-phenyl |
| 1259. | cyclopropylmethyl | 4-((R)-2,2,2-trifluoro-1-methylethyl)-phenyl |
| 1260. | cyclopropylmethyl | 4-(2-fluoro-3-fluoromethylethyl)-phenyl |
| 1261. | cyclopropylmethyl | 4-(1-difluoromethyl-2,2-difluoroethyl)-phenyl |
| 1262. | cyclopropylmethyl | 4-(1,1-dimethyl-2-fluoroethyl)-phenyl |
| 1263. | cyclopropylmethyl | 4-methoxyphenyl |
| 1264. | cyclopropylmethyl | 4-ethoxyphenyl |
| 1265. | cyclopropylmethyl | 4-propoxyphenyl |
| 1266. | cyclopropylmethyl | 4-isopropoxyphenyl |
| 1267. | cyclopropylmethyl | 4-butoxyphenyl |
| 1268. | cyclopropylmethyl | 4-(fluoromethoxy)-phenyl |
| 1269. | cyclopropylmethyl | 4-(difluoromethoxy)-phenyl |
| 1270. | cyclopropylmethyl | 4-(trifluoromethoxy)-phenyl |
| 1271. | cyclopropylmethyl | 3-(trifluoromethoxy)-phenyl |
| 1272. | cyclopropylmethyl | 4-(2-fluoroethoxy)-phenyl |
| 1273. | cyclopropylmethyl | 4-(2,2-difluoroethoxy)-phenyl |
| 1274. | cyclopropylmethyl | 4-(2,2,2-trifluoroethoxy)-phenyl |
| 1275. | cyclopropylmethyl | 4-(1,1,2,2-tetrafluoroethoxy)-phenyl |
| 1276. | cyclopropylmethyl | 4-cyclopropylphenyl |
| 1277. | cyclopropylmethyl | 4-cyclobutylphenyl |
| 1278. | cyclopropylmethyl | 4-cyclopentylphenyl |
| 1279. | cyclopropylmethyl | 4-(2,2-difluorocyclopropyl)-phenyl |
| 1280. | cyclopropylmethyl | 3,4-difluorophenyl |
| 1281. | cyclopropylmethyl | 4-bromo-3-fluorophenyl |
| 1282. | cyclopropylmethyl | 4-bromo-2-fluorophenyl |
| 1283. | cyclopropylmethyl | 4-bromo-2,5-difluorophenyl |
| 1284. | cyclopropylmethyl | 2-fluoro-4-isopropylphenyl |
| 1285. | cyclopropylmethyl | 3-fluoro-4-isopropylphenyl |
| 1286. | cyclopropylmethyl | 4-(1-hydroxy-1-methylethyl)-phenyl |
| 1287. | cyclopropylmethyl | 4-(2-hydroxy-2-methylpropyl)-phenyl |
| 1288. | cyclopropylmethyl | 4-acetylphenyl |
| 1289. | cyclopropylmethyl | 4-carboxyphenyl |
| 1290. | cyclopropylmethyl | 4-cyanophenyl |
| 1291. | cyclopropylmethyl | 4-hydroxyphenyl |
| 1292. | cyclopropylmethyl | 4-(O-benzyl)-phenyl |
| 1293. | cyclopropylmethyl | 4-(2-methoxyethoxy)-phenyl |
| 1294. | cyclopropylmethyl | 4-($CH_2$—$N(CH_3)_2$)-phenyl |
| 1295. | cyclopropylmethyl | 4-(NH—CO—$NH_2$)-phenyl |
| 1296. | cyclopropylmethyl | 4-(methylsulfanyl)-phenyl |
| 1297. | cyclopropylmethyl | 4-(fluoromethylsulfanyl)-phenyl |
| 1298. | cyclopropylmethyl | 4-(difluoromethylsulfanyl)-phenyl |
| 1299. | cyclopropylmethyl | 4-(trifluoromethylsulfanyl)-phenyl |
| 1300. | cyclopropylmethyl | 4-(methylsulfonyl)-phenyl |
| 1301. | cyclopropylmethyl | 4-(N-methoxy-N-methyl-amino)-phenyl |
| 1302. | cyclopropylmethyl | 4-(methoxyamino)-phenyl |
| 1303. | cyclopropylmethyl | 4-(ethoxyamino)-phenyl |
| 1304. | cyclopropylmethyl | 4-(N-methylaminooxy)-phenyl |
| 1305. | cyclopropylmethyl | 4-(N,N-dimethylaminooxy)-phenyl |
| 1306. | cyclopropylmethyl | 4-(azetidin-1-yl)-phenyl |
| 1307. | cyclopropylmethyl | 4-(2-methylazetidin-1-yl)-phenyl |
| 1308. | cyclopropylmethyl | 4-((S)-2-methylazetidin-1-yl)-phenyl |
| 1309. | cyclopropylmethyl | 4-((R)-2-methylazetidin-1-yl)-phenyl |
| 1310. | cyclopropylmethyl | 4-(3-fluoroazetidin-1-yl)-phenyl |
| 1311. | cyclopropylmethyl | 4-(3-methoxyazetidin-1-yl)-phenyl |
| 1312. | cyclopropylmethyl | 4-(3-hydroxyazetidin-1-yl)-phenyl |
| 1313. | cyclopropylmethyl | 4-(pyrrolidin-1-yl)-phenyl |
| 1314. | cyclopropylmethyl | 4-(pyrrolidin-2-yl)-phenyl |
| 1315. | cyclopropylmethyl | 4-((S)-pyrrolidin-2-yl)-phenyl |
| 1316. | cyclopropylmethyl | 4-((R)-pyrrolidin-2-yl)-phenyl |
| 1317. | cyclopropylmethyl | 4-(pyrrolidin-3-yl)-phenyl |
| 1318. | cyclopropylmethyl | 4-((S)-pyrrolidin-3-yl)-phenyl |
| 1319. | cyclopropylmethyl | 4-((R)-pyrrolidin-3-yl)-phenyl |
| 1320. | cyclopropylmethyl | 4-(2-fluoropyrrolidin-1-yl)-phenyl |
| 1321. | cyclopropylmethyl | 4-((S)-2-fluoropyrrolidin-1-yl)-phenyl |
| 1322. | cyclopropylmethyl | 4-((R)-2-fluoropyrrolidin-1-yl)-phenyl |
| 1323. | cyclopropylmethyl | 4-(3-fluoropyrrolidin-1-yl)-phenyl |
| 1324. | cyclopropylmethyl | 4-((S)-3-fluoropyrrolidin-1-yl)-phenyl |
| 1325. | cyclopropylmethyl | 4-((R)-3-fluoropyrrolidin-1-yl)-phenyl |
| 1326. | cyclopropylmethyl | 4-(2,2-difluoropyrrolidin-1-yl)-phenyl |
| 1327. | cyclopropylmethyl | 4-(3,3-difluoropyrrolidin-1-yl)-phenyl |
| 1328. | cyclopropylmethyl | 4-(2-methylpyrrolidin-1-yl)-phenyl |
| 1329. | cyclopropylmethyl | 4-((S)-2-methylpyrrolidin-1-yl)-phenyl |
| 1330. | cyclopropylmethyl | 4-((R)-2-methylpyrrolidin-1-yl)-phenyl |
| 1331. | cyclopropylmethyl | 4-(3-methylpyrrolidin-1-yl)-phenyl |
| 1332. | cyclopropylmethyl | 4-((S)-3-methylpyrrolidin-1-yl)-phenyl |
| 1333. | cyclopropylmethyl | 4-((R)-3-methylpyrrolidin-1-yl)-phenyl |
| 1334. | cyclopropylmethyl | 4-(1-methylpyrrolidin-2-yl)-phenyl |
| 1335. | cyclopropylmethyl | 4-((S)-1-methylpyrrolidin-2-yl)-phenyl |
| 1336. | cyclopropylmethyl | 4-((R)-1-methylpyrrolidin-2-yl)-phenyl |
| 1337. | cyclopropylmethyl | 4-(1-methylpyrrolidin-3-yl)-phenyl |
| 1338. | cyclopropylmethyl | 4-((S)-1-methylpyrrolidin-3-yl)-phenyl |
| 1339. | cyclopropylmethyl | 4-((R)-1-methylpyrrolidin-3-yl)-phenyl |
| 1340. | cyclopropylmethyl | 4-(2,2-dimethylpyrrolidin-1-yl)-phenyl |
| 1341. | cyclopropylmethyl | 4-(3,3-dimethylpyrrolidin-1-yl)-phenyl |
| 1342. | cyclopropylmethyl | 4-(2-trifluoromethylpyrrolidin-1-yl)-phenyl |
| 1343. | cyclopropylmethyl | 4-((S)-2-trifluoromethylpyrrolidin-1-yl)-phenyl |
| 1344. | cyclopropylmethyl | 4-((R)-2-trifluoromethylpyrrolidin-1-yl)-phenyl |
| 1345. | cyclopropylmethyl | 4-(3-trifluoromethylpyrrolidin-1-yl)-phenyl |
| 1346. | cyclopropylmethyl | 4-((S)-3-trifluoromethylpyrrolidin-1-yl)-phenyl |
| 1347. | cyclopropylmethyl | 4-((R)-3-trifluoromethylpyrrolidin-1-yl)-phenyl |
| 1348. | cyclopropylmethyl | 4-(2-oxopyrrolidin-1-yl)-phenyl |
| 1349. | cyclopropylmethyl | 4-(2-oxo-oxazolidin-3-yl)-phenyl |
| 1350. | cyclopropylmethyl | 4-(piperidin-1-yl)-phenyl |
| 1351. | cyclopropylmethyl | 4-(2-methylpiperidin-1-yl)-phenyl |
| 1352. | cyclopropylmethyl | 4-((S)-2-methylpiperidin-1-yl)-phenyl |
| 1353. | cyclopropylmethyl | 4-((R)-2-methylpiperidin-1-yl)-phenyl |
| 1354. | cyclopropylmethyl | 4-(piperazin-1-yl)-phenyl |
| 1355. | cyclopropylmethyl | 4-(4-methylpiperazin-1-yl)-phenyl |
| 1356. | cyclopropylmethyl | 4-(morpholin-4-yl)-phenyl |
| 1357. | cyclopropylmethyl | 4-(thiomorpholin-4-yl)-phenyl |
| 1358. | cyclopropylmethyl | 4-(1-oxo-thiomorpholin-4-yl)-phenyl |
| 1359. | cyclopropylmethyl | 4-(1,1-dioxo-thiomorpholin-4-yl)-phenyl |
| 1360. | cyclopropylmethyl | 4-(pyrrol-1-yl)-phenyl |
| 1361. | cyclopropylmethyl | 4-(pyrrol-2-yl)-phenyl |
| 1362. | cyclopropylmethyl | 4-(pyrrol-3-yl)-phenyl |
| 1363. | cyclopropylmethyl | 4-(1-methylpyrrol-2-yl)-phenyl |

TABLE A-continued

| No. | R¹ | Ar |
|---|---|---|
| 1364. | cyclopropylmethyl | 4-(1-methylpyrrol-3-yl)-phenyl |
| 1365. | cyclopropylmethyl | 4-(furan-2-yl)-phenyl |
| 1366. | cyclopropylmethyl | 4-(furan-3-yl)-phenyl |
| 1367. | cyclopropylmethyl | 4-(thiophen-2-yl)-phenyl |
| 1368. | cyclopropylmethyl | 4-(thiophen-3-yl)-phenyl |
| 1369. | cyclopropylmethyl | 4-(5-propylthien-2-yl)-phenyl |
| 1370. | cyclopropylmethyl | 4-(pyrazol-1-yl)-phenyl |
| 1371. | cyclopropylmethyl | 4-(pyrazol-3-yl)-phenyl |
| 1372. | cyclopropylmethyl | 4-(pyrazol-4-yl)-phenyl |
| 1373. | cyclopropylmethyl | 4-(1-methyl-1H-pyrazol-4-yl)-phenyl |
| 1374. | cyclopropylmethyl | 4-(1-ethyl-1H-pyrazol-4-yl)-phenyl |
| 1375. | cyclopropylmethyl | 4-(1-methyl-1H-pyrazol-5-yl)-phenyl |
| 1376. | cyclopropylmethyl | 4-(1H-imidazol-2-yl)-phenyl |
| 1377. | cyclopropylmethyl | 4-(imidazol-1-yl)-phenyl |
| 1378. | cyclopropylmethyl | 4-(1-methylimidazol-2-yl)-phenyl |
| 1379. | cyclopropylmethyl | 4-(oxazol-2-yl)-phenyl |
| 1380. | cyclopropylmethyl | 4-(oxazol-4-yl)-phenyl |
| 1381. | cyclopropylmethyl | 4-(oxazol-5-yl)-phenyl |
| 1382. | cyclopropylmethyl | 4-(isoxazol-3-yl)-phenyl |
| 1383. | cyclopropylmethyl | 4-(isoxazol-4-yl)-phenyl |
| 1384. | cyclopropylmethyl | 4-(isoxazol-5-yl)-phenyl |
| 1385. | cyclopropylmethyl | 4-([1,2,3]-triazol-1-yl)-phenyl |
| 1386. | cyclopropylmethyl | 4-([1,2,4]-triazol-1-yl)-phenyl |
| 1387. | cyclopropylmethyl | 4-([1,2,3]-triazol-2-yl)-phenyl |
| 1388. | cyclopropylmethyl | 4-(4H-[1,2,4]-triazol-3-yl)-phenyl |
| 1389. | cyclopropylmethyl | 4-([1,2,4]-triazol-4-yl)-phenyl |
| 1390. | cyclopropylmethyl | 4-(2H-[1,2,3]-triazol-4-yl)-phenyl |
| 1391. | cyclopropylmethyl | 4-(4-methyl-4H-[1,2,4]-triazol-3-yl)-phenyl |
| 1392. | cyclopropylmethyl | 4-(2-methyl-2H-[1,2,3]-triazol-4-yl)-phenyl |
| 1393. | cyclopropylmethyl | 4-([1,3,4]-oxadiazol-2-yl)-phenyl |
| 1394. | cyclopropylmethyl | 4-([1,2,4]-oxadiazol-3-yl)-phenyl |
| 1395. | cyclopropylmethyl | 4-([1,2,4]-oxadiazol-5-yl)-phenyl |
| 1396. | cyclopropylmethyl | 4-([1,2,3]-oxadiazol-4-yl)-phenyl |
| 1397. | cyclopropylmethyl | 4-([1,2,3]-oxadiazol-5-yl)-phenyl |
| 1398. | cyclopropylmethyl | 4-([1,2,3]-thiadiazol-4-yl)-phenyl |
| 1399. | cyclopropylmethyl | 4-(1H-tetrazol-5-yl)-phenyl |
| 1400. | cyclopropylmethyl | 4-(tetrazol-1-yl)-phenyl |
| 1401. | cyclopropylmethyl | 4-(2-methyl-2H-tetrazol-5-yl)-phenyl |
| 1402. | cyclopropylmethyl | 4-(1-methyl-1H-tetrazol-5-yl)-phenyl |
| 1403. | cyclopropylmethyl | 4-furazan-3-yl-phenyl |
| 1404. | cyclopropylmethyl | 4-(pyrid-2-yl)-phenyl |
| 1405. | cyclopropylmethyl | 4-(pyrid-3-yl)-phenyl |
| 1406. | cyclopropylmethyl | 4-(pyrid-4-yl)-phenyl |
| 1407. | cyclopropylmethyl | 4-(pyrimidin-2-yl)-phenyl |
| 1408. | cyclopropylmethyl | 4-(pyrimidin-4-yl)-phenyl |
| 1409. | cyclopropylmethyl | 4-(pyrimidin-5-yl)-phenyl |
| 1410. | cyclopropylmethyl | 5-isopropylthiophen-2-yl |
| 1411. | cyclopropylmethyl | 2-chlorothiophen-5-yl |
| 1412. | cyclopropylmethyl | 2,5-dichlorothiophen-4-yl |
| 1413. | cyclopropylmethyl | 2,3-dichlorothiophen-5-yl |
| 1414. | cyclopropylmethyl | 2-chloro-3-nitrothiophen-5-yl |
| 1415. | cyclopropylmethyl | 2-(phenylsulfonyl)-thiophen-5-yl |
| 1416. | cyclopropylmethyl | 2-(pyridin-2-yl)thiophen-5-yl |
| 1417. | cyclopropylmethyl | 2-(5-(trifluoromethyl)isoxazol-3-yl)-thiophen-5-yl |
| 1418. | cyclopropylmethyl | 2-(2-methylthiazol-4-yl)-thiophen-5-yl |
| 1419. | cyclopropylmethyl | 1-methyl-1H-imidazol-4-yl |
| 1420. | cyclopropylmethyl | 1,2-dimethyl-1H-imidazol-4-yl |
| 1421. | cyclopropylmethyl | 3,5-dimethylisoxazol-4-yl |
| 1422. | cyclopropylmethyl | thiazol-2-yl |
| 1423. | cyclopropylmethyl | 4-methylthiazol-2-yl |
| 1424. | cyclopropylmethyl | 4-isopropylthiazol-2-yl |
| 1425. | cyclopropylmethyl | 4-trifluoromethylthiazol-2-yl |
| 1426. | cyclopropylmethyl | 5-methylthiazol-2-yl |
| 1427. | cyclopropylmethyl | 5-isopropylthiazol-2-yl |
| 1428. | cyclopropylmethyl | 5-trifluoromethylthiazol-2-yl |
| 1429. | cyclopropylmethyl | 2,4-dimethylthiazol-5-yl |
| 1430. | cyclopropylmethyl | 2-acetamido-4-methylthiazol-5-yl |
| 1431. | cyclopropylmethyl | 4H-[1,2,4]triazol-3-yl |
| 1432. | cyclopropylmethyl | 5-methyl-4H-[1,2,4]triazol-3-yl |
| 1433. | cyclopropylmethyl | 4-methyl-4H-[1,2,4]triazol-3-yl |
| 1434. | cyclopropylmethyl | 5-isopropyl-4H-[1,2,4]triazol-3-yl |
| 1435. | cyclopropylmethyl | 5-trifluoromethyl-4H-[1,2,4]triazol-3-yl |
| 1436. | cyclopropylmethyl | 4,5-dimethyl-4H-[1,2,4]triazol-3-yl |
| 1437. | cyclopropylmethyl | 5-isopropyl-4-methyl-4H-[1,2,4]triazol-3-yl |
| 1438. | cyclopropylmethyl | 5-trifluoromethyl-4-methyl-4H-[1,2,4]triazol-3-yl |
| 1439. | cyclopropylmethyl | [1,3,4]thiadiazol-2-yl |
| 1440. | cyclopropylmethyl | 5-methyl-[1,3,4]thiadiazol-2-yl |
| 1441. | cyclopropylmethyl | 5-isopropyl-[1,3,4]thiadiazol-2-yl |
| 1442. | cyclopropylmethyl | 5-trifluoromethyl-[1,3,4]thiadiazol-2-yl |
| 1443. | cyclopropylmethyl | 3-bromo-2-chloropyrid-5-yl |
| 1444. | cyclopropylmethyl | 2-(4-morpholino)-pyrid-5-yl |
| 1445. | cyclopropylmethyl | 2-phenoxypyrid-5-yl |
| 1446. | cyclopropylmethyl | (2-isopropyl)-pyrimidin-5-yl |
| 1447. | cyclopropylmethyl | (5-isopropyl)-pyrimidin-2-yl |
| 1448. | cyclopropylmethyl | 8-quinolyl |
| 1449. | cyclopropylmethyl | 5-isoquinolyl |
| 1450. | cyclopropylmethyl | 2-(trifluoroacetyl)-1,2,3,4-tetrahydroisoquinolin-7-yl |
| 1451. | cyclopropylmethyl | 5-chloro-3-methylbenzothiophen-2-yl |
| 1452. | cyclopropylmethyl | 3,4-dihydro-4-methyl-2H-benzo[b][1,4]oxazinyl |
| 1453. | cyclopropylmethyl | benzothiazol-6-yl |
| 1454. | cyclopropylmethyl | benzo[2,1,3]oxadiazol-4-yl |
| 1455. | cyclopropylmethyl | 5-chlorobenzo[2,1,3]oxadiazol-4-yl |
| 1456. | cyclopropylmethyl | 7-chlorobenzo[2,1,3]oxadiazol-4-yl |
| 1457. | cyclopropylmethyl | benzo[2,1,3]thiadiazol-4-yl |
| 1458. | cyclopropylmethyl | 6-chloroimidazo[2,1-b]thiazolyl |
| 1459. | allyl | 4-methylphenyl |
| 1460. | allyl | 4-ethylphenyl |
| 1461. | allyl | 4-propylphenyl |
| 1462. | allyl | 4-isopropylphenyl |
| 1463. | allyl | 4-sec-butylphenyl |
| 1464. | allyl | 4-isobutylphenyl |
| 1465. | allyl | 4-(1,1-dimethylpropyl)-phenyl |
| 1466. | allyl | 4-vinylphenyl |
| 1467. | allyl | 4-isopropenylphenyl |
| 1468. | allyl | 4-fluorophenyl |
| 1469. | allyl | 4-chlorophenyl |
| 1470. | allyl | 4-bromophenyl |
| 1471. | allyl | 4-(fluoromethyl)phenyl |
| 1472. | allyl | 3-(fluoromethyl)phenyl |
| 1473. | allyl | 2-(fluoromethyl)phenyl |
| 1474. | allyl | 4-(difluoromethyl)phenyl |
| 1475. | allyl | 3-(difluoromethyl)phenyl |
| 1476. | allyl | 2-(difluoromethyl)phenyl |
| 1477. | allyl | 4-(trifluoromethyl)phenyl |
| 1478. | allyl | 3-(trifluoromethyl)phenyl |
| 1479. | allyl | 2-(trifluoromethyl)phenyl |
| 1480. | allyl | 4-(1-fluoroethyl)-phenyl |
| 1481. | allyl | 4-((S)-1-fluoroethyl)-phenyl |
| 1482. | allyl | 4-((R)-1-fluoroethyl)-phenyl |
| 1483. | allyl | 4-(2-fluoroethyl)-phenyl |
| 1484. | allyl | 4-(1,1-difluoroethyl)-phenyl |
| 1485. | allyl | 4-(2,2-difluoroethyl)-phenyl |
| 1486. | allyl | 4-(2,2,2-trifluoroethyl)-phenyl |
| 1487. | allyl | 4-(3-fluoropropyl)-phenyl |
| 1488. | allyl | 4-(2-fluoropropyl)-phenyl |
| 1489. | allyl | 4-((S)-2-fluoropropyl)-phenyl |
| 1490. | allyl | 4-((R)-2-fluoropropyl)-phenyl |
| 1491. | allyl | 4-(3,3-difluoropropyl)-phenyl |
| 1492. | allyl | 4-(3,3,3-trifluoropropyl)-phenyl |
| 1493. | allyl | 4-(1-fluoro-1-methylethyl)-phenyl |
| 1494. | allyl | 4-(2-fluoro-1-methylethyl)-phenyl |
| 1495. | allyl | 4-((S)-2-fluoro-1-methylethyl)-phenyl |
| 1496. | allyl | 4-((R)-2-fluoro-1-methylethyl)-phenyl |
| 1497. | allyl | 4-(2,2-difluoro-1-methylethyl)-phenyl |
| 1498. | allyl | 4-((S)-2,2-difluoro-1-methylethyl)-phenyl |
| 1499. | allyl | 4-((R)-2,2-difluoro-1-methylethyl)-phenyl |
| 1500. | allyl | 4-(2,2,2-trifluoro-1-methylethyl)-phenyl |
| 1501. | allyl | 4-((S)-2,2,2-trifluoro-1-methylethyl)-phenyl |
| 1502. | allyl | 4-((R)-2,2,2-trifluoro-1-methylethyl)-phenyl |
| 1503. | allyl | 4-(2-fluoro-1-fluoromethylethyl)-phenyl |
| 1504. | allyl | 4-(1-difluoromethyl-2,2-difluoroethyl)-phenyl |
| 1505. | allyl | 4-(1,1-dimethyl-2-fluoroethyl)-phenyl |
| 1506. | allyl | 4-methoxyphenyl |
| 1507. | allyl | 4-ethoxyphenyl |
| 1508. | allyl | 4-propoxyphenyl |
| 1509. | allyl | 4-isopropoxyphenyl |
| 1510. | allyl | 4-butoxyphenyl |
| 1511. | allyl | 4-(fluoromethoxy)-phenyl |
| 1512. | allyl | 4-(difluoromethoxy)-phenyl |
| 1513. | allyl | 4-(trifluoromethoxy)-phenyl |

TABLE A-continued

| No. | R¹ | Ar |
|---|---|---|
| 1514. | allyl | 3-(trifluoromethoxy)-phenyl |
| 1515. | allyl | 4-(2-fluoroethoxy)-phenyl |
| 1516. | allyl | 4-(2,2-difluoroethoxy)-phenyl |
| 1517. | allyl | 4-(2,2,2-trifluoroethoxy)-phenyl |
| 1518. | allyl | 4-(1,1,2,2-tetrafluoroethoxy)-phenyl |
| 1519. | allyl | 4-cyclopropylphenyl |
| 1520. | allyl | 4-cyclobutylphenyl |
| 1521. | allyl | 4-cyclopentylphenyl |
| 1522. | allyl | 4-(2,2-difluorocyclopropyl)-phenyl |
| 1523. | allyl | 3,4-difluorophenyl |
| 1524. | allyl | 4-bromo-3-fluorophenyl |
| 1525. | allyl | 4-bromo-2-fluorophenyl |
| 1526. | allyl | 4-bromo-2,5-difluorophenyl |
| 1527. | allyl | 2-fluoro-4-isopropylphenyl |
| 1528. | allyl | 3-fluoro-4-isopropylphenyl |
| 1529. | allyl | 4-(1-hydroxy-1-methylethyl)-phenyl |
| 1530. | allyl | 4-(2-hydroxy-2-methylpropyl)-phenyl |
| 1531. | allyl | 4-acetylphenyl |
| 1532. | allyl | 4-carboxyphenyl |
| 1533. | allyl | 4-cyanophenyl |
| 1534. | allyl | 4-hydroxyphenyl |
| 1535. | allyl | 4-(O-benzyl)-phenyl |
| 1536. | allyl | 4-(2-methoxyethoxy)-phenyl |
| 1537. | allyl | 4-(CH₂—N(CH₃)₂)-phenyl |
| 1538. | allyl | 4-(NH—CO—NH₂)-phenyl |
| 1539. | allyl | 4-(methylsulfanyl)-phenyl |
| 1540. | allyl | 4-(fluoromethylsulfanyl)-phenyl |
| 1541. | allyl | 4-(difluoromethylsulfanyl)-phenyl |
| 1542. | allyl | 4-(trifluoromethylsulfanyl)-phenyl |
| 1543. | allyl | 4-(methylsulfonyl)-phenyl |
| 1544. | allyl | 4-(N-methoxy-N-methyl-amino)-phenyl |
| 1545. | allyl | 4-(methoxyamino)-phenyl |
| 1546. | allyl | 4-(ethoxyamino)-phenyl |
| 1547. | allyl | 4-(N-methylaminooxy)-phenyl |
| 1548. | allyl | 4-(N,N-dimethylaminooxy)-phenyl |
| 1549. | allyl | 4-(azetidin-1-yl)-phenyl |
| 1550. | allyl | 4-(2-methylazetidin-1-yl)-phenyl |
| 1551. | allyl | 4-((S)-2-methylazetidin-1-yl)-phenyl |
| 1552. | allyl | 4-((R)-2-methylazetidin-1-yl)-phenyl |
| 1553. | allyl | 4-(3-fluoroazetidin-1-yl)-phenyl |
| 1554. | allyl | 4-(3-methoxyazetidin-1-yl)-phenyl |
| 1555. | allyl | 4-(3-hydroxyazetidin-1-yl)-phenyl |
| 1556. | allyl | 4-(pyrrolidin-1-yl)-phenyl |
| 1557. | allyl | 4-(pyrrolidin-2-yl)-phenyl |
| 1558. | allyl | 4-((S)-pyrrolidin-2-yl)-phenyl |
| 1559. | allyl | 4-((R)-pyrrolidin-2-yl)-phenyl |
| 1560. | allyl | 4-(pyrrolidin-3-yl)-phenyl |
| 1561. | allyl | 4-((S)-pyrrolidin-3-yl)-phenyl |
| 1562. | allyl | 4-((R)-pyrrolidin-3-yl)-phenyl |
| 1563. | allyl | 4-(2-fluoropyrrolidin-1-yl)-phenyl |
| 1564. | allyl | 4-((S)-2-fluoropyrrolidin-1-yl)-phenyl |
| 1565. | allyl | 4-((R)-2-fluoropyrrolidin-1-yl)-phenyl |
| 1566. | allyl | 4-(3-fluoropyrrolidin-1-yl)-phenyl |
| 1567. | allyl | 4-((S)-3-fluoropyrrolidin-1-yl)-phenyl |
| 1568. | allyl | 4-((R)-3-fluoropyrrolidin-1-yl)-phenyl |
| 1569. | allyl | 4-(2,2-difluoropyrrolidin-1-yl)-phenyl |
| 1570. | allyl | 4-(3,3-difluoropyrrolidin-1-yl)-phenyl |
| 1571. | allyl | 4-(2-methylpyrrolidin-1-yl)-phenyl |
| 1572. | allyl | 4-((S)-2-methylpyrrolidin-1-yl)-phenyl |
| 1573. | allyl | 4-((R)-2-methylpyrrolidin-1-yl)-phenyl |
| 1574. | allyl | 4-(3-methylpyrrolidin-1-yl)-phenyl |
| 1575. | allyl | 4-((S)-3-methylpyrrolidin-1-yl)-phenyl |
| 1576. | allyl | 4-((R)-3-methylpyrrolidin-1-yl)-phenyl |
| 1577. | allyl | 4-(1-methylpyrrolidin-2-yl)-phenyl |
| 1578. | allyl | 4-((S)-1-methylpyrrolidin-2-yl)-phenyl |
| 1579. | allyl | 4-((R)-1-methylpyrrolidin-2-yl)-phenyl |
| 1580. | allyl | 4-(1-methylpyrrolidin-3-yl)-phenyl |
| 1581. | allyl | 4-((S)-1-methylpyrrolidin-3-yl)-phenyl |
| 1582. | allyl | 4-((R)-1-methylpyrrolidin-3-yl)-phenyl |
| 1583. | allyl | 4-(2,2-dimethylpyrrolidin-1-yl)-phenyl |
| 1584. | allyl | 4-(3,3-dimethylpyrrolidin-1-yl)-phenyl |
| 1585. | allyl | 4-(2-trifluoromethylpyrrolidin-1-yl)-phenyl |
| 1586. | allyl | 4-((S)-2-trifluoromethylpyrrolidin-1-yl)-phenyl |
| 1587. | allyl | 4-((R)-2-trifluoromethylpyrrolidin-1-yl)-phenyl |
| 1588. | allyl | 4-(3-trifluoromethylpyrrolidin-1-yl)-phenyl |
| 1589. | allyl | 4-((S)-3-trifluoromethylpyrrolidin-1-yl)-phenyl |
| 1590. | allyl | 4-((R)-3-trifluoromethylpyrrolidin-1-yl)-phenyl |
| 1591. | allyl | 4-(2-oxopyrrolidin-1-yl)-phenyl |
| 1592. | allyl | 4-(2-oxo-oxazolidin-3-yl)-phenyl |
| 1593. | allyl | 4-(piperidin-1-yl)-phenyl |
| 1594. | allyl | 4-(2-methylpiperidin-1-yl)-phenyl |
| 1595. | allyl | 4-((S)-2-methylpiperidin-1-yl)-phenyl |
| 1596. | allyl | 4-((R)-2-methylpiperidin-1-yl)-phenyl |
| 1597. | allyl | 4-(piperazin-1-yl)-phenyl |
| 1598. | allyl | 4-(4-methylpiperazin-1-yl)-phenyl |
| 1599. | allyl | 4-(morpholin-4-yl)-phenyl |
| 1600. | allyl | 4-(thiomorpholin-4-yl)-phenyl |
| 1601. | allyl | 4-(1-oxo-thiomorpholin-4-yl)-phenyl |
| 1602. | allyl | 4-(1,1-dioxo-thiomorpholin-4-yl)-phenyl |
| 1603. | allyl | 4-(pyrrol-1-yl)-phenyl |
| 1604. | allyl | 4-(pyrrol-2-yl)-phenyl |
| 1605. | allyl | 4-(pyrrol-3-yl)-phenyl |
| 1606. | allyl | 4-(1-methylpyrrol-2-yl)-phenyl |
| 1607. | allyl | 4-(1-methylpyrrol-3-yl)-phenyl |
| 1608. | allyl | 4-(furan-2-yl)-phenyl |
| 1609. | allyl | 4-(furan-3-yl)-phenyl |
| 1610. | allyl | 4-(thiophen-2-yl)-phenyl |
| 1611. | allyl | 4-(thiophen-3-yl)-phenyl |
| 1612. | allyl | 4-(5-propylthien-2-yl)-phenyl |
| 1613. | allyl | 4-(pyrazol-1-yl)-phenyl |
| 1614. | allyl | 4-(pyrazol-3-yl)-phenyl |
| 1615. | allyl | 4-(pyrazol-4-yl)-phenyl |
| 1616. | allyl | 4-(1-methyl-1H-pyrazol-4-yl)-phenyl |
| 1617. | allyl | 4-(1-ethyl-1H-pyrazol-4-yl)-phenyl |
| 1618. | allyl | 4-(1-methyl-1H-pyrazol-5-yl)-phenyl |
| 1619. | allyl | 4-(1H-imidazol-2-yl)-phenyl |
| 1620. | allyl | 4-(imidazol-1-yl)-phenyl |
| 1621. | allyl | 4-(1-methylimidazol-2-yl)-phenyl |
| 1622. | allyl | 4-(oxazol-2-yl)-phenyl |
| 1623. | allyl | 4-(oxazol-4-yl)-phenyl |
| 1624. | allyl | 4-(oxazol-5-yl)-phenyl |
| 1625. | allyl | 4-(isoxazol-3-yl)-phenyl |
| 1626. | allyl | 4-(isoxazol-4-yl)-phenyl |
| 1627. | allyl | 4-(isoxazol-5-yl)-phenyl |
| 1628. | allyl | 4-([1,2,3]-triazol-1-yl)-phenyl |
| 1629. | allyl | 4-([1,2,4]-triazol-1-yl)-phenyl |
| 1630. | allyl | 4-([1,2,3]-triazol-2-yl)-phenyl |
| 1631. | allyl | 4-(4H-[1,2,4]-triazol-3-yl)-phenyl |
| 1632. | allyl | 4-([1,2,4]-triazol-4-yl)-phenyl |
| 1633. | allyl | 4-(2H-[1,2,3]-triazol-4-yl)-phenyl |
| 1634. | allyl | 4-(4-methyl-4H-[1,2,4]-triazol-3-yl)-phenyl |
| 1635. | allyl | 4-(2-methyl-2H-[1,2,3]-triazol-4-yl)-phenyl |
| 1636. | allyl | 4-([1,3,4]-oxadiazol-2-yl)-phenyl |
| 1637. | allyl | 4-([1,2,4]-oxadiazol-3-yl)-phenyl |
| 1638. | allyl | 4-([1,2,4]-oxadiazol-5-yl)-phenyl |
| 1639. | allyl | 4-([1,2,3]-oxadiazol-4-yl)-phenyl |
| 1640. | allyl | 4-([1,2,3]-oxadiazol-5-yl)-phenyl |
| 1641. | allyl | 4-([1,2,3]-thiadiazol-4-yl)-phenyl |
| 1642. | allyl | 4-(1H-tetrazol-5-yl)-phenyl |
| 1643. | allyl | 4-(tetrazol-1-yl)-phenyl |
| 1644. | allyl | 4-(2-methyl-2H-tetrazol-5-yl)-phenyl |
| 1645. | allyl | 4-(1-methyl-1H-tetrazol-5-yl)-phenyl |
| 1646. | allyl | 4-furazan-3-yl-phenyl |
| 1647. | allyl | 4-(pyrid-2-yl)-phenyl |
| 1648. | allyl | 4-(pyrid-3-yl)-phenyl |
| 1649. | allyl | 4-(pyrid-4-yl)-phenyl |
| 1650. | allyl | 4-(pyrimidin-2-yl)-phenyl |
| 1651. | allyl | 4-(pyrimidin-4-yl)-phenyl |
| 1652. | allyl | 4-(pyrimidin-5-yl)-phenyl |
| 1653. | allyl | 5-isopropylthiophen-2-yl |
| 1654. | allyl | 2-chlorothiophen-5-yl |
| 1655. | allyl | 2,5-dichlorothiophen-4-yl |
| 1656. | allyl | 2,3-dichlorothiophen-5-yl |
| 1657. | allyl | 2-chloro-3-nitrothiophen-5-yl |
| 1658. | allyl | 2-(phenylsulfonyl)-thiophen-5-yl |
| 1659. | allyl | 2-(pyridin-2-yl)thiophen-5-yl |
| 1660. | allyl | 2-(5-(trifluoromethyl)isoxazol-3-yl)-thiophen-5-yl |
| 1661. | allyl | 2-(2-methylthiazol-4-yl)-thiophen-5-yl |
| 1662. | allyl | 1-methyl-1H-imidazol-4-yl |

TABLE A-continued

| No. | R¹ | Ar |
|---|---|---|
| 1663. | allyl | 1,2-dimethyl-1H-imidazol-4-yl |
| 1664. | allyl | 3,5-dimethylisoxazol-4-yl |
| 1665. | allyl | thiazol-2-yl |
| 1666. | allyl | 4-methylthiazol-2-yl |
| 1667. | allyl | 4-isopropylthiazol-2-yl |
| 1668. | allyl | 4-trifluoromethylthiazol-2-yl |
| 1669. | allyl | 5-methylthiazol-2-yl |
| 1670. | allyl | 5-isopropylthiazol-2-yl |
| 1671. | allyl | 5-trifluoromethylthiazol-2-yl |
| 1672. | allyl | 2,4-dimethylthiazol-5-yl |
| 1673. | allyl | 2-acetamido-4-methylthiazol-5-yl |
| 1674. | allyl | 4H-[1,2,4]triazol-3-yl |
| 1675. | allyl | 5-methyl-4H-[1,2,4]triazol-3-yl |
| 1676. | allyl | 4-methyl-4H-[1,2,4]triazol-3-yl |
| 1677. | allyl | 5-isopropyl-4H-[1,2,4]triazol-3-yl |
| 1678. | allyl | 5-trifluoromethyl-4H-[1,2,4]triazol-3-yl |
| 1679. | allyl | 4,5-dimethyl-4H-[1,2,4]triazol-3-yl |
| 1680. | allyl | 5-isopropyl-4-methyl-4H-[1,2,4]triazol-3-yl |
| 1681. | allyl | 5-trifluoromethyl-4-methyl-4H-[1,2,4]triazol-3-yl |
| 1682. | allyl | [1,3,4]thiadiazol-2-yl |
| 1683. | allyl | 5-methyl-[1,3,4]thiadiazol-2-yl |
| 1684. | allyl | 5-isopropyl-[1,3,4]thiadiazol-2-yl |
| 1685. | allyl | 5-trifluoromethyl-[1,3,4]thiadiazol-2-yl |
| 1686. | allyl | 3-bromo-2-chloropyrid-5-yl |
| 1687. | allyl | 2-(4-morpholino)-pyrid-5-yl |
| 1688. | allyl | 2-phenoxypyrid-5-yl |
| 1689. | allyl | (2-isopropyl)-pyrimidin-5-yl |
| 1690. | allyl | (5-isopropyl)-pyrimidin-2-yl |
| 1691. | allyl | 8-quinolyl |
| 1692. | allyl | 5-isoquinolyl |
| 1693. | allyl | 2-(trifluoroacetyl)-1,2,3,4-tetrahydroisoquinolin-7-yl |
| 1694. | allyl | 5-chloro-3-methylbenzothiophen-2-yl |
| 1695. | allyl | 3,4-dihydro-4-methyl-2H-benzo[b][1,4]oxazinyl |
| 1696. | allyl | benzothiazol-6-yl |
| 1697. | allyl | benzo[2,1,3]oxadiazol-4-yl |
| 1698. | allyl | 5-chlorobenzo[2,1,3]oxadiazol-4-yl |
| 1699. | allyl | 7-chlorobenzo[2,1,3]oxadiazol-4-yl |
| 1700. | allyl | benzo[2,1,3]thiadiazol-4-yl |
| 1701. | allyl | 6-chloroimidazo[2,1-b]thiazolyl |
| 1702. | H | 4-(trifluoromethoxy)-phenyl |
| 1703. | H | 3-(trifluoromethoxy)-phenyl |
| 1704. | H | 4-cyanophenyl |
| 1705. | H | 4-methylphenyl |
| 1706. | H | 4-ethylphenyl |
| 1707. | H | 4-propylphenyl |
| 1708. | H | 4-methoxyphenyl |
| 1709. | H | 4-fluorophenyl |
| 1710. | H | 4-chlorophenyl |
| 1711. | H | 4-bromophenyl |
| 1712. | H | 3-(trifluoromethyl)phenyl |
| 1713. | H | 4-(trifluoromethyl)phenyl |
| 1714. | H | 2-(trifluoromethyl)phenyl |
| 1715. | H | 3,4-difluorophenyl |
| 1716. | H | 4-bromo-3-fluorophenyl |
| 1717. | H | 4-bromo-2-fluorophenyl |
| 1718. | H | 4-bromo-2,5-difluorophenyl |
| 1719. | H | 2-fluoro-4-isopropylphenyl |
| 1720. | H | 4-hydroxyphenyl |
| 1721. | H | 4-isopropylphenyl |
| 1722. | H | 4-sec-butylphenyl |
| 1723. | H | 4-isobutylphenyl |
| 1724. | H | 4-(1,1-dimethylpropyl)-phenyl |
| 1725. | H | 4-vinylphenyl |
| 1726. | H | 4-isopropenylphenyl |
| 1727. | H | 4-(fluoromethyl)phenyl |
| 1728. | H | 3-(fluoromethyl)phenyl |
| 1729. | H | 2-(fluoromethyl)phenyl |
| 1730. | H | 4-(difluoromethyl)phenyl |
| 1731. | H | 3-(difluoromethyl)phenyl |
| 1732. | H | 2-(difluoromethyl)phenyl |
| 1733. | H | 4-(1-fluoroethyl)-phenyl |
| 1734. | H | 4-((S)-1-fluoroethyl)-phenyl |
| 1735. | H | 4-((R)-1-fluoroethyl)-phenyl |
| 1736. | H | 4-(2-fluoroethyl)-phenyl |
| 1737. | H | 4-(1,1-difluoroethyl)-phenyl |
| 1738. | H | 4-(2,2-difluoroethyl)-phenyl |
| 1739. | H | 4-(2,2,2-trifluoroethyl)-phenyl |
| 1740. | H | 4-(3-fluoropropyl)-phenyl |
| 1741. | H | 4-(2-fluoropropyl)-phenyl |
| 1742. | H | 4-((S)-2-fluoropropyl)-phenyl |
| 1743. | H | 4-((R)-2-fluoropropyl)-phenyl |
| 1744. | H | 4-(3,3-difluoropropyl)-phenyl |
| 1745. | H | 4-(3,3,3-trifluoropropyl)-phenyl |
| 1746. | H | 4-(1-fluoro-1-methylethyl)-phenyl |
| 1747. | H | 4-(2-fluoro-1-methylethyl)-phenyl |
| 1748. | H | 4-((S)-2-fluoro-1-methylethyl)-phenyl |
| 1749. | H | 4-((R)-2-fluoro-1-methylethyl)-phenyl |
| 1750. | H | 4-(2,2-difluoro-1-methylethyl)-phenyl |
| 1751. | H | 4-((S)-2,2-difluoro-1-methylethyl)-phenyl |
| 1752. | H | 4-((R)-2,2-difluoro-1-methylethyl)-phenyl |
| 1753. | H | 4-(2,2,2-trifluoro-1-methylethyl)-phenyl |
| 1754. | H | 4-((S)-2,2,2-trifluoro-1-methylethyl)-phenyl |
| 1755. | H | 4-((R)-2,2,2-trifluoro-1-methylethyl)-phenyl |
| 1756. | H | 4-(2-fluoro-1-fluoromethyl-ethyl)-phenyl |
| 1757. | H | 4-(1-difluoromethyl-2,2-difluoroethyl)-phenyl |
| 1758. | H | 4-(1,1-dimethyl-2-fluoroethyl)-phenyl |
| 1759. | H | 4-ethoxyphenyl |
| 1760. | H | 4-propoxyphenyl |
| 1761. | H | 4-isopropoxyphenyl |
| 1762. | H | 4-butoxyphenyl |
| 1763. | H | 4-(fluoromethoxy)-phenyl |
| 1764. | H | 4-(difluoromethoxy)-phenyl |
| 1765. | H | 4-(2-fluoroethoxy)-phenyl |
| 1766. | H | 4-(2,2-difluoroethoxy)-phenyl |
| 1767. | H | 4-(2,2,2-trifluoroethoxy)-phenyl |
| 1768. | H | 4-(1,1,2,2-tetrafluoroethoxy)-phenyl |
| 1769. | H | 4-cyclopropylphenyl |
| 1770. | H | 4-cyclobutylphenyl |
| 1771. | H | 4-cyclopentylphenyl |
| 1772. | H | 4-(2,2-difluorocyclopropyl)-phenyl |
| 1773. | H | 3-fluoro-4-isopropylphenyl |
| 1774. | H | 4-(1-hydroxy-1-methylethyl)-phenyl |
| 1775. | H | 4-(2-hydroxy-2-methylpropyl)-phenyl |
| 1776. | H | 4-acetylphenyl |
| 1777. | H | 4-carboxyphenyl |
| 1778. | H | 4-(O-benzyl)-phenyl |
| 1779. | H | 4-(2-methoxyethoxy)-phenyl |
| 1780. | H | 4-(CH₂—N(CH₃)₂)-phenyl |
| 1781. | H | 4-(NH—CO—NH₂)-phenyl |
| 1782. | H | 4-(methylsulfanyl)-phenyl |
| 1783. | H | 4-(fluoromethylsulfanyl)-phenyl |
| 1784. | H | 4-(difluoromethylsulfanyl)-phenyl |
| 1785. | H | 4-(trifluoromethylsulfanyl)-phenyl |
| 1786. | H | 4-(methylsulfonyl)-phenyl |
| 1787. | H | 4-(N-methoxy-N-methyl-amino)-phenyl |
| 1788. | H | 4-(methoxyamino)-phenyl |
| 1789. | H | 4-(ethoxyamino)-phenyl |
| 1790. | H | 4-(N-methylaminooxy)-phenyl |
| 1791. | H | 4-(N,N-dimethylaminooxy)-phenyl |
| 1792. | H | 4-(azetidin-1-yl)-phenyl |
| 1793. | H | 4-(2-methylazetidin-1-yl)-phenyl |
| 1794. | H | 4-((S)-2-methylazetidin-1-yl)-phenyl |
| 1795. | H | 4-((R)-2-methylazetidin-1-yl)-phenyl |
| 1796. | H | 4-(3-fluoroazetidin-1-yl)-phenyl |
| 1797. | H | 4-(3-methoxyazetidin-1-yl)-phenyl |
| 1798. | H | 4-(3-hydroxyazetidin-1-yl)-phenyl |
| 1799. | H | 4-(pyrrolidin-1-yl)-phenyl |
| 1800. | H | 4-(pyrrolidin-2-yl)-phenyl |
| 1801. | H | 4-((S)-pyrrolidin-2-yl)-phenyl |
| 1802. | H | 4-((R)-pyrrolidin-2-yl)-phenyl |
| 1803. | H | 4-(pyrrolidin-3-yl)-phenyl |
| 1804. | H | 4-((S)-pyrrolidin-3-yl)-phenyl |
| 1805. | H | 4-((R)-pyrrolidin-3-yl)-phenyl |
| 1806. | H | 4-(2-fluoropyrrolidin-1-yl)-phenyl |
| 1807. | H | 4-((S)-2-fluoropyrrolidin-1-yl)-phenyl |
| 1808. | H | 4-((R)-2-fluoropyrrolidin-1-yl)-phenyl |
| 1809. | H | 4-(3-fluoropyrrolidin-1-yl)-phenyl |
| 1810. | H | 4-((S)-3-fluoropyrrolidin-1-yl)-phenyl |
| 1811. | H | 4-((R)-3-fluoropyrrolidin-1-yl)-phenyl |
| 1812. | H | 4-(2,2-difluoropyrrolidin-1-yl)-phenyl |
| 1813. | H | 4-(3,3-difluoropyrrolidin-1-yl)-phenyl |
| 1814. | H | 4-(2-methylpyrrolidin-1-yl)-phenyl |

TABLE A-continued

| No. | R¹ | Ar |
|---|---|---|
| 1815. | H | 4-((S)-2-methylpyrrolidin-1-yl)-phenyl |
| 1816. | H | 4-((R)-2-methylpyrrolidin-1-yl)-phenyl |
| 1817. | H | 4-(3-methylpyrrolidin-1-yl)-phenyl |
| 1818. | H | 4-((S)-3-methylpyrrolidin-1-yl)-phenyl |
| 1819. | H | 4-((R)-3-methylpyrrolidin-1-yl)-phenyl |
| 1820. | H | 4-(1-methylpyrrolidin-2-yl)-phenyl |
| 1821. | H | 4-((S)-1-methylpyrrolidin-2-yl)-phenyl |
| 1822. | H | 4-((R)-1-methylpyrrolidin-2-yl)-phenyl |
| 1823. | H | 4-(1-methylpyrrolidin-3-yl)-phenyl |
| 1824. | H | 4-((S)-1-methylpyrrolidin-3-yl)-phenyl |
| 1825. | H | 4-((R)-1-methylpyrrolidin-3-yl)-phenyl |
| 1826. | H | 4-(2,2-dimethylpyrrolidin-1-yl)-phenyl |
| 1827. | H | 4-(3,3-dimethylpyrrolidin-1-yl)-phenyl |
| 1828. | H | 4-(2-trifluoromethylpyrrolidin-1-yl)-phenyl |
| 1829. | H | 4-((S)-2-trifluoromethylpyrrolidin-1-yl)-phenyl |
| 1830. | H | 4-((R)-2-trifluoromethylpyrrolidin-1-yl)-phenyl |
| 1831. | H | 4-(3-trifluoromethylpyrrolidin-1-yl)-phenyl |
| 1832. | H | 4-((S)-3-trifluoromethylpyrrolidin-1-yl)-phenyl |
| 1833. | H | 4-((R)-3-trifluoromethylpyrrolidin-1-yl)-phenyl |
| 1834. | H | 4-(2-oxopyrrolidin-1-yl)-phenyl |
| 1835. | H | 4-(2-oxo-oxazolidin-3-yl)-phenyl |
| 1836. | H | 4-(piperidin-1-yl)-phenyl |
| 1837. | H | 4-(2-methylpiperidin-1-yl)-phenyl |
| 1838. | H | 4-((S)-2-methylpiperidin-1-yl)-phenyl |
| 1839. | H | 4-((R)-2-methylpiperidin-1-yl)-phenyl |
| 1840. | H | 4-(piperazin-1-yl)-phenyl |
| 1841. | H | 4-(4-methylpiperazin-1-yl)-phenyl |
| 1842. | H | 4-(morpholin-4-yl)-phenyl |
| 1843. | H | 4-(thiomorpholin-4-yl)-phenyl |
| 1844. | H | 4-(1-oxo-thiomorpholin-4-yl)-phenyl |
| 1845. | H | 4-(1,1-dioxo-thiomorpholin-4-yl)-phenyl |
| 1846. | H | 4-(pyrrol-1-yl)-phenyl |
| 1847. | H | 4-(pyrrol-2-yl)-phenyl |
| 1848. | H | 4-(pyrrol-3-yl)-phenyl |
| 1849. | H | 4-(1-methylpyrrol-2-yl)-phenyl |
| 1850. | H | 4-(1-methylpyrrol-3-yl)-phenyl |
| 1851. | H | 4-(furan-2-yl)-phenyl |
| 1852. | H | 4-(furan-3-yl)-phenyl |
| 1853. | H | 4-(thiophen-2-yl)-phenyl |
| 1854. | H | 4-(thiophen-3-yl)-phenyl |
| 1855. | H | 4-(5-propylthien-2-yl)-phenyl |
| 1856. | H | 4-(pyrazol-1-yl)-phenyl |
| 1857. | H | 4-(pyrazol-3-yl)-phenyl |
| 1858. | H | 4-(pyrazol-4-yl)-phenyl |
| 1859. | H | 4-(1-methyl-1H-pyrazol-4-yl)-phenyl |
| 1860. | H | 4-(1-ethyl-1H-pyrazol-4-yl)-phenyl |
| 1861. | H | 4-(1-methyl-1H-pyrazol-5-yl)-phenyl |
| 1862. | H | 4-(1H-imidazol-2-yl)-phenyl |
| 1863. | H | 4-(imidazol-1-yl)-phenyl |
| 1864. | H | 4-(1-methylimidazol-2-yl)-phenyl |
| 1865. | H | 4-(oxazol-2-yl)-phenyl |
| 1866. | H | 4-(oxazol-4-yl)-phenyl |
| 1867. | H | 4-(oxazol-5-yl)-phenyl |
| 1868. | H | 4-(isoxazol-3-yl)-phenyl |
| 1869. | H | 4-(isoxazol-4-yl)-phenyl |
| 1870. | H | 4-(isoxazol-5-yl)-phenyl |
| 1871. | H | 4-([1,2,3]-triazol-1-yl)-phenyl |
| 1872. | H | 4-([1,2,4]-triazol-1-yl)-phenyl |
| 1873. | H | 4-([1,2,3]-triazol-2-yl)-phenyl |
| 1874. | H | 4-(4H-[1,2,4]-triazol-3-yl)-phenyl |
| 1875. | H | 4-([1,2,4]-triazol-4-yl)-phenyl |
| 1876. | H | 4-(2H-[1,2,3]-triazol-4-yl)-phenyl |
| 1877. | H | 4-(4-methyl-4H-[1,2,4]-triazol-3-yl)-phenyl |
| 1878. | H | 4-(2-methyl-2H-[1,2,3]-tiazol-4-yl)-phenyl |
| 1879. | H | 4-([1,3,4]-oxadiazol-2-yl)-phenyl |
| 1880. | H | 4-([1,2,4]-oxadiazol-3-yl)-phenyl |
| 1881. | H | 4-([1,2,4]-oxadiazol-5-yl)-phenyl |
| 1882. | H | 4-([1,2,3]-oxadiazol-4-yl)-phenyl |
| 1883. | H | 4-([1,2,3]-oxadiazol-5-yl)-phenyl |
| 1884. | H | 4-([1,2,3]-thiadiazol-4-yl)-phenyl |
| 1885. | H | 4-(1H-tetrazol-5-yl)-phenyl |
| 1886. | H | 4-(tetrazol-1-yl)-phenyl |
| 1887. | H | 4-(2-methyl-2H-tetrazol-5-yl)-phenyl |
| 1888. | H | 4-(1-methyl-1H-tetrazol-5-yl)-phenyl |
| 1889. | H | 4-furazan-3-yl-phenyl |
| 1890. | H | 4-(pyrid-2-yl)-phenyl |
| 1891. | H | 4-(pyrid-3-yl)-phenyl |
| 1892. | H | 4-(pyrid-4-yl)-phenyl |
| 1893. | H | 4-(pyrimidin-2-yl)-phenyl |
| 1894. | H | 4-(pyrimidin-4-yl)-phenyl |
| 1895. | H | 4-(pyrimidin-5-yl)-phenyl |
| 1896. | H | 5-isopropylthiophen-2-yl |
| 1897. | H | 2-chlorothiophen-5-yl |
| 1898. | H | 2,5-dichlorothiophen-4-yl |
| 1899. | H | 2,3-dichlorothiophen-5-yl |
| 1900. | H | 2-chloro-3-nitrothiophen-5-yl |
| 1901. | H | 2-(phenylsulfonyl)-thiophen-5-yl |
| 1902. | H | 2-(pyridin-2-yl)thiophen-5-yl |
| 1903. | H | 2-(5-(trifluoromethyl)isoxazol-3-yl)-thiophen-5-yl |
| 1904. | H | 2-(2-methylthiazol-4-yl)-thiophen-5-yl |
| 1905. | H | 1-methyl-1H-imidazol-4-yl |
| 1906. | H | 1,2-dimethyl-1H-imidazol-4-yl |
| 1907. | H | 3,5-dimethylisoxazol-4-yl |
| 1908. | H | thiazol-2-yl |
| 1909. | H | 4-methylthiazol-2-yl |
| 1910. | H | 4-isopropylthiazol-2-yl |
| 1911. | H | 4-trifluoromethylthiazol-2-yl |
| 1912. | H | 5-methylthiazol-2-yl |
| 1913. | H | 5-isopropylthiazol-2-yl |
| 1914. | H | 5-trifluoromethylthiazol-2-yl |
| 1915. | H | 2,4-dimethylthiazol-5-yl |
| 1916. | H | 2-acetamido-4-methylthiazol-5-yl |
| 1917. | H | 4H-[1,2,4]triazol-3-yl |
| 1918. | H | 5-methyl-4H-[1,2,4]triazol-3-yl |
| 1919. | H | 4-methyl-4H-[1,2,4]triazol-3-yl |
| 1920. | H | 5-isopropyl-4H-[1,2,4]triazol-3-yl |
| 1921. | H | 5-trifluoromethyl-4H-[1,2,4]triazol-3-yl |
| 1922. | H | 4,5-dimethyl-4H-[1,2,4]triazol-3-yl |
| 1923. | H | 5-isopropyl-4-methyl-4H-[1,2,4]triazol-3-yl |
| 1924. | H | 5-trifluoromethyl-4-methyl-4H-[1,2,4]triazol-3-yl |
| 1925. | H | [1,3,4]thiadiazol-2-yl |
| 1926. | H | 5-methyl-[1,3,4]thiadiazol-2-yl |
| 1927. | H | 5-isopropyl-[1,3,4]thiadiazol-2-yl |
| 1928. | H | 5-trifluoromethyl-[1,3,4]thiadiazol-2-yl |
| 1929. | H | 3-bromo-2-chloropyrid-5-yl |
| 1930. | H | 2-(4-morpholino)-pyrid-5-yl |
| 1931. | H | 2-phenoxypyrid-5-yl |
| 1932. | H | (2-isopropyl)-pyrimidin-5-yl |
| 1933. | H | (5-isopropyl)-pyrimidin-2-yl |
| 1934. | H | 8-quinolyl |
| 1935. | H | 5-isoquinolyl |
| 1936. | H | 2-(trifluoroacetyl)-1,2,3,4-tetrahydroisoquinolin-7-yl |
| 1937. | H | 5-chloro-3-methylbenzothiophen-2-yl |
| 1938. | H | 3,4-dihydro-4-methyl-2H-benzo[b][1,4]oxazinyl |
| 1939. | H | benzothiazol-6-yl |
| 1940. | H | benzo[2,1,3]oxadiazol-4-yl |
| 1941. | H | 5-chlorobenzo[2,1,3]oxadiazol-4-yl |
| 1942. | H | 7-chlorobenzo[2,1,3]oxadiazol-4-yl |
| 1943. | H | benzo[2,1,3]thiadiazol-4-yl |
| 1944. | H | 6-chloroimidazo[2,1-b]thiazolyl |

Table B-1: Compounds of the formula Iu, wherein Ar has the meaning given in one of the rows of table B.

Table B-2: Compounds of the formula Iv, wherein Ar has the meaning given in one of the rows of table B.

Table B-3: Compounds of the formula Iw, wherein Ar has the meaning given in of the rows of table B.

Table B-4: Compounds of the formula Ix, wherein Ar has the meaning given in one of the rows of table B.

Table B-5: Compounds of the formula Iy, wherein Ar has the meaning given in one of the rows of table B.

Table B-6: Compounds of the formula Iz, wherein Ar has the meaning given in one of the rows of table B.

TABLE B

| No. | Ar |
|---|---|
| 1945. | 4-(trifluoromethoxy)-phenyl |
| 1946. | 3-(trifluoromethoxy)-phenyl |
| 1947. | 4-cyanophenyl |
| 1948. | 4-methylphenyl |
| 1949. | 4-ethylphenyl |
| 1950. | 4-propylphenyl |
| 1951. | 4-methoxyphenyl |
| 1952. | 4-fluorophenyl |
| 1953. | 4-chlorophenyl |
| 1954. | 4-bromophenyl |
| 1955. | 3-(trifluoromethyl)phenyl |
| 1956. | 4-(trifluoromethyl)phenyl |
| 1957. | 2-(trifluoromethyl)phenyl |
| 1958. | 3,4-difluorophenyl |
| 1959. | 4-bromo-3-fluorophenyl |
| 1960. | 4-bromo-2-fluorophenyl |
| 1961. | 4-bromo-2,5-difluorophenyl |
| 1962. | 2-fluoro-4-isopropylphenyl |
| 1963. | 4-hydroxyphenyl |
| 1964. | 4-isopropylphenyl |
| 1965. | 4-sec-butylphenyl |
| 1966. | 4-isobutylphenyl |
| 1967. | 4-(1,1-dimethylpropyl)-phenyl |
| 1968. | 4-vinylphenyl |
| 1969. | 4-isopropenylphenyl |
| 1970. | 4-(fluoromethyl)phenyl |
| 1971. | 3-(fluoromethyl)phenyl |
| 1972. | 2-(fluoromethyl)phenyl |
| 1973. | 4-(difluoromethyl)phenyl |
| 1974. | 3-(difluoromethyl)phenyl |
| 1975. | 2-(difluoromethyl)phenyl |
| 1976. | 4-(1-fluoroethyl)-phenyl |
| 1977. | 4-((S)-1-fluoroethyl)-phenyl |
| 1978. | 4-((R)-1-fluoroethyl)-phenyl |
| 1979. | 4-(2-fluoroethyl)-phenyl |
| 1980. | 4-(1,1-difluoroethyl)-phenyl |
| 1981. | 4-(2,2-difluoroethyl)-phenyl |
| 1982. | 4-(2,2,2-trifluoroethyl)-phenyl |
| 1983. | 4-(3-fluoropropyl)-phenyl |
| 1984. | 4-(2-fluoropropyl)-phenyl |
| 1985. | 4-((S)-2-fluoropropyl)-phenyl |
| 1986. | 4-((R)-2-fluoropropyl)-phenyl |
| 1987. | 4-(3,3-difluoropropyl)-phenyl |
| 1988. | 4-(3,3,3-trifluoropropyl)-phenyl |
| 1989. | 4-(1-fluoro-1-methylethyl)-phenyl |
| 1990. | 4-(2-fluoro-1-methylethyl)-phenyl |
| 1991. | 4-((S)-2-fluoro-1-methylethyl)-phenyl |
| 1992. | 4-((R)-2-fluoro-1-methylethyl)-phenyl |
| 1993. | 4-(2,2-difluoro-1-methylethyl)-phenyl |
| 1994. | 4-((S)-2,2-difluoro-1-methylethyl)-phenyl |
| 1995. | 4-((R)-2,2-difluoro-1-methylethyl)-phenyl |
| 1996. | 4-(2,2,2-trifluoro-1-methylethyl)-phenyl |
| 1997. | 4-((S)-2,2,2-trifluoro-1-methylethyl)-phenyl |
| 1998. | 4-((R)-2,2,2-trifluoro-1-methylethyl)-phenyl |
| 1999. | 4-(2-fluoro-1-fluoromethylethyl)-phenyl |
| 2000. | 4-(1-difluoromethyl-2,2-difluoroethyl)-phenyl |
| 2001. | 4-(1,1-dimethyl-2-fluoroethyl)-phenyl |
| 2002. | 4-ethoxyphenyl |
| 2003. | 4-propoxyphenyl |
| 2004. | 4-isopropoxyphenyl |
| 2005. | 4-butoxyphenyl |
| 2006. | 4-(fluoromethoxy)-phenyl |
| 2007. | 4-(difluoromethoxy)-phenyl |
| 2008. | 4-(2-fluoroethoxy)-phenyl |
| 2009. | 4-(2,2-difluoroethoxy)-phenyl |
| 2010. | 4-(2,2,2-trifluoroethoxy)-phenyl |
| 2011. | 4-(1,1,2,2-tetrafluoroethoxy)-phenyl |
| 2012. | 4-cyclopropylphenyl |
| 2013. | 4-cyclobutylphenyl |
| 2014. | 4-cyclopentylphenyl |
| 2015. | 4-(2,2-difluorocyclopropyl)-phenyl |
| 2016. | 3-fluoro-4-isopropylphenyl |
| 2017. | 4-(1-hydroxy-1-methylethyl)-phenyl |
| 2018. | 4-(2-hydroxy-2-methylpropyl)-phenyl |
| 2019. | 4-acetylphenyl |
| 2020. | 4-carboxyphenyl |
| 2021. | 4-(O-benzyl)-phenyl |
| 2022. | 4-(2-methoxyethoxy)-phenyl |
| 2023. | 4-($CH_2$—$N(CH_3)_2$)-phenyl |
| 2024. | 4-(NH—CO—$NH_2$)-phenyl |
| 2025. | 4-(methylsulfanyl)-phenyl |
| 2026. | 4-(fluoromethylsulfanyl)-phenyl |
| 2027. | 4-(difluoromethylsulfanyl)-phenyl |
| 2028. | 4-(trifluoromethylsulfanyl)-phenyl |
| 2029. | 4-(methylsulfonyl)-phenyl |
| 2030. | 4-(N-methoxy-N-methyl-amino)-phenyl |
| 2031. | 4-(methoxyamino)-phenyl |
| 2032. | 4-(ethoxyamino)-phenyl |
| 2033. | 4-(N-methylaminooxy)-phenyl |
| 2034. | 4-(N,N-dimethylaminooxy)-phenyl |
| 2035. | 4-(azetidin-1-yl)-phenyl |
| 2036. | 4-(2-methylazetidin-1-yl)-phenyl |
| 2037. | 4-((S)-2-methylazetidin-1-yl)-phenyl |
| 2038. | 4-((R)-2-methylazetidin-1-yl)-phenyl |
| 2039. | 4-(3-fluoroazetidin-1-yl)-phenyl |
| 2040. | 4-(3-methoxyazetidin-1-yl)-phenyl |
| 2041. | 4-(3-hydroxyazetidin-1-yl)-phenyl |
| 2042. | 4-(pyrrolidin-1-yl)-phenyl |
| 2043. | 4-(pyrrolidin-2-yl)-phenyl |
| 2044. | 4-((S)-pyrrolidin-2-yl)-phenyl |
| 2045. | 4-((R)-pyrrolidin-2-yl)-phenyl |
| 2046. | 4-(pyrrolidin-3-yl)-phenyl |
| 2047. | 4-((S)-pyrrolidin-3-yl)-phenyl |
| 2048. | 4-((R)-pyrrolidin-3-yl)-phenyl |
| 2049. | 4-(2-fluoropyrrolidin-1-yl)-phenyl |
| 2050. | 4-((S)-2-fluoropyrrolidin-1-yl)-phenyl |
| 2051. | 4-((R)-2-fluoropyrrolidin-1-yl)-phenyl |
| 2052. | 4-(3-fluoropyrrolidin-1-yl)-phenyl |
| 2053. | 4-((S)-3-fluoropyrrolidin-1-yl)-phenyl |
| 2054. | 4-((R)-3-fluoropyrrolidin-1-yl)-phenyl |
| 2055. | 4-(2,2-difluoropyrrolidin-1-yl)-phenyl |
| 2056. | 4-(3,3-difluoropyrrolidin-1-yl)-phenyl |
| 2057. | 4-(2-methylpyrrolidin-1-yl)-phenyl |
| 2058. | 4-((S)-2-methylpyrrolidin-1-yl)-phenyl |
| 2059. | 4-((R)-2-methylpyrrolidin-1-yl)-phenyl |
| 2060. | 4-(3-methylpyrrolidin-1-yl)-phenyl |
| 2061. | 4-((S)-3-methylpyrrolidin-1-yl)-phenyl |
| 2062. | 4-((R)-3-methylpyrrolidin-1-yl)-phenyl |
| 2063. | 4-(1-methylpyrrolidin-2-yl)-phenyl |
| 2064. | 4-((S)-1-methylpyrrolidin-2-yl)-phenyl |
| 2065. | 4-((R)-1-methylpyrrolidin-2-yl)-phenyl |
| 2066. | 4-(1-methylpyrrolidin-3-yl)-phenyl |
| 2067. | 4-((S)-1-methylpyrrolidin-3-yl)-phenyl |
| 2068. | 4-((R)-1-methylpyrrolidin-3-yl)-phenyl |
| 2069. | 4-(2,2-dimethylpyrrolidin-1-yl)-phenyl |
| 2070. | 4-(3,3-dimethylpyrrolidin-1-yl)-phenyl |
| 2071. | 4-(2-trifluoromethylpyrrolidin-1-yl)-phenyl |
| 2072. | 4-((S)-2-trifluoromethylpyrrolidin-1-yl)-phenyl |
| 2073. | 4-((R)-2-trifluoromethylpyrrolidin-1-yl)-phenyl |
| 2074. | 4-(3-trifluoromethylpyrrolidin-1-yl)-phenyl |
| 2075. | 4-((S)-3-trifluoromethylpyrrolidin-1-yl)-phenyl |
| 2076. | 4-((R)-3-trifluoromethylpyrrolidin-1-yl)-phenyl |
| 2077. | 4-(2-oxopyrrolidin-1-yl)-phenyl |
| 2078. | 4-(2-oxo-oxazolidin-3-yl)-phenyl |
| 2079. | 4-(piperidin-1-yl)-phenyl |
| 2080. | 4-(2-methylpiperidin-1-yl)-phenyl |
| 2081. | 4-((S)-2-methylpiperidin-1-yl)-phenyl |
| 2082. | 4-((R)-2-methylpiperidin-1-yl)-phenyl |
| 2083. | 4-(piperazin-1-yl)-phenyl |
| 2084. | 4-(4-methylpiperazin-1-yl)-phenyl |
| 2085. | 4-(morpholin-4-yl)-phenyl |
| 2086. | 4-(thiomorpholin-4-yl)-phenyl |
| 2087. | 4-(1-oxo-thiomorpholin-4-yl)-phenyl |
| 2088. | 4-(1,1-dioxo-thiomorpholin-4-yl)-phenyl |
| 2089. | 4-(pyrrol-1-yl)-phenyl |
| 2090. | 4-(pyrrol-2-yl)-phenyl |
| 2091. | 4-(pyrrol-3-yl)-phenyl |
| 2092. | 4-(1-methylpyrrol-2-yl)-phenyl |
| 2093. | 4-(1-methylpyrrol-3-yl)-phenyl |
| 2094. | 4-(furan-2-yl)-phenyl |
| 2095. | 4-(furan-3-yl)-phenyl |
| 2096. | 4-(thiophen-2-yl)-phenyl |
| 2097. | 4-(thiophen-3-yl)-phenyl |
| 2098. | 4-(5-propylthien-2-yl)-phenyl |
| 2099. | 4-(pyrazol-1-yl)-phenyl |
| 2100. | 4-(pyrazol-3-yl)-phenyl |

TABLE B-continued

| No. | Ar |
|-----|-----|
| 2101. | 4-(pyrazol-4-yl)-phenyl |
| 2102. | 4-(1-methyl-1H-pyrazol-4-yl)-phenyl |
| 2103. | 4-(1-ethyl-1H-pyrazol-4-yl)-phenyl |
| 2104. | 4-(1-methyl-1H-pyrazol-5-yl)-phenyl |
| 2105. | 4-(1H-imidazol-2-yl)-phenyl |
| 2106. | 4-(imidazol-1-yl)-phenyl |
| 2107. | 4-(1-methylimidazol-2-yl)-phenyl |
| 2108. | 4-(oxazol-2-yl)-phenyl |
| 2109. | 4-(oxazol-4-yl)-phenyl |
| 2110. | 4-(oxazol-5-yl)-phenyl |
| 2111. | 4-(isoxazol-3-yl)-phenyl |
| 2112. | 4-(isoxazol-4-yl)-phenyl |
| 2113. | 4-(isoxazol-5-yl)-phenyl |
| 2114. | 4-([1,2,3]-triazol-1-yl)-phenyl |
| 2115. | 4-([1,2,4]-triazol-1-yl)-phenyl |
| 2116. | 4-([1,2,3]-triazol-2-yl)-phenyl |
| 2117. | 4-(4H-[1,2,4]-triazol-3-yl)-phenyl |
| 2118. | 4-([1,2,4]-triazol-4-yl)-phenyl |
| 2119. | 4-(2H-[1,2,3]-triazol-4-yl)-phenyl |
| 2120. | 4-(4-methyl-4H-[1,2,4]-triazol-3-yl)-phenyl |
| 2121. | 4-(2-methyl-2H-[1,2,3]-triazol-4-yl)-phenyl |
| 2122. | 4-([1,3,4]-oxadiazol-2-yl)-phenyl |
| 2123. | 4-([1,2,4]-oxadiazol-3-yl)-phenyl |
| 2124. | 4-([1,2,4]-oxadiazol-5-yl)-phenyl |
| 2125. | 4-([1,2,3]-oxadiazol-4-yl)-phenyl |
| 2126. | 4-([1,2,3]-oxadiazol-5-yl)-phenyl |
| 2127. | 4-([1,2,3]-thiadiazol-4-yl)-phenyl |
| 2128. | 4-(1H-tetrazol-5-yl)-phenyl |
| 2129. | 4-(tetrazol-1-yl)-phenyl |
| 2130. | 4-(2-methyl-2H-tetrazol-5-yl)-phenyl |
| 2131. | 4-(1-methyl-1H-tetrazol-5-yl)-phenyl |
| 2132. | 4-furazan-3-yl-phenyl |
| 2133. | 4-(pyrid-2-yl)-phenyl |
| 2134. | 4-(pyrid-3-yl)-phenyl |
| 2135. | 4-(pyrid-4-yl)-phenyl |
| 2136. | 4-(pyrimidin-2-yl)-phenyl |
| 2137. | 4-(pyrimidin-4-yl)-phenyl |
| 2138. | 4-(pyrimidin-5-yl)-phenyl |
| 2139. | 5-isopropylthiophen-2-yl |
| 2140. | 2-chlorothiophen-5-yl |
| 2141. | 2,5-dichlorothiophen-4-yl |
| 2142. | 2,3-dichlorothiophen-5-yl |
| 2143. | 2-chloro-3-nitrothiophen-5-yl |
| 2144. | 2-(phenylsulfonyl)-thiophen-5-yl |
| 2145. | 2-(pyridin-2-yl)thiophen-5-yl |
| 2146. | 2-(5-(trifluoromethyl)isoxazol-3-yl)-thiophen-5-yl |
| 2147. | 2-(2-methylthiazol-4-yl)-thiophen-5-yl |
| 2148. | 1-methyl-1H-imidazol-4-yl |
| 2149. | 1,2-dimethyl-1H-imidazol-4-yl |
| 2150. | 3,5-dimethylisoxazol-4-yl |
| 2151. | thiazol-2-yl |
| 2152. | 4-methylthiazol-2-yl |
| 2153. | 4-isopropylthiazol-2-yl |
| 2154. | 4-trifluoromethylthiazol-2-yl |
| 2155. | 5-methylthiazol-2-yl |
| 2156. | 5-isopropylthiazol-2-yl |
| 2157. | 5-trifluoromethylthiazol-2-yl |
| 2158. | 2,4-dimethylthiazol-5-yl |
| 2159. | 2-acetamido-4-methylthiazol-5-yl |
| 2160. | 4H-[1,2,4]triazol-3-yl |
| 2161. | 5-methyl-4H-[1,2,4]triazol-3-yl |
| 2162. | 4-methyl-4H-[1,2,4]triazol-3-yl |
| 2163. | 5-isopropyl-4H-[1,2,4]triazol-3-yl |
| 2164. | 5-trifluoromethyl-4H-[1,2,4]triazol-3-yl |
| 2165. | 4,5-dimethyl-4H-[1,2,4]triazol-3-yl |
| 2166. | 5-isopropyl-4-methyl-4H-[1,2,4]triazol-3-yl |
| 2167. | 5-trifluoromethyl-4-methyl-4H-[1,2,4]triazol-3-yl |
| 2168. | [1,3,4]thiadiazol-2-yl |
| 2169. | 5-methyl-[1,3,4]thiadiazol-2-yl |
| 2170. | 5-isopropyl-[1,3,4]thiadiazol-2-yl |
| 2171. | 5-trifluoromethyl-[1,3,4]thiadiazol-2-yl |
| 2172. | 3-bromo-2-chloropyrid-5-yl |
| 2173. | 2-(4-morpholino)-pyrid-5-yl |
| 2174. | 2-phenoxypyrid-5-yl |
| 2175. | (2-isopropyl)-pyrimidin-5-yl |
| 2176. | (5-isopropyl)-pyrimidin-2-yl |
| 2177. | 8-quinolyl |
| 2178. | 5-isoquinolyl |
| 2179. | 2-(trifluoroacetyl)-1,2,3,4-tetrahydroisoquinolin-7-yl |
| 2180. | 5-chloro-3-methylbenzothiophen-2-yl |
| 2181. | 3,4-dihydro-4-methyl-2H-benzo[b][1,4]oxazinyl |
| 2182. | benzothiazol-6-yl |
| 2183. | benzo[2,1,3]oxadiazol-4-yl |
| 2184. | 5-chlorobenzo[2,1,3]oxadiazol-4-yl |
| 2185. | 7-chlorobenzo[2,1,3]oxadiazol-4-yl |
| 2186. | benzo[2,1,3]thiadiazol-4-yl |
| 2187. | 6-chloroimidazo[2,1-b]thiazolyl |

The compounds of the formula I where $R^3$ and $R^{1a}$ both are hydrogen can be prepared by analogy to methods which are well known in the art. A preferred method for the preparation of compounds I is outlined in scheme 1:

Scheme 1

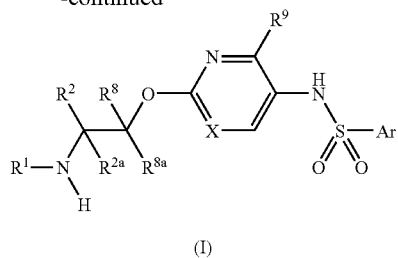

(I)

In scheme 1 $R^1$, $R^2$, $R^{2a}$, $R^8$, $R^{8a}$, $R^9$, X and Ar have the meanings as given above. PG is an amino-protecting group such as tert.-butoxycarbonyl or benzyl. Suitable protecting groups are disclosed, for example, in P. Kocienski, Protecting Groups, Thieme-Verlag, Stuttgart 2000, Chapter 6. Hal is halogen, in particular bromine or chlorine.

According to scheme 1, following standard methods for nucleophilic aromatic substitution reactions, compound II is reacted in step a) with an aminoalcohol VIII in the presence of a base, such as sodium hydride, sodium alkoxide or potassium carbonate in an organic solvent such as dimethylformamide, dioxane or tetrahydrofurane (see e.g. WO 2004/000830).

Alternatively, compounds III can be prepared from compounds II and VIII via palladium-catalyzed reactions described in the literature, for example in J. Am. Chem. Soc. 2001, 123, pp. 10770-10771. One example for a suitable Pd(0) catalyst is Pd(OAc)$_2$ which is customarily used in the presence of a ligand like for example [1,1']binaphthalenyl-2-yl-di-tert-butyl-phosphane in solvents like for example toluene or 1,2-dimethoxy ethane.

The so obtained nitro compound III is reduced in step b) by conventional means to give the corresponding amino compound IV. The required reaction conditions correspond to the customary conditions for reducing aromatic nitro groups which have been described extensively in the literature (see, for example, J. March, Advanced Organic Chemistry, 3rd ed., J. Wiley & Sons, New-York, 1985, p. 1183 and the literature cited in this reference). The reduction is achieved, for example, by reacting the nitro compound III with a metal such as iron, zinc or tin under acidic reaction conditions, i.e. using nascent hydrogen, or using a complex hydride such as lithium aluminum hydride or sodium borohydride, preferably in the presence of transition metal compounds of nickel or cobalt such as NiCl$_2$(P(phenyl)$_3$)$_2$, or COCl$_2$, (see Ono et al. Chem. Ind. (London), 1983 p. 480), or using NaBH$_2$S$_3$ (see Lalancette et al., Can. J. Chem. 49, 1971, p. 2990), with it being possible to carry out these reductions, depending on the given reagent, in substance or in a solvent or diluent. Alternatively, the reduction of III to IV can be carried out with hydrogen in the presence of a transition metal catalyst, e.g. using hydrogen in the presence of catalysts based on platinum, palladium, nickel, ruthenium or rhodium. The catalysts can contain the transition metal in elemental form or in the form of a complex compound, of a salt or of an oxide of the transition metal, with it being possible, for the purpose of modifying the activity, to use customary coligands, e.g. organic phosphine compounds, such as triphenylphosphine, tricyclohexylphosphine or tri-n-butylphosphines or phosphites. The catalyst is customarily employed in quantities of from 0.001 to 1 mol per mol of compound III, calculated as catalyst metal. In a preferred variant, the reduction is effected using tin(II) chloride in analogy with the methods described in Bioorganic and Medicinal Chemistry Letters, 2002, 12(15), pp. 1917-1919 and J. Med. Chem. 2002, 45(21), pp. 4679-4688. The reaction of III with tin(II) chloride is preferably carried out in an inert organic solvent, preferably an alcohol such as methanol, ethanol, isopropanol or butanol.

The thus obtained compound IV is reacted with an arylsulfonylchloride Cl—SO$_2$—Ar, preferably in the presence of a base, according to standard procedures of the art to afford compound V. The reaction depicted in scheme 1 step c) takes place under the reaction conditions which are customary for preparing arylsulfonamide compounds or arylsulfonic esters, respectively, and which are described, for example, in J. March, Advanced Organic Chemistry, 3$^{rd}$ edition, John Wiley & Sons, New York, 1985 p 444 and the literature cited therein, European J. Org. Chem. 2002 (13), pp. 2094-2108, Tetrahedron 2001, 57 (27) pp. 5885-5895, Bioorganic and Medicinal Chemistry Letters, 2000, 10(8), pp. 835-838 and Synthesis 2000 (1), pp. 103-108. The reaction customarily takes place in an inert solvent, for example in an ether, such as diethyl ether, diisopropyl ether, methyl tert-butyl ether or tetrahydrofuran, a halohydrocarbon, such as dichloromethane, an aliphatic or cycloaliphatic hydrocarbon, such as pentane, hexane or cyclohexane, or an aromatic hydrocarbon, such as toluene, xylene, cumene and the like, or in a mixture of the abovementioned solvents. The reaction of IV with Cl—SO$_2$—Ar is customarily carried out in the presence of an auxiliary base. Suitable bases are inorganic bases, such as sodium carbonate or potassium carbonate, or sodium hydrogencarbonate or potassium hydrogencarbonate, and organic bases, for example trialkylamines, such as triethylamine, or pyridine compounds, such as pyridine, lutidine and the like. The latter compounds can at the same time serve as solvents. The auxiliary base is customarily employed in at least equimolar quantities, based on the amine compound IV.

In step d) the protecting group PG is cleaved by conventional means (see e.g. P. Kocienski, Protecting Groups, Thieme-Verlag, Stuttgart 2000, Chapter 6) thereby affording a compound I, wherein $R^{1a}$ is hydrogen.

Scheme 2

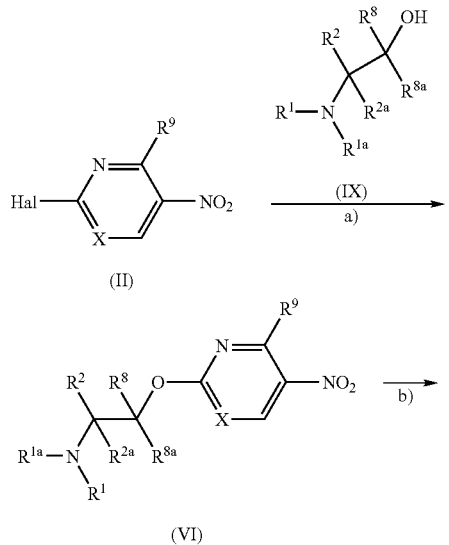

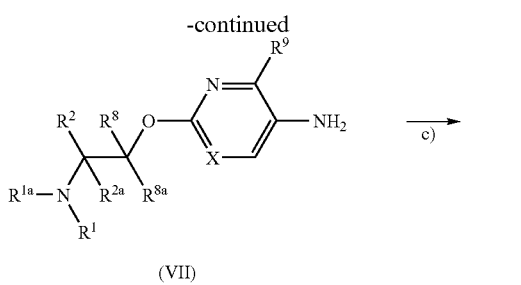

(VII)

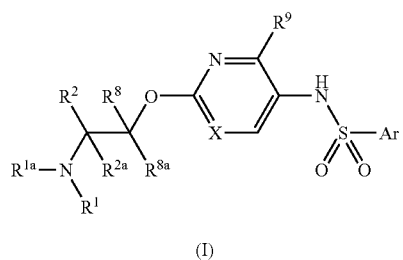

(I)

In scheme 2 is depicted the synthesis of compounds of the formula I where $R^1$, $R^{1a}$, $R^2$, $R^{2a}$, $R^8$, $R^{8a}$, $R^9$, X and Ar have the meanings as given above. Hal is halogen, in particular bromine and chlorine. The reaction steps a), b), and c) to obtain compounds I in scheme 2 follow the reaction steps a), b), and c) described for scheme 1.

The compounds II can be obtained from commercial sources.

Scheme 3

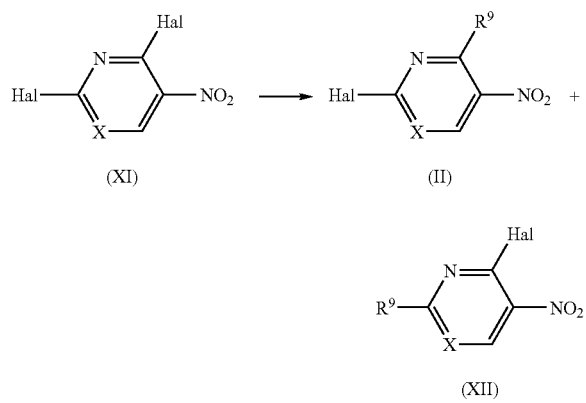

If $R^9$ is alkoxy, compounds II also can be synthesised according to scheme 3. Following standard methods, commercially available compounds XI, wherein Hal is halogen, in particular bromine or chlorine, are reacted with an alkali salt of an alcohol, e.g. sodium or potassium salt of e.g. methanol, ethanol or n-propanol, in the corresponding alcohol as a solvent, e.g. methanol, ethanol or n-propanol. The so obtained mixture of compounds II and XII can be separated for example by means of recrystallizing from a solvent or by means of chromatography to provide the desired compound II.

Protected aminoalcohols VIII are either commercially available or can be obtained from commercially available aminoalcohols by selectively protecting the amino group of these compounds according to standard methods (see e.g. P. Kocienski, Protecting Groups, loc. cit.).

Aminoalcohols IX are either commercially available or can be prepared by analogy to methods which are well known in the art.

A skilled person will also appreciate that compounds of the formula I wherein $R^3$ is different from hydrogen, can be obtained by selective alkylation of the sulfonamide group in the compounds of the formulae V or I.

If $R^1$ or $R^{1a}$ in compound I is (are) allyl the allyl group(s) can be cleaved to obtain a compound I' or I" wherein R is hydrogen. The cleavage of the allyl group is achieved, for example, by reacting I [$R^1$=allyl] with an allyl trapping agent, such as mercaptobenzoic acid or 1,3-dimethylbarbituric acid, in the presence of catalytic quantities of palladium (0) compounds or palladium compounds which are able to form a palladium(0) compound under reaction conditions, e.g. palladium dichloride, tetrakis(triphenylphosphine)palladium(0) or tris(dibenzylideneacetone)dipalladium(0), advantageously in combination with phosphine ligands, e.g. triarylphosphines, such as triphenylphosphine, trialkylphosphines, such as tributylphosphine, and cycloalkylphosphines, such as tricyclohexylphosphine, and especially with phosphine chelate ligands, such as 2,2'-bis(diphenylphosphino)-1,1'-binaphthyl or 1,4-bis(diphenylphosphino)butane, using methods known from the literature (with regard to eliminating N-allyl in the presence of mercaptobenzoic acid, see WO 94/24088; with regard to eliminating in the presence of 1,3-dimethylbarbituric acid, see J. Am. Chem. Soc. 2001, 123 (28), pp. 6801-6808 and J. Org. Chem. 2002, 67(11) pp. 3718-3723). Alternatively, the cleavage of N-allyl can also be effected by reacting in the presence of rhodium compounds, such as tris(triphenylphosphine)chlororhodium(I), using methods known from the literature (see J. Chem. Soc., Perkin Transaction I: Organic and Bio-Organic Chemistry 1999 (21) pp. 3089-3104 and Tetrahedron Asymmetry 1997, 8(20), pp. 3387-3391). If $R^1$ or $R^{1a}$ in compound I is (are) allyl the allyl group can be also converted into a n-propyl group by hydrogenation in the presence of Pd—C as a catalyst.

If not indicated otherwise, the above-described reactions are generally carried out in a solvent at temperatures between room temperature and the boiling temperature of the solvent employed. Alternatively, the activation energy which is required for the reaction can be introduced into the reaction mixture using microwaves, something which has proved to be of value, in particular, in the case of the reactions catalyzed by transition metals (with regard to reactions using microwaves, see Tetrahedron 2001, 57, p. 9199 ff. p. 9225 ff. and also, in a general manner, "Microwaves in Organic Synthesis", André Loupy (Ed.), Wiley-VCH 2002.

The sulfonylchlorides Cl—$SO_2$—Ar are either commercially available or can be prepared according to standard synthetic methods. Sulfonylchlorides containing a fluorinated radical $R^a$ may be prepared by different synthetic routes, e.g. by reacting suitable hydroxy or oxo precursor (e.g. a compound Cl—$SO_2$—Ar, carrying a hydroxy or oxo substituted radical) with fluorinating reagents like DAST (diethylaminosulfurtrifluoride), morpholine-DAST, deoxofluor (bis(2-methoxyethyl)aminosulfur trifluoride), Ishikawa's reagent (N,N-diethyl-(1,1,2,3,3,3-hexafluoropropyl) amine; Journal of Fluorine Chemistry, 1989, 43, 371-377).

More conventionally, the hydroxy group of an aromatic compound which carries a hydroxy substituted radical but not a chlorosulfonyl group, is transformed into a leaving group which is then replaced by a fluoride ion (J. Org. Chem., 1994, 59, 2898-22901; Tetrahedron Letters, 1998, 7305-6; J. Org. Chem., 1998, 63, 9587-9589, Synthesis, 1987, 920-21)). Subsequent direct chlorosulfonylation with chlorosulfonic acid (Heterocycles, 2001, 55, 9, 1789-1803; J. Org. Chem., 2000, 65, 1399-1406) or a two step process preparing first the sulfonic acid derivatives which are then transformed to the sulfonylchlorides with e.g. chlorosulfonic acid, phosphorus pentachloride (Eur. J. Med. Chem., 2002, 36, 809-828) and the like, yields the desired sulfonylchloride (Tetrahedron Letters, 1991, 33, 50 7787-7788). Sulfonylchlorides may also be prepared by diazotation of suitable amine precursor Ar—$NH_2$ with sodium nitrite under acidic conditions and reaction with sulfur dioxide in acetic acid (scheme (iii); J. Org. Chem., 1960, 25, 1824-26;); by oxidation of suitable heteroaryl-thiols HS—Ar or heteroaryl-benzyl-thioethers $C_6H_5$—$CH_2$—S—Ar with chlorine (Synthesis, 1998, 36-38; J. Am. Chem. Soc., 1950, 74, 4890-92;) directly to the corresponding sulfonyl chlorides. The further are known in the art or may be prepared by standard methods. E.g. mercapto-pyrimidines or pyrimidinyl-benzylthioether precursors can e.g. be prepared according to literature (Chemische Berichte, 1960, 1208-11; Chemische Berichte, 1960, 95, 230-235; Collection Czechoslow. Chem. Comm., 1959, 24, 1667-1671; Austr. J. Chem., 1966, 19, 2321-30; Chemiker-Zeitung, 101, 6, 1977, 305-7; Tetrahedron, 2002, 58, 887-890; Synthesis, 1983, 641-645.

A skilled person will readily appreciate that compounds of the formula I can also be obtained from structurally similar compounds by functional group interconversion. In particular N-bound radicals $R^a$ can be introduced into compounds of the formula I by reacting the corresponding halogen compound, i.e. a compound of the formula I, which instead of $R^a$ carries a halogen atom, in particular a bromine or iodine atom, with a primary or secondary amine in the presence of a base, preferably also in the presence of a palladium catalyst in terms of a Buchwald-Hartwig reaction.

In the following schemes 4 to 6 several routes are shown which are suitable to prepare benzenesulfonyl chlorides carrying a fluorinated propyl radical.

The 4-(1,1-difluoropropan-2-yl)benzene-1-sulfonyl chloride intermediate can be prepared from the commercially available 2-phenylpropanoic acid. In the first step a) the 2-phenylpropanoic acid is converted to the alkyl ester by esterification with an alcohol (e.g. methanol or ethanol) under acid catalysis (e.g. HCl, $SO_2Cl_2$). The ester can be reduced to the corresponding 2-phenyl propanal by a reducing agent such as DIBAL (diisobutylaluminium hydride). The aldehyde is converted to the 1,1-difluoro-2-propyl derivative by reaction with a suitable fluorinating reagent like DAST (diethylaminosulfurtrifluoride), morpholine-DAST, deoxofluor (bis(2-methoxyethyl)aminosulfur trifluoride), Ishikawa's reagent (N,N-diethyl-(1,1,2,3,3,3-hexafluoropropyl)amine; Journal of Fluorine Chemistry, 1989, 43, 371-377) (step b). The thus obtained 1,1-difluoro-2-phenylpropane can be converted into 4-(1,1-difluoro-2-propyl)benzenesulfonyl chloride by either direct chlorosulfonylation with chlorosulfonic acid (Heterocycles, 2001, 55, 9, 1789-1803; J. Org. Chem., 2000, 65, 1399-1406) (step c) or by a two step process preparing first the sulfonic acid derivatives (step d) which are then transformed to the sulfonylchlorides (step e) by reaction with e.g. chlorosulfonic acid, phosphorous pentachloride (Eur. J. Med. Chem., 2002, 36, 809-828); through diazotisation of suitable amine precursors with sodium nitrite under acidic conditions and reaction with sulfur dioxide in acetic acid (J. Org. Chem., 1960, 25, 1824-26); oxidation of suitable heteroaryl-thiols or heteroaryl-benzyl-thioethers with chlorine (Synthesis, 1998, 36-38; J. Am. Chem. Soc., 1950, 74, 4890-92) directly to the corresponding sulfonyl chlorides.

The synthesis shown in scheme 4 can also be performed using (R)-2-phenylpropanoic acid and (S)-2-phenylpropanoic acid, respectively, to give the corresponding chiral 4-(1,1-difluoropropan-2-yl)benzene-1-sulfonyl chlorides.

Scheme 5:

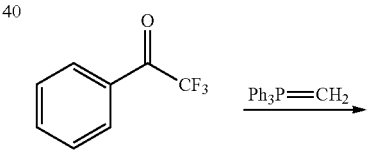

Scheme 4:

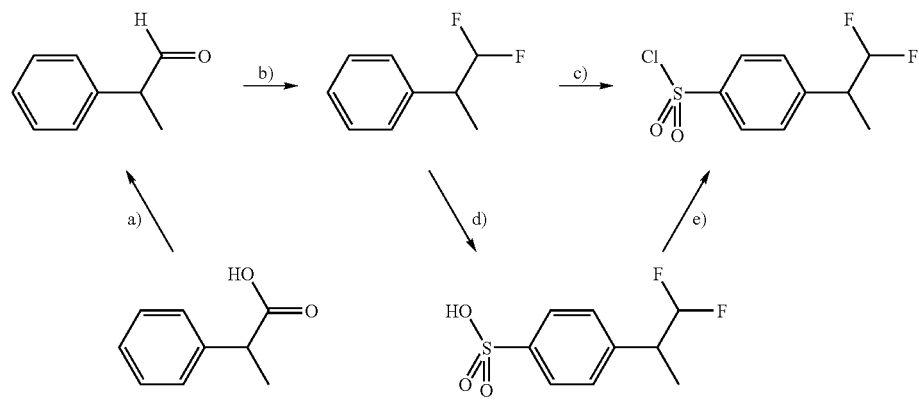

-continued

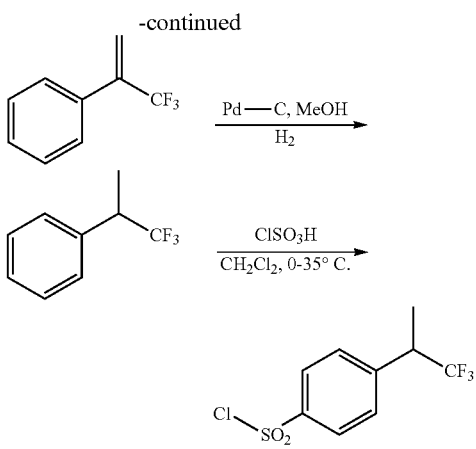

4-(1,1,1-Trifluoropropan-2-yl)benzene-1-sulfonyl chloride intermediate can be prepared from the commercially available 2,2,2-trifluoro-1-phenylethanone by a synthetic route shown in scheme 5. The ketone can be converted to the 3,3,3-trifluoro-2-phenylpropene by a Wittig reaction with a suitable ylide such as methylene-triphenylphosphane (prepared by reaction of methyltriphenylphosphonium halide and a suitable base such as lithium diisopropylamide or potassium tert-butoxide) or according to a Horner-Emmons reaction by reacting the ketone with a suitable phosphonate such as diethyl methylphosphonate and a suitable base such as lithium diisopropylamide or potassium tert-butoxide. The thus obtained 3,3,3-trifluoro-2-phenylpropene can then be reduced to the saturated alkane by catalytic hydrogenation (e.g. Pd—C) followed by conversion to the sulfonyl chloride by the methods described in scheme 4.

The synthesis of scheme 5 can also be performed using a chiral catalyst for the alkene hydrogenation to allow the preparation of the corresponding chiral 4-(1,1,1-triifluoropropan-2-yl)benzene-1-sulfonyl chlorides.

Scheme 6:

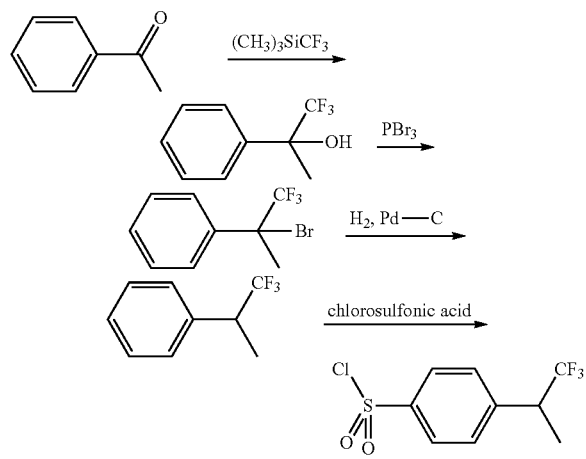

The 4-(1,1,1-trifluoropropan-2-yl)benzene-1-sulfonyl chloride can be also prepared from the commercially available 1-phenyl-ethanone by a four step procedure as shown in scheme 6. The ketone can be converted to the trifluoromethyl hydroxyl intermediate by reaction with trimethyl-trifluoromethyl-silane (Journal of Organic Chemistry, 2000, 65, 8848-8856; Journal of Fluorine Chemistry, 2003, 122, 243-246) which can then be converted to the trifluoromethyl bromide (Journal of the American Chemical Society, 1987, 109, 2435-4). Dehalogenation by catalytic hydrogenation (e.g. Pd—C) can then be followed by conversion to the sulfonyl chloride by the methods discussed above.

Examples of solvents which can be used are ethers, such as diethyl ether, diisopropyl ether, methyl tert-butyl ether or tetrahydrofuran, aprotic polar solvent, such as dimethylformamide, dimethyl sulfoxide, dimethoxyethane, and acetonitrile, aromatic hydrocarbons, such as toluene and xylene, ketones, such as acetone or methyl ethyl ketone, halohydrocarbons, such as dichloromethane, trichloromethane and dichloroethane, esters, such as ethyl acetate and methyl butyrate, carboxylic acids, such as acetic acid or propionic acid, and alcohols, such as methanol, ethanol, n-propanol, isopropanol, n-butanol, isobutanol, 2-butanol and tert.-butanol.

If desired, it is possible for a base to be present in order to neutralize protons which are released in the reactions. Suitable bases include inorganic bases, such as sodium carbonate, potassium carbonate, sodium hydrogen carbonate or potassium hydrogen carbonate, and, in addition, alkoxides, such as sodium methoxide or sodium ethoxide, alkali metal hydrides, such as sodium hydride, and also organometallic compounds, such as butyllithium compounds or alkylmagnesium compounds, or organic nitrogen bases, such as triethylamine or pyridine. The latter compounds can at the same time serve as solvents.

The crude product is isolated in a customary manner, for example by filtering, distilling off the solvent or extracting from the reaction mixture, etc. The resulting compounds can be purified in a customary manner, for example by means of recrystallizing from a solvent, by means of chromatography or by means of converting into an acid addition salt.

The acid addition salts are prepared in a customary manner by mixing the free base with a corresponding acid, where appropriate in solution in an organic solvent, for example a lower alcohol, such as methanol, ethanol or propanol, an ether, such as methyl tert-butyl ether or diisopropyl ether, a ketone, such as acetone or methyl ethyl ketone, or an ester, such as ethyl acetate.

The compounds according to the invention of the formula I are surprisingly highly selective dopamine $D_3$ receptor ligands which, because of their low affinity for other receptors such as $D_1$ receptors, $D_4$ receptors, α1-adrenergic and/or α2-adrenergic receptors, muscarinergic receptors, histamine receptors, opiate receptors and, in particular, dopamine $D_2$ receptors, give rise to fewer side-effects than do the classic neuroleptics, which are $D_2$ receptor antagonists. A compound of the invention can be a dopamine $D_3$ receptor agonist, including partial agonistic activity, or a dopamine $D_3$ receptor antagonist, including partial antagonistic activity.

The high affinity of the compounds according to the invention for $D_3$ receptors is reflected in very low in-vitro receptor binding constants ($K_i(D_3)$ values) of as a rule less than 50 nM (nmol/l), preferably of less than 10 nM and, in particular of less than 5 nM. The displacement of [$^{125}$I]-iodosulpride can, for example, be used in receptor binding studies for determining binding affinities for $D_3$ receptors.

The selectivity of the compounds according to the invention, i.e. the ratio $K_i(D_2)/K_i(D_3)$ of the receptor binding constants, is as a rule at least 50, preferably at least 100, even better at least 150. The displacement of [$^3$H]SCH23390, [$^{125}$I] iodosulpride or [$^{125}$I] spiperone can be used, for example, for carrying out receptor binding studies on $D_1$, $D_2$ and $D_4$ receptors.

Because of their binding profile, the compounds can be used for treating diseases which respond to dopamine $D_3$ receptor ligands (or which are susceptible to treatment with a dopamine $D_3$ receptor ligand, respectively), i.e. they are effective for treating those medical disorders or diseases in which exerting an influence on (modulating) the dopamine $D_3$ receptors leads to an improvement in the clinical picture or to the disease being cured. Examples of these diseases are disorders or diseases of the central nervous system.

Disorders or diseases of the central nervous system are understood as meaning disorders which affect the spinal chord and, in particular, the brain. Within the meaning of the invention, the term "disorder" denotes disturbances and/or anomalies which are as a rule regarded as being pathological conditions or functions and which can manifest themselves in the form of particular signs, symptoms and/or malfunctions. While the treatment according to the invention can be directed toward individual disorders, i.e. anomalies or pathological conditions, it is also possible for several anomalies, which may be causatively linked to each other, to be combined into patterns, i.e. syndromes, which can be treated in accordance with the invention.

The disorders which can be treated in accordance with the invention are, in particular, psychiatric and neurological disturbances. These disturbances include, in particular, organic disturbances, including symptomatic disturbances, such as psychoses of the acute exogenous reaction type or attendant psychoses of organic or exogenous cause, e.g., in association with metabolic disturbances, infections and endocrinopathogies; endogenous psychoses, such as schizophrenia and schizotype and delusional disturbances; affective disturbances, such as depressions, mania and/or manic-depressive conditions; and also mixed forms of the above-described disturbances; neurotic and somatoform disturbances and also disturbances in association with stress; dissociative disturbances, e.g. loss of consciousness, clouding of consciousness, double consciousness and personality disturbances; disturbances in attention and waking/sleeping behavior, such as behavioral disturbances and emotional disturbances whose onset lies in childhood and youth, e.g. hyperactivity in children, intellectual deficits, in particular attention disturbances (attention deficit disorders), memory disturbances and cognitive disturbances, e.g. impaired learning and memory (impaired cognitive function), dementia, narcolepsy and sleep disturbances, e.g. restless legs syndrome; development disturbances; anxiety states, delirium; sexlife disturbances, e.g. impotence in men; eating disturbances, e.g. anorexia or bulimia; addiction; and other unspecified psychiatric disturbances.

The disorders which can be treated in accordance with the invention also include Parkinson's disease and epilepsy and, in particular, the affective disturbances connected thereto.

The addiction diseases include psychic disorders and behavioral disturbances which are caused by the abuse of psychotropic substances, such as pharmaceuticals or narcotics, and also other addiction diseases, such as addiction to gaming (impulse control disorders not elsewhere classified). Examples of addictive substances are: opioids (e.g. morphine, heroin and codeine), cocaine; nicotine; alcohol; substances which interact with the GABA chloride channel complex, sedatives, hypnotics and tranquilizers, for example benzodiazepines; LSD; cannabinoids; psychomotor stimulants, such as 3,4-methylenedioxy-N-methylamphetamine (ecstasy); amphetamine and amphetamine-like substances such as methylphenidate and other stimulants including caffeine. Addictive substances which come particularly into consideration are opioids, cocaine, amphetamine or amphetamine-like substances, nicotine and alcohol.

With regard to the treatment of addiction diseases, particular preference is given to those compounds according to the invention of the formula I which themselves do not possess any psychotropic effect. This can also be observed in a test using rats, which, after having been administered compounds which can be used in accordance with the invention, reduce their self administration of psychotropic substances, for example cocaine.

According to another aspect of the present invention, the compounds according to the invention are suitable for treating disorders whose causes can at least partially be attributed to an anomalous activity of dopamine $D_3$ receptors.

According to another aspect of the present invention, the treatment is directed, in particular, toward those disorders which can be influenced, within the sense of an expedient medicinal treatment, by the binding of preferably exogeneously administered binding partners (ligands) to dopamine $D_3$ receptors.

The diseases which can be treated with the compounds according to the invention are frequently characterized by progressive development, i.e. the above-described conditions change over the course of time; as a rule, the severity increases and conditions may possibly merge into each other or other conditions may appear in addition to those which already exist.

The compounds according to the invention can be used to treat a large number of signs, symptoms and/or malfunctions which are connected with the disorders of the central nervous system and, in particular, the abovementioned conditions. These signs, symptoms and/or malfunctions include, for example, a disturbed relationship to reality, lack of insight and ability to meet customary social norms or the demands made by life, changes in temperament, changes in individual drives, such as hunger, sleep, thirst, etc., and in mood, disturbances in the ability to observe and combine, changes in personality, in particular emotional lability, hallucinations, ego-disturbances, distractedness, ambivalence, autism, depersonalization and false perceptions, delusional ideas, chanting speech, lack of synkinesia, short-step gait, flexed posture of trunk and limbs, tremor, poverty of facial expression, monotonous speech, depressions, apathy, impeded spontaneity and decisiveness, impoverished association ability, anxiety, nervous agitation, stammering, social phobia, panic disturbances, withdrawal symptoms in association with dependency, maniform syndromes, states of excitation and confusion, dysphoria, dyskinetic syndromes and tic disorders, e.g. Huntington's chorea and Gilles-de-la-Tourette's syndrome, vertigo syndromes, e.g. peripheral positional, rotational and oscillatory vertigo, melancholia, hysteria, hypochondria and the like.

Within the meaning of the invention, a treatment also includes a preventive treatment (prophylaxis), in particular as relapse prophylaxis or phase prophylaxis, as well as the treatment of acute or chronic signs, symptoms and/or malfunctions. The treatment can be orientated symptomatically, for example as the suppression of symptoms. It can be effected over a short period, be orientated over the medium term or can be a long-term treatment, for example within the context of a maintenance therapy.

Therefore the compounds according to the invention are preferentially suitable for treating diseases of the central nervous system, in particular for treating affective disorders; neurotic disturbances, stress disturbances and somatoform disturbances and psychoses, and, in particular, for treating schizophrenia and depression. Because of their high selectivity with regard to the D₃ receptor, the compounds I according to the invention are also suitable for treating disturbances of kidney function, in particular disturbances of kidney function which are caused by diabetes mellitus (see WO 00/67847) and, especially, diabetic nephropathy.

Particularly, the compounds of the invention are suitable for treating following disorders: Parkinson's disease, schizophrenia, cognitive disturbances, depression, anxiety, addiction, kidney function disturbances, eating disturbances and epilepsy.

Within the context of the treatment, the use according to the invention of the described compounds involves a method. In this method, an effective quantity of one or more compounds, as a rule formulated in accordance with pharmaceutical and veterinary practice, is administered to the individual to be treated, preferably a mammal, in particular a human being, productive animal or domestic animal. Whether such a treatment is indicated, and in which form it is to take place, depends on the individual case and is subject to medical assessment (diagnosis) which takes into consideration signs, symptoms and/or malfunctions which are present, the risks of developing particular signs, symptoms and/or malfunctions, and other factors.

As a rule, the treatment is effected by means of single or repeated daily administration, where appropriate together, or alternating, with other active compounds or active compound-containing preparations such that a daily dose of preferably from about 0.1 to 1000 mg/kg of bodyweight, in the case of oral administration, or of from about 0.1 to 100 mg/kg of bodyweight, in the case of parenteral administration, is supplied to an individual to be treated.

The invention also relates to the production of pharmaceutical compositions for treating an individual, preferably a mammal, in particular a human being, productive animal or domestic animal. Thus, the ligands are customarily administered in the form of pharmaceutical compositions which comprise a pharmaceutically acceptable excipient together with at least one compound according to the invention and, where appropriate, other active compounds. These compositions can, for example, be administered orally, rectally, transdermally, subcutaneously, intravenously, intramuscularly or intranasally.

Examples of suitable pharmaceutical formulations are solid medicinal forms, such as powders, granules, tablets, in particular film tablets, lozenges, sachets, cachets, sugar-coated tablets, capsules, such as hard gelatin capsules and soft gelatin capsules, suppositories or vaginal medicinal forms, semisolid medicinal forms, such as ointments, creams, hydrogels, pastes or plasters, and also liquid medicinal forms, such as solutions, emulsions, in particular oil-in-water emulsions, suspensions, for example lotions, injection preparations and infusion preparations, and eyedrops and eardrops. Implanted release devices can also be used for administering inhibitors according to the invention. In addition, it is also possible to use liposomes or microspheres.

When producing the compositions, the compounds according to the invention are optionally mixed or diluted with one or more excipients. Excipients can be solid, semisolid or liquid materials which serve as vehicles, carriers or medium for the active compound.

Suitable excipients are listed in the specialist medicinal monographs. In addition, the formulations can comprise pharmaceutically acceptable carriers or customary auxiliary substances, such as glidants; wetting agents; emulsifying and suspending agents; preservatives; antioxidants; antiirritants; chelating agents; coating auxiliaries; emulsion stabilizers; film formers; gel formers; odor masking agents; taste corrigents; resin; hydrocolloids; solvents; solubilizers; neutralizing agents; diffusion accelerators; pigments; quaternary ammonium compounds; refatting and overfatting agents; raw materials for ointments, creams or oils; silicone derivatives; spreading auxiliaries; stabilizers; sterilants; suppository bases; tablet auxiliaries, such as binders, fillers, glidants, disintegrants or coatings; propellants; drying agents; opacifiers; thickeners; waxes; plasticizers and white mineral oils. A formulation in this regard is based on specialist knowledge as described, for example, in Fiedler, H. P., Lexikon der Hilfsstoffe für Pharmazie, Kosmetik und angrenzende Gebiete [Encyclopedia of auxiliary substances for pharmacy, cosmetics and related fields], 4$^{th}$ edition, Aulendorf: ECV-Editio-Kantor-Verlag, 1996.

The following examples serve to explain the invention without limiting it.

The compounds were either characterized via proton-NMR in d₆-dimethylsulfoxid or d-chloroform, if not stated otherwise, on a 400 MHz or 500 MHz NMR instrument (Bruker AVANCE), or by mass spectrometry, generally recorded via HPLC-MS in a fast gradient on C18-material (electrospray-ionisation (ESI) mode), or melting point.

The magnetic nuclear resonance spectral properties (NMR) refer to the chemical shifts (δ) expressed in parts per million (ppm). The relative area of the shifts in the $^1$H NMR spectrum corresponds to the number of hydrogen atoms for a particular functional type in the molecule. The nature of the shift, as regards multiplicity, is indicated as singlet (s), broad singlet (s. br.), doublet (d), broad doublet (d br.), triplet (t), broad triplet (t br.), quartet (q), quintet (quint.) and multiplet (m).

PREPARATION EXAMPLES

I. Intermediates a. [2-(5-Amino-6-methoxy-pyridin-2-yloxy)-ethyl]-propyl-carbamic Acid Tert-Butyl Ester a.1 [2-(6-Methoxy-5-nitro-pyridin-2-yloxy)-ethyl]-propyl-carbamic Acid Tert-Butyl Ester A mixture of 6-bromo-2-methoxy-3-nitropyridine (5 g, 21.46 mmol), (2-hydroxy-ethyl)-propyl-carbamic acid tert-butyl ester (4.36 g, 21.46 mmol) and K₂CO₃ (2.97 g, 21.46 mmol) in dimethylformamide (DMF) (60 ml) was stirred at room temperature for 24 h and at 40° C. for 4 h. After evaporation of the solvent under reduced pressure the residue was purified by silica gel chromatography with dichloromethane/methanol (10:0; 9:1; 7:3; 0:10) as eluent to provide 2.81 g (36.9%) of the product.

MS (ESI) m/z: 356.25 [M+H(—BOC)]⁺ a.2 [2-(5-Amino-6-methoxy-pyridin-2-yloxy)-ethyl]-propyl-carbamic Acid Tert-Butyl Ester A mixture of [2-(6-methoxy-5-nitro-pyridin-2-yloxy)-ethyl]-propyl-carbamic acid tert-butyl ester (1.12 g, 3.16 mmol) and 10% palladium on charcoal (0.34 g, 0.316 mmol) in ethanol (80 ml) was hydrogenated at atmospheric pressure until the consumption of hydrogen was complete. After filtration and evaporation of the solvent under reduced pressure 960 mg (93.5%) of the title compound were obtained.

MS (ESI) m/z: 326.25 [M+H]⁺ b. 6-(1-Benzyl-pyrrolidin-3-yloxy)-2-methoxy-pyridin-3-ylamine b.1 6-(1-Benzyl-pyrrolidin-3-yloxy)-2-methoxy-3-nitro-pyridine

A mixture of 6-bromo-2-methoxy-3-nitropyridine (1.5 g, 6.44 mmol), 1-benzyl-pyrrolidin-3-ol (1.14 g, 6.44 mmol) and $K_2CO_3$ (0.89 g, 6.44 mmol) in dimethylformamide (DMF) (20 ml) was stirred at room temperature for 24 h and at 40° C. for 4 h. After evaporation of the solvent under reduced pressure the residue was purified by silica gel chromatography with dichloromethane/methanol (10:0; 9:1; 7:3; 0:10) as eluent to provide 380 mg (18.1%) of the product.
MS (ESI) m/z: 330.15 [M+H]$^+$ b.2 6-(1-Benzyl-pyrrolidin-3-yloxy)-2-methoxy-pyridin-3-ylamine

To a solution of 6-(1-benzyl-pyrrolidin-3-yloxy)-2-methoxy-3-nitro-pyridine (0.38 g, 1.15 mmol) in acetic acid (4 ml) at 80° C. was added iron (0.32 g, 5.77 mmol) slowly in portions. The exothermic reaction was stirred for 3 h at 80° C. After evaporation of the solvent under reduced pressure the solid residue was dissolved in 1N NaOH, which was extracted 6 times with dichloromethane. The combined organic layers were dried over $MgSO_4$, filtered and the solvent evaporated to obtain 240 mg (68.9%) of the title compound.
MS (ESI) m/z: 300.15 [M+H]$^+$ c. 2-Methoxy-6-(2-pyrrolidin-1-yl-ethoxy)-pyridin-3-ylamine

The desired product was obtained following the synthetic procedure analogous to that described for the preparation of intermediate a. starting from 6-bromo-2-methoxy-3-nitropyridine and 2-pyrrolidin-1-yl-ethanol.
MS (ESI) m/z: 268.15 [M+H]$^+$ d. [2-(5-Amino-4-methoxy-pyrimidin-2-yloxy)-ethyl]-propyl-carbamic Acid Tert-Butyl Ester d.1 2-Chloro-4-methoxy-5-nitro-pyrimidine

To a solution of 2,4-dichloro-5-nitropyrimidine (10 g, 51.55 mmol) in methanol (150 ml) at −10° C. a solution of potassium methanolate (3.62 g, 51.55 mmol) in methanol (150 ml) was added over a period of 10 minutes. The mixture was allowed to warm to 0° C. and the solvent was evaporated under reduced pressure at 30° C. The residue was purified by silica gel chromatography with n-heptane/ethyl acetate (3:1) as eluent affording 3.7 g (37.9%) of the title compound. 1.34 g (13.7%) 4-chloro-2-methoxy-5-nitropyrimidine was obtained as a side product
MS (ESI) m/z: 196.15 [M+H]$^+$ d.2 [2-(4-Methoxy-5-nitro-pyrimidin-2-yloxy)-ethyl]-propyl-carbamic acid tert-butyl ester To a solution of (2-hydroxy-ethyl)-propyl-carbamic acid tert-butyl ester (1.07 g, 5.28 mmol) in THF (40 ml) at 0° C. was added NaH (0.25 g, 5.80 mmol). After stirring the suspension at 0° C. for 30 minutes a solution of 2-chloro-4-methoxy-5-nitropyrimidine (1 g, 5.28 mmol) in THF (10 ml) was added and the mixture was stirred at room temperature for 16 h. The mixture was added to water, which was extracted three times with dichloromethane. The combined organic layers were dried over $MgSO_4$, filtered and concentrated under reduced pressure to obtain the title compound.
MS (ESI) m/z: 357.15 [M+H]$^+$ d.3 [2-(5-Amino-4-methoxy-pyrimidin-2-yloxy)-ethyl]-propyl-carbamic Acid Tert-Butyl Ester To a mixture of crude [2-(4-methoxy-5-nitro-pyrimidin-2-yloxy)-ethyl]-propyl-carbamic acid tert-butyl ester (1.76 g, 4.94 mmol) and 10% palladium on charcoal (200 mg) in water (15 ml) was slowly added a solution of ammonium formate (3.12 g, 49.44 mmol) in water (10 ml) at 80° C. After stirring for 1 h at 80° C. the mixture was filtered and concentrated under reduced pressure. The aqueous layer was extracted three times with dichloromethane. The combined organic layers were dried over $MgSO_4$, filtered and the solvent was evaporated under reduced pressure. The residue was purified by silica gel chromatography with toluene/THF/MeOH (4:1:1)/2.5% triethylamine to give 720 mg (44.7%) of the title compound.
MS (ESI) m/z: 327.15 [M+H]$^+$ e. 6-(2-Dimethylamino-ethoxy)-pyridin-3-ylamine

The desired product was obtained following the synthetic procedure analogous to that described for the preparation of intermediate a. starting from 2-chloro-5-nitropyridine and 2-dimethylaminoethanol.
MS (ESI) m/z: 182.15 [M+H]$^+$ f. [2-(5-Amino-pyridin-2-yloxy)-ethyl]-propyl-carbamic Acid Tert-Butyl Ester The desired product was obtained following the synthetic procedure analogous to that described for the preparation of intermediate a. starting from 2-chloro-5-nitropyridine and (2-hydroxy-ethyl)-propyl-carbamic acid tert-butyl ester.
MS (ESI) m/z: 326.15 [M+H]$^+$ g. 4-((S)-2-Fluoro-1-methyl-ethyl)-benzenesulfonyl Chloride g.1 Toluene-4-sulfonic Acid (S)-2-phenyl-propyl Ester

To a solution of 20 g of (S)-(−)-2-phenyl-1-propanol in 240 ml of dichloromethane were added in portions 28 g of p-toluenesulfonyl chloride (146.8 mmol). After stirring for 18 h at room temperature, the organic phase was washed with 100 ml of water, dried over magnesium sulfate, filtered, and the solvent was evaporated under reduced pressure to yield 43 g of the title compound.
$^1$H-NMR (CDCl$_3$, 400 MHz): δ [ppm] 7.65 (d, 2H), 7.15-7.3 (m, 5H), 7.1 (d, 2H), 4.0-4.1 (m, 2H), 3.1 (m, 1H), 2.4 (s, 3H), 1.3 (d, 3H).

g.2 ((S)-2-Fluoro-1-methyl-ethyl)-benzene 9.62 g of toluene-4-sulfonic acid (S)-2-phenyl-propyl ester (33.13 mmol) were dissolved in 80 ml of polyethylenglycol 400. 9.62 g of potassium fluoride (165.6 mmol) were added and the reaction mixture was stirred at 50° C. for 3 days and another 2 days at 55-70° C. The reaction was treated with 150 ml of saturated aqueous sodium chloride solution, extracted three times with diethyl ether, and the combined organic layers were dried over magnesium sulfate, filtered, and the solvent was evaporated under reduced pressure. The crude product was purified via silica gel chromatography using cyclohexyane/ethyl acetate 15% as eluent. 2.85 g of the desired product were isolated, containing ~25% of the elimination side product.

$^1$H-NMR (CDCl$_3$, 400 MHz): δ [ppm] 7.2-7.4 (m, 5H), 4.3-4.6 (several m, 2H), 3.15 (m, 1H). 1.3 (m, 3H).

g.3 4-((S)-2-Fluoro-1-methyl-ethyl)-benzenesulfonyl Chloride 3.5 g of ((S)-2-fluoro-1-methyl-ethyl)-benzene (25.32 mmol) were dissolved in 80 ml of dichloromethane. At 0-5° C., 11.81 g of chlorosulfonic acid (101.31 mmol), dissolved in 20 ml of dichloromethane, were added dropwise. The reaction mixture was stirred for 30 min at room temperature and 2 h at 30° C. The solvent was evaporated. 150 ml of diethyl ether were added to the residue, washed once with 150 ml of water, and the organic layer was dried over magnesium sulfate, filtered, and the solvent was evaporated under reduced pressure. The crude product was purified via silica gel chromatography with n-heptane-dichloromethane (6:4) as eluent to give 1.5 g of the title compound.

$^1$H-NMR (CDCl$_3$, 400 MHz): δ [ppm] 8.0 (d, 2H), 7.5 (d, 2H), 4.5 (dd, 2H), 3.25 (m, 1H), 1.4 (d, 3H).

h. 4-((R)-2-Fluoro-1-methyl-ethyl)-benzenesulfonyl Chloride h.1 Toluene-4-sulfonic Acid (R)-2-phenyl-propyl Ester

Following the procedure analogous to that used for the synthesis of toluene-4-sulfonic acid (S)-2-phenyl-propyl ester, but using (R)-2-phenyl-1-propanol as starting compound, the title compound was prepared.

h.2 ((R)-2-Fluoro-1-methyl-ethyl)-benzene

The title compound was prepared as described above for the synthesis of ((S)-2-fluoro-1-methyl-ethyl)-benzene, but using toluene-4-sulfonic acid (R)-2-phenyl-propyl ester instead of toluene-4-sulfonic acid (S)-2-phenyl-propyl ester.

$^1$H-NMR (CDCl$_3$, 400 MHz): δ [ppm] 7.2-7.4 (m, 5H), 4.3-4.6 (several m, 2H), 3.15 (m, 1H). 1.3 (m, 3H).

h.3 4-((R)-2-Fluoro-1-methyl-ethyl)-benzenesulfonyl chloride 1.3 g of ((R)-2-fluoro-1-methyl-ethyl)-benzene (9.4 mmol) were dissolved in 50 ml of dichloromethane. At 0-5° C., 1.1 g of chlorosulfonic acid (9.4 mmol), dissolved in 10 ml of dichloromethane were added dropwise. The reaction mixture was stirred for 20 min at 0-5° C. and then added to a solution of 2.15 g of phosphorous pentachloride dissolved in 40 ml of dichloromethane. The reaction mixture was stirred for 30 min at 0-5° C. and 1 h at room temperature. The solvent was evaporated, 100 ml of diethyl ether were added, the mixture was washed once with 150 ml of water, and the organic layer was dried over magnesium sulfate, filtered, and the solvent was evaporated under reduced pressure. The crude product was purified via silica gel chromatography with n-heptane-dichloromethane (1:1) as eluent to give 0.261 g of the title compound.

$^1$H-NMR (CDCl$_3$, 400 MHz): δ [ppm] 8.0 (d, 2H), 7.5 (d, 2H), 4.5 (dd, 2H), 3.25 (m, 1H), 1.4 (d, 3H).

i. 4-(2-Fluoro-1-methyl-ethyl)-benzenesulfonyl Chloride

Following the procedures analogous to that used for the preparation of 4-((S)-2-fluoro-1-methyl-ethyl)-benzenesulfonyl chloride, but starting with 2-phenyl-1-propanol in step a.3.g.1, the title compound was prepared.

$^1$H-NMR (CDCl$_3$, 400 MHz): δ [ppm] 8.0 (d, 2H), 7.5 (d, 2H), 4.5 (dd, 2H), 3.25 (m, 1H), 1.4 (d, 3H).

k. 4-(3-Fluoropropyl)-benzenesulfonyl Chloride k.1 (3-Fluoropropyl)-benzene 15.6 g of diethylaminosulfurtrifluoride (DAST, 96.91 mmol) were dissolved in 18 ml of dichloromethane. At 0-5° C., 12 g of 3-phenyl-1-propanol (88.1 mmol) dissolved in 30 ml of dichloromethane were added dropwise. The reaction mixture was stirred for 18 h, and, after addition of 30 ml of dichloromethane, poured onto 100 ml of ice water. The organic layer was separated, dried over magnesium sulfate, filtered, and the solvent was evaporated. The crude product was purified by distillation at a bath temperature of 106° C. at 20 mm to yield 7.4 g of the title compound.

$^1$H-NMR (CDCl$_3$, 400 MHz): δ [ppm] 7.1-7.3 (m, 5H), 4.4 (dt, 2H), 2.7 (m, 2H). 2.0 (m, 2H).

k.2 4-(3-Fluoropropyl)-benzenesulfonyl Chloride 4.1 g of (3-fluoro-propyl)-benzene (29.67 mmol) were dissolved in 40 ml of dichloromethane. At 0-5° C., 6.91 g of chlorosulfonic acid (59.34 mmol), dissolved in 10 ml of dichloromethane, were added dropwise. The reaction mixture was stirred for 45 min at 0-5° C. and then added to a solution of 6.8 g of phosphorous pentachloride (32.63 mmol) dissolved in 50 ml of dichloromethane. The reaction mixture was stirred for 1 h at 5-10° C. The solvent was evaporated, 150 ml of diethyl ether were added, the solution was washed once with 150 ml of ice water, and the organic layer was dried over magnesium sulfate, filtered, and the solvent was evaporated under reduced pressure. The crude product was purified via silica gel chromatography with n-heptane-dichloromethane (11:9) as eluent to give 5.5 g of the title compound.

$^1$H-NMR (CDCl$_3$, 400 MHz): δ [ppm] 7.95 (d, 2H), 7.45 (d, 2H), 4.5 (dt, 2H), 2.9 (t, 2H), 2.05 (m, 2H).

m. 4-(2-Fluoroethyl)-benzenesulfonyl Chloride m.1 (2-Fluoroethyl)-benzene 6.8 g of the title compound were obtained from commercially available 2-phenyl-ethanol following the procedure used for the synthesis of (3-fluoropropyl)-benzene.

$^1$H-NMR (CDCl$_3$, 400 MHz): δ [ppm] 7.1-7.3 (m, 5H), 4.6 (m, 1H), 4.45 (m, 1H), 2.95 (m, 1H), 2.9 (m, 1H).

m.2 4-(2-Fluoroethyl)-benzenesulfonyl Chloride 3.55 g were obtained following the procedure used for the synthesis of 4-((R)-2-fluoro-1-methyl-ethyl)-benzenesulfonyl chloride.

$^1$H-NMR (CDCl$_3$, 400 MHz): δ [ppm] 8.0 (d, 2H), 7.5 (d, 2H), 4.7 (dt, 2H), 3.05-3.2 (dt, 2H).

n. 4-(1,1,1-Trifluoropropan-2-yl)benzenesulfonyl Chloride and 2-(1,1,1-trifluoropropan-2-yl)benzenesulfonyl Chloride Prepared on a 14 g scale following the procedure outlined in Scheme 5. 2-(1,1,1-Trifluoropropan-2-yl)benzenesulfonyl chloride is a by-product of the reaction.
4-(1,1,1-Trifluoropropan-2-yl)benzenesulfonyl chloride:
MS (ESI) m/z: 273.1 [M+H]$^+$
$^1$H-NMR (DMSO-d$_6$): δ [ppm] 7.62 (d, 2H), 7.33 (d, 2H), 3.81 (m, 1H), 1.42 (d, 3H).
2-(1,1,1-Trifluoropropan-2-yl)benzenesulfonyl chloride:
MS (ESI) m/z: 273.1 [M+H]$^+$ o. 4-Oxazol-4-yl-benzenesulfonyl Chloride

A solution of 2-bromo-1-phenyl-ethanone (40 g, 201 mmol) and ammonium formiate (44.35 g, 703 mmol) in formic acid (75 ml) was heated to reflux for 2 h. The reaction mixture was evaporated under reduced pressure, and the residue was added to water, which was extracted three times with dichloromethane. The crude product was purified by silica gel chromatography using ethyl acetate/heptane (0:10; 1:9) as eluent. At 0° C., 4-pPhenyloxazole (3 g, 20.67 mmol) was added slowly to 24.08 g of chlorosulfonic acid (206.67 mmol). The reaction mixture was stirred for 20 min at 0-5° C. and then warmed to room temperature, and finally stirred at 45° C. for 2 h. The reaction mixture was then added cautiously (!) to ice water. The precipitate was filtered, washed with water and dried in a vacuum oven at 30° C. to give the title compound (4.3 g, 76.8%).
MS (ESI) m/z: 240.15 [M+H]$^+$ (4-Oxazol-4-yl-benzenesulfonic acid methyl ester)

p. 6-[2-(Benzyl-propyl-amino)-ethoxy]-2-methoxy-pyridin-3-ylamine p.1 Benzyl-[2-(6-methoxy-5-nitro-pyridin-2-yloxy)-ethyl]-propyl-amine

To a mixture of Pd(OAc)$_2$ (112 mg, 0.5 mmol) and [1,1'] binaphthalen-2-yl-di-tert-butyl-phosphane (30 mg, 0.75 mmol) in toluene (40 ml) was added 6-bromo-2-methoxy-3-pyridine (2.92 g, 12.54 mmol), Cs$_2$CO$_3$ (20.4 g, 62.68 mmol), and 2-(benzyl-propyl-amino)-ethanol (3.63 g, 18.8 mmol). The mixture was stirred under nitrogen at room temperature for 24 h.
After evaporation of the solvent under reduced pressure the residue was dissolved in water and extracted five times with dichloromethane. The residue was purified by silica gel chromatography with n-heptane/dichloromethane (10:0; 7:3; 0:10) as eluent to provide 2.92 g (67.3%) of the product.
MS (ESI) m/z: 346.15 [M+H]$^+$ p.2 6-[2-(Benzyl-propyl-amino)-ethoxy]-2-methoxy-pyridin-3-ylamine

To a solution of benzyl-[2-(6-methoxy-5-nitro-pyridin-2-yloxy)-ethyl]-propyl-amine (2.92 g, 8.45 mmol) in acetic acid (120 ml) at 80° C. iron (2.36 g, 42.27 mmol) was slowly added in portions. The exothermic reaction was stirred for 2 h at 80° C. After evaporation of the solvent under reduced pressure, the solid residue was dissolved in aq. NaHCO$_3$, which was extracted 6 times with dichloromethane. The residue was purified by silica gel chromatography with dichloromethane/methanol (10:0; 8:2; 6.5:3.5; 0:10) as eluent to provide 1.4 g (52.5%) of the product.
MS (ESI) m/z: 316.15 [M+H]$^+$ q. (S)-2-(5-Amino-6-methoxy-pyridin-2-yloxymethyl)-pyrrolidine-1-carboxylic Acid Tert-Butyl Ester q.1 (S)-2-(6-Methoxy-5-nitro-pyridin-2-yloxymethyl)-pyrrolidine-1-carboxylic Acid Tert-Butyl Ester To a mixture of Pd(OAc)$_2$ (0.08 g, 0.34 mmol) and [1,1'] binaphthalen-2-yl-di-tert-butyl-phosphane (0.14 g, 0.34 mmol) in toluene (10 ml) was added 6-bromo-2-methoxy-3-nitropyridine(1.0 g, 4.29 mmol), Cs$_2$CO$_3$ (3.5 g, 10.73 mmol), and (S)-2-hydroxymethyl-pyrrolidine-1-carboxylic acid tert-butyl ester (1.73 g, 8.58 mmol). The mixture was stirred under nitrogen at room temperature for 24 h. After evaporation of the solvent under reduced pressure, the residue was purified by silica gel chromatography with dichloromethane/ethyl acetate/methanol (10:0:0; 9:0.5:0.5; 7:1.5: 1.5; 0:5:5) as eluent to provide 0.11 g (7.5%) of the product.
MS (ESI) m/z: 354.15 [M+H]$^+$ q.2 (S)-2-(5-Amino-6-methoxy-pyridin-2-yloxymethyl)-pyrrolidine-1-carboxylic Acid Tert-Butyl Ester A solution of (S)-2-(6-methoxy-5-nitro-pyridin-2-yloxymethyl)-pyrrolidine-1-carboxylic acid tert-butyl ester (0.11 g, 0.32 mmol) in methanol (11 ml) was hydrogenated using the ThalesNano H-Cube® hydrogenation reactor employing a 10% palladium on charcoal catalyst cartridge. After concentration of the solution under reduced pressure 0.10 g (92.6%) of the title compound were obtained.
MS (ESI) m/z: 324.15 [M+H]$^+$ r. (R)-2-(5-Amino-6-methoxy-pyridin-2-yloxymethyl)-pyrrolidine-1-carboxylic Acid Tert-Butyl Ester The desired product was obtained following the synthetic procedure analogous to that described for the preparation of intermediate q starting from 6-bromo-2-methoxy-3-nitropyridine and (R)-2-hydroxymethylpyrrolidine-1-carboxylic acid tert-butyl ester.
MS (ESI) m/z: 324.15 [M+H]$^+$ s. (S)-2-(5-Amino-6-methyl-pyridin-2-yloxymethyl)-pyrrolidine-1-carboxylic Acid Tert-Butyl Ester The desired product was obtained following the synthetic procedure analogous to that described for the preparation of intermediate q starting from 6-chloro-2-methyl-3-nitropyridine and (S)-2-hydroxymethyl-pyrrolidine-1-carboxylic acid tert-butyl ester.
MS (ESI) m/z: 340.15 [M+H]$^+$ t. (R)-2-(5-Amino-6-methyl-pyridin-2-yloxymethyl)-pyrrolidine-1-carboxylic Acid Tert-Butyl Ester The desired product was obtained following the synthetic procedure analogous to that described for the preparation of intermediate q starting from 6-chloro-2-methyl-3-nitro-pyridine and (R)-2-hydroxymethyl-pyrrolidine-1-carboxylic acid tert-butyl ester.
MS (ESI) m/z: 340.15 [M+H]$^+$ u. [2-(5-Amino-6-methyl-pyridin-2-yloxy)-ethyl]-propyl-carbamic Acid Tert-Butyl Ester u.1 [2-(6-Methyl-5-nitro-pyridin-2-yloxy)-ethyl]-propyl-carbamic Acid Tert-Butyl Ester A mixture of 6-chloro-2-methyl-3-nitro-pyridine (1 g, 5.79 mmol), (2-hydroxyethyl)-propyl-carbamic acid tert-butyl ester (1.18 g, 5.79 mmol) and lithium hydride (0.05 g, 6.37 mmol) in toluene (5 ml) was stirred at 90° C. for 4 h. After evaporation of the solvent under reduced pressure the residue was purified by silica gel chromatography with heptane/ethyl acetate (10:0; 8:2; 0:10) as eluent to provide 1.38 g (70.2%) of the product.

MS (ESI) m/z: 284.15 [M+H(-[tert-butyl])]$^+$ u.2 [2-(5-Amino-6-methyl-pyridin-2-yloxy)-ethyl]-propyl-carbamic Acid Tert-Butyl Ester A solution of [2-(6-methyl-5-nitro-pyridin-2-yloxy)-ethyl]-propyl-carbamic acid tert-butyl ester (300 mg, 0.88 mmol) in methanol (10 ml) was hydrogenated using the ThalesNano H-Cube® hydrogenation reactor employing a 10% palladium on charcoal catalyst cartridge. After concentration of the solution under reduced pressure, 230 mg (84.2%) of the title compound were obtained.

v. 6-[2-(Benzyl-propyl-amino)-ethoxy]-2-methyl-pyridin-3-ylamine

The desired product was obtained following the synthetic procedure analogous to that described for the preparation of intermediate p starting from 6-chloro-2-methyl-3-nitropyridine and 2-(benzyl-propyl-amino)-ethanol.

MS (ESI) m/z: 300.15 [M+H]$^+$ w. 6-[2-(Benzyl-propyl-amino)-ethoxy]-4-methyl-pyridin-3-ylamine

The desired product was obtained following the synthetic procedure analogous to that described for the preparation of intermediate p starting from 2-chloro-4-methyl-5-nitropyridine and 2-(benzyl-propyl-amino)-ethanol.

MS (ESI) m/z: 300.15 [M+H]$^+$ x. 6-[2-(Benzyl-propyl-amino)-ethoxy]-5-methyl-pyridin-3-ylamine

The desired product was obtained following the synthetic procedure analogous to that described for the preparation of intermediate p starting from 2-bromo-3-methyl-5-nitropyridine and 2-(benzyl-propyl-amino)-ethanol.

MS (ESI) m/z: 300.15 [M+H]$^+$ y. 4-(2-Fluoro-ethoxy)-benzenesulfonylchloride

At 0° C., (2-fluoro-ethoxy)-benzene (20 mmol) was added slowly to chlorosulfonic acid (200 mmol). The reaction mixture was stirred for 20 min at 0-5° C. and then warmed to room temperature, and finally stirred at 45° C. for 2 h. Then the reaction mixture was cautiously (!) added to ice water. The precipitate was filtered, washed with water and dried in a vacuum oven at 30° C. to give the title compound.

$^1$H-NMR (CDCl$_3$): δ [ppm] 4.21-4.45 (m, 2H), 4.65-5.00 (m, 2H), 7.08 (d, 2H), 8.00 (d, 2H).

z. 4-(2,2-Difluoro-ethoxy)-benzenesulfonylchloride

The desired product was obtained following the synthetic procedure analogous to that described for the preparation of intermediate y.

$^1$H-NMR (CDCl$_3$): δ [ppm] 4.21-4.40 (m, 2H), 5.82-6.45 (m, 1H), 7.08 (d, 2H), 8.02 (d, 2H).

zz. 4-(2,2,2-Trifluoro-ethoxy)-benzenesulfonylchloride

The desired product was obtained following the synthetic procedure analogous to that described for the preparation of intermediate y.

$^1$H-NMR (CDCl$_3$): δ [ppm] 4.40-4.55 (m, 2H), 7.10 (d, 2H), 8.02 (d, 2H).

II. Preparation of Compounds I

Example 1

4-(3-Fluoro-propyl)-N-[2-methoxy-6-(2-propylamino-ethoxy)-pyridin-3-yl]-benzenesulfonamide×HCl After a solution of [2-(5-Amino-6-methoxy-pyridin-2-yloxy)-ethyl]-propyl-carbamic acid tert-butyl ester (200 mg, 0.62 mmol) in pyridine (3 ml) was stirred at room temperature for 30 minutes 4-(3-Fluoro-propyl)-benzenesulfonyl chloride (160 mg, 0.68 mmol) was added. The mixture was stirred at room temperature for 16 h, after which the solvent was evaporated under reduced pressure. The residue was taken up in toluene and the solvent was evaporated again. This procedure was repeated once. The residue was purified by silica gel chromatography with n-hexane/ethyl acetate (1:0; 1:1; 0:1)/ 0.2% triethylamine as eluent. The residue was dissolved in dichloromethane (5 ml). At 0° C. to this solution HCl in diethylether (1 ml) was added slowly. The mixture was stirred at room temperature for 6 h. After concentration under reduced pressure, the residue was purified by chromatography (Chromabond-C18) with H$_2$O/acetonitrile (95:5; 0:100; 95:5)/0.1% acetic acid as eluent. The solution of the so obtained oil in 1N NaOH was extracted three times with dichloromethane (45 ml). The combined organic layers were concentrated to 30 ml and HCl in diethylether (2 ml) was added. The solid formed was filtered and dried in a vacuum oven to obtain 88.9 mg (35.6%) of the title compound.

MS (ESI) m/z: 426.25 [M+H]$^+$ $^1$H-NMR (MeOD): δ [ppm] 7.70 (m, 1H), 7.60 (d, 2H), 7.35 (d, 2H), 6.45 (d, 1H), 4.50-4.60 (m, 2H), 4.35-4.50 (m, 2H), 3.60 (s, 3H), 3.40-3.45 (m, 2H), 3.00-3.10 (m, 2H), 2.75-2.80 (m, 2H), 1.90-2.10 (m, 2H), 1.70-1.85 (m, 2H), 1.05 (t, 3H).

Example 2

N-[2-Methoxy-6-(2-propylamino-ethoxy)-pyridin-3-yl]-4-trifluoromethoxy-benzenesulfonamide×HCl The desired product was obtained following the synthetic procedure analogous to that described for example 1 starting from [2-(5-Amino-6-methoxy-pyridin-2-yloxy)-ethyl]-propyl-carbamic acid tert-butyl ester and 4-trifluoromethoxy-benzenesulfonyl chloride.

MS (ESI) m/z: 449.25 [M+H]$^+$

¹H-NMR (D₆-DMSO): δ [ppm] 7.75 (d, 2H), 7.56 (d, 2H), 7.45 (d, 1H), 6.30 (d, 1H), 4.15-4.25 (m, 2H), 3.40 (s, 3H), 2.80-2.90 (m, 2H), 2.50-2.55 (m, 2H), 1.35-1.45 (m, 2H), 0.85 (t, 3H).

Example 3

N-[2-Methoxy-6-(2-propylamino-ethoxy)-pyridin-3-yl]-4-(2,2,2-trifluoro-1-methylethyl)-benzenesulfonamide×HCl The desired product was obtained following the synthetic procedure analogous to that described for example 1 starting from [2-(5-Amino-6-methoxy-pyridin-2-yloxy)-ethyl]-propyl-carbamic acid tert-butyl ester and 4-(2,2,2-trifluoro-1-methyl-ethyl)-benzenesulfonyl chloride.

MS (ESI) m/z: 462.15 [M+H]⁺

¹H-NMR (CDCl₃): δ [ppm] 9.90 (s br., 2H), 7.70 (d, 1H), 7.65 (d, 2H), 7.40 (d, 2H), 6.45 (d, 1H), 4.60-4.70 (m, 2H), 3.55 (s, 3H), 3.35-3.50 (m, 1H), 3.30-3.35 (m, 2H), 2.95-3.05 (m, 2H), 1.90-2.00 (m, 2H), 1.50 (d, 3H), 0.95 (t, 3H).

Example 4

4-Isopropyl-N-[2-methoxy-6-(2-propylamino-ethoxy)-pyridin-3-yl]-benzenesulfonamide×HCl The desired product was obtained following the synthetic procedure analogous to that described for example 1 starting from [2-(5-Amino-6-methoxy-pyridin-2-yloxy)-ethyl]-propyl-carbamic acid tert-butyl ester and 4-Isopropyl-benzenesulfonyl chloride.

MS (ESI) m/z: 408.25 [M+H]⁺

Example 5

4-Difluoromethoxy-N-[2-methoxy-6-(2-propylamino-ethoxy)-pyridin-3-yl]-benzenesulfonamide×HCl The desired product was obtained following the synthetic procedure analogous to that described for example 1 starting from [2-(5-Amino-6-methoxy-pyridin-2-yloxy)-ethyl]-propyl-carbamic acid tert-butyl ester and 4-difluoromethoxy-benzenesulfonyl chloride.

MS (ESI) m/z: 432.15 [M+H]⁺

¹H-NMR (MeOD): δ [ppm] 7.70-7.80 (m, 3H), 7.25 (d, 2H), 7.70 (t, 1H), 6.45 (d, 1H), 4.50-4.55 (m, 2H), 3.60 (s, 3H), 3.40-3.45 (m, 2H), 3.00-3.10 (m, 2H), 1.70-1.85 (m, 2H), 1.05 (t, 3H).

Example 6

4-(2-Fluoro-ethyl)-N-[2-methoxy-6-(2-propylamino-ethoxy)-pyridin-3-yl]-benzenesulfonamide×HCl The desired product was obtained following the synthetic procedure analogous to that described for example 1 starting from [2-(5-Amino-6-methoxy-pyridin-2-yloxy)-ethyl]-propyl-carbamic acid tert-butyl ester and 4-(2-fluoro-ethyl)-benzenesulfonyl chloride.

MS (ESI) m/z: 412.25 [M+H]⁺

¹H-NMR (D₆-DMSO): δ [ppm] 9.45 (s br., 3H), 7.55 (d, 2H), 7.40-7.50 (m, 3H), 7.10 (d, 2H), 6.40 (d, 1H), 4.60-4.75 (m, 2H), 4.45-4.55 (m, 2H), 3.50 (s, 3H), 3.20-3.30 (m, 2H), 3.00-3.10 (m, 2H), 2.85 (t, 2H), 1.65-1.75 (m, 2H), 0.90 (t, 3H).

Example 7

N-[2-Methoxy-6-(2-propylamino-ethoxy)-pyridin-3-yl]-4-oxazol-5-yl-benzenesulfonamide×HCl The desired product was obtained following the synthetic procedure analogous to that described for example 1 starting from [2-(5-Amino-6-methoxy-pyridin-2-yloxy)-ethyl]-propyl-carbamic acid tert-butyl ester and 4-oxazol-5-yl-benzenesulfonyl chloride.

MS (ESI) m/z: 433.25 [M+H]⁺

¹H-NMR (MeOD): δ [ppm] 8.35 (s, 1H), 7.85 (d, 2H), 7.80 (d, 2H), 7.70-7.75 (m, 3H), 6.45 (d, 1H), 4.50-4.55 (m, 2H), 3.60 (s, 3H), 3.40-3.45 (m, 2H), 3.00-3.05 (m, 2H), 1.60-1.70 (m, 2H), 1.05 (t, 3H).

Example 8

4-(2-Fluoro-ethoxy)-N-[2-methoxy-6-(2-propylamino-ethoxy)-pyridin-3-yl]-benzenesulfonamide×HCl The desired product was obtained following the synthetic procedure analogous to that described for example 1 starting from [2-(5-Amino-6-methoxy-pyridin-2-yloxy)-ethyl]-propyl-carbamic acid tert-butyl ester and 4-(2-Fluoro-ethoxy)-benzenesulfonyl chloride.

MS (ESI) m/z: 428.10 [M+H]⁺

¹H-NMR (D₆-DMSO): δ [ppm] 9.40 (s, 1H), 9.25 (s br., 2H), 7.60 (d, 2H), 7.45 (d, 1H), 7.10 (d, 2H), 6.35 (d, 1H), 4.75 (d, 2H), 4.50 (m, 2H), 4.30 (d, 2H), 3.55 (s, 3H), 3.25 (s br., 2H), 2.85 (s br., 2H), 1.60-1.70 (m, 2H), 0.90 (t, 3H).

Example 9

4-(2,2-Difluoro-ethoxy)-N-[2-methoxy-6-(2-propylamino-ethoxy)-pyridin-3-yl]-benzenesulfonamid×HCl The desired product was obtained following the synthetic procedure analogous to that described for example 1 starting from [2-(5-Amino-6-methoxy-pyridin-2-yloxy)-ethyl]-propyl-carbamic acid tert-butyl ester and 4-(2,2-Difluoro-ethoxy)-benzenesulfonyl chloride.

MS (ESI) m/z: 446.05 [M+H]⁺

¹H-NMR (D₆-DMSO): δ [ppm] 9.40 (s, 1H), 9.15 (s br., 2H), 7.60 (d, 2H), 7.45 (d, 1H), 7.15 (d, 2H), 6.40 (t, 1H), 6.39 (d, 1H), 4.47 (m, 2H), 4.40 (t, 2H), 3.55 (s, 3H), 3.25 (s br., 2H), 2.88 (s br., 2H), 1.60-1.70 (m, 2H), 0.90 (t, 3H).

Example 10

N-[2-Methoxy-6-(2-propylamino-ethoxy)-pyridin-3-yl]-4-(2,2,2-trifluoro-ethoxy)-benzenesulfonamide×HCl The desired product was obtained following the synthetic procedure analogous to that described for example 1 starting from [2-(5-Amino-6-methoxy-pyridin-2-yloxy)-ethyl]-propyl-carbamic acid tert-butyl ester and 4-(2,2,2-trifluoro-ethoxy)-benzenesulfonyl chloride.

MS (ESI) m/z: 464.05 [M+H]⁺

¹H-NMR (D₆-DMSO): δ [ppm] 9.45 (s, 1H), 9.15 (s br., 2H), 7.60 (d, 2H), 7.45 (d, 1H), 7.25 (d, 2H), 6.39 (d, 1H), 4.85-4.90 (m, 2H), 4.45-4.50 (m, 2H), 3.55 (s, 3H), 3.25 (s br., 2H), 2.88 (s br., 2H), 1.60-1.70 (m, 2H), 0.90 (t, 3H).

Example 11

4-((R)-2-Fluoro-1-methyl-ethyl)-N-[2-methoxy-6-(2-propylamino-ethoxy)-pyridin-3-yl]-benzenesulfonamide×HCl The desired product was obtained following the synthetic procedure analogous to that described for example 1 starting from [2-(5-Amino-6-methoxy-pyridin-2-yloxy)-ethyl]-propyl-carbamic acid tert-butyl ester and 4-((R)-2-Fluoro-1-methyl-ethyl)-benzenesulfonyl chloride.

MS (ESI) m/z: 426.15 [M+H]$^+$ $^1$H-NMR (D$_6$-DMSO): δ [ppm] 9.49 (s, 1H), 9.15 (s br., 2H), 7.60 (d, 2H), 7.50 (d, 1H), 7.45 (d, 2H), 6.40 (d, 1H), 4.45-4.60 (m, 4H), 3.45 (s, 3H), 3.20-3.30 (m, 3H), 2.90 (s br., 2H), 1.60-1.70 (m, 2H), 1.22 (d, 3H), 0.90 (t, 3H).

Example 12

4-((S)-2-Fluoro-1-methyl-ethyl)-N-[2-methoxy-6-(2-propylamino-ethoxy)-pyridin-3-yl]-benzenesulfonamide×HCl To a solution of 6-[2-(benzyl-propyl-amino)-ethoxy]-2-methoxy-pyridin-3-ylamine (60 mg, 0.20 mmol) in pyridine (0.8 ml) was added 4-((S)-2-fluoro-1-methyl-ethyl)-benzenesulfonyl chloride (50 mg, 0.20 mmol) at 0° C. The mixture was stirred at room temperature for 16 h, after which the solvent was evaporated under reduced pressure. The residue was purified by silica gel chromatography with dichloromethane/ethyl acetate (10:0; 9:1; 0:100)/0.2% triethylamine as eluent. A mixture of the so obtained oil was hydrogenated using the ThalesNano H-Cube® hydrogenation reactor employing a 10% palladium on charcoal catalyst cartridge.

After filtration and evaporation of the solvent under reduced pressure the residue was purified by chromatography (Chromabond-C18) with H$_2$O/acetonitrile (95:5; 0:100; 95:5)/0.1% acetic acid as eluent. To a solution of the so obtained oil in 2-propanol, HCl in diethylether was added. The solid formed was filtered and dried in a vacuum oven to give 10 mg (20.3%) of the title compound.

MS (ESI) m/z: 426.15 [M+H]$^+$ $^1$H-NMR (D$_6$-DMSO): δ [ppm] 9.49 (s, 1H), 9.15 (s br., 2H), 7.60 (d, 2H), 7.50 (d, 1H), 7.45 (d, 2H), 6.40 (d, 1H), 4.45-4.60 (m, 4H), 3.45 (s, 3H), 3.20-3.30 (m, 3H), 2.90 (s br., 2H), 1.60-1.70 (m, 2H), 1.22 (d, 3H), 0.90 (t, 3H).

Example 13

4-Isopropyl-N-[2-methoxy-6-(pyrrolidin-3-yloxy)-pyridin-3-yl]-benzenesulfonamide×HCl After a solution of 6-(1-Benzyl-pyrrolidin-3-yloxy)-2-methoxy-pyridin-3-ylamine (120 mg, 0.40 mmol) in pyridine (2 ml) was stirred at room temperature for 30 minutes 4-isopropyl-benzenesulfonyl chloride (100 mg, 0.44 mmol) was added. The mixture was stirred at room temperature for 16 h, after which the solvent was evaporated under reduced pressure. The residue was taken up in toluene and the solvent was evaporated. This procedure was repeated once. The residue was purified by silica gel chromatography with dichloromethane/ethyl acetate (10:0; 9:1; 0:10)/0.2% triethylamine as eluent. A mixture of the so obtained oil and 10% Palladium on charcoal (20 mg, 0.02 mmol) in ethanol (20 ml) was hydrogenated at atmospheric pressure until the consumption of hydrogen was complete. After filtration and evaporation of the solvent under reduced pressure the residue was purified by silica gel chromatography with dichloromethane/methanol (10:0; 0:10; 10:0) as eluent. To a solution of the so obtained oil in methanol HCl in diethylether was added, and the solution was concentrated under reduced pressure to obtain 31 mg (33.2%) of the title compound.

MS (ESI) m/z: 392.35 [M+H]$^+$ $^1$H-NMR (MeOD): δ [ppm] 7.65 (d, 1H), 7.60 (d, 2H), 7.35 (d, 2H), 6.35 (d, 1H), 5.55 (s br., 1H), 3.45-3.60 (m, 4H), 3.55 (s, 3H), 2.90-3.05 (m, 1H), 2.30-2.40 (m, 2H), 1.60-1.70 (m, 2H), 1.25 (d, 3H).

Example 14

N-[2-methoxy-6-(pyrrolidin-3-yloxy)-pyridin-3-yl]-4-trifluormethoxy-benzenesulfonamide×HCl The desired product was obtained following the synthetic procedure analogous to that described for example 13 starting from 6-(1-Benzyl-pyrrolidin-3-yloxy)-2-methoxy-pyridin-3-ylamine and 4-trifluoromethoxy-benzenesulfonyl chloride.

MS (ESI) m/z: 434.35 [M+H]$^+$ $^1$H-NMR (MeOD): δ [ppm] 7.92 (d, 1H), 7.80 (d, 2H), 7.405 (d, 2H), 6.40 (d, 1H), 5.57 (s br., 1H), 3.45-3.60 (m, 4H), 3.55 (s, 3H), 2.30-2.40 (m, 2H).

Example 15

4-(3-Fluoro-propyl)-N-[2-methoxy-6-(2-pyrrolidin-1-yl-ethoxy)-pyridin-3-yl]-benzenesulfonamide After a solution of 2-Methoxy-6-(2-pyrrolidin-1-yl-ethoxy)-pyridin-3-ylamine (200 mg, 0.84 mmol) in pyridine (3 ml) was stirred at room temperature for 30 minutes 4-(3-fluoro-propyl)-benzenesulfonyl chloride (200 mg, 0.84 mmol) was added. The mixture was stirred at room temperature for 16 h, thereafter the solvent was evaporated under reduced pressure. The residue was taken up in toluene and the solvent was evaporated. This procedure was repeated once. The residue was purified by silica gel chromatography with dichloromethane/methanol (100:0; 95:5; 0:100) as eluent to give 20 mg (5.4%) of the title compound.

MS (ESI) m/z: 438.15 [M+H]$^+$ $^1$H-NMR (CDCl$_3$): δ [ppm] 7.72 (d, 1H), 7.60 (d, 2H), 7.25 (d, 2H), 6.60 (s, 1H), 6.30 (d, 1H), 4.60-4.65 (m, 2H), 4.35-4.50 (m, 2H), 3.85-3.95 (m, 2H), 3.60 (s, 3H), 3.40-3.45 (m, 2H), 2.90-3.00 (m, 2H), 2.05-2.20 (m, 4H), 1.95-2.05 (m, 2H).

Example 16

4-Isopropyl-N-[2-methoxy-6-(2-pyrrolidin-1-yl-ethoxy)-pyridin-3-yl]-benzenesulfonamide×HCl The desired product was obtained following the synthetic procedure analogous to that described for example 15 starting from 2-Methoxy-6-(2-pyrrolidin-1-yl-ethoxy)-pyridin-3-ylamine and 4-isopropyl-benzenesulfonyl chloride.

MS (ESI) m/z: 420.15 [M+H]$^+$

Example 17

4-((R)-2-Fluoro-1-methyl-ethyl)-N-[2-methoxy-6-(2-pyrrolidin-1-yl-ethoxy)-pyridin-3-yl]-benzenesulfonamide The desired product was obtained following the synthetic procedure analogous to that described for example 15 starting from 2-Methoxy-6-(2-pyrrolidin-1-yl-ethoxy)-pyridin-3-ylamine and 4-((R)-2-fluoro-1-methyl-ethyl)-benzenesulfonyl chloride.

MS (ESI) m/z: 438.15 [M+H]$^+$ $^1$H-NMR (CDCl$_3$): δ [ppm] 7.65 (d, 2H), 7.15-7.30 (m, 3H), 6.20-6.35 (d, 1H), 4.35-4.50 (m, 2H), 4.25-4.35 (m, 2H), 3.55 (s, 3H), 3.05-3.20 (m, 1H), 2.70-2.85 (m, 2H), 2.55-2.60 (m, 4H), 1.75-1.80 (m, 4H), 1.30 (d, 3H).

Example 18

N-[2-Methoxy-6-(2-pyrrolidin-1-yl-ethoxy)-pyridin-3-yl]-4-(2,2,2-trifluoro-1-methyl-ethyl)-benzenesulfonamide The desired product was obtained following the synthetic procedure analogous to that described for example 15 starting from 2-Methoxy-6-(2-pyrrolidin-1-yl-ethoxy)-pyridin-3-ylamine and 4-(2,2,2-trifluoro-1-methyl-ethyl)-benzenesulfonyl chloride.

MS (ESI) m/z: 474.25 [M+H]$^+$ $^1$H-NMR (CDCl$_3$): δ [ppm] 7.70 (d, 1H), 7.65 (d, 2H), 7.35 (d, 2H), 6.35 (d, 1H), 4.35-4.40 (m, 2H), 3.50 (s, 3H), 2.85-2.92 (m, 2H), 2.60-2.73 (m, 4H), 1.80-1.90 (m, 4H), 1.50 (d, 3H).

Example 19

N-[2-Methoxy-6-(2-pyrrolidin-1-yl-ethoxy)-pyridin-3-yl]-4-oxazol-5-yl-benzenesulfonamide The desired product was obtained following the synthetic procedure analogous to that described for example 15 starting from 2-Methoxy-6-(2-pyrrolidin-1-yl-ethoxy)-pyridin-3-ylamine and 4-oxazol-5-yl-benzenesulfonyl chloride.

MS (ESI) m/z: 445.15 [M+H]$^+$ $^1$H-NMR (MeOD): δ [ppm] 8.35 (s, 1H), 7.85 (d, 2H), 7.75 (d, 2H), 7.71 (d, 1H), 7.69 (s, 1H), 6.45 (d, 1H), 4.55-4.60 (m, 2H), 3.65-3.75 (m, 2H), 3.60 (s, 3H), 3.60-3.65 (m, 2H), 3.15-3.25 (m, 2H), 2.00-2.25 (m, 4H).

Example 20

4-isopropyl-N-[4-methoxy-2-(2-propylamino-ethoxy)-pyrimidin-5-yl]-benzenesulfonamide The desired product was obtained following the synthetic procedure analogous to that described for example 1 starting from [2-(5-Amino-4-methoxy-pyrimidin-2-yloxy)-ethyl]-propyl-carbamic acid tert-butyl ester and 4-isopropyl-benzenesulfonyl chloride.

MS (ESI) m/z: 409.15 [M+H]$^+$ $^1$H-NMR (DMSO): δ [ppm] 8.00 (s, 1H), 7.55 (d, 2H), 7.48 (d, 2H), 4.25-4.30 (m, 2H), 3.50 (s, 3H), 2.90-3.00 (m, 1H), 2.85-2.92 (m, 2H), 2.55-2.60 (m, 2H), 1.37-1.50 (m, 2H), 1.20 (d, 6H), 0.85 (t, 3H).

Example 21

N-[4-Methoxy-2-(2-propylamino-ethoxy)-pyrimidin-5-yl]-4-trifluoromethoxy-benzenesulfonamide The desired product was obtained following the synthetic procedure analogous to that described for example 1 starting from [2-(5-Amino-4-methoxy-pyrimidin-2-yloxy)-ethyl]-propyl-carbamic acid tert-butyl ester and 4-trifluoromethoxy-benzenesulfonyl chloride.

MS (ESI) m/z: 451.15 [M+H]$^+$ $^1$H-NMR (MeOD): δ [ppm] 8.02 (s, 1H), 7.74 (d, 2H), 7.28 (d, 2H), 4.30-4.35 (m, 2H), 3.55 (s, 3H), 2.95-3.00 (m, 2H), 2.60-2.67 (m, 2H), 1.48-1.52 (m, 2H), 0.87 (t, 3H).

Example 22

N-[6-(2-Dimethylamino-ethoxy)-pyridin-3-yl]-4-isopropyl-benzenesulfonamide×HCl

The desired product was obtained following the synthetic procedure analogous to that described for example 15 starting from 6-(2-Dimethylamino-ethoxy)-pyridin-3-ylamine and 4-isopropyl-benzenesulfonyl chloride.

MS (ESI) m/z: 364.15 [M+H]$^+$

Example 23

4-Isopropyl-N-[6-(2-propylamino-ethoxy)-pyridin-3-yl]-benzenesulfonamide×HCl

The desired product was obtained following the synthetic procedure analogous to that described for example 1 starting from [2-(5-Amino-pyridin-2-yloxy)-ethyl]-propyl-carbamic acid tert-butyl ester and 4-isopropyl-benzenesulfonyl chloride.

MS (ESI) m/z: 378.15 [M+H]$^+$

Example 24

N-[6-(2-Dipropylamino-ethoxy)-pyridin-3-yl]-4-isopropyl-benzenesulfonamide×HCl

To a solution of 4-Isopropyl-N-[6-(2-propylamino-ethoxy)-pyridin-3-yl]-benzenesulfonamide (81 mg, 0.21 mmol), propionaldehyde (13.71 mg, 0.24 mmol) and acetic acid (0.02 ml) in dichloromethane (5 ml) was added sodium trisacetoxy borohydride (68.22 mg, 0.32 mmol). The mixture was stirred at room temperature for 1 h. After evaporation of the solvent under reduced pressure, the residue was dissolved in 1N NaOH, which was extracted three times with diethylether. The combined organic layers were dried over MgSO$_4$, filtered and the solvent evaporated under reduced pressure. To a solution of the residue in diethylether at 0° C. HCl in diethylether was added. The solid formed was filtered and dried in a vacuum oven to give 66 mg (67.4%) of the title compound.

MS (ESI) m/z: 420.25 [M+H]$^+$ $^1$H-NMR (DMSO): δ [ppm] 10.20 (s br., 2H), 7.85 (s, 1H), 7.65 (d, 2H), 7.50 (d, 1H), 7.45 (d, 2H), 6.80 (d, 1H), 4.50-4.57 (m, 2H), 3.40-3.50 (m, 2H), 3.00-3.10 (m, 4H), 2.90-3.00 (m, 1H), 1.60-1.70 (m, 4H), 1.20 (d, 6H), 0.90 (t, 6H).

The following examples were obtained according to the synthetic procedure analogous to that described for example 1.

Example 25

4-Isopropyl-N-[2-methoxy-6-((R)-1-pyrrolidin-2-ylmethoxy)-pyridin-3-yl]-benzenesulfonamide×HCl MS (ESI) m/z: 392.1 [M+H]$^+$ $^1$H-NMR (DMSO): δ [ppm] 9.20-9.70 (m, 2H), 7.60 (d, 2H), 7.50 (d, 1H), 7.40 (d, 2H), 6.40 (d, 1H), 4.38-4.48 (m, 2H), 3.85-88 (m, 1H), 3.52 (s, 3H), 3.12-3.22 (m, 2H), 2.97-2.99 (m, 1H), 2.05-2.15 (m, 1H), 1.85-2.05 (m, 2H), 1.68-1.70 (m, 1H), 1.23 (d, 6H).

Example 26

4-(2-Fluoro-ethoxy)-N-[2-methoxy-6-((R)-1-pyrrolidin-2-ylmethoxy)-pyridin-3-yl]-benzenesulfonamide×HCl MS (ESI) m/z: 426.1 [M+H]$^+$
$^1$H-NMR (DMSO): δ [ppm] 9.98 (bs, 1H), 9.32-9.38 (m, 2H), 7.58 (d, 2H), 7.38 (d, 1H), 7.09 (d, 2H), 6.36 (d, 1H), 4.68-4.80 (m, 2H), 4.36-4.45 (m, 2H), 4.27-4.35 (m, 2H), 3.80-3.86 (m, 1H), 3.55 (s, 3H), 3.12-3.20 (m, 2H), 2.03-2.10 (m, 1H), 1.83-1.97 (m, 2H), 1.64-1.72 (m, 1H).

Example 27

N-[2-Methoxy-6-((R)-1-pyrrolidin-2-ylmethoxy)-pyridin-3-yl]-4-oxazol-5-yl-benzenesulfonamide×HCl MS (ESI) m/z: 431.1 [M+H]$^+$
$^1$H-NMR (DMSO): δ [ppm] 9.82-9.92 (m, 1H), 9.63 (s, 1H), 9.22-9.28 (m, 1H), 8.53 (s, 1H), 7.88 (d, 2H), 7.87 (s, 1H), 7.48 (d, 1H), 6.38 (d, 1H), 4.32-4.46 (m, 2H), 3.80-88 (m, 1H), 3.49 (s, 3H), 3.12-3.22 (m, 2H), 2.02-2.10 (m, 1H), 1.82-1.98 (m, 2H), 1.62-1.72 (m, 1H).

Example 28

4-Isopropyl-N-[2-methoxy-6-((S)-1-pyrrolidin-2-ylmethoxy)-pyridin-3-yl]-benzenesulfonamide×HCl MS (ESI) m/z: 392.1 [M+H]$^+$
$^1$H-NMR (DMSO): δ [ppm] 9.20-9.70 (m, 2H), 7.60 (d, 2H), 7.50 (d, 1H), 7.40 (d, 2H), 6.40 (d, 1H), 4.38-4.48 (m, 2H), 3.85-88 (m, 1H), 3.52 (s, 3H), 3.12-3.22 (m, 2H), 2.97-2.99 (m, 1H), 2.05-2.15 (m, 1H), 1.85-2.05 (m, 2H), 1.68-1.70 (m, 1H), 1.23 (d, 6H).

Example 29

4-Isopropyl-N-[2-methyl-6-(2-propylamino-ethoxy)-pyridin-3-yl]-benzenesulfonamide×HCl MS (ESI) m/z: 392.1 [M+H]$^+$
$^1$H-NMR (MeOD): δ [ppm] 7.63 (d, 2H), 7.47 (d, 1H), 7.43 (d, 2H), 6.78 (d, 1H), 4.58-4.62 (m, 2H), 3.45-3.51 (m, 2H), 3.00-3.10 (m, 3H), 2.14 (s, 3H), 1.72-1.85 (m, 2H), 1.30 (d, 6H), 1.07 (t, 3H).

Example 30

N-[2-Methyl-6-(2-propylamino-ethoxy)-pyridin-3-yl]-4-trifluoromethoxy-benzenesulfonamide×HCl MS (ESI) m/z: 434.1 [M+H]$^+$
$^1$H-NMR (MeOD): δ [ppm] 7.81 (d, 2H), 7.46 (d, 2H), 7.40 (d, 1H), 6.72 (d, 1H), 4.57-4.59 (m, 2H), 3.44-3.46 (m, 2H), 3.05-3.08 (m, 2H), 2.14 (s, 3H), 1.72-1.81 (m, 2H), 1.05 (t, 3H).

Example 31

4-Difluoromethoxy-N-[2-methyl-6-(2-propylamino-ethoxy)-pyridin-3-yl]-benzenesulfonamide×HCl MS (ESI) m/z: 416.1 [M+H]$^+$
$^1$H-NMR (DMSO): δ [ppm] 9.85 (s, 1H), 9.33 (bs, 2H), 7.71 (d, 2H), 7.42 (t, 1H), 7.36 (d, 2H), 7.22 (d, 1H), 6.63 (d, 1H), 4.47-4.49 (m, 2H), 3.24-3.27 (m, 2H), 2.85-2.91 (m, 2H), 2.10 (s, 3H), 1.63-1.72 (m, 2H), 0.90 (t, 3H).

Example 32

4-(2,2-Difluoro-ethoxy)-N-[2-methyl-6-(2-propylamino-ethoxy)-pyridin-3-yl]-benzenesulfonamide×HCl MS (ESI) m/z: 430.1 [M+H]$^+$
$^1$H-NMR (DMSO): δ [ppm] 9.66 (s, 1H), 9.34 (bs, 2H), 7.61 (d, 2H), 7.23 (d, 1H), 7.18 (d, 2H), 6.63 (d, 1H), 6.31-6.55 (m, 1H), 4.40-4.50 (m, 4H), 3.24-3.30 (m, 2H), 2.85-2.95 (m, 2H), 2.11 (s, 3H), 1.65-1.75 (m, 2H), 0.90 (t, 3H).

Example 33

4-(2-Fluoro-ethoxy)-N-[2-methyl-6-(2-propylamino-ethoxy)-pyridin-3-yl]-benzenesulfonamide×HCl MS (ESI) m/z: 412.1 [M+H]$^+$
$^1$H-NMR (DMSO): δ [ppm] 9.62 (s, 1H), 9.32 (bs, 2H), 7.60 (d, 2H), 7.23 (d, 1H), 7.13 (d, 2H), 6.64 (d, 1H), 4.70-4.85 (m, 2H), 4.48-4.50 (m, 2H), 4.30-4.39 (m, 2H), 3.24-3.32 (m, 2H), 2.85-2.95 (m, 2H), 2.11 (s, 3H), 1.65-1.75 (m, 2H), 0.90 (t, 3H).

Example 34

4-((R)-2-Fluoro-1-methyl-ethyl)-N-[2-methyl-6-(2-propylamino-ethoxy)-pyridin-3-yl]-benzenesulfonamide×HCl MS (ESI) m/z: 410.1 [M+H]$^+$
$^1$H-NMR (DMSO): δ [ppm] 9.74 (s, 1H), 9.35 (bs, 2H), 7.61 (d, 2H), 7.50 (d, 2H), 7.26 (d, 1H), 6.63 (d, 1H), 4.40-4.62 (m, 4H), 3.20-3.30 (m, 2H), 3.05-3.08 (m, 1H), 2.85-2.95 (m, 2H), 2.04 (s, 3H), 1.65-1.75 (m, 2H), 1.24 (d, 3H), 0.91 (t, 3H).

Example 35

4-((S)-2-Fluoro-1-methyl-ethyl)-N-[2-methyl-6-(2-propylamino-ethoxy)-pyridin-3-yl]-benzenesulfonamide×HCl MS (ESI) m/z: 410.1 [M+H]$^+$
$^1$H-NMR (DMSO): δ [ppm] 9.77 (s, 1H), 9.38 (bs, 2H), 7.61 (d, 2H), 7.50 (d, 2H), 7.26 (d, 1H), 6.63 (d, 1H), 4.40-4.62 (m, 4H), 3.20-3.30 (m, 3H), 2.85-2.95 (m, 2H), 2.04 (s, 3H), 1.65-1.75 (m, 2H), 1.24 (d, 3H), 0.89 (t, 3H)

Example 36

N-[2-Methyl-6-(2-propylamino-ethoxy)-pyridin-3-yl]-4-oxazol-5-yl-benzenesulfonamide×HCl MS (ESI) m/z: 417.1 [M+H]$^+$
$^1$H-NMR (DMSO): δ [ppm] 9.92 (s, 1H), 9.35 (bs, 2H), 8.57 (s, 1H), 7.93 (d, 2H), 7.92 (s, 1H), 7.45 (d, 2H), 7.24 (d, 1H), 6.64 (d, 1H), 4.47-4.50 (m, 2H), 3.24-3.30 (m, 2H), 2.85-2.92 (m, 2H), 2.11 (s, 3H), 1.64-1.73 (m, 2H), 0.90 (t, 3H).

Example 37

N-[2-Methyl-6-(2-propylamino-ethoxy)-pyridin-3-yl]-4-oxazol-4-yl-benzenesulfonamide×HCl MS (ESI) m/z: 417.1 [M+H]+
¹H-NMR (DMSO): δ [ppm] 9.86 (s, 1H), 9.31 (bs, 2H), 8.84 (s, 1H), 8.54 (s, 1H), 7.99 (d, 2H), 7.72 (d, 2H), 7.25 (d, 1H), 6.65 (d, 1H), 4.47-4.50 (m, 2H), 3.20-3.30 (m, 2H), 2.85-2.92 (m, 2H), 2.11 (s, 3H), 1.64-1.72 (m, 2H), 0.90 (t, 3H).

Example 38

N-[2-Methyl-6-((S)-1-pyrrolidin-2-ylmethoxy)-pyridin-3-yl]-4-oxazol-5-yl-benzenesulfonamide×HCl MS (ESI) m/z: 379.1 [M+H]+
¹H-NMR (DMSO): δ [ppm] 9.60-9.80 (m, 2H), 9.00-9.10 (m, 1H), 8.52 (bs, 1H), 7.85-7.90 (m, 3H), 7.69 (d, 2H), 7.21 (d, 1H), 6.60 (d, 1H), 4.28-4.41 (m, 2H), 3.80-3.90 (m, 1H), 3.10-3.20 (m, 2H), 2.05-2.10 (m, 4H), 1.80-1.95 (m, 2H), 1.65-1.75 (m, 1H).

Example 39

4-(2,2-Difluoro-ethoxy)-N-[2-methyl-6-((S)-1-pyrrolidin-2-ylmethoxy)-pyridin-3-yl]-benzenesulfonamide×HCl MS (ESI) m/z: 428.1 [M+H]+
¹H-NMR (DMSO): δ [ppm] 9.50-9.60 (m, 2H), 8.90-9.00 (m, 1H), 7.89 (d, 2H), 7.24 (d, 1H), 7.18 (d, 2H), 6.64 (d, 1H), 6.28-6.57 (m, 1H), 4.28-4.48 (m, 4H), 3.80-3.90 (m, 1H), 3.15-3.25 (m, 2H), 2.05-2.15 (m, 4H), 1.85-2.00 (m, 2H), 1.70-1.80 (m, 1H).

Example 40

4-(2-Fluoro-ethoxy)-N-[2-methyl-6-((S)-1-pyrrolidin-2-ylmethoxy)-pyridin-3-yl]-benzenesulfonamide×HCl MS (ESI) m/z: 410.1 [M+H]+
¹H-NMR (DMSO): δ [ppm] 9.60-9.70 (m, 1H), 9.54 (s, 1H), 8.95-9.05 (m, 1H), 7.58 (d, 2H), 7.24 (d, 1H), 7.13 (d, 2H), 6.64 (d, 1H), 4.71-4.85 (m, 2H), 4.30-4.50 (m, 4H), 3.80-3.90 (m, 1H), 3.15-3.25 (m, 2H), 2.05-2.15 (m, 4H), 1.85-2.00 (m, 2H), 1.70-1.80 (m, 1H).

Example 41

N-[2-Methyl-6-((S)-1-pyrrolidin-2-ylmethoxy)-pyridin-3-yl]-4-trifluoromethoxy-benzenesulfonamide×HCl MS (ESI) m/z: 432.1 [M+H]+
¹H-NMR (DMSO): δ [ppm] 9.90 (s, 1H), 9.60-9.70 (m, 1H), 8.95-9.05 (m, 1H), 7.79 (d, 2H), 7.60 (d, 2H), 7.27 (d, 1H), 6.66 (d, 1H), 4.31-4.47 (m, 2H), 3.85-3.95 (m, 1H), 3.15-3.25 (m, 2H), 2.05-2.15 (m, 4H), 1.85-2.00 (m, 2H), 1.70-1.80 (m, 1H).

Example 42

4-((R)-2-Fluoro-1-methyl-ethyl)-N-[2-methyl-6-((S)-1-pyrrolidin-2-ylmethoxy)-pyridin-3-yl]-benzenesulfonamide×HCl MS (ESI) m/z: 408.1 [M+H]+
¹H-NMR (DMSO): δ [ppm] 9.65 (s, 1H), 9.45-9.55 (m, 1H), 8.85-8.95 (m, 1H), 7.60 (d, 2H), 7.51 (d, 2H), 7.28 (d, 1H), 6.65 (d, 1H), 4.48-4.62 (m, 2H), 4.30-4.47 (m, 2H), 3.85-3.95 (m, 1H), 3.20-3.30 (m, 2H), 2.08-2.15 (m, 1H), 2.04 (s, 3H), 1.85-2.00 (m, 2H), 1.70-1.80 (m, 1H), 1.27 (d, 3H).

Example 43

4-Isopropyl-N-[2-methyl-6-((S)-1-pyrrolidin-2-ylmethoxy)-pyridin-3-yl]-benzenesulfonamide×HCl MS (ESI) m/z: 390.1 [M+H]+
¹H-NMR (DMSO): δ [ppm] 9.55-9.65 (m, 2H), 8.93-9.02 (m, 1H), 7.57 (d, 2H), 7.45 (d, 2H), 7.28 (d, 1H), 6.65 (d, 1H), 4.30-4.45 (m, 4H), 3.85-3.95 (m, 1H), 3.15-3.25 (m, 2H), 2.95-3.05 (m, 1H), 2.08-2.15 (m, 1H), 2.04 (s, 3H), 1.85-2.00 (m, 2H), 1.70-1.80 (m, 1H), 1.24 (d, 3H).

Example 44

N-[2-Methyl-6-((R)-1-pyrrolidin-2-ylmethoxy)-pyridin-3-yl]-4-oxazol-5-yl-benzenesulfonamide×HCl MS (ESI) m/z: 379.1 [M+H]+
¹H-NMR (DMSO): δ [ppm] 9.75 (s, 1H), 9.14-9.24 (m, 1H), 8.64-8.74 (m, 1H), 8.57 (s, 1H), 7.90-7.95 (m, 3H), 7.73 (d, 2H), 7.27 (d, 1H), 6.65 (d, 1H), 4.26-4.47 (m, 2H), 3.85-3.94 (m, 1H), 3.20-3.25 (m, 2H), 2.07-2.15 (m, 4H), 1.90-2.10 (m, 2H), 1.70-1.80 (m, 1H).

Example 45

4-Isopropyl-N-[2-methyl-6-((R)-1-pyrrolidin-2-ylmethoxy)-pyridin-3-yl]-benzenesulfonamide×HCl MS (ESI) m/z: 354.1 [M+H]+
¹H-NMR (DMSO): δ [ppm] 9.59 (s, 1H), 9.36-9.44 (m, 1H), 8.78-8.86 (m, 1H), 7.57 (d, 2H), 7.45 (d, 2H), 7.28 (d, 1H), 6.65 (d, 1H), 4.28-4.47 (m, 4H), 3.85-3.94 (m, 1H), 3.18-3.25 (m, 2H), 2.95-3.05 (m, 1H), 2.08-2.15 (m, 1H), 2.04 (s, 3H), 1.88-2.00 (m, 2H), 1.70-1.80 (m, 1H), 1.24 (d, 3H).

The following examples were obtained according to the synthetic procedure analogous to that described for example 12.

Example 46

4-((R)-2,2-Difluoro-1-methyl-ethyl)-N-[2-methoxy-6-(2-propylamino-ethoxy)-pyridin-3-yl]-benzenesulfonamide×HCl MS (ESI) m/z: 444.1 [M+H]+
¹H-NMR (DMSO): δ [ppm] 9.54 (s, 1H), 9.44 (bs, 2H), 7.61-7.63 (m, 2H), 7.49-7.52 (m, 3H), 6.40 (d, 1H), 6.10-6.34 (m, 1H), 4.50-4.52 (m, 2H), 3.43 (s, 3H), 3.32-3.40 (m, 1H), 3.25-3.28 (m, 2H), 2.85-2.90 (m, 2H), 1.65-1.73 (m, 2H), 1.31 (d, 3H), 0.89 (t, 3H).

Example 47

4-((S)-2,2-Difluoro-1-methyl-ethyl)-N-[2-methoxy-6-(2-propylamino-ethoxy)-Iyridin-3-yl]-benzenesulfonamide×HCl MS (ESI) m/z: 444.1 [M+H]+

¹H-NMR (DMSO): δ [ppm] 9.54 (s, 1H), 9.44 (bs, 2H), 7.61-7.63 (m, 2H), 7.49-7.52 (m, 3H), 6.40 (d, 1H), 6.10-6.34 (m, 1H), 4.50-4.52 (m, 2H), 3.43 (s, 3H), 3.32-3.40 (m, 1H), 3.25-3.28 (m, 2H), 2.85-2.90 (m, 2H), 1.65-1.73 (m, 2H), 1.31 (d, 3H), 0.89 (t, 3H).

Example 48

N-[2-Methoxy-6-(2-propylamino-ethoxy)-pyridin-3-yl]-4-oxazol-4-yl-benzenesulfonamide×HCl MS (ESI) m/z: 433.1 [M+H]$^+$
¹H-NMR (DMSO): δ [ppm] 9.58 (s, 1H), 9.25 (bs, 2H), 8.81 (s, 1H), 8.54 (s, 1H), 7.96 (d, 2H), 7.71 (d, 2H), 7.49 (d, 1H), 6.40 (d, 1H), 6.10-6.34 (m, 1H), 4.48-4.51 (m, 2H), 3.52 (s, 3H), 3.25-3.28 (m, 2H), 2.85-2.90 (m, 2H), 1.63-1.71 (m, 2H), 0.90 (t, 3H).

Example 49

N-[2-Methoxy-6-(2-propylamino-ethoxy)-pyridin-3-yl]-4-pyrazol-1-yl-benzenesulfonamide×HCl MS (ESI) m/z: 432.1 [M+H]$^+$
¹H-NMR (DMSO): δ [ppm] 9.59 (s, 1H), 8.94 (bs, 2H), 8.61 (d, 1H), 8.01 (d, 2H), 7.82 (s, 1H), 7.75 (d, 2H), 7.50 (d, 1H), 6.61 (bs, 1H), 6.40 (d, 1H), 4.42-4.47 (m, 2H), 3.54 (s, 3H), 3.25-3.30 (m, 2H), 2.85-2.95 (m, 2H), 1.56-1.68 (m, 2H), 0.89 (t, 3H).

Example 50

4-(3-Fluoro-propyl)-N-[2-methyl-6-(2-propylamino-ethoxy)-pyridin-3-yl]-benzenesulfonamide×HCl MS (ESI) m/z: 410.1 [M+H]$^+$
¹H-NMR (DMSO): δ [ppm] 9.72 (s, 1H), 9.36 (bs, 2H), 7.56 (d, 2H), 7.41 (d, 2H), 7.22 (d, 1H), 6.61 (d, 1H), 4.35-4.48 (m, 4H), 3.20-3.30 (m, 2H), 2.83-2.90 (m, 2H), 2.70-2.76 (m, 2H), 2.03 (s, 3H), 1.85-2.00 (m, 2H), 1.62-1.71 (m, 2H), 0.89 (t, 3H).

Example 51

N-[2-Methyl-6-(2-propylamino-ethoxy)-pyridin-3-yl]-4-((R)-2,2,2-trifluoro-1-methyl-ethyl)-benzenesulfonamide×HCl MS (ESI) m/z: 446.1 [M+H]$^+$
¹H-NMR (DMSO): δ [ppm] 9.86 (s, 1H), 9.36 (bs, 2H), 7.66 (d, 2H), 7.60 (d, 2H), 7.25 (d, 1H), 6.62 (d, 1H), 4.45-4.48 (m, 2H), 3.90-4.02 (m, 1H), 3.20-3.30 (m, 2H), 2.83-2.90 (m, 2H), 1.98 (s, 3H), 1.62-1.71 (m, 2H), 1.44 (d, 3H), 0.89 (t, 3H).

Example 52

4-((R)-2,2-Difluoro-1-methyl-ethyl)-N-[2-methyl-6-(2-propylamino-ethoxy)-pyridin-3-yl]-benzenesulfonamide×HCl MS (ESI) m/z: 428.1 [M+H]$^+$
¹H-NMR (DMSO): δ [ppm] 9.81 (s, 1H), 9.36 (bs, 2H), 7.62 (d, 2H), 7.52 (d, 2H), 7.24 (d, 1H), 6.62 (d, 1H), 6.09-6.32 (m, 1H), 4.45-4.48 (m, 2H), 3.34-3.42 (m, 1H), 3.22-3.27 (m, 2H), 2.83-2.90 (m, 2H), 2.01 (s, 3H), 1.62-1.71 (m, 2H), 1.30 (d, 3H), 0.89 (t, 3H).

Example 53

N-[2-Methyl-6-(2-propylamino-ethoxy)-pyridin-3-yl]-4-(2,2,2-trifluoro-ethoxy)-benzenesulfonamide×HCl MS (ESI) m/z: 412.1 [M+H]$^+$
¹H-NMR (DMSO): δ [ppm] 9.68 (s, 1H), 9.31 (bs, 2H), 7.62 (d, 2H), 7.22-7.24 (m, 3H), 6.63 (d, 1H), 4.87-4.92 (m, 2H), 4.46-4.51 (m, 2H), 3.24-3.30 (m, 2H), 2.85-2.95 (m, 2H), 2.11 (s, 3H), 1.65-1.74 (m, 2H), 0.92 (t, 3H).

Example 54

4-((R)-2,2-Difluoro-1-methyl-ethyl)-N-[4-methyl-6-(2-propylamino-ethoxy)-pyridin-3-yl]-benzenesulfonamide×HCl MS (ESI) m/z: 428.1 [M+H]$^+$
¹H-NMR (DMSO): δ [ppm] 9.70 (s, 1H), 8.60-8.66 (m, 2H), 7.64-7.69 (m, 3H), 7.56 (d, 2H), 6.70 (s, 1H), 6.09-6.39 (m, 1H), 4.45-4.48 (m, 2H), 3.30-3.45 (m, 3H), 2.90-3.00 (m, 2H), 1.94 (s, 3H), 1.60-1.70 (m, 2H), 1.35 (d, 3H), 0.94 (t, 3H).

Example 55

N-[4-Methyl-6-(2-propylamino-ethoxy)-pyridin-3-yl]-4-oxazol-4-yl-benzenesulfonamide×HCl MS (ESI) m/z: 381.1 [M+H]$^+$
¹H-NMR (DMSO): δ [ppm] 9.73 (s, 1H), 8.83 (s, 1H), 8.56-8.65 (m, 2H), 8.01 (d, 2H), 7.73 (d, 2H), 7.66 (s, 1H), 6.71 (s, 1H), 4.44-4.47 (m, 2H), 3.30-3.45 (m, 2H), 2.90-3.00 (m, 2H), 2.01 (s, 3H), 1.60-1.68 (m, 2H), 0.93 (t, 3H).

Example 56

4-(2,2-Difluoro-ethoxy)-N-[4-methyl-6-(2-propylamino-ethoxy)-pyridin-3-yl]-benzenesulfonamide×HCl MS (ESI) m/z: 394.1 [M+H]$^+$
¹H-NMR (DMSO): δ [ppm] 9.70 (s, 1H), 9.35 (bs, 2H), 7.58-7.62 (m, 3H), 7.17 (d, 1H), 6.69 (s, 1H), 6.29-6.55 (m, 1H), 4.38-4.50 (m, 4H), 3.21-3.28 (m, 2H), 2.82-2.90 (m, 2H), 1.99 (s, 3H), 1.62-1.71 (m, 2H), 0.89 (t, 3H).

Example 57

4-((R)-2-Fluoro-1-methyl-ethyl)-N-[4-methyl-6-(2-propylamino-ethoxy)-pyridin-3-yl]-benzenesulfonamide×HCl MS (ESI) m/z: 410.1 [M+H]$^+$
¹H-NMR (DMSO): δ [ppm] 9.76 (s, 1H), 9.32 (bs, 2H), 7.60-7.62 (m, 3H), 7.50 (d, 2H), 6.68 (s, 1H), 4.45-4.59 (m, 4H), 3.20-3.30 (m, 3H), 2.84-2.91 (m, 2H), 1.92 (s, 3H), 1.63-1.71 (m, 2H), 1.23 (d, 3H), 0.89 (t, 3H).

Example 58

N-[4-Methyl-6-(2-propylamino-ethoxy)-pyridin-3-yl]-4-trifluoromethoxy-benzenesulfonamide×HCl MS (ESI) m/z: 434.1 [M+H]$^+$ $^1$H-NMR (DMSO): δ [ppm] 9.88 (s, 1H), 8.80-8.90 (m, 1H), 7.79 (d, 2H), 7.58-7.63 (m, 3H), 6.70 (s, 1H), 4.43-4.46 (m, 2H), 3.44-3.46 (m, 2H), 3.25-3.35 (m, 2H), 2.85-2.95 (m, 2H), 1.95 (s, 3H), 1.58-1.68 (m, 2H), 0.91 (t, 3H).

Example 59

4-Isopropyl-N-[4-methyl-6-(2-propylamino-ethoxy)-pyridin-3-yl]-benzenesulfonamide×HCl MS (ESI) m/z: 392.1 [M+H]$^+$
$^1$H-NMR (MeOD): δ [ppm] 7.73 (s, 1H), 7.63 (d, 2H), 7.42 (d, 2H), 6.81 (s, 1H), 4.55-4.58 (m, 2H), 3.44-3.46 (m, 2H), 3.00-3.10 (m, 3H), 2.05 (s, 3H), 1.72-1.80 (m, 2H), 1.29 (d, 6H), 1.05 (t, 3H).

Example 60

4-(2-Fluoro-ethoxy)-N-[5-methyl-6-(2-propylamino-ethoxy)-pyridin-3-yl]-benzenesulfonamide×HCl MS (ESI) m/z: 376.1 [M+H]$^+$
$^1$H-NMR (DMSO): δ [ppm] 10.10 (s, 1H), 9.30 (bs, 2H), 7.62-7.66 (m, 3H), 7.31 (d, 1H), 7.09 (d, 2H), 4.70-4.80 (m, 2H), 4.48-4.50 (m, 2H), 4.30-4.39 (m, 2H), 3.24-3.30 (m, 2H), 2.85-2.90 (m, 2H), 2.12 (s, 3H), 1.62-1.72 (m, 2H), 0.90 (t, 3H).

Example 61

4-Isopropyl-N-{2-methyl-6-[(1-propylpyrrolidin-3-yl)oxy]pyridin-3-yl}benzenesulfonamide (2E)-but-2-enedioate 61.1
2-Methyl-3-nitro-6-(pyrrolidin-3-yloxy)pyridine 6-Methyl-5-nitropyridin-2-ol (5 g) was dissolved in tetrahydrofuran and DL-3-pyrrolidinol (2.83 g) and triphenylphosphine (12.76 g) were added. Di-tert-butyl (E)-diazene-1,2-dicarboxylate (11.21 g) dissolved in tetrahydrofuran (15 mL) was added dropwise over 15 min. The reaction mixture was stirred at room temperature for 50 h. The reaction mixture was concentrated in vacuo. The remaining residue was suspended in dichloromethane and trifluoroacetic acid (7.55 mL) was added dropwise. The reaction mixture was stirred for 12 h at room temperature. The reaction mixture was concentrated in vacuo, redissolved in dichloromethane and extracted several times with 1N hydrochloric acid. The combined aqueous extracts were treated with 1N NaOH to pH 10 and extracted with ethyl acetate (3×). The combined ethyl acetate extracts were successively washed with water and brine and dried (sodium sulfate). After concentration in vacuo, the crude product was purified by flash chromatography (silica, dichloromethane, 1-10% methanol gradient). Yield: 1.5 g (18.6%, pale yellow oil).

61.2. 2-Methyl-3-nitro-6-[(1-propionylpyrrolidin-3-yl)oxy]pyridine

2-Methyl-3-nitro-6-(pyrrolidin-3-yloxy)pyridine (1.3 g) was dissolved in dichloromethane (20 ml) and triethylamine (1.57 ml) was added. The solution was cooled to 0° C. and a solution of propionyl chloride (574 mg) in dichloromethane (5 ml) was added dropwise over 5 min. The reaction mixture was allowed to come to room temperature and was stirred for another 5 min. Water (10 ml) was added. After stirring for 3 min, the phases were separated and the aqueous layer was extracted with dichloromethane. The combined organic layers were dried (sodium sulfate) and concentrated in vacuo. The crude product was purified by flash chromatography (silica, dichloromethane/methanol=98/2). Yield: 950 mg (64.9%, pale yellow oil).

61.3 2-Methyl-6-[(1-propionylpyrrolidin-3-yl)oxy]pyridin-3-amine

2-Methyl-3-nitro-6-[(1-propionylpyrrolidin-3-yl)oxy]pyridine (940 mg) was dissolved in methanol (50 mL) and hydrogenated (H-cube from ThalesNano, 10% Pd/C, 60° C., 50 bar, 1 mL/min). The methanol was removed in vacuo. Yield: 800 mg (95%, colorless oil).

61.4 4-Isopropyl-N-{2-methyl-6-[(1-propionylpyrrolidin-3-yl)oxy]pyridin-3-yl}-benzenesulfonamide 2-Methyl-6-[(1-propionylpyrrolidin-3-yl)oxy]pyridin-3-amine (340 mg) was dissolved in pyridine (3.3 mL) and 4-isopropylbenzenesulfonyl chloride (358 mg) was slowly added under stirring. After 19 h stirring at room temperature, the reaction mixture was diluted with dichloromethane and 2 M aqueous NaOH was added. After stirring for 1 h at room temperature the phases were separated. The organic phase was dried (sodium sulfate), concentrated and the crude product purified by flash chromatography (silica, dichloromethane, 0.5 to 5% methanol gradient). Yield: 460 mg (78%, pale yellow oil).

61.5 4-Isopropyl-N-{2-methyl-6-[(1-propylpyrrolidin-3-yl)oxy]pyridin-3-yl}-benzenesulfonamide (2E)-but-2-enedioate Lithium aluminium hydride (88 mg) was suspended in tetrahydrofuran (1 mL) and 4-isopropyl-N-{2-methyl-6-[(1-propionylpyrrolidin-3-yl)oxy]pyridin-3-yl}benzene-sulfonamide (250 mg) dissolved in tetrahydrofuran (1 ml) was added dropwise at room temperature over 5 min. After stirring for another 30 min, the reaction was quenched with a solution of 1% water in tetrahydrofuran and concentrated. The residue was taken up in dichloromethane, washed with water and the organic phase was dried (sodium sulfate) and concentrated in vacuo. The crude product was purified by flash chromatography (silica, dichloromethane/methanol=97/3). The product (70 mg) was dissolved in methanol and (2E)-but-2-enedioic acid (19 mg) was added. After stirring for 1 h at 40° C. methanol was removed in vacuo. Yield: 89 mg (26%, colorless solid).

MS (ESI) m/z: 418.1 [M+H]$^+$

Example 62

4-(2-Fluoroethoxy)-N-{2-methyl-6-[(1-propylpyrrolidin-3-yl)oxy]pyridin-3-yl}-benzenesulfonamide (2E)-but-2-enedioate 4-(2-Fluoroethoxy)-N-{2-methyl-6-[(1-propylpyrrolidin-3-yl)oxy]pyridin-3-yl}-benzenesulfonamide (2E)-but-2-enedioate was prepared analogously to example 61 from 2-methyl-6-[(1-propylpyrrolidin-3-yl)oxy]pyridin-3-amine and 4-(2-fluoroethoxy)benzenesulfonyl chloride.

MS (ESI) m/z: 438.1 [M+H]$^+$

Example 63

4-(2,2-Difluoroethoxy)-N-{2-methyl-6-[(1-propylpyrrolidin-3-yl)oxy]pyridin-3-yl}-benzenesulfonamide (2E)-but-2-enedioate

4-(2,2-Difluoroethoxy)-N-{2-methyl-6-[(1-propylpyrrolidin-3-yl)oxy]pyridin-3-yl}-benzenesulfonamide (2E)-but-2-enedioate was prepared analogously to example example 61 from 2-methyl-6-[(1-propionylpyrrolidin-3-yl)oxy]pyridin-3-amine and 4-(2,2-difluoroethoxy)benzenesulfonyl chloride.

MS (ESI) m/z: 456.1 [M+H]$^+$

Example 64

4-[(1S)-2,2-Difluoro-1-methylethyl]-N-{2-methyl-6-[(1-propylpyrrolidin-3-yl)-oxy]pyridin-3-yl}benzenesulfonamide (2E)-but-2-enedioate

4-[(1S)-2,2-Difluoro-1-methylethyl]-N-{2-methyl-6-[(1-propylpyrrolidin-3-yl)-oxy]pyridin-3-yl}benzenesulfonamide (2E)-but-2-enedioate was prepared analogously to example 61 from 2-methyl-6-[(1-propionylpyrrolidin-3-yl)oxy]pyridin-3-amine and 4-[(1S)-2,2-difluoro-1-methylethyl]benzenesulfonyl chloride.

MS (ESI) m/z: 454.1 [M+H]$^+$

III. Examples of Galenic Administration Forms

A) Tablets

Tablets of the following composition are pressed on a tablet press in the customary manner:
40 mg of substance from Example 8
120 mg of corn starch
13.5 mg of gelatin
45 mg of lactose
2.25 mg of Aerosil® (chemically pure silicic acid in submicroscopically fine dispersion)
6.75 mg of potato starch (as a 6% paste)

B) Sugar-Coated Tablets
20 mg of substance from Example 8
60 mg of core composition
70 mg of saccharification composition The core composition consists of 9 parts of corn starch, 3 parts of lactose and 1 part of 60:40 vinylpyrrolidone/vinyl acetate copolymer. The saccharification composition consists of 5 parts of cane sugar, 2 parts of corn starch, 2 parts of calcium carbonate and 1 part of talc. The sugar-coated tablets which had been prepared in this way are subsequently provided with a gastric juice-resistant coating.

IV. Biolociical Investigations

Receptor Binding Studies:

The substance to be tested was either dissolved in methanol/Chremophor® (BASF-AG) or in dimethyl sulfoxide and then diluted with water to the desired concentration.

Dopamine D$_3$ Receptor:

The assay mixture (0.250 ml) was composed of membranes derived from ~10$^6$ HEK-293 cells possessing stably expressed human dopamine D$_3$ receptors, 0.1 nM [$^{125}$I]-iodosulpride and incubation buffer (total binding) or, in addition, test substance (inhibition curve) or 1 μM spiperone (nonspecific binding). Each assay mixture was run in triplicate.

The incubation buffer contained 50 mM tris, 120 mM NaCl, 5 mM KCl, 2 mM CaCl$_2$, 2 mM MgCl$_2$ and 0.1% bovine serum albumin, 10 μM quinolone and 0.1% ascorbic acid (prepared fresh daily). The buffer was adjusted to pH 7.4 with HCl.

Dopamine D$_{2L}$ Receptor:

The assay mixture (1 ml) was composed of membranes from ~10$^6$ HEK-293 cells possessing stably expressed human dopamine D$_{2L}$ receptors (long isoform) and 0.01 nM [$^{125}$I] iodospiperone and incubation buffer (total binding) or, in addition, test substance (inhibition curve) or 1 μM haloperidol (nonspecific binding). Each assay mixture was run in triplicate.

The incubation buffer contained 50 mM tris, 120 mM NaCl, 5 mM KCl, 2 mM CaCl$_2$, 2 mM MgCl$_2$ and 0.1% bovine serum albumin. The buffer was adjusted to pH 7.4 with HCl.

Measurement and Analysis:

After having been incubated at 25° C. for 60 minutes, the assay mixtures were filtered through a Whatman GF/B glass fiber filter under vacuum using a cell collecting device. The filters were transferred to scintillation viols using a filter transfer system. After 4 ml of Ultima Gold® (Packard) have been added, the samples were shaken for one hour and the radioactivity was then counted in a Beta-Counter (Packard, Tricarb 2000 or 2200CA). The cpm values were converted into dpm using a standard quench series and the program belonging to the instrument.

The inhibition curves were analyzed by means of iterative nonlinear regression analysis using the Statistical Analysis System (SAS) which is similar to the "LIGAND" program described by Munson and Rodbard.

The results of the receptor binding studies are expressed as receptor binding constants $K_i(D_2)$ and $K_i(D_3)$, respectively, as herein before described, and given in table 3.

In these tests, the compounds according to the invention exhibit very good affinities for the D$_3$ receptor (<10 nM, frequently <5 nM) and bind selectively to the D$_3$ receptor.

The results of the binding tests are given in table 1.

TABLE 1

| Example | $K_i(D3)$* | $K_i(D2)$*/$K_i(D3)$* |
|---|---|---|
| 1 | ++++ | ++ |
| 2 | +++ | + |
| 3 | +++ | ++ |
| 4 | ++++ | ++ |
| 5 | +++ | ++ |
| 6 | +++ | ++ |
| 7 | ++++ | ++++ |
| 8 | +++ | ++++ |
| 9 | +++ | ++++ |
| 10 | +++ | ++++ |
| 11 | ++++ | ++++ |
| 13 | + | + |
| 15 | ++ | + |
| 16 | +++ | + |
| 17 | +++ | ++ |
| 18 | +++ | + |
| 19 | ++ | + |
| 20 | +++ | + |
| 21 | + | ++ |
| 22 | + | n.d. |
| 23 | ++ | + |
| 24 | ++ | ++ |
| 27 | +++ | +++ |
| 29 | ++++ | ++++ |
| 34 | +++ | ++++ |
| 36 | ++ | ++++ |
| 43 | +++ | +++ |

TABLE 1-continued

| | | |
|---|---|---|
| 57 | ++ | ++ |
| 61 | +++ | + |

*Receptor binding constants obtained according to the assays described herein before
Key:

$K_i(D3)$*

| | |
|---|---|
| + | between 50 and 150 nM |
| ++ | between 10 and 50 nM |
| +++ | between 1 and 10 nM |
| ++++ | <1 nM |

$K_i(D2)*/K_i(D3)*$

| | |
|---|---|
| + | between 10 and 50 |
| ++ | between 50 and 100 |
| +++ | between 100 and 150 |
| ++++ | >150 |

We claim:

1. An aryloxyethylamine compound of the formula I

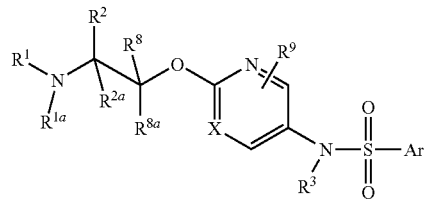

(I)

wherein

Ar is phenyl or an aromatic 5- or 6-membered C-bound heteroaromatic radical, wherein Ar may carry 1 radical $R^a$ and wherein Ar may also carry 1 or 2 radicals $R^b$;

$R^a$ is selected from the group consisting of $C_1$-$C_6$-alkyl, fluorinated $C_1$-$C_6$-alkyl, $C_2$-$C_6$-alkenyl, fluorinated $C_2$-$C_6$-alkenyl, $C_3$-$C_6$-cycloalkyl, fluorinated $C_3$-$C_6$-cycloalkyl, $C_1$-$C_6$-alkoxy, fluorinated $C_1$-$C_6$-alkoxy, $C_1$-$C_6$-hydroxyalkyl, $C_1$-$C_6$-alkoxy-$C_1$-$C_4$-alkyl, $C_1$-$C_6$-hydroxyalkoxy, $C_1$-$C_6$-alkoxy-$C_1$-$C_4$-alkoxy, COOH, $NR^4R^5$, $CH_2NR^4R^5$, $ONR^4R^5$, $NHC(O)NR^4R^5$, $C(O)NR^4R^5$, $SO_2NR^4R^5$, $C_1$-$C_6$-alkylcarbonyl, fluorinated $C_1$-$C_6$-alkylcarbonyl, $C_1$-$C_6$-alkylcarbonylamino, fluorinated $C_1$-$C_6$-alkylcarbonylamino, $C_1$-$C_6$-alkylcarbonyloxy, fluorinated $C_1$-$C_6$-alkylcarbonyloxy, $C_1$-$C_6$-alkoxycarbonyl, fluorinated $C_1$-$C_6$-alkoxycarbonyl, $C_1$-$C_6$-alkylthio, fluorinated $C_1$-$C_6$-alkylthio, $C_1$-$C_6$-alkylsulfinyl, fluorinated $C_1$-$C_6$-alkylsulfinyl, $C_1$-$C_6$-alkylsulfonyl, fluorinated $C_1$-$C_6$-alkylsulfonyl, phenylsulfonyl, phenyl, phenoxy, benzyloxy, pyridin-2-yloxy and a 3- to 7-membered heterocyclic radical, wherein the phenyl groups, the pyridyl group and the heterocyclyl group in the six last mentioned radicals may carry 1, 2, 3 or 4 radicals selected from halogen, cyano, OH, oxo, CN, and a radical $R^{aa}$, wherein $R^{aa}$ is selected from $C_1$-$C_6$-alkyl, fluorinated $C_1$-$C_6$-alkyl, $C_2$-$C_6$-alkenyl, fluorinated $C_2$-$C_6$-alkenyl, $C_3$-$C_6$-cycloalkyl, fluorinated $C_3$-$C_6$-cycloalkyl, $C_1$-$C_6$-alkoxy, fluorinated $C_1$-$C_6$-alkoxy, $C_1$-$C_6$-hydroxyalkyl, $C_1$-$C_6$-alkoxy-$C_1$-$C_4$-alkyl, $C_1$-$C_6$-hydroxyalkoxy, $C_1$-$C_6$-alkoxy-$C_1$-$C_4$-alkoxy, COOH, $NR^4R^5$, $CH_2NR^4R^5$, $ONR^4R^5$, $NHC(O)NR^4R^5 C(O)NR^4R^5$, $SO_2NR^4R^5 C_1$-$C_6$-alkylcarbonyl, fluorinated $C_1$-$C_6$-alkylcarbonyl, $C_1$-$C_6$-alkylcarbonylamino, fluorinated $C_1$-$C_6$-alkylcarbonylamino, $C_1$-$C_6$-alkylcarbonyloxy, fluorinated $C_1$-$C_6$-alkylcarbonyloxy, $C_1$-$C_6$-alkoxycarbonyl, fluorinated $C_1$-$C_6$-alkoxycarbonyl, $C_1$-$C_6$-alkylthio, fluorinated $C_1$-$C_6$-alkylthio, $C_1$-$C_6$-alkylsulfinyl, fluorinated $C_1$-$C_6$-alkylsulfinyl, $C_1$-$C_6$-alkylsulfonyl, fluorinated $C_1$-$C_6$-alkylsulfonyl, each $R^b$ is selected from halogen, cyano, nitro, OH, methyl, methoxy, fluoromethyl, difluoromethyl, trifluoromethyl, fluormethoxy, difluoromethoxy and trifluoromethoxy, or the radical $R^a$ and one radical $R^b$, if present, which are bound to two adjacent carbon atoms of phenyl, may form a 5- or 6-membered heterocyclic or carbocyclic ring which is fused to the phenyl ring and which is unsubstituted or which may carry 1, 2 or 3 radicals selected from halogen, $NO_2$, $NH_2$, OH, CN, $C_1$-$C_6$-alkyl, fluorinated $C_1$-$C_6$-alkyl, $C_3$-$C_6$-cycloalkyl, fluorinated $C_3$-$C_6$-cycloalkyl, $C_1$-$C_6$-alkoxy, fluorinated $C_1$-$C_6$-alkoxy, $C_1$-$C_6$-hydroxyalkyl, $C_1$-$C_4$-alkoxy-$C_2$-$C_4$-alkyl, $C_1$-$C_6$-hydroxyalkoxy, $C_1$-$C_4$-alkoxy-$C_2$-$C_4$-alkoxy, $C_1$-$C_6$-alkylcarbonyl, fluorinated $C_1$-$C_6$-alkylcarbonyl, $C_1$-$C_6$-alkylamino, di-$C_1$-$C_6$-alkylamino, $C_1$-$C_6$-alkylaminocarbonyl, di-$C_1$-$C_6$-alkylaminocarbonyl, $C_1$-$C_6$-alkylcarbonylamino, fluorinated $C_1$-$C_6$-alkylcarbonylamino, $C_1$-$C_6$-alkylcarbonyloxy, fluorinated $C_1$-$C_6$-alkylcarbonyloxy, $C_1$-$C_6$-alkoxycarbonyl, $C_1$-$C_6$-alkylthio, fluorinated $C_1$-$C_6$-alkylthio, $C_1$-$C_6$-alkylsulfinyl, fluorinated $C_1$-$C_6$-alkylsulfinyl, $C_1$-$C_6$-alkylsulfonyl and fluorinated $C_1$-$C_6$-alkylsulfonyl;

X is N or CH;

$R^1$ is H, $C_1$-$C_4$-alkyl, $C_3$-$C_4$-cycloalkyl, $C_3$-$C_4$-cycloalkylmethyl, $C_3$-$C_4$-alkenyl, fluorinated $C_1$-$C_4$-alkyl, fluorinated $C_3$-$C_4$-cycloalkyl, fluorinated $C_3$-$C_4$-cycloalkylmethyl, fluorinated $C_3$-$C_4$-alkenyl, formyl or $C_1$-$C_3$-alkylcarbonyl;

$R^{1a}$ is H, $C_1$-$C_4$-alkyl, $C_3$-$C_4$-cycloalkyl, $C_3$-$C_4$-cycloalkylmethyl, $C_3$-$C_4$-alkenyl, fluorinated $C_1$-$C_4$-alkyl, fluorinated $C_3$-$C_4$-cycloalkyl, fluorinated $C_3$-$C_4$-cycloalkylmethyl, or fluorinated $C_3$-$C_4$-alkenyl; or $R^1$ and $R^{1a}$ together are $(CR^6R^7)_r$ with r being 3, 4 or 5;

$R^2$ and $R^{2a}$ are independently of each other H, fluorine, $C_1$-$C_4$-alkyl or fluorinated $C_1$-$C_4$-alkyl or $R^{2a}$ and $R^2$ together may form a ring member $(CR^6R^7)_m$ with m being 2, 3, 4 or 5; or $R^{1a}$ and $R^{2a}$ together are $(CR^6R^7)_n$ with n being 2, 3 or 4;

$R^3$ is H or $C_1$-$C_4$-alkyl;

$R^4$, $R^5$ independently of each other and independently of their individual occurrence are selected from H, $C_1$-$C_3$-alkyl, $C_1$-$C_3$-alkoxy and fluorinated $C_1$-$C_3$-alkyl;

$R^6$, $R^7$ independently of each other and independently of their individual occurrence are selected from H, fluorine, $C_1$-$C_4$-alkyl and fluorinated $C_1$-$C_4$-alkyl;

$R^8$, $R^{8a}$ independently of each other are H, fluorine, $C_1$-$C_4$-alkyl or fluorinated $C_1$-$C_4$-alkyl or $R^{1a}$ and $R^{8a}$ together may form a ring member $(CR^6R^7)_q$ with q being 2, 3, 4 or 5; or $R^{1a}$ and $R^{8a}$ together are $(CR^6R^7)_s$ with s being 2 or 3;

$R^9$ is H, $C_1$-$C_4$-alkyl, fluorinated $C_1$-$C_4$-alkyl, $C_1$-$C_4$-alkoxy or fluorinated $C_1$-$C_4$-alkoxy;

and the physiologically tolerated acid addition salts of these compounds.

2. The compound as claimed in claim 1, wherein Ar is phenyl or an aromatic 5- or 6-membered C-bound heteroaromatic radical, comprising 1 nitrogen atom as ring member and 0, 1, 2 or 3 further heteroatoms selected from O, S and N as ring members, wherein Ar carries one radical $R^a$ which is selected from the group consisting of $C_1$-$C_6$-alkyl, fluorinated $C_1$-$C_6$-alkyl, $C_3$-$C_6$-cycloalkyl, fluorinated $C_3$-$C_6$-cycloalkyl, $C_1$-$C_6$-alkoxy, fluorinated $C_1$-$C_6$-alkoxy, $NR^4R^5$, 1-aziridinyl, azetidin-1-yl, pyrrolidin-1-yl or piperidin-1-yl, wherein the last four mentioned radicals may be fluorinated, a phenyl group and an aromatic 5- or 6-membered C-bound heteroaromatic radical comprising 1 nitrogen atom as ring member and 0, 1, 2 or 3 further heteroatoms selected from O, S and N as ring members, wherein the last two mentioned radicals may carry 1, 2, 3 or 4 radicals selected from halogen and a radical $R^{aa}$, wherein $R^{aa}$ is selected from $C_1$-$C_6$-alkyl, fluorinated $C_1$-$C_6$-alkyl, $C_3$-$C_6$-cycloalkyl, fluorinated $C_3$-$C_6$-cycloalkyl, $C_1$-$C_6$-alkoxy, fluorinated $C_1$-$C_6$-alkoxy and $NR^4R^5$; and wherein Ar may carry 1 or 2 further radicals $R^b$, which are independently of each other selected from halogen, cyano, methyl, fluoromethyl, difluoromethyl, trifluoromethyl, difluoromethoxy and trifluoromethoxy; and wherein $R^4$, $R^5$, independently of each other and independently of each individual occurrence, are selected from H, $C_1$-$C_3$-alkyl and fluorinated $C_1$-$C_3$-alkyl.

3. The compound as claimed in claim 1 or 2, wherein Ar carries one radical $R^a$ of the formula $R^{a'}$

wherein
Y is N, CH or CF,
$R^{a1}$ and $R^{a2}$ are independently of each other selected from $C_1$-$C_2$-alkyl, $C_1$-$C_2$-alkoxy, fluorinated $C_1$-$C_2$-alkyl, provided for Y being CH or CF one of the radicals $R^{a1}$ or $R^{a2}$ may also be hydrogen or fluorine, or
$R^{a1}$ and $R^{a2}$ together form a ring member $(CH_2)_k$ wherein 1 or 2 of the hydrogen atoms may be replaced by fluorine, hydroxy, oxo, $C_1$-$C_2$-alkyl or $C_1$-$C_2$-alkoxy, and wherein one $CH_2$ moiety may be replaced by O, S, S=O, $SO_2$ or N–$R^c$, with $R^c$ being hydrogen or $C_1$-$C_2$-alkyl, and wherein k is 2, 3, 4, 5 or 6.

4. The compound as claimed in claim 3, wherein the radical $R^{a'}$ is selected from isopropyl, (R)-1-fluoroethyl, (S)-1-fluoroethyl, 2-fluoroethyl, 1,1-difluoroethyl, 2,2-difluoroethyl, 2,2,2-trifluoroethyl, (R)-1-fluoropropyl, (S)-1-fluoropropyl, 2-fluoropropyl, 3-fluoropropyl, 1,1-difluoropropyl, 2,2-difluoropropyl, 3,3-difluoropropyl, 3,3,3-trifluoropropyl, (R)-2-fluoro-1-methylethyl, (S)-2-fluoro-1-methylethyl, (R)-2,2-difluoro-1-methylethyl, (S)-2,2-difluoro-1-methylethyl, (R)-1,2-difluoro-1-methylethyl, (S)-1,2-difluoro-1-methylethyl, (R)-2,2,2-trifluoro-1-methylethyl, (S)-2,2,2-trifluoro-1-methylethyl, 2-fluoro-1-(fluoromethyhethyl, 1-(difluoromethyl)-2,2-difluoroethyl, cyclopropyl, cyclobutyl, 1-fluorocyclopropyl, and 2-fluorocyclopropyl.

5. The compound as claimed in claim 3, wherein the radical $R^{a'}$ is selected from 4-morpholinyl, 4-thiomorpholinyl, 4-(1,1-dioxo)thiomorpholinyl, piperazin-1-yl, 4-methylpiperazin-1-yl, azetidin-1-yl, 2-methylazetidin-1-yl, (S)-2-methylazetidin-1-yl, (R)-2-methylazetidin-1-yl, 3-fluoroazetidin-1-yl, 3-methoxyazetidin-1-yl, 3-hydroxyazetidin-1-yl, 1,3-oxazol-5-yl, pyrrolidin-1-yl, pyrrolidin-2-yl, (S)-pyrrolidin-2-yl, (R)-pyrrolidin-2-yl, pyrrolidin-3-yl, (S)-pyrrolidin-3-yl, (R)-pyrrolidin-3-yl, 2-fluoropyrrolidin-1-yl, (S)-2-fluoropyrrolidin-1-yl, (R)-2-fluoropyrrolidin-1-yl, 3-fluoropyrrolidin-1-yl, (S)-3-fluoropyrrolidin-1-yl, (R)-3-fluoropyrrolidin-1-yl, 2,2-difluoropyrrolidin-1-yl, 3,3-difluoropyrrolidin-1-yl, 2-methylpyrrolidin-1-yl, (S)-2-methylpyrrolidin-1-yl, (R)-2-methylpyrrolidin-1-yl, 3-methylpyrrolidin-1-yl, (S)-3-methylpyrrolidin-1-yl, (R)-3-methylpyrrolidin-1-yl, 1-methylpyrrolidin-2-yl, (S)-1-methylpyrrolidin-2-yl, (R)-1-methylpyrrolidin-2-yl, 1-methylpyrrolidin-3-yl, (S)-1-methylpyrrolidin-3-yl, (R)-1-methylpyrrolidin-3-yl, 2,2-dimethylpyrrolidin-1-yl, 3,3-dimethylpyrrolidin-1-yl, 2-trifluoromethylpyrrolidin-1-yl, (S)-2-trifluoromethylpyrrolidin-1-yl, (R)-2-trifluoromethylpyrrolidin-1-yl, 3-trifluoromethylpyrrolidin-1-yl, (S)-3-trifluoromethylpyrrolidin-1-yl, (R)-3-trifluoromethylpyrrolidin-1-yl, 2-oxopyrrolidin-1-yl, 2-oxo-oxazolidin-3-yl, piperidin-1-yl, 2-methylpiperidin-1-yl, (S)-2-methylpiperidin-1-yl and (R)-2-methylpiperidin-1-yl.

6. The compound as claimed in claim 3, wherein the radical $R^{a'}$ carries 1, 2, 3 or 4 fluorine atoms.

7. The compound as claimed in claim 1 wherein Ar is unsubstituted or carries one radical $R^a$, which is selected from the group consisting of $(CH_2)_vCF_3$, $(CH_2)_vCHF_2$, $(CH_2)_vCH_2F$, $O(CH_2)_vCF_3$, $O(CH_2)_vCHF_2$ and $O(CH_2)_vCH_2F$, with v being 0, 1, 2 or 3.

8. The compound as claimed in claim 1, wherein Ar is unsubstituted or carries one radical $R^a$, which is selected from 5- or 6-membered heteroaromatic radicals having as ring member 1 heteroatom selected from O, S and N and which may further have 1, 2 or 3 nitrogen atoms as ring members, and wherein the 5- or 6-membered heteroaromatic radical may carry 1, 2 or 3 substituents selected from halogen, $NO_2$, $NH_2$, OH, CN, $C_1$-$C_6$-alkyl, fluorinated $C_1$-$C_6$-alkyl, $C_3$-$C_6$-cycloalkyl, fluorinated $C_3$-$C_6$-cycloalkyl, $C_1$-$C_6$-alkoxy, fluorinated $C_1$-$C_6$-alkoxy, $C_1$-$C_6$-hydroxyalkyl, $C_1$-$C_4$-alkoxy-$C_1$-$C_4$-alkyl, $C_1$-$C_6$-hydroxyalkoxy, $C_1$-$C_4$-alkoxy-$C_2$-$C_4$-alkoxy, $C_1$-$C_6$-alkylcarbonyl, fluorinated $C_1$-$C_6$-alkylcarbonyl, $C_1$-$C_6$-alkylamino, di-$C_1$-$C_6$-alkylamino, $C_1$-$C_6$-alkylaminocarbonyl, di-$C_1$-$C_6$-alkyl-aminocarbonyl, $C_1$-$C_6$-alkylcarbonylamino, fluorinated $C_1$-$C_6$-alkylcarbonylamino, $C_1$-$C_6$-alkylcarbonyloxy, fluorinated $C_1$-$C_6$-alkylcarbonyloxy, $C_1$-$C_6$-alkoxycarbonyl, $C_1$-$C_6$-alkylthio, fluorinated $C_1$-$C_6$-alkylthio, $C_1$-$C_6$-alkylsulfinyl, fluorinated $C_1$-$C_6$-alkylsulfinyl, $C_1$-$C_6$-alkylsulfonyl and fluorinated $C_1$-$C_6$-alkylsulfonyl.

9. The compound as claimed in claim 8, wherein Ar carries one heteroaromatic radical $R^a$, which is selected from furanyl, thienyl, pyrrolyl, pyrazolyl, imidazolyl, oxazolyl, isoxazolyl, [1,3,4]-thiadiazolyl, [1,2,4]-triazolyl, [1,2,3]-triazolyl and tetrazolyl, where the heteroaromatic radical may be unsubstituted or may carry 1 to 3 substituents selected from halogen, $C_1$-$C_4$-alkyl, $C_1$-$C_4$-alkoxy, fluorinated $C_1$-$C_4$-alkyl and fluorinated $C_1$-$C_4$-alkoxy.

10. The compound as claimed in claim 1, wherein Ar is phenyl.

11. The compound as claimed in claim 10, wherein Ar carries one radical $R^a$ in the 4-position of the phenyl ring.

12. The compound as claimed in claim 1, wherein X is CH.

13. The compound as claimed in claim 1, wherein $R^9$ is hydrogen, methoxy or methyl.

14. The compound as claimed in claim 1, wherein $R^9$ is located at the 2-position relative to the 1-position of the nitrogen ring atom and to the 3-position of the —$NR^3$—$SO_2$—Ar group.

15. The compound as claimed in claim 1, wherein $R^1$ is H, methyl, n-propyl, fluorinated $C_2$-$C_3$-alkyl or 1-propen-3-yl.

16. The compound as claimed in claim 1, wherein $R^{1a}$ is hydrogen or $C_1$-$C_4$-alkyl.

17. The compound as claimed in claim 1, wherein $R^{2a}$ is hydrogen.

18. The compound as claimed in claim 1, wherein $R^2$ is hydrogen.

19. The compound as claimed in claim 1, wherein $R^{8a}$ is hydrogen.

20. The compound as claimed in claim 1, wherein $R^8$ is hydrogen.

21. The compound as claimed in claim 1, wherein $R^{2a}$ and $R^{1a}$ together form an alkylene group $(CH_2)_n$ with n being 2, 3 or 4.

22. The compound as claimed in claim 1, wherein $R^{8a}$ and $R^{1a}$ together form an alkylene group $(CH_2)_s$ with s being 2 or 3.

23. The compound as claimed in claim 1, wherein $R^1$ and $R^{1a}$ together form an alkylene group $(CH_2)_r$ with r being 3, 4 or 5.

24. The compound as claimed in claim 1, wherein $R^{1a}$, $R^2$, $R^{2a}$, $R^8$ and $R^{8a}$ are each H, $R^1$ is propyl, $R^9$ is methoxy.

25. The compound as claimed in claim 1, wherein $R^{1a}$, $R^2$, $R^{2a}$, $R^8$ and $R^{8a}$ are H, $R^1$ is propyl, $R^9$ is methyl.

26. A pharmaceutical composition comprising at least one compound of the formula I or a pharmaceutically acceptable salt thereof as claimed in claim 1, optionally together with at least one physiologically acceptable carrier or auxiliary substance.

27. A method for treating the acute or chronic signs, symptoms and/or malfunctions of a medical disorder susceptible to treatment with a dopamine D3 receptor ligand, wherein the disorder is selected from the group consisting of Parkinson's disease, schizophrenia, impaired learning and memory, depression, anxiety, psychic disorders and behavioral disturbances caused by the abuse of psychotropic substances, and diabetic nephropathy, said method comprising administering an effective amount of at least one compound of the formula I or a pharmaceutically acceptable salt thereof as claimed in claim 1 to a subject in need thereof.

28. A method for suppressing the symptoms of a medical disorder susceptible to treatment with a dopamine D3 receptor ligand, wherein the disorder is selected from the group consisting of Parkinson's disease, schizophrenia, impaired learning and memory, depression, anxiety, psychic disorders and behavioral disturbances caused by the abuse of psychotropic substances, and diabetic nephropathy, said method comprising administering an effective amount of at least one compound of the formula I or a pharmaceutically acceptable salt thereof as claimed in claim 1 to a subject in need thereof.

* * * * *